US008367689B2

(12) United States Patent
Bauer et al.

(10) Patent No.: US 8,367,689 B2
(45) Date of Patent: Feb. 5, 2013

(54) INHIBITORS OF JAK

(75) Inventors: Shawn M. Bauer, Pacifica, CA (US);
Jack W. Rose, San Mateo, CA (US);
Yonghong Song, Foster City, CA (US);
Qing Xu, Foster City, CA (US);
Mukund Mehrotra, South San Francisco, CA (US); Wolin Huang, Foster City, CA (US); Anjali Pandey, Fremont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 21 days.

(21) Appl. No.: 12/775,358

(22) Filed: May 6, 2010

(65) Prior Publication Data
US 2011/0005947 A1    Jan. 13, 2011

Related U.S. Application Data

(60) Provisional application No. 61/176,077, filed on May 6, 2009, provisional application No. 61/256,239, filed on Oct. 29, 2009.

(51) Int. Cl.
*A01N 43/54* (2006.01)
*A61K 31/505* (2006.01)
(52) U.S. Cl. .................. 514/275; 544/323; 546/308
(58) Field of Classification Search .................. 544/330, 544/331
See application file for complete search history.

(56) References Cited

U.S. PATENT DOCUMENTS

| 7,122,542 | B2 | 10/2006 | Singh et al. |
| 7,517,886 | B2 | 4/2009 | Singh et al. |
| 2004/0029902 | A1 | 2/2004 | Singh et al. |
| 2005/0234049 | A1 | 10/2005 | Singh et al. |
| 2005/0272753 | A1* | 12/2005 | Nagashima et al. ........... 514/275 |
| 2009/0318407 | A1* | 12/2009 | Bauer et al. ............... 514/210.18 |
| 2010/0029610 | A1* | 2/2010 | Singh et al. ............... 514/210.18 |
| 2010/0048567 | A1* | 2/2010 | Jia et al. ...................... 514/235.8 |
| 2010/0249092 | A1* | 9/2010 | Singh et al. ............... 514/210.18 |
| 2011/0237590 | A1* | 9/2011 | Kitamura et al. ........... 514/237.2 |

FOREIGN PATENT DOCUMENTS

| EP | 1 054 004 A1 | 11/2000 |
| WO | WO 02/092571 A1 | 11/2002 |
| WO | WO 03/063794 A2 | 8/2003 |
| WO | WO 2004/014382 A1 | 2/2004 |
| WO | WO 2005/012294 A1 | 2/2005 |
| WO | WO 2005/016893 A2 | 2/2005 |
| WO | WO 2005/095400 A1 | 10/2005 |
| WO | WO 2008/009458 A1 | 1/2008 |
| WO | WO 2008/135786 A1 | 11/2008 |
| WO | WO 2009/145856 A1 | 12/2009 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
Blair, A. et al., "Lack of Expression of Thy-1 (CD90) on Acute Myeloid Leukemia Cells With Long-Term Proliferative Ability In Vitro and In Vivo," *Blood*, May 1, 1997, vol. 89, No. 9, pp. 3104-3112.
Constantinescu, S.N. et al., "Mining for JAK-STAT mutations in cancer," *Trends in Biochemical Sciences*, 2007, vol. 33, No. 3, pp. 122-131.
Eleveld, M.B. et al., "Diastereoselective Synthesis of Chiral Secondary Amines with Two Chiral Centers Directly Attached to the Nitrogen Atom," *J. Org. Chem.*, 1986, vol. 51, No. 19, pp. 3635-3642.
Haura, E.B. et al., "Mechanisms of Disease: insights into the emerging role of signal transducers and activators of transcription in cancer," *Nature Clinical Practice Oncology*, Jun. 2005, vol. 2, No. 6, pp. 315-324.
International Search Report mailed on Sep. 22, 2010, for International Application No. PCT/US2010/033921 filed on May 6, 2010, 5 pages.
Mócsai, A. et al., "Syk Is Required for Integrin Singnaling in Neutrophils," *Immunity*, Apr. 2002, vol. 16, pp. 547-558.
Passegué, E. et al., "Normal and leukemic hematopoiesis: Are leukemias a stem cell disorder or a reacquisition of stem cell characteristics?" *PNAS*, Sep. 30, 2003, vol. 100, Suppl. 1, pp. 11842-11849.
Turhan, A.G. et al., "Highly Purified Primitive Hematpoietic Stem Cells Are PML-RARA Negative and Generate Nonclonal Progenitors in Acute Promyelocytic Leukemia," *Blood*, Apr. 15, 1995, vol. 85, No. 8, pp. 2154-2161.
Turner, M. et al., "Tyrosine kinase SYK: essential functions for immunoreceptor signaling," *Immunology Today*, Mar. 2000, vol. 21, No. 3, pp. 148-154.
Turner, S.D. et al., "Fusion tyrosine kinase mediated signalling pathways in the transformation of haematopoietic cells," *Leukemia*, 2006, vol. 20, pp. 572-582.
U.S. Appl. No. 60/630,808, filed Nov. 24, 2004, for Robin Cooper et al.
U.S. Appl. No. 60/645,424, filed Jan. 19, 2005, for Rajinder Singh et al.
U.S. Appl. No. 60/654,620, filed Feb. 18, 2005, for Rajinder Singh et al.

* cited by examiner

*Primary Examiner* — James O Wilson
*Assistant Examiner* — Alexander R Pagano
(74) *Attorney, Agent, or Firm* — Kilpatrick Townsend & Stockton LLP

(57) ABSTRACT

The present invention is directed to compounds of formula I and tautomers and pharmaceutically acceptable salts thereof which are selective inhibitors of JAK. The present invention is also directed to intermediates used in making such compounds, the preparation of such a compound, pharmaceutical compositions containing such a compound, methods of inhibition JAK activity, and methods to prevent or treat a number of conditions mediated at least in part by JAK activity.

27 Claims, No Drawings

INHIBITORS OF JAK

CROSS-REFERENCES TO RELATED APPLICATIONS

This application claims the benefit of priority under 35 U.S.C. 119(e) to U.S. Provisional Application No. 61/176,077 filed on May 6, 2009 and U.S. Provisional Application No. 61/256,239 filed on Oct. 29, 2009 which are herein incorporated in their entirety by reference.

BACKGROUND OF THE INVENTION

This invention is directed to pyrimidine and pyridine-based compounds which act as inhibitors of JAK. This invention is also directed to pharmaceutical compositions containing the pyrimidine and pyridine-based compounds and methods of using the compounds or compositions to treat a condition mediated at least in part by JAK activity. The invention is also directed to methods of making the compounds described herein.

Janus tyrosine kinases (JAKs) are a small family of structurally and functionally related non-receptor, cytoplasmic protein tyrosine kinases, including JAK1, JAK2, JAK3, and tyrosine kinase 2 (TYK2). JAKs play pivotal roles in the initiation of cytokine-triggered signaling events by signal transducers and activators of transcriptions (STATs) via tyrosine phosphorylation. JAK-mediated tyrosine phosphorylations of cytokine receptors and STATs are the important signal transduction pathways used by many cytokines, growth factors, and interferons. Upon phosphorylation, the STATs dimerize and translocate to the nucleus where they can then induce transcription of the corresponding cytokine-responsive genes. This association with relevant cytokine signaling pathways makes JAK3 an important target for therapeutic intervention in the treatment of autoimmune disorders, inflammatory diseases, cell proliferative disorder and organ transplant rejection such as rheumatoid arthritis, psoriasis, Crohn's disease, multiple sclerosis, asthma and acute myeloid leukemias (AML).

JAK-3 in particular plays an essential role in the function of lymphocytes, macrophages and mast cells. The compounds that inhibit JAK-3 can be therapeutically useful in treatment of, leukemia, lymphoma where JAK3 is hyperactivated. JAK3 inhibition will be useful as immunosuppressive agent for treatment of chronic and/or acute organ transplant and autoimmune diseases such as rheumatoid arthritis, Type 1 diabetes, systemic lupus, multiple sclerosis, Crohn's disease and inflammatory diseases such as, asthma, psoriasis, chronic obstructive pulmonary disease.

An important feature of JAK3 is that it specifically associates with the common cytokine receptor gamma (γ) chain (cc) which is a shared component of the receptors for IL-2, IL-4, IL-7, IL-9, and IL-15. Unlike the other JAK family members, that are more widely expressed in many mammalian tissues, JAK3 expression seems to be mainly limited to the endoplasmic membranes of hematopoietic cells.

The pivotal roles in signaling through the gamma chain of γc containing cytokine receptors cytokine receptors and its limited expression and unique tissue distribution make JAK3 an attractive therapeutic target relative to the other JAK family members to manage the abnormal cytokine activities implicated in many cancer cells and inflammatory lymphocytes.

In the relatively young field of Janus kinase inhibition, Pfizer has already progressed their JAK3 inhibitor, Tasocitinib (CP-690,550), into Phase III clinical trials for acute rejection in kidney transplant patients. Other JAK3 inhibitors have been reported, such as the non-selective (within JAK family) but very potent tetracyclic pyridone 2, reported by Merck. Aventis has published an oxindole JAK3 inhibitor that shows good enzymatic selectivity vs JAK2. However, this oxindole inhibitor also shows very strong inhibition vs a panel of CDK kinases. Vertex has described aza indoles as JAK inhibitors (WO2005/95400). AstraZeneca has published quinoline 3-carboxamides as JAK 3 inhibitors (WO2002/92571) and other compounds for inhibition of all JAKs for the treatment of cancer (WO2008/135786).

Several mutated forms of JAK2 have been identified in a variety of disease settings, for example translocations resulting in the fusion of the JAK2 kianse domain with an oligo-meriaztiondomain, TEL-JAK2, Bcr-JAK2 and PCM1-JAK2 have been implicated in the pathogenesis of various hematological malignancies (SD Turner and Alesander DR, Leukemia, 2006, 20, 572-582). Recently a unique mutation encoding a valine to phenylalanine substitution in JAK2 was detected in a significant number of myleoproliferative diseases such as polycythemia vera (PV), essential thrombocythemia (ET) and idiopathic myelofibrosis patients.

Constitutive activation of the STAT family, in particular STAT3 and STAT5 have been detected in a wide range of cancers and hyperproliferative diseases (Haura et al, Oncology, 2005, 2(6), 315-324). Further, aberrant activation of the JAK/STAT pathway provides an important proliferative and/or anti-apoptotic drive downstream of many kinases (e.g. Flt3, EGFR) whose constitutive activation have been implicated as key drivers in a variety of cancers and hyperproliferative disorders. Potent and specific inhibitors of JAK1 and JAK2 will be useful in the treatment of cancers including multiple myeloma, prostate, breat and lung cancer, B-cell Chronic Lymphocytic Leukemia, metastatic melanoma, multiple myeloma, and hepatoma.

While progress has been made in this field, there remains a need in the art for compounds that inhibit JAK kinase, as well as for methods for treating conditions in a patient, such as rheumatoid arthritis, psoriasis, Crohn's disease, multiple sclerosis, asthma, acute myeloid leukemias (AML) and/or inflammation that can benefit from such inhibition. Moreover, the availability of compounds that selectively inhibit one of these kinases as compared to other kinases would also be desirable. The present invention satisfies this and other needs.

BRIEF SUMMARY OF THE INVENTION

The present invention provides novel compounds having activity as inhibitors of JAK kinase activity (also referred to herein as "JAK inhibitors"), as well as to methods for their preparation and use, and to pharmaceutical compositions containing the same. Such compounds have the following structure (I):

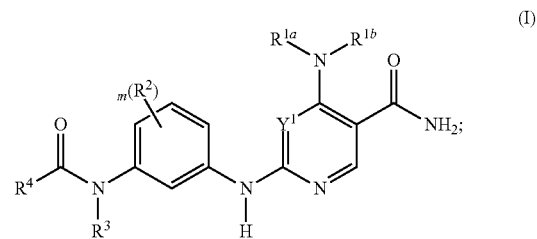

or a pharmaceutically acceptable salt thereof, wherein each $R^{1a}$, $R^{1b}$, $R^2$, $R^3$, $R^4$, $Y^1$ and m are as defined below.

The present invention also provides a pharmaceutical composition comprising a therapeutically effective amount of a compound of formula I, or a pharmaceutical acceptable salt thereof, and a pharmaceutically acceptable carrier and/or diluent.

The compounds of the present invention have utility over a wide range of therapeutic applications, and may be used to treat a variety of conditions, mediated at least in part by JAK activity, in both men and women, as well as a mammal in general (also referred to herein as a "subject"). For example, such conditions include, but are not limited to, those associated with cardiovascular disease, inflammatory disease or autoimmune disease. More specifically, the compounds of the present invention have utility for treating conditions or disorders including, but not limited to: allergy, asthma, rheumatoid arthritis, Crohn's disease, anti-phospholipid syndrome, lupus, psoriasis, multiple sclerosis, and chronic lymphocytic leukemia. Thus, in one embodiment, methods are disclosed which include the administration of an effective amount of a compound of formula (I), typically in the form of a pharmaceutical composition, to a subject in need thereof.

The present invention also provides a method for inhibiting the JAK activity of a blood sample comprising contacting said sample with a compound of the present invention.

The present invention further provides compounds in purified forms, as well as chemical intermediates.

These and other aspects, objects, features and advantages of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As used herein, the below terms have the following meanings unless specified otherwise:

1. Abbreviations and Definitions

The abbreviations used herein are conventional, unless otherwise defined. The following abbreviations are used: AcOH=acetic acid, AIBN=azobisisobutyronitrile (also azobisisobutylonitrile), aq.=aqueous, Boc=t-butylcarboxy, Bz-benzyl, BOP=benzotriazol-1-yloxytris(dimethylamino)-phosphonium hexafluorophosphate, BPO=benzoyl peroxide, nBuOH=n-butanol, $CBr_4$=tetrabromomethane, mCPBA=m-chloroperoxybenzoic acid, $CH_2Cl_2$ or DCM=dichloromethane, $Cs_2CO_3$=cesium carbonate, $CuCl_2$=copper chloride; DIBAL=diisobutylaluminum hydride, DIEA=Hunig's base or diisopropyl ethylamine, DME=dimethoxy ethane, DMF=dimethyl formamide, DMSO=dimethyl sulfoxide, $Et_3N$=triethylamine, EtOAc=ethyl acetate, g=gram, HATU=2-(1H 7-Azabenzotriazol-1-yl)-1,1,3,3-tetramethyl uronium hexafluorophosphate, $H_2$=hydrogen; $H_2O$=water; HBr=hydrogen bromide; HCl=hydrogen chloride, HIV=human immunodeficiency virus, HPLC=high pressure liquid chromatography, h=hour, IgE=immunoglobulin E, $IC_{50}$=The concentration of an inhibitor that is required for 50% inhibition of an enzyme in vitro, IPA=isopropyl alcohol, kg=kilogram, KCN=potassium cyanide, KOH=potassium hydroxide, $K_2PO_4$=potassium phosphate, LDA=lithium diisopropylamide, $LiAlH_4$=lithium aluminum hydride=LiOH: lithium hydroxide; MeCN=acetonitrile; MS=Mass Spec, m/z=mass to charge ratio, MHz=Mega Hertz, MeOH=methanol, µM=micromolar, µL=microliter, mg=milligram, mm=millimeter, mM=millimolar, mmol=millimole, mL=milliliter, mOD/min=millioptical density units per minute, min=minute, M=molar, $Na_2CO_3$=sodium carbonate, ng=nanogram, $NaHCO_3$=sodium bicarbonate; $NaNO_2$=sodium nitrite; NaOH=sodium hydroxide; $Na_2S_2O_3$=sodium thiosulfate; $Na_2SO_4$=sodium sulfate; NBS=N-bromosuccinimide; $NH_4Cl$=ammonium chloride; $NH_4OAc$=ammonium acetate; NaSMe=sodium methylthiolate, NBS=N-bromosuccinamide, n-BuLi=n-butyl lithium, nm=nanometer, nM=nanomolar, N=Normal, NMP=N-methyl-2-pyrrolidone, NMR=nuclear magnetic resonance, Pd/C=palladium on carbon, $Pd(PPh_3)_4$=Tetrakis-(triphenylphosphine)-palladium, pM=picomolar, Pin=pinacolato, PEG=polyethylene glycol, $PPh_3$ or $Ph_3P$=triphenyl phosphine, RLV=Raucher leukemia virus, Ra—Ni=Rainey Nickel, $SOCl_2$=thionyl chloride, RT=room temperature, TEA=triethylamine, THF=tetrahydrofuran, TFA=trifluoroacetic acid, TLC=thin layer chromatography, TMS=trimethylsilyl, Tf=trifluoromethylsulfonyl and TSC=trisodium citrate.

It is noted here that as used in this specification and the appended claims, the singular forms "a," "an," and "the" include plural reference unless the context clearly dictates otherwise.

"Alkyl," by itself or as part of another substituent, means, unless otherwise stated, a straight or branched chain, fully saturated aliphatic hydrocarbon radical having the number of carbon atoms designated. For example, "$C_{1-8}$alkyl" refers to a hydrocarbon radical straight or branched, containing from 1 to 8 carbon atoms that is derived by the removal of one hydrogen atom from a single carbon atom of a parent alkane. The phrase "unsubstituted alkyl" refers to alkyl groups that do not contain groups other than fully saturated aliphatic hydrocarbon radicals. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkenyl" by itself or as part of another substituent refers to a straight or branched chain, which may be mono- or poly-unsaturated, having the number of carbon atoms designated. For example, "$C_2$-$C_8$ alkenyl" means an alkenyl radical having from 2, 3, 4, 5, 6, 7 or 8 atoms that is derived by the removal of one hydrogen atom from a single carbon atom of a parent alkene. Examples include, but are not limited to vinyl, 2-propenyl i.e. —CH═C(H)($CH_3$), —CH═C($CH_3$)$_2$, —C($CH_3$)═C(H)$_2$, —C($CH_3$)═C(H)($CH_3$), —C($CH_2CH_3$)═$CH_2$, butadienyl e.g. 2-(butadienyl), pentadienyl e.g. 2,4-pentadienyl and 3-(1,4-pentadienyl), and hexadienyl, among others, and higher homologs and stereoisomers thereof. A "substituted" alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon. Each site of unsaturation may be either cis or trans configuration about the double bond(s).

The term "alkynyl", by itself or as part of another substituent, means a straight or branched chain hydrocarbon radical, which may be mono- or polyunsaturated, having the number of carbon atoms designated. For example, "$C_2$-$C_8$ alkynyl" means an alkynyl radical having from 2 to 8 carbon atoms that is derived by the removal of one hydrogen atom from a single carbon atom of a parent alkyne. "Unsubstituted alkynyl" refers to straight and branched chain groups such as those described with respect to unsubstituted alkyl groups as defined above, except that at least one triple bond exists between two carbon atoms. Examples include, but are not limited to ethynyl e.g. —C≡C(H), 1-propynyl e.g. —C≡C (CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others, and higher homologs and isomers thereof. A "substituted" alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

"Alkylene" by itself or as part of another substituent means a divalent radical derived from an alkane, as exemplified by —CH$_2$CH$_2$CH$_2$CH$_2$—. Typically, an alkylene group will have from 1, 2, 3, 4, 5, 6, 7 or 8 carbon atoms that is derived by the removal of one hydrogen atom from a single carbon atom of a parent alkyl.

"Cycloalkyl" or "carbocycle", by themselves or in combination with other terms, represent, unless otherwise stated, cyclic versions of "alkyl", "alkenyl" and "alkynyl" in which all ring atoms are carbon. "Cycloalkyl" or "carbocycle" refers to a mono- or polycyclic group. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s). The term "cycloalkenyl" refers to a cycloalkyl group that has at least one site of alkenyl unsaturation between the ring vertices. The term "cycloalkynyl" refers to a cycloalkyl group that has at least one site of alkynyl unsaturation between the ring vertices. When "cycloalkyl" is used in combination with "alkyl", as in $C_{3-8}$cycloalkyl$C_{3-8}$alkylene-, the cycloalkyl portion is meant to have the stated number of carbon atoms (e.g., from three to eight carbon atoms), while the alkylene portion has from one to eight carbon atoms. Typical cycloalkyl substituents have from 3 to 8 ring atoms. Examples of cycloalkyl include cyclopropyl, cyclobutyl, cyclpentyl, cyclohexyl, 1-cyclohexenyl, 3-cyclohexenyl, cycloheptyl, and the like.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of unsubstituted aryl groups include phenyl, 1-naphthyl, 2-naphthyl and 4-biphenyl. "Substituted aryl group" includes, for example, —CH$_2$OH (one carbon atom and one heteroatom replacing a carbon atom) and —CH$_2$SH. The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalky groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "heterocycle", "heterocyclyl" or "heterocyclic" refer to a saturated or unsaturated non-aromatic cyclic group containing at least one heteroatom. As used herein, the term "heteroatom" is meant to include oxygen (O), nitrogen (N), sulfur (S) and silicon (Si). Each heterocycle can be attached at any available ring carbon or heteroatom. Each heterocycle may have one or more rings. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imidazoline, pyrazol-5-one, pyrrolidine-2,5-dione, imidazolidine-2,4-dione, pyrrolidine, tetrahydroquinolinyl, decahydroquinolinyl, tetrahydrobenzooxazepinyl dihydrodibenzooxepin and the like.

"Heteroaryl" refers to a cyclic or polycyclic aromatic radical that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein. "Substituted heteroaryl" refers to a unsubstituted heteroaryl group as defined above in which one or more of the ring members is bonded to a non-hydrogen atom such as described above with respect to substituted alkyl groups and substituted aryl groups. Representative substituents include straight and branched chain alkyl groups-CH$_3$, —C$_2$H$_5$, —CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$ and halo.

In each of the above embodiments designating a number of atoms e.g. "$C_{1-8}$" is meant to include all possible embodiments that have one fewer atom. Non-limiting examples include $C_{1-7}$, $C_{2-8}$, $C_{2-7}$, $C_{3-8}$, $C_{3-7}$ and the like.

Each of the terms herein (e.g., "alkyl," "heteroalkyl," "aryl" and "heteroaryl") is meant to include both "unsubstituted" and optionally "substituted" forms of the indicated radical, unless otherwise indicated. Typically each radical is substituted with 0, 1, 2 3 4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other representative "substituents" include those in which one or more bonds to a carbon(s) or hydrogen(s) atoms is replaced by a bond to an alkyl, cycloalkyl, aryl, heteroaryl, or heterocyclyl group.

The herein-defined groups may include prefixes and/or suffixes that are commonly used in the art to create additional well-recognized substituent groups. As examples, "alkylamino" refers to a group of the formula —$NR^a R^b$. Unless stated otherwise, for the following groups containing $R^a$, $R^b$, $R^c$, $R^d$ and $R^e$: $R^a$, and $R^b$ are each independently selected from H, alkyl, alkoxy, thioalkoxy, cycloalkyl, aryl, heteroaryl, or heterocyclyl or are optionally joined together with the atom(s) to which they are attached to form a cyclic group. When $R^a$ and $R^b$ are attached to the same nitrogen atom, they can be combined with the nitrogen atom to form a 5-, 6- or 7-membered ring. For example, —$NR^a R^b$ is meant to include 1-pyrrolidinyl and 4-morpholinyl.

$R^c$, $R^d$, $R^e$ and $R^f$ are each independently selected from alkyl, alkenyl, alkynyl, cycloalkyl, cycloalkenyl, aryl, heteroaryl, heterocyclyl or alkylenearyl as defined herein.

Typically, a particular radical will have 0, 1, 2 or 3 substituents, with those groups having two or fewer substituents being preferred in the present invention. More preferably, a radical will be unsubstituted or monosubstituted. Most preferably, a radical will be unsubstituted.

"Substituents" for the alkyl and heteroalkyl radicals (as well as those groups referred to as alkylene, alkenyl, heteroalkylene, heteroalkenyl, alkynyl, cycloalkyl, heterocyclyl) can be a variety of groups selected from: —$OR^a$, =O, =$NR^a$, =N—$OR^a$, —$NR^a R^b$, —$SR^a$, halogen, —$SiR^a R^b R^c$, —OC(O)$R^a$, —C(O)$R^a$, —$CO_2 R^a$, —CONR$^a$R$^b$, —OC(O)NR$^a$R$^b$, —NR$^b$C(O)R$^a$, —NR$^a$—C(O)NR$^b$R$^c$, —NR$^a$—SO$_2$NR$^b$R$^c$, —NR$^b$CO$_2$R$^a$, —NH—C(NH$_2$)=NH, —NR$^a$C(NH$_2$)=NH, —NH—C(NH$_2$)=NR$^a$, —S(O)R$^a$, —SO$_2$R$^a$, —SO$_2$NR$^a$R$^b$, —NR$^b$SO$_2$R, —CN and —NO$_2$, in a number ranging from zero to three, with those groups having zero, one or two substituents being particularly preferred.

In some embodiments, "substituents" for the alkyl and heteroalkyl radicals are selected from: —OR$^a$, =O, —NR$^a$R$^b$, —SR$^a$, halogen, —SiR$^a$R$^b$R$^c$, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^b$CO$_2$R$^a$, —NR$^a$—SO$_2$NR$^b$R$^c$, —S(O) R$^a$, —SO$_2$R$^a$, —SO$_2$NR$^a$R$^b$, —NR$^c$SO$_2$R, —CN and —NO$_2$, where R$^a$ and R$^b$ are as defined above. In some embodiments, substituents are selected from: —OR$^a$, =O, —NR$^a$R$^b$, halogen, —OC(O)R$^a$, —CO$_2$R$^a$, —CONR$^a$R$^b$, —OC(O)NR$^a$R$^b$, —NR$^b$C(O)R$^a$, —NR$^b$CO$_2$R$^a$, —NR$^a$—SO$_2$NR$^b$R$^c$, —SO$_2$R$^a$, —SO$_2$NR$^a$R$^b$, —NR"SO$_2$R, —CN and —NO$_2$.

Examples of substituted alkyl are: —(CH$_2$)$_3$NH$_2$, —(CH$_2$)$_3$NH(CH$_3$), —(CH$_2$)$_3$NH(CH$_3$)$_2$, —CH$_2$C(=CH$_2$)CH$_2$NH$_2$, —CH$_2$C(=O)CH$_2$NH$_2$, —CH$_2$S(=O)$_2$CH$_3$, —CH$_2$OCH$_2$NH$_2$, —CO$_2$H. Examples of substituents of substituted alkyl are: CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$, and halo.

Similarly, "substituents" for the aryl and heteroaryl groups are varied and are selected from: -halogen, —OR$^a$, —OC(O) R$^a$, —NR$^a$R$^b$, —SR$^a$, —R$^a$, —CN, —NO$_2$, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^a$, —NR$^a$—C(O)NR$^b$R$^c$, —NH—C(NH$_2$) =NH, —NR$^a$C(NH$_2$)=NH, —NH—C(NH$_2$)=NR$^a$, —S(O)R$^a$, —S(O)$_2$R$^a$, —S(O)$_2$NR$^a$R$^b$, —N$_3$, —CH(Ph)$_2$, perfluoroC$_{1-8}$alkoxy, and perfluoroC$_{1-8}$alkyl, in a number ranging from zero to the total number of open valences on the aromatic ring system; and where R$^a$, R$^b$ and R$^c$ are independently selected from hydrogen, C$_{1-6}$alkyl and heteroalkyl, unsubstituted aryl and heteroaryl, (unsubstituted aryl)-C$_{1-8}$alkyl, and (unsubstituted aryl)oxy-C$_{1-8}$alkyl.

Two of the "substituents" on adjacent atoms of the aryl or heteroaryl ring may optionally be replaced with a substituent of the formula -T—C(O)—(CH$_2$)q-U—, wherein T and U are independently —NH—, —O—, —CH$_2$— or a single bond, and q is 0, 1 or 2. Alternatively, two of the substituents on adjacent atoms of the aryl or heteroaryl ring may optionally be replaced with a substituent of the formula -A-(CH$_2$)$_r$-B—, wherein A and B are independently —CH$_2$—, —O—, —NH—, —S—, —S(O)—, —S(O)$_2$—, S(O)$_2$NR$^a$— or a single bond, and r is 1, 2 or 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$-X—(CH$_2$)$_t$-—, where s and t are independently integers of from 0 to 3, and X is —O—, —NR$^a$—, —S—, —S(O)—, —S(O)$_2$—, or —S(O)$_2$NR$^a$—. The substituent R$^a$ in —NR$^a$— and —S(O)$_2$NR$^a$— is selected from hydrogen or unsubstituted C$_{1-6}$alkyl. Otherwise, R' is as defined above.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

"Alkoxy" refers to —OR$^d$ wherein R$^d$ is alkyl as defined herein. Representative examples of alkoxy groups include methoxy, ethoxy, t-butoxy, trifluoromethoxy, and the like.

"Amino" refers to the group —NR$^a$R$^b$ where R$^a$ and R$^b$ are independently H, alkyl, aryl, heterocyclyl and the like; or can also be combined to form a 3-7 membered ring with the nitrogen atom to which each is attached. The term "alkylamino" refers to the group —NR$^a$R$^b$ where R$^a$ is alkyl and R$^b$ is H or alkyl. The term "arylamino" refers to the group —NR$^a$R$^b$ where R$^a$ is aryl and R$^b$ is hydrogen, alkyl, aryl, or heterocyclyl. The term "(alkyl)(aryl)amino" refers to the group —NR$^a$R$^b$ where R$^a$ is alkyl and R$^b$ is aryl. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

"Aminocarbonyl" or "aminoacyl" refers to the amide —C(=O)—NR$^a$R$^b$ where R$^a$ is H and R$^b$ is H. The term "alkylaminocarbonyl" refers herein to the group —C(=O)—NR$^a$R$^b$ where R$^a$ is alkyl and R$^b$ is H or alkyl. The term "arylaminocarbonyl" refers herein to the group —C(=O)—NR$^a$R$^b$ where R$^a$ or R$^b$ is aryl. Representative aminocarbonyl groups include, for example, those shown below. These aminocarbonyl group can be further substituted as will be apparent to those having skill in the organic and medicinal chemistry arts in conjunction with the disclosure herein.

"Bond" when used a element in a Markush group means that the corresponding group does not exist, and the groups of both sides are directly linked.

"Carbonyl" refers to the divalent group —C(=O)—.

"Carboxy" or "carboxyl" refers to the group —CO$_2$H.

"Carboxyl ester" or "carboxy ester" refers to the groups —C(=O)OR$^c$.

"(Carboxyl ester)amino" refers to the groups —NR$^a$—C(O)OR$^c$, where R$^a$ is alkyl or hydrogen.

"Cyano" refers to —CN.

"Ester" refers to —C(=O)OR$^d$ wherein R$^d$ is alkyl, cycloalkyl, aryl, heteroaryl, or heterocyclyl.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "haloC$_{1-8}$alkyl" is meant to include trifluoromethyl, 2,2,2-trifluoroethyl, 4-chlorobutyl, 3-bromopropyl, and the like. The term "perhaloalkyl" means, unless otherwise stated, alkyl substituted with (2m'+1) halogen atoms, where m' is the total number of carbon atoms in the alkyl group. For example, the term "perhaloC$_{1-8}$alkyl", is meant to include trifluoromethyl, pentachloroethyl, 1,1,1-trifluoro-2-bromo-2-chloroethyl, and the like. Additionally, term "haloalkoxy" refers to an alkoxy radical substituted with one or more halogen atoms.

"Heteroalkyl" means an alkyl radical as defined herein with one, two or three components independently selected from cyano, oxo, —O—, —OR$^w$, —NR$^x$—, —NR$^x$R$^y$, —S(O)$_n$— and —S(O)$_n$R$^z$ (where n is an integer from 0 to 2), with the understanding that the point of attachment of the heteroalkyl radical is through a carbon, nitrogen, oxygen or sulfur atom of the heteroalkyl radical. R$^w$ is hydrogen, alkyl, cycloalkyl, cycloalkyl-alkyl, aryl, araalkyl, alkoxycarbonyl, aryloxycarbonyl, carboxamido, or mono- or di-alkylcarbamoyl. R$^x$ is hydrogen, alkyl, cycloalkyl, cycloalkyl-alkyl, aryl or araalkyl. Ry is hydrogen, alkyl, cycloalkyl, cycloalkyl-alkyl, aryl, araalkyl, alkoxycarbonyl, aryloxycarbonyl, carboxamido, mono- or di-alkylcarbamoyl or alkylsulfonyl. R$^z$ is hydrogen (provided that n is 0), alkyl, cycloalkyl, cycloalkyl-alkyl, aryl, araalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^w$, R$^x$, R$^y$, and R$^z$ can be further substituted by amino, fluorine, alkylamino, di-alkylamino, OH or alkoxy. Additionally, the prefix indicating the number of carbon atoms (e.g., C$_1$-C$_{10}$) refers to the total number of carbon atoms in the portion of the heteroalkyl group exclusive of the cyano, oxo, —O—, —OR$^w$, —NR$^x$—, —NR$^x$R$^y$, —S(O)$_n$— and —S(O)$_n$R$^z$ portions. Examples include alkoxy, alkoxyalkylene, amino, aminoalkylene, aminocarbonyl, alkylcarbonylamino, and the like.

"Heterocyclylcarbonyl" refers to the —C(=O)R$^c$ where R$^c$ is heterocyclyl.

"Hydroxy" or "hydroxyl" refers to the group —OH.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or disubstituted with an alkyl group and situations where the heterocyclo group is not substituted with the alkyl group.

"Optionally substituted" means a ring which is optionally substituted independently with substituents. A site of a group that is unsubstituted may be substituted with hydrogen.

"Oxo" refers to the divalent group =O.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, $3^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug ester form. "Prodrug"s of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

A wide variety of progroups, as well as the resultant promoieties, suitable for masking functional groups in the active JAK selective inhibitory compounds to yield prodrugs are well-known in the art. For example, a hydroxyl functional group may be masked as a sulfonate, ester (such as acetate or maleate) or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including methyl, ethyl, pivaloyloxymethyl, silyl esters and thioesters), amide or hydrazide promoiety, which may be hydrolyzed in vivo to provide the carboxyl group. The invention includes those esters and acyl groups known in the art for modifying the solubility or hydrolysis characteristics for use as sustained-release or prodrug formulations. Other specific examples of suitable progroups and their respective promoieties will be apparent to those of skill in the art.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystalization or chromatagraphic means well known in the art, and subsequent recovery of the pure enantiomers.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

An "agonist" or "activator" refers to an agent or molecule that binds to a receptor of the invention, stimulates, increases, opens, activates, facilitates, enhances activation or enzymatic activity, sensitizes or up regulates the activity of a receptor of the invention.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of JAK" and related terms and phrases refer to a condition or disorder associated with inappropriate, e.g., less than or greater than normal, activity of JAK and at least partially responsive to or affected by modulation of JAK (e.g., JAK antagonist or agonist results in some improvement in patient well-being in at least some patients). Inappropriate functional activity of JAK might arise as the result of expression of JAK in cells which normally do not express the receptor, greater than normal production of JAK, or slower than normal metabolic inactivation or elimination of JAK or its active metabolites, increased expression of JAK or degree of intracellular activation (leading to, e.g., inflammatory and immune-related disorders and conditions) or decreased expression of JAK. A condition or disorder associated with JAK may include a "JAK-mediated condition or disorder".

As used herein, the phrases "a condition or disorder mediated at least in part by JAK activity", and related phrases and terms refer to a condition or disorder characterized by inappropriate, e.g., greater than normal, JAK activity. Inappropriate JAK functional activity might arise as the result of JAK expression in cells which normally do not express JAK or increased JAK expression or degree of intracellular activation (leading to, e.g., inflammatory and immune-related disorders and conditions). A condition or disorder mediated at least in part by JAK activity may be completely or partially mediated by inappropriate JAK functional activity. However, a condition or disorder mediated at least in part by JAK activity is one in which modulation of JAK results in some effect on the underlying condition or disorder (e.g., an JAK antagonist results in some improvement in patient well-being in at least some patients).

The term "inflammation" as used herein refers to infiltration of white blood cells (e.g., leukocytes, monocytes, etc.) into the area being treated for restenosis.

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

As used herein, the term "JAK" refers to a Janus kinase (RefSeq Accession No. P-43408) or a variant thereof that is capable of mediating gene expression in vitro or in vivo. JAK variants include proteins substantially homologous to native JAK, i.e., proteins having one or more naturally or non-naturally occurring amino acid deletions, insertions or substitutions (e.g., JAK derivatives, homologs and fragments). The amino acid sequence of JAK variant preferably is at least about 80% identical to a native JAK, more preferably at least about 90% identical, and most preferably at least about 95% identical.

The term "leukocyte" refers to any of the various blood cells that have a nucleus and cytoplasm, separate into a thin white layer when whole blood is centrifuged, and help protect the body from infection and disease. Examples of leukocytes include, without limitation, neutrophils, eosinophils, basophils, lymphocytes, and monocytes.

The term "mammal" includes, without limitation, humans, domestic animals (e.g., dogs or cats), farm animals (cows, horses, or pigs), monkeys, rabbits, mice, and laboratory animals.

The terms "modulate", "modulation" and the like refer to the ability of a compound to increase or decrease the function and/or expression of JAK, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with JAK, either directly or indirectly, and/or the upregulation or downregulation of the expression of JAK, either directly or indirectly. In a preferred embodiment, the modulation is direct Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of JAK can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100% Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Patient" refers to human and non-human animals, especially mammals. Examples of patients include, but are not limited to, humans, cows, dogs, cats, goats, sheep, pigs and rabbits.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

The terms "prevent", "preventing", "prevention" and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or reacquiring a disorder or condition or one or more of its attendant symptoms.

The phrase "selectively" or "specifically" when referring to binding to a receptor, refers to a binding reaction that is determinative of the presence of the receptor, often in a heterogeneous population of receptors and other biologics. Thus, under designated conditions, the compounds bind to a particular receptor at least two times the background and more typically more than 10 to 100 times background. Specific binding of a compound under such conditions requires a compound that is selected for its specificity for a particular receptor. For example, small organic molecules can be screened to obtain only those compounds that specifically or selectively bind to a selected receptor and not with other receptors or proteins. A variety of assay formats may be used to select compounds that are selective for a particular receptor. For example, High-throughput screening assays are routinely used to select compounds that are selective for a particular a receptor.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "treat", "treating", "treatment" and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

The term "vessel" refers to any channel for carrying a fluid, such as an artery or vein. For example, a "blood vessel" refers to any of the vessels through which blood circulates in the body. The lumen of a blood vessel refers to the inner open space or cavity of the blood vessel.

2. Embodiments of the Invention a. Compounds

The present invention provides one group of embodiments, a compound having the formula I:

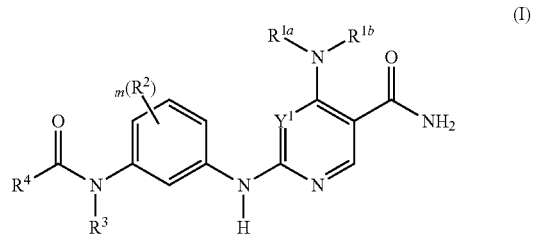

(I)

or a tautomer or pharmaceutically acceptable salt thereof, wherein:

$Y^1$ is N or $CR^{1c}$;

$R^{1a}$ is (a) $C_{3-8}$cycloalkyl, optionally substituted with from 1 to 3 substituents $R^{1d}$ wherein each $R^{1d}$ is independently selected from the group consisting of $C_{1-8}$alkyl, $C_{2-8}$alkenyl, $C_{2-8}$alkynyl, hydroxyl, halogen, $C_{1-8}$heteroalkyl, cyano, aryl, heteroaryl, heterocyclyl and heterocyclylcarbonyl; or if on adjacent carbon atoms of the $C_{3-8}$cycloalkyl, may be combined with the atoms to which each are attached to form an aryl group;

(b) $C_{1-8}$alkyl, optionally substituted with from 1 to 3 substituents selected from the group consisting of $C_{2-8}$alkenyl, $C_{2-8}$alkynyl, amino, hydroxyl, halogen, $C_{1-8}$heteroalkyl, cyano, $C_{3-8}$cycloalkyl, aryl, haloaryl, $C_{1-8}$alkylaryl, $C_{1-8}$alkoxyaryl, heteroaryl, $C_{3-8}$heterocyclyl and $C_{3-8}$ heterocyclylcarbonyl;

(c) heterocyclyl, optionally substituted with from 1 to 3 substituents selected from the group consisting of $C_{1-8}$alkyl, $C_{2-8}$alkenyl, $C_{2-8}$alkynyl, hydroxyl, halogen, $C_{1-8}$heteroalkyl, cyano, aryl, heteroaryl, heterocyclyl and heterocyclylcarbonyl;

(d) aryl, optionally substituted with from 1 to 3 substituents selected from the group consisting of $C_{1-8}$alkyl, $C_{2-8}$alkenyl, $C_{2-8}$alkynyl, hydroxyl, halogen, $C_{1-8}$heteroalkyl, cyano, aryl, heteroaryl, heterocyclyl and heterocyclylcarbonyl, amino and alkylsulfonyl; and (e) heteroaryl, optionally substituted with from 1 to 3 substituents selected from the group consisting of $C_{1-8}$alkyl, $C_{2-8}$alkenyl, $C_{2-8}$alkynyl, hydroxyl, halogen, $C_{1-8}$heteroalkyl, cyano, aryl, heteroaryl, heterocyclyl and heterocyclylcarbonyl;

$R^{1b}$ is H or $C_{1-8}$alkyl;
$R^{1c}$ is H, $C_{1-8}$alkyl or halogen;
$R^2$ is H, $C_{1-8}$alkyl, $C_{1-8}$heteroalkyl, heterocyclyl$C_{1-8}$alkoxy, halogen or heterocyclyl;
$R^3$ is H or $C_{1-8}$alkyl or $C_{3-8}$cycloalkyl;
$R^4$ is selected from the group consisting amino, $C_{1-8}$alkyl, amino$C_{1-8}$alkyl, $C_{2-8}$alkenyl, $C_{2-8}$alkynyl, $C_{1-8}$heteroalkyl, $C_{3-8}$cycloalkyl, aryl, heteroaryl and $C_{3-8}$heterocyclyl; and
m is 0, 1, 2 or 3.

The present invention provides another group of embodiments, a compound having the formula I:

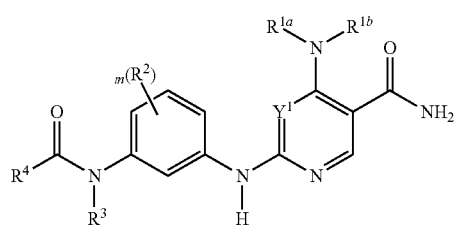

(I)

or a tautomer or pharmaceutically acceptable salt thereof, wherein:

$Y^1$ is N or $CR^{1c}$;

$R^{1a}$ is (a) $C_{3-8}$cycloalkyl, optionally substituted with from 1 to 3 substituents $R^{1d}$ wherein each $R^{1d}$ is independently selected from the group consisting of $C_{1-8}$alkyl, $C_{2-8}$alkenyl, $C_{2-8}$alkynyl, hydroxyl, halogen, $C_{1-8}$heteroalkyl, cyano, aryl, heteroaryl, heterocyclyl and heterocyclylcarbonyl; or if on adjacent carbon atoms of the $C_{3-8}$cycloalkyl, may be combined with the atoms to which each are attached to form an aryl group;

(b) $C_{1-8}$alkyl, optionally substituted with from 1 to 3 substituents selected from the group consisting of $C_{2-8}$alkenyl, $C_{2-8}$alkynyl, amino, hydroxyl, halogen, $C_{1-8}$heteroalkyl, cyano, $C_{3-8}$cycloalkyl, aryl, haloaryl, $C_{1-8}$alkylaryl, $C_{1-8}$alkoxyaryl, heteroaryl, $C_{3-8}$heterocyclyl and $C_{3-8}$ heterocyclylcarbonyl;

$R^{1b}$ is H or $C_{1-8}$alkyl;
$R^{1c}$ is H, $C_{1-8}$alkyl or halogen;
$R^2$ is H, $C_{1-8}$alkyl, $C_{1-8}$alkoxy or halogen;
$R^3$ is H or $C_{1-8}$alkyl;

$R^4$ is selected from the group consisting amino, $C_{1-8}$alkyl, $C_{2-8}$alkenyl, $C_{2-8}$alkynyl, $C_{1-8}$ heteroalkyl, $C_{3-8}$cycloalkyl, aryl, heteroaryl and $C_{3-8}$heterocyclyl; and
m is 0, 1, 2 or 3.

The present invention provides another group of embodiments, a compound wherein $Y^1$ is N. In another group of embodiments, $Y^1$ is CH.

The present invention provides one group of embodiments, a compound having the formula Ia:

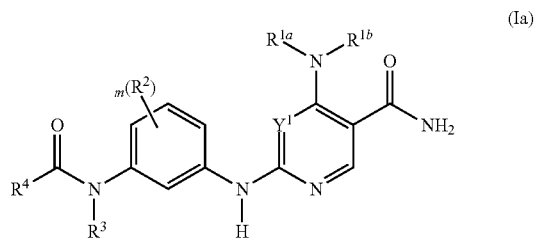

(Ia)

or a tautomer or pharmaceutically acceptable salt thereof, wherein:

$R^{1a}$ is (a) $C_{3-8}$cycloalkyl, optionally substituted with from 1 to 3 substituents $R^{1d}$ wherein each $R^{1d}$ is independently selected from the group consisting of $C_{1-8}$alkyl, $C_{2-8}$alkenyl, $C_{2-8}$alkynyl, hydroxyl, halogen, $C_{1-8}$heteroalkyl, cyano, aryl, heteroaryl, heterocyclyl and heterocyclylcarbonyl; or if on adjacent carbon atoms of the $C_{3-8}$cycloalkyl, may be combined with the atoms to which each are attached to form an aryl group;

(b) $C_{1-8}$alkyl, optionally substituted with from 1 to 3 substituents selected from the group consisting of $C_{2-8}$alkenyl, $C_{2-8}$alkynyl, amino, hydroxyl, halogen, $C_{1-8}$heteroalkyl, cyano, $C_{3-8}$cycloalkyl, aryl, haloaryl, $C_{1-8}$alkylaryl, $C_{1-8}$alkoxyaryl, heteroaryl, $C_{3-8}$heterocyclyl and $C_{3-8}$ heterocyclylcarbonyl;

$R^{1b}$ is H or $C_{1-8}$alkyl;
$R^2$ is H, $C_{1-8}$alkyl, $C_{1-8}$alkoxy or halogen;
$R^3$ is H or $C_{1-8}$alkyl;
$R^4$ is selected from the group consisting $C_{1-8}$alkyl, $C_{1-8}$heteroalkyl, $C_{3-8}$cycloalkyl, and amino; and
m is 0, 1, 2 or 3.

The present invention provides another group of embodiments, a compound wherein $R^3$ is H.

The present invention provides another group of embodiments, a compound having the formula (Ib):

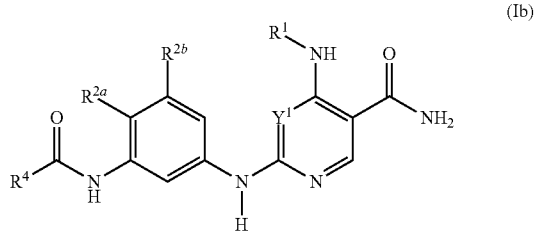

(Ib)

or a tautomer or pharmaceutically acceptable salt thereof, wherein:

$R^1$ is (a) $C_{3-8}$cycloalkyl, optionally substituted with hydroxyl and aryl;

(b) $C_{1-8}$alkyl, optionally substituted with from 1 to 3 substituents selected from the group consisting of $C_{2-8}$alkynyl, hydroxyl, halogen, $C_{1-8}$alkoxy, cyano, aminocarbonyl, $C_{3-8}$ cyclopropyl, aryl, haloaryl, $C_{1-8}$alkylaryl, $C_{1-8}$alkoxyaryl, heteroaryl, and heterocyclyl, heterocyclylcarbonyl;

$R^{2a}$ H, $C_{1-8}$alkyl, $C_{1-8}$alkoxy or halogen;

$R^{2b}$ is H, $C_{1-8}$alkyl, $C_{1-8}$alkoxy or halogen;

$R^4$ is selected from the group consisting $C_{1-8}$alkyl, $C_{1-8}$alkoxyC$_{1-8}$alkylene, $C_{3-8}$ cycloalkyl, $C_{1-8}$alkoxy, and amino.

In another group of embodiments, $R^1$ is $C_{3-8}$cycloalkyl, optionally substituted with hydroxy. In another group of embodiments, $R^1$ is cyclopropyl, cyclobutyl, cyclopentyl or cyclohexyl, optionally substituted with hydroxy. In another group of embodiments, $R^1$ is $C_{1-8}$ alkyl, optionally substituted with from 1 to 3 substituents selected from the group consisting of $C_{2-8}$alkynyl, hydroxy, halogen, $C_{1-8}$alkoxy, cyano, aminocarbonyl, $C_{3-8}$cycloalkyl, aryl, haloaryl, heteroaryl, heterocyclyl and heterocyclylcarbonyl. In another group of embodiments, $R^1$ is —CH$_3$, CH$_2$CH$_3$, —CH(CH$_3$)$_2$, —C(CH$_3$)$_3$ or —CH$_2$CH$_2$CH(CH$_3$)$_2$. In another group of embodiments, $R^1$ is $C_{1-8}$alkyl, optionally substituted with from 1 to 3 substituents selected from the group consisting of $C_{2-8}$alkynyl, hydroxy, halogen, $C_{1-8}$alkoxy, cyano, aminocarbonyl and $C_{3-8}$cycloalkyl. In another group of embodiments, $R^1$ is —CH$_2$C≡CH, —CH$_2$CF$_3$, —CH$_2$-cPr, —CH$_2$CH$_2$OCH$_3$ or CH$_2$CH$_2$CH$_2$OCH$_3$. In another group of embodiments, $R^1$ is $C_{1-8}$alkyl, substituted with from 1 to 3 substituents selected from the group consisting of aryl, haloaryl, $C_{1-8}$alkylaryl, $C_{1-8}$alkoxyaryl, heteroaryl, heterocyclyl and heterocyclylcarbonyl.

In another group of embodiments, $R^{2a}$ is H, methyl, methoxy, fluoro or chloro and $R^{2b}$ is H, methyl, methoxy, fluoro or chloro. In another group of embodiments, $R^{2a}$ is chloro and $R^{2b}$ is H.

The present invention provides another group of embodiments, a compound having the formula (Ic):

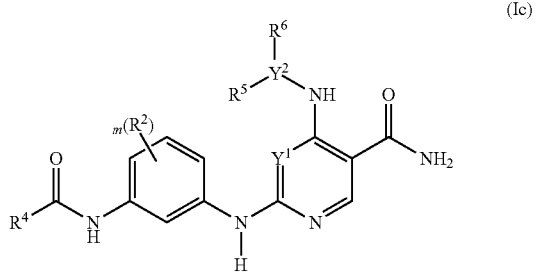

(Ic)

or a tautomer or pharmaceutically acceptable salt thereof, wherein:

$Y^2$ is —CH or —CH—CH—;

$R^5$ is H, $C_{1-8}$alkyl or hydroxyC$_{1-8}$alkylene; and $R^6$ is $C_{2-8}$alkynyl, hydroxyl, halogen, $C_{1-8}$alkoxy, cyano, aminocarbonyl, $C_{3-8}$ cyclopropyl, aryl, haloaryl, heteroaryl, heterocyclyl and heterocyclylcarbonyl or $C_{1-8}$alkyl, optionally substituted with from 1 to 3 substituents selected from the group consisting of $C_{2-8}$ alkynyl, hydroxyl, halogen, $C_{1-8}$alkoxy, cyano, aminocarbonyl, $C_{3-8}$cyclopropyl, aryl, haloaryl, $C_{1-8}$alkylaryl, $C_{1-8}$alkoxyaryl, heteroaryl, heterocyclyl and heterocyclylcarbonyl.

In another group of embodiments, $R^4$ is $C_{1-8}$heteroalkyl, selected from the group consisting of $C_{1-8}$alkoxy and $C_{1-8}$alkoxyC$_{1-8}$alkylene. In another group of embodiments, $R^5$ is CH$_3$; and $R^6$ is Ph or

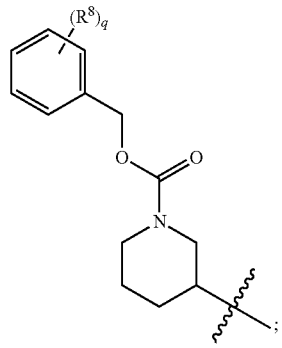

$R^8$ is selected from the group consisting of $C_{1-8}$alkyl, halogen, $C_{1-8}$alkoxy, or may be taken together to form a heterocyclic ring; and q is 0, 1, 2 or 3; the wavy line indicates the point of attachment to the rest of the molecule.

The present invention provides another group of embodiments, a compound having the formula (Id):

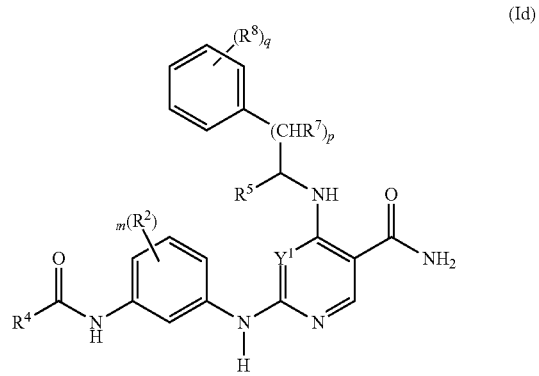

(Id)

or a tautomer or pharmaceutically acceptable salt thereof, wherein:

$R^5$ is $C_{1-8}$alkyl or hydroxyC$_{1-8}$alkylene; or may be taken together with $R^8$ to form a cyclic ring;

$R^7$ is $C_{1-8}$alkyl, hydroxyl or $C_{1-8}$alkoxy;

$R^8$ is selected from the group consisting of $C_{1-8}$alkyl, halogen and $C_{1-8}$alkoxy, or may be taken together to form a heterocyclic ring; and p is 0, 1, 2, or 3; and q is 0, 1, 2 or 3.

The present invention provides another group of embodiments, a compound having the formula (Ie):

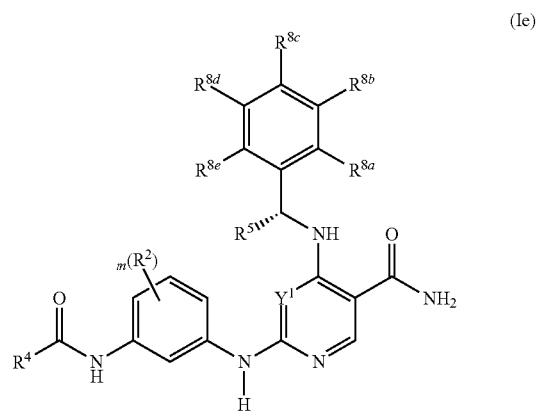

(Ie)

or a tautomer or pharmaceutically acceptable salt thereof, wherein:

$R^5$ is $C_{1-8}$alkyl or hydroxyC$_{1-8}$alkylene; or may be taken together with $R^{8a}$ or $R^{8b}$ to form a cyclic ring;

$R^{8a}$ is H, halogen, or may be taken together with $R^5$ to form 5-6 membered carbocyclic ring;

$R^{8b}$ is H, halogen or, or may be taken together with $R^{8a}$ to form a heterocyclic ring;

$R^{8c}$ is H, $C_{1-8}$alkyl, halogen or $C_{1-8}$alkoxy, or may be taken together with $R^{8b}$ to form a heterocyclic ring;

$R^{8d}$ is H; and $R^{8e}$ is H, halogen or may be taken together with $R^5$ to form 5-6 membered carbocyclic ring.

The present invention provides another group of embodiments, a compound having the formula If:

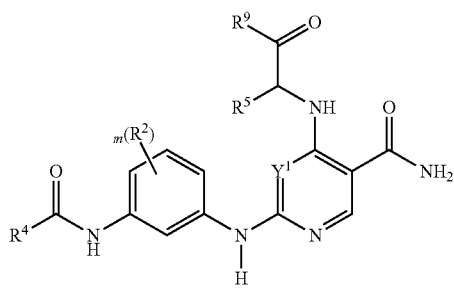

(If)

or a tautomer or pharmaceutically acceptable salt thereof, wherein:

$R^9$ is hetero$C_{1-8}$alkyl.

The present invention provides another group of embodiments, a compound having the formula Ig:

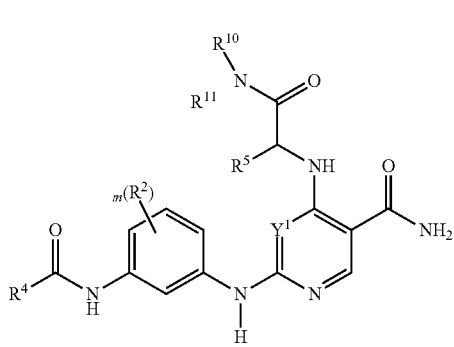

(Ig)

or a tautomer or pharmaceutically acceptable salt thereof, wherein:

$R^{10}$ is H or $C_{1-8}$alkyl; or may be taken together with $R^{11}$ and the nitrogen atom to which each is attached to form a heterocyclic ring; and $R^{11}$ is H or $C_{1-8}$alkyl; or may be taken together with $R^{10}$ and the nitrogen atom to which each is attached to form a heterocyclic ring.

In another group of embodiments, the compound has the formula Ih:

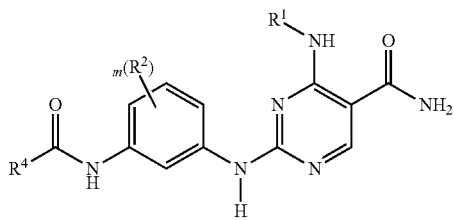

(Ih)

or a tautomer or pharmaceutically acceptable salt thereof, wherein:

$R^1$ and $R^4$ are $C_{3-8}$cycloalkyl.

In another group of embodiments, the compound has the formula (Ii):

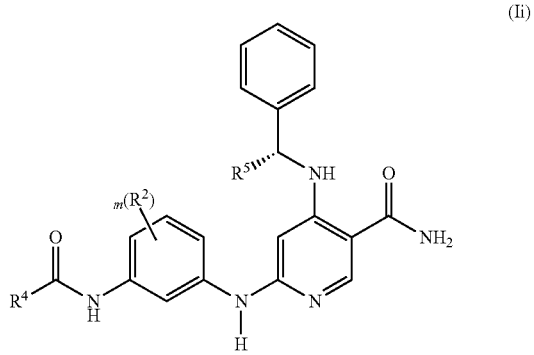

(Ii)

or a tautomer or pharmaceutically acceptable salt thereof, wherein:

$R^5$ is H or $C_{1-8}$alkyl;

$R^4$ is $C_{1-8}$alkyl or heterocyclyl

In another group of embodiments, $R^4$ is selected from the group consisting of —$CH_3$, —$CH_2CH_3$, —$NH_2$, —$NHCH_3$, —$NCH_2CH_3$, —$N(CH_3)_2$, —$OCH_3$, —$OCH_2CH_3$, —$OCH(CH_3)_2$, —$CH_2OCH_3$, —$CH_2CONH_2$, cPr and cBu. In another group of embodiments, $R^4$ has the formula:

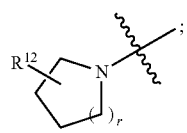

wherein $R^{12}$ is selected from the group consisting of H and OH, r is 0 or 1; and the wavy line indicates the point of attachment to the rest of the molecule. In another group of embodiments, $R^4$ has the formula:

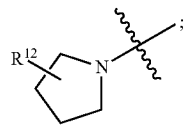

wherein $R^{12}$ is selected from the group consisting of H and OH; and the wavy line indicates the point of attachment to the rest of the molecule.

The present invention provides another group of embodiments, a compound selected from the group consisting of: Methyl 3-(5-carbamoyl-4-(2,2,2-trifluoroethylamino)pyrimidin-2-ylamino)phenylcarbamate; 2-(3-(cyclopropanecarboxamido)phenylamino)-4-(2,2,2-trifluoroethylamino)pyrimidine-5-carboxamide; 2-(3-(2-methoxyacetamido)phenylamino)-4-(2,2,2-trifluoroethylamino)pyrimidine-5-carboxamide; 2-(3-acetamidophenylamino)-4-(2,2,2-trifluoroethylamino)pyrimidine-5-carboxamide; 2-(3-acetamidophenylamino)-4-(methylamino)pyrimidine-5-carboxamide; 2-(3-acetamidophenylamino)-4-(ethylamino)pyrimidine-5-carboxamide; 2-(3-acetamidophenylamino)-4-(prop-2-ynylamino)pyrimidine-5-carboxamide; 2-(3- acetamidophenylamino)-4-(isopropylamino)pyrimidine-5-carboxamide; 2-(3-acetamidophenylamino)-4-(cyclopropylmethylamino)pyrimidine-5-carboxamide; 2-(3-acetamidophenylamino)-4-(tert-butylamino)pyrimidine-5-carboxamide; 2-(3-acetamidophenylamino)-4-(2-methoxyethylamino)pyrimidine-5-carboxamide; 2-(3-acetamidophenylamino)-4-(cyclopentylamino)pyrimidine-5-carboxamide; 2-(3-acetamidophenylamino)-4-(3-methoxypropylamino)pyrimidine-5-carboxamide; 2-(3-acetamidophenylamino)-4-(benzylamino)pyrimidine-5-carboxamide; methyl 5-(5-carbamoyl-4-(2,2,2-trifluoroethylamino)pyrimidin-2-ylamino)-2-chlorophenylcarbamate; 4-(cyclopentylamino)-2-(3-(cyclopropanecarboxamido)phenylamino)pyrimidine-5-carboxamide; 2-(3-cyclobutanecarboxamido)phenylamino)-4-(cyclopentylamino)pyrimidine-5-carboxamide; 4-(cyclopentylamino)-2-(3-propionamidophenylamino)pyrimidine-5-carboxamide; 4-(cyclopentylamino)-2-(3-(2-methoxyacetamido)phenylamino)pyrimidine-5-carboxamide; methyl 3-(5-carbamoyl-4-(cyclopentylamino)pyrimidin-2-ylamino)phenylcarbamate; ethyl 3-(5-carbamoyl-4-(cyclopentylamino)pyrimidin-2-ylamino)phenylcarbamate; methyl 5-(5-carbamoyl-4-(cyclopentylamino)pyrimidin-2-ylamino)-2-chlorophenylcarbamate; 4-(benzylamino)-2-(3-(cyclopropanecarboxamido)phenylamino)pyrimidine-5-carboxamide; 4-(benzylamino)-2-(3-(cyclobutanecarboxamido)phenylamino)pyrimidine-5-carboxamide; 4-(benzylamino)-2-(3-propionamidophenylamino)pyrimidine-5-carboxamide; 4-(benzylamino)-2-(3-(2-methoxyacetamido)phenylamino)pyrimidine-5-carboxamide; methyl 3-(4-(benzylamino)-5-carbamoylpyrimidin-2-ylamino)phenylcarbamate; ethyl 3-(4-(benzylamino)-5-carbamoylpyrimidin-2-ylamino)phenylcarbamate; methyl 5-(4-(benzylamino)-5-carbamoylpyrimidin-2-ylamino)-2-chlorophenylcarbamate; 4-(cyclopentylamino)-2-(3-ureidophenylamino)pyrimidine-5-carboxamide; 4-(cyclopentylamino)-2-(3-(3-methylureido)phenylamino)pyrimidine-5-carboxamide; 4-(cyclopentylamino)-2-(3-(3,3-dimethylureido)phenylamino)pyrimidine-5-carboxamide; 4-(cyclopentylamino)-2-(3-(3-ethylureido)phenylamino)pyrimidine-5-carboxamide; 4-(cyclopentylamino)-2-(3-(pyrrolidine-1-carboxamido)phenylamino)pyrimidine-5-carboxamide; 4-(benzylamino)-2-(3-ureidophenylamino)pyrimidine-5-carboxamide; 4-(benzylamino)-2-(3-(3-methylureido)phenylamino)pyrimidine-5-carboxamide; 4-(benzylamino)-2-(3-(pyrrolidine-1-carboxamido)phenylamino)pyrimidine-5-carboxamide; isopropyl 3-(4-(benzylamino)-5-carbamoylpyrimidin-2-ylamino)phenylcarbamate; (S)-2-(3-(2-methoxyacetamido)phenylamino)-4-(1-phenylethylamino)pyrimidine-5-carboxamide; 2-(3-(2-methoxyacetamido)phenylamino)-4-(4-methylbenzylamino)pyrimidine-5-carboxamide; 2-(3-(2-methoxyacetamido)phenylamino)-4-(4-methoxybenzylamino)pyrimidine-5-carboxamide; 4-(4-chlorobenzylamino)-2-(3-(2-methoxyacetamido)phenylamino)pyrimidine-5-carboxamide; 4-(3,4-dichlorobenzylamino)-2-(3-(2-methoxyacetamido)phenylamino)pyrimidine-5-carboxamide; (R)-2-(3-(2-methoxyacetamido)phenylamino)-4-(1-phenylethylamino)pyrimidine-5-carboxamide; (S)-2-(3-acetamidophenylamino)-4-(2-hydroxy-2-phenylethylamino)pyrimidine-5-carboxamide; (R)-2-(3-acetamidophenylamino)-4-(2-hydroxy-2-phenylethylamino)pyrimidine-5-carboxamide; 2-(3-acetamidophenylamino)-4-(2-amino-2-oxoethylamino)pyrimidine-5-carboxamide; 2-(3-acetamidophenylamino)-4-(2-phenylcyclopropylamino)pyrimidine-5-carboxamide; 2-(3-acetamidophenylamino)-4-(cyclohexylamino)pyrimidine-5-carboxamide; 2-(3-acetamidophenylamino)-4-((trans)-2-hydroxycyclopentylamino)pyrimidine-5-carboxamide; 2-(3-acetamidophenylamino)-4-(benzyl(methyl)amino)pyrimidine-5-carboxamide; 4-(cyclobutylamino)-2-(3-(2-methoxyacetamido)phenylamino)pyrimidine-5-carboxamide; 2-(3-acetamidophenylamino)-4-(cyclobutylamino)pyrimidine-5-carboxamide; 2-(3-acetamidophenylamino)-4-(phenethylamino)pyrimidine-5-carboxamide; 4-(isopropylamino)-2-(3-(2-methoxyacetamido)phenylamino)pyrimidine-5-carboxamide; 2-(3-(2-methoxyacetamido)phenylamino)-4-(2,3,6-trifluorobenzylamino)pyrimidine-5-carboxamide; 2-(3-acetamidophenylamino)-4-(2,3,6-trifluorobenzylamino)pyrimidine-5-carboxamide; (S)-2-(3-acetamidophenylamino)-4-(2-phenylpropylamino)pyrimidine-5-carboxamide; (S)-2-(3-acetamidophenylamino)-4-(1-hydroxy-3-(1H-imidazol-5-yl)propan-2-ylamino)pyrimidine-5-carboxamide; 2-(3-acetamidophenylamino)-4-(3-amino-3-oxopropylamino)pyrimidine-5-carboxamide; (R)-2-(3-acetamidophenylamino)-4-(1-hydroxy-4-methylpentan-2-ylamino)pyrimidine-5-carboxamide; 2-(3-acetamidophenylamino)-4-(2-(pyrrolidin-1-yl)ethylamino)pyrimidine-5-carboxamide; (S)-2-(3-acetamidophenylamino)-4-(1-phenylethylamino)pyrimidine-5-carboxamide; 2-(3-acetamidophenylamino)-4-(2-oxo-2-(pyrrolidin-1-yl)ethylamino)pyrimidine-5-carboxamide; (R)-2-(3-acetamidophenylamino)-4-(piperidin-3-ylamino)pyrimidine-5-carboxamide; 2-(3-acetamidophenylamino)-4-(4-methylbenzylamino)pyrimidine-5-carboxamide; 2-(3-acetamidophenylamino)-4-(4-methoxybenzylamino)pyrimidine-5-carboxamide; 2-(3-acetamidophenylamino)-4-(4-chlorobenzylamino)pyrimidine-5-carboxamide; 2-(3-acetamidophenylamino)-4-(3,4-dichlorobenzylamino)pyrimidine-5-carboxamide; (R)-2-(3-acetamidophenylamino)-4-(1-phenylethylamino)pyrimidine-5-carboxamide; 2-(3-acetamidophenylamino)-4-(2-(methylamino)-2-oxoethylamino)pyrimidine-5-carboxamide; 2-(3-acetamidophenylamino)-4-((2S,3S)-1-hydroxy-3-methylpentan-2-ylamino)pyrimidine-5-carboxamide; 2-(3-acetamidophenylamino)-4-(cyanomethylamino)pyrimidine-5-carboxamide; 2-(3-acetamidophenylamino)-4-(tetrahydro-2H-pyran-4-ylamino)pyrimidine-5-carboxamide; (S)-2-(3-acetamidophenylamino)-4-(1-hydroxy-3-phenylpropan-2-ylamino)pyrimidine-5-carboxamide; 4-(isopropylamino)-2-(3-(N-methylacetamido)phenylamino)pyrimidine-5-carboxamide; 4-(cyclopentylamino)-2-(3-(N-methylacetamido)phenylamino)pyrimidine-5-carboxamide; 4-(benzylamino)-2-(3-(N-methylacetamido)phenylamino)pyrimidine-5-carboxamide; 2-(3-acetamidophenylamino)-4-(2-morpholinoethylamino)pyrimidine-5-carboxamide; (R)-2-(3-acetamidophenylamino)-4-(2-phenylpropylamino)pyrimidine-5-carboxamide; (S)-2-(3-acetamidophenylamino)-4-(2-hydroxypropylamino)pyrimidine-5-carboxamide; (R)-2-(3-acetamidophenylamino)-4-(2,3-dihydroxypropylamino)pyrimidine-5-carboxamide; 2-(3-acetamidophenylamino)-4-(2-methoxy-2-phenylethylamino)pyrimidine-5-carboxamide; (S)-2-(3-acetamidophenylamino)-4-(1-amino-1-oxopropan-2-ylamino)pyrimidine-5-carboxamide; (R)-2-(3-(2-methoxy-N-methylacetamido)phenylamino)-4-(1-phenylethylamino)pyrimidine-5-carboxamide; (R)-2-(3-(N-methylacetamido)phenylamino)-4-(1-phenylethylamino)pyrimidine-5-carboxamide; 4-(isopropylamino)-2-(3-(2-methoxy-N-methylacetamido)phenylamino)pyrimidine-5-carboxamide; 4-(cyclopentylamino)-2-(3-(2-methoxy-N-methylacetamido)phenylamino)pyrimidine-5-carboxamide; 4-(benzylamino)-2-(3-(2-methoxy-N-methylacetamido)phenylamino)pyrimidine-5-carboxamide; (R)-2-(3-acetamidophenylamino)-4-(1-amino-1-oxopropan-2-ylamino)pyrimidine-5-carboxamide; 2-(3-acetamidophenylamino)-4-(2,3-dihydro-1H-inden-2-ylamino)pyrimidine-5-carboxamide; (S)-2-(3-acetamidophenylamino)-4-(2-hydroxy-1-phenylethylamino)pyrimidine-5-carboxamide; 2-(3-acetamidophenylamino)-4-(3-fluorobenzylamino)pyrimidine-5-carboxamide; 2-(3-acetamidophenylamino)-4-(2,3-difluorobenzylamino)pyrimidine-5-carboxamide; (S)-2-(3-acetamidophenylamino)-4-(2,3-dihydro-1H-inden-1-ylamino)pyrimidine-5-carboxamide; (R)-2-(3-acetamidophenylamino)-4-(2,3-dihydro-1H-inden-1-ylamino)pyrimidine-5-carboxamide; (R)-2-(3-acetamidophenylamino)-4-(2-hydroxy-1-phenylethylamino)pyrimidine-5-carboxamide; 2-(3-acetamidophenylamino)-4-(benzo[d][1,3]dioxol-5-ylmethylamino)pyrimidine-5-carboxamide; 2-2-(3-acetamidophenylamino)-4-(2-fluorobenzylamino)pyrimidine-5-carboxamide; 2-(3-acetamidophenylamino)-4-(3-chlorobenzylamino)pyrimidine-5-carboxamide; 2-(3-acetamidophenylamino)-4-(2,5-difluorobenzylamino)pyrimidine-5-carboxamide; 2-(3-acetamidophenylamino)-4-(4-fluorobenzylamino)pyrimidine-5-carboxamide; 4-(4-fluorobenzylamino)-2-(3-(2-methoxyacetamido)phenylamino)pyrimidine-5-carboxamide; (R)-4-(1-phenylethylamino)-2-(3-(pyrrolidine-1-carboxamido)phenylamino)pyrimidine-5-carboxamide; 2-(3-acetamido-4-chlorophenylamino)-4-(benzylamino)pyrimidine-5-carboxamide; 4-(benzylamino)-2-(4-chloro-3-(2-methoxyacetamido)phenylamino)pyrimidine-5-carboxamide; 4-(benzylamino)-2-(4-chloro-3-(3-cyclobutylureido)phenylamino)pyrimidine-5-carboxamide; (R)-2-(3-acetamido-4-chlorophenylamino)-4-(1-phenylethylamino)pyrimidine-5-carboxamide; (R)-2-(4-chloro-3-(2-methoxyacetamido)phenylamino)-4-(1-phenylethylamino)pyrimidine-5-carboxamide; (R)-2-(4-chloro-3-(cyclopropanecarboxamido)phenylamino)-4-(1-phenylethylamino)pyrimidine-5-carboxamide; (R)-2-(4-chloro-3-(3-cyclobutylureido)phenylamino)-4-(1-phenylethylamino)pyrimidine-5-carboxamide; 2-(3-acetamidophenylamino)-4-(benzylamino)-N-methylpyrimidine-5-carboxamide; 4-(benzylamino)-2-(3-(2-methoxyacetamido)phenylamino)-N-methylpyrimidine-5-carboxamide; methoxyacetamido)phenylamino)-N-methylpyrimidine-5-carboxamide; benzyl 3-((2-(3-acetamidophenylamino)-5-carbamoylpyrimidin-4-ylamino)methyl)piperidine-1-carboxylate; and 6-(3-acetamidophenylamino)-4-(benzylamino)nicotinamide.

The present invention provides another group of embodiments, a compound selected from the group consisting of: 2-(3-acetamidophenylamino)-4-(piperidin-3-ylmethylamino)pyrimidine-5-carboxamide; 2-(3-acetamidophenylamino)-4-((1-carbamoylpiperidin-3-yl)methylamino)pyrimidine-5-carboxamide; 2-(3-acetamidophenylamino)-4-((1-(4-fluorophenylcarbamoyl)piperidin-3-yl)methylamino)pyrimidine-5-carboxamide; 2-(3-acetamidophenylamino)-4-((1-acetylpiperidin-3-yl)methylamino)pyrimidine-5-carboxamide; 2-(3-acetamidophenylamino)-4-((1-(methylsulfonyl)piperidin-3-yl)methylamino)pyrimidine-5-carboxamide; (R)-2-(3-(2,5-dihydro-1H-pyrrole-1-carboxamido)phenylamino)-4-(1-phenylethylamino)pyrimidine-5-carboxamide; (R)-2-(3-(N-methylpyrrolidine-1-carboxamido)phenylamino)-4-(1-phenylethylamino)pyrimidine-5-carboxamide; 4-(cyclopropylmethylamino)-2-(3-(pyrrolidine-1-carboxamido)phenylamino) pyrimidine-5-carboxamide; 4-(cyclopropylmethylamino)-2-(3-(2-methoxyacetamido)phenylamino)pyrimidine-5-carboxamide; 4-(cyclopropylmethylamino)-2-(3-(2-methoxy-N-methylacetamido)phenylamino)pyrimidine-5-carboxamide; 4-(cyclopropylmethylamino)-2-(3-(N-methylacetamido)phenylamino)pyrimidine-5-carboxamide; 4-(cyclopropylmethylamino)-2-(3-(N-methylpyrrolidine-1-carboxamido)phenylamino)pyrimidine-5-carboxamide; 2-(3-((S)-3-hydroxypyrrolidine-1-carboxamido)phenylamino)-4-((R)-1-phenylethylamino)pyrimidine-5-carboxamide; (R)-methyl 5-(5-carbamoyl-4-(1-phenylethylamino)pyrimidin-2-ylamino)-2-chlorophenylcarbamate; 4-(benzylamino)-2-(4-chloro-3-(pyrrolidine-1-carboxamido)phenylamino)pyrimidine-5-carboxamide; 4-(benzylamino)-2-(4-chloro-3-(3-methylureido)phenylamino)pyrimidine-5-carboxamide; (R)-2-(4-chloro-3-(3-methylureido)phenylamino)-4-(1-phenylethylamino)pyrimidine-5-carboxamide; 4-(methylamino)-2-(3-(pyrrolidine-1-carboxamido)phenylamino)pyrimidine-5-carboxamide; 4-(ethylamino)-2-(3-(pyrrolidine-1-carboxamido)phenylamino)pyrimidine-5-carboxamide; 4-(butylamino)-2-(3-(pyrrolidine-1-carboxamido)phenylamino)pyrimidine-5-carboxamide; 2-(3-(pyrrolidine-1-carboxamido)phenylamino)-4-(2,2,2-trifluoroethylamino)pyrimidine-5-carboxamide; 2-(3-((S)-2-methylpyrrolidine-1-carboxamido)phenylamino)-4-((R)-1-phenylethylamino)pyrimidine-5-carboxamide; 2-(3-((S)-2-(methoxymethyl)pyrrolidine-1-carboxamido)phenylamino)-4-((R)-1-phenylethylamino) pyrimidine-5-carboxamide; (S)-4-(benzylamino)-2-(3-(2-methylpyrrolidine-1-carboxamido)phenylamino)pyrimidine-5-carboxamide; (S)-4-(benzylamino)-2-(3-(2-(methoxymethyl)pyrrolidine-1-carboxamido)phenylamino)pyrimidine-5-carboxamide; 4-(benzylamino)-2-(3-(N-methylpyrrolidine-1-carboxamido)phenylamino)pyrimidine-5-carboxamide; 4-(benzylamino)-2-(3-(2,5-dihydro-1H-pyrrole-1-carboxamido)phenylamino)pyrimidine-5-carboxamide; (S)-4-(benzylamino)-2-(3-(3-hydroxypyrrolidine-1-carboxamido)phenylamino)pyrimidine-5-carboxamide; (S)-4-(sec-butylamino)-2-(3-(2-methoxyacetamido)phenylamino)pyrimidine-5-carboxamide; (R)-4-(benzylamino)-2-(3-(2-methylpyrrolidine-1-carboxamido) phenylamino) pyrimidine-5-carboxamide; (R)-4-(benzylamino)-2-(3-(2-(methoxymethyl)pyrrolidine-1-carboxamido)phenylamino)pyrimidine-5-carboxamide; 2-(3-((R)-2-methylpyrrolidine-1-carboxamido)phenylamino)-4-((R)-1-phenylethylamino)pyrimidine-5-carboxamide; 2-(3-((R)-2-(methoxymethyl)pyrrolidine-1-carboxamido)phenylamino)-4-((R)-1-phenylethylamino)pyrimidine-5-carboxamide; 4-(benzylamino)-2-(3-(N-cyclopropyl-2-methoxyacetamido)phenylamino)pyrimidine-5-carboxamide; 4-(benzylamino)-2-(3-(N-cyclopropylcyclopropanecarboxamido)phenylamino)pyrimidine-5-carboxamide; (R)-2-(3-acetamidophenylamino)-4-(cyclopropyl(phenyl)methylamino)pyrimidine-5-carboxamide; 4-(benzylamino)-2-(4-chloro-3-(3-cyclopropylureido)phenylamino)pyrimidine-5-carboxamide; 2-(3-acetamido-4-methylphenylamino)-4-(benzylamino)pyrimidine-5-carboxamide; 2-(3-acetamido-4-fluorophenylamino)-4-(benzylamino)pyrimidine-5-carboxamide; 4-(benzylamino)-2-(4-methyl-3-(3-methylureido)phenylamino)pyrimidine-5-carboxamide; (R)-2-(3-(N-cyclopropylacetamido)phenylamino)-4-(1-phenylethylamino) pyrimidine-5-carboxamide; (R)-2-(3-(N-cyclopropyl-2-methoxyacetamido)phenylamino)-4-(1-phenylethylamino)pyrimidine-5-carboxamide; 4-(benzylamino)-2-(4-methoxy-3-(pyrrolidine-1-carboxamido)phenylamino)pyrimidine-5-carboxamide; 4-(benzylamino)-2-(4-methoxy-3-(3-methylureido)phenylamino)pyrimidine-5-carboxamide; 2-(4-chloro-3-(3-methylureido)phenylamino)-4-(3-chlorobenzylamino)pyrimidine-5-carboxamide; 2-(4-chloro-3-(3-methylureido)phenylamino)-4-(cyclopentylamino)pyrimidine-5-carboxamide; 2-(4-chloro-3-(pyrrolidine-1-carboxamido)phenylamino)-4-(cyclopentylamino)pyrimidine-5-carboxamide; 2-(4-chloro-3-(pyrrolidine-1-carboxamido)phenylamino)-4-(3-chlorobenzylamino)pyrimidine-5-carboxamide; 2-(4-chloro-3-(pyrrolidine-1- carboxamido)phenylamino)-4-(cyclopropylmethylamino) pyrimidine-5-carboxamide; (S)-4-(sec-butylamino)-2-(4-chloro-3-(3-methylureido)phenylamino)pyrimidine-5-carboxamide; (S)-4-(sec-butylamino)-2-(4-chloro-3-(pyrrolidine-1-carboxamido)phenylamino)pyrimidine-5-carboxamide; 2-(4-chloro-3-(pyrrolidine-1-carboxamido) phenylamino)-4-(3-fluorobenzylamino)pyrimidine-5-carboxamide; 2-(4-chloro-3-(3-methylureido) phenylamino)-4-(cyclopropylmethylamino)pyrimidine-5-carboxamide; 4-(3-fluorobenzylamino)-2-(3-(pyrrolidine-1-carboxamido)phenylamino)pyrimidine-5-carboxamide; 4-(3-chlorobenzylamino)-2-(3-(pyrrolidine-1-carboxamido) phenylamino)pyrimidine-5-carboxamide; 4-(2-fluorobenzylamino)-2-(3-(3-methylureido)phenylamino)pyrimidine-5-carboxamide; N-(5-(4-(benzylamino)-5-carbamoylpyrimidin-2-ylamino)-2-chlorophenyl) morpholine-4-carboxamide; (R)-N-(5-(5-carbamoyl-4-(1-phenylethylamino)pyrimidin-2-ylamino)-2-chlorophenyl) morpholine-4-carboxamide; 2-(3-acetamidophenylamino)-4-(1-methyl-1H-indol-4-ylamino)pyrimidine-5-carboxamide; 2-(3-acetamidophenylamino)-4-(1-ethyl-1H-indol-4-ylamino)pyrimidine-5-carboxamide; 2-(3-acetamidophenylamino)-4-(2-methyl-2H-indazol-4-ylamino)pyrimidine-5-carboxamide; 2-(3-acetamidophenylamino)-4-(piperidin-4-ylmethylamino) pyrimidine-5-carboxamide; 2-(3-acetamidophenylamino)-4-(1-methyl-1H-indazol-4-ylamino)pyrimidine-5-carboxamide; 2-(3-acetamidophenylamino)-4-(benzo[c][1,2,5]thiadiazo-4-ylamino)pyrimidine-5-carboxamide; (R)-2-(4-chloro-3-ureidophenylamino)-4-(1-phenylethylamino) pyrimidine-5-carboxamide; 4-(benzylamino)-2-(4-chloro-3-ureidophenylamino)pyrimidine-5-carboxamide; (R)-2-(4-chloro-3-(3,3-dimethylureido)phenylamino)-4-(1-phenylethylamino) pyrimidine-5-carboxamide; 4-(benzylamino)-2-(4-chloro-3-(3,3-dimethylureido)phenylamino) pyrimidine-5-carboxamide; 4-(benzylamino)-2-(2-fluoro-5-(3-methylureido)phenylamino)pyrimidine-5-carboxamide; 4-(benzylamino)-2-(5-(3,3-dimethylureido)-2-fluorophenylamino)pyrimidine-5-carboxamide; (R)-4-(benzylamino)-2-(3-(tetrahydrofuran-2-carboxamido)phenylamino)pyrimidine-5-carboxamide; 4-(benzylamino)-2-(3-(tetrahydrofuran-3-carboxamido)phenylamino)pyrimidine-5-carboxamide; 4-(benzylamino)-2-(2-fluoro-5-(pyrrolidine-1-carboxamido)phenylamino)pyrimidine-5-carboxamide; (R)-2-(4-chloro-3-(piperidine-1-carboxamido)phenylamino)-4-(1-phenylethylamino) pyrimidine-5-carboxamide; (S)-4-(benzylamino)-2-(3-(tetrahydrofuran-2-carboxamido) phenylamino)pyrimidine-5-carboxamide; 4-((R)-1-phenylethylamino)-2-(3-((S)-tetrahydrofuran-2-carboxamido)phenylamino)pyrimidine-5-carboxamide; (S)-4-(3-fluorobenzylamino)-2-(3-(tetrahydrofuran-2-carboxamido)phenylamino)pyrimidine-5-carboxamide; 4-(benzylamino)-2-(4-chloro-3-(piperidine-1-carboxamido)phenylamino)pyrimidine-5-carboxamide; (R)-4-(benzylamino)-2-(3-(3-(dimethylamino)pyrrolidine-1-carboxamido)phenylamino)pyrimidine-5-carboxamide; (R)-4-(benzylamino)-2-(3-(3-hydroxypiperidine-1-carboxamido)phenylamino)pyrimidine-5-carboxamide; (R)-2-(3-(4-hydroxypiperidine-1-carboxamido)phenylamino)-4-(1-phenylethylamino)pyrimidine-5-carboxamide; 4-(benzylamino)-2-(3-(4-methylpiperazine-1-carboxamido) phenylamino)pyrimidine-5-carboxamide; N-(3-(4-(benzylamino)-5-carbamoylpyrimidin-2-ylamino)phenyl)morpholine-4-carboxamide; 4-(benzylamino)-2-(3-(piperidine-1-carboxamido)phenylamino)pyrimidine-5-carboxamide; 2-(3-(azetidine-1-carboxamido)phenylamino)-4-(benzylamino)pyrimidine-5-carboxamide; (R)-4-(1-phenylethylamino)-2-(3-(piperidine-1-carboxamido)phenylamino)pyrimidine-5-carboxamide; (R)-2-(4-chloro-3-(pyrrolidine-1-carboxamido)phenylamino)-4-(1-phenylethylamino) pyrimidine-5-carboxamide; 2-(3-(azetidine-1-carboxamido)phenylamino)-4-(benzylamino)pyrimidine-5-carboxamide; 2-(3-acetamido-4-(2-(pyrrolidin-1-yl)ethoxy)phenylamino)-4-(3-fluorobenzylamino)pyrimidine-5-carboxamide; 2-(3-acetamido-4-(2-(pyrrolidin-1-yl)ethoxy)phenylamino)-4-(2-methyl-2H-indazol-4-ylamino)pyrimidine-5-carboxamide; tert-butyl 3-((2-(3-acetamidophenylamino)-5-carbamoylpyrimidin-4-ylamino)methyl)pyrrolidine-1-carboxylate; 2-(3-acetamidophenylamino)-4-(pyrrolidin-3-ylmethylamino) pyrimidine-5-carboxylic acid; 2-(3-acetamido-4-(2-(pyrrolidin-1-yl)ethoxy)phenylamino)-4-(benzo[c][1,2,5]thiadiazo-4-ylamino)pyrimidine-5-carboxamide; 2-(3-acetamido-4-(2-(dimethylamino)ethoxy)phenylamino)-4-(3-fluorobenzylamino)pyrimidine-5-carboxamide; 2-(3-acetamido-4-(2-(dimethylamino)ethoxy)phenylamino)-4-(2-methyl-2H-indazol-4-ylamino)pyrimidine-5-carboxamide; 2-(3-acetamido-4-(2-(dimethylamino)ethoxy) phenylamino)-4-(benzo[c][1,2,5]thiadiazo-4-ylamino) pyrimidine-5-carboxamide; 2-(3-acetamido-4-(2-(piperidin-1-yl)propoxy)phenylamino)-4-(3-fluorobenzylamino) pyrimidine-5-carboxamide; 2-(3-acetamido-4-(2-(piperidin-1-yl)propoxy)phenylamino)-4-(2-methyl-2H-indazol-4-ylamino)pyrimidine-5-carboxamide; 2-(3-(azetidine-1-carboxamido)-4-chlorophenylamino)-4-(benzylamino) pyrimidine-5-carboxamide; 2-(3-(azetidine-1-carboxamido)-4-fluorophenylamino)-4-(benzylamino) pyrimidine-5-carboxamide; 2-(3-acetamidophenylamino)-4-(isobutylamino)pyrimidine-5-carboxamide; 2-(4-chloro-3-(pyrrolidine-1-carboxamido)phenylamino)-4-(isobutylamino)pyrimidine-5-carboxamide; (R)-4-(sec-butylamino)-2-(4-chloro-3-(pyrrolidine-1-carboxamido) phenylamino)pyrimidine-5-carboxamide; (R)-2-(3-acetamidophenylamino)-4-(sec-butylamino)pyrimidine-5-carboxamide; 4-(benzylamino)-2-(4-methoxy-3-(N-methylpyrrolidine-1-carboxamido)phenylamino) pyrimidine-5-carboxamide; 4-(3-fluorobenzylamino)-2-(4-methoxy-3-(N-methylpyrrolidine-1-carboxamido) phenylamino)pyrimidine-5-carboxamide; 4-(benzylamino)-2-(4-chloro-3-(N-methylpyrrolidine-1-carboxamido) phenylamino)pyrimidine-5-carboxamide; 2-(4-chloro-3-(N-methylpyrrolidine-1-carboxamido)phenylamino)-4-(3-fluorobenzylamino)pyrimidine-5-carboxamide; 2-(3-acetamido-4-(2-(piperidin-1-yl)propoxy)phenylamino)-4-(benzo[c][1,2,5]thiadiazo-4-ylamino)pyrimidine-5-carboxamide; 2-(3-acetamido-4-(2-(pyrrolidin-1-yl)ethoxy) phenylamino)-4-(benzylamino)pyrimidine-5-carboxamide; 2-(3-acetamido-4-(2-acetamido-(piperidin-1-yl)propoxy) phenylamino)-4-(benzylamino)pyrimidine-5-carboxamide; 2-(3-acetamido-4-(2-(piperidin-1-yl)propoxy)phenylamino)-4-(1-methyl-1H-indazol-4-ylamino)pyrimidine-5-carboxamide; (S)-2-(3-acetamidophenylamino)-4-(3-methylbutan-2-ylamino)pyrimidine-5-carboxamide; (S)-2-(4-chloro-3-(pyrrolidine-1-carboxamido)phenylamino)-4-(3-methylbutan-2-ylamino)pyrimidine-5-carboxamide; 2-(3-acetamidophenylamino)-4-(2-methylbutylamino) pyrimidine-5-carboxamide; 2-(4-chloro-3-(pyrrolidine-1-carboxamido)phenylamino)-4-(2-methylbutylamino) pyrimidine-5-carboxamide; 2-(3-acetamidophenylamino)-4-(isopentylamino)pyrimidine-5-carboxamide; (R)-2-(3-acetamidophenylamino)-4-(3-methylbutan-2-ylamino) pyrimidine-5-carboxamide; (R)-2-(4-chloro-3-(pyrrolidine-1-carboxamido)phenylamino)-4-(3-methylbutan-2-ylamino)pyrimidine-5-carboxamide; (R)-2-(3-(4-methylpiperazine-1-carboxamido)phenylamino)-4-(1-phenylethylamino)pyrimidine-5-carboxamide; (R)-N-(3-(5-carbamoyl-4-(1-phenylethylamino)pyrimidin-2-ylamino) phenyl)morpholine-4-carboxamide; 4-(3-fluorobenzylamino)-2-(3-(4-methylpiperazine-1-carboxamido) phenylamino)pyrimidine-5-carboxamide; 2-(3-(2-cyanoacetamido)phenylamino)-4-(3-fluorobenzylamino)-pyrimidine- 5-carboxamide; N-(3-(5-carbamoyl-4-(3-fluorobenzylamino)pyrimidin-2-ylamino)phenyl)morpholine-4-carboxamide; 2-(3-acetamido-5-chlorophenylamino)-4-(benzylamino)pyrimidine-5-carboxamide; 2-(3-acetamido-5-chlorophenylamino)-4-(3-fluorobenzylamino)pyrimidine-5-carboxamide; 2-(3-acetamidophenylamino)-4-(cyclobutylmethylamino)pyrimidine-5-carboxamide; 2-(4-chloro-3-(pyrrolidine-1-carboxamido)phenylamino)-4-(cyclobutylmethylamino)pyrimidine-5-carboxamide; 2-(3-acetamidophenylamino)-4-(4-aminophenylamino)pyrimidine-5-carboxamide; 4-(benzylamino)-2-(4-fluoro-3-(3-methylureido)phenylamino)pyrimidine-5-carboxamide; 4-(3-fluorobenzylamino)-2-(3-(3,3,3-trifluoropropanamido)phenylamino)pyrimidine-5-carboxamide; benzyl 3-(5-carbamoyl-4-(3-fluorobenzylamino)pyrimidin-2-ylamino)phenylcarbamate; 2-(3-(1-cyanocyclopropanecarboxamido)phenylamino)-4-(3-fluorobenzylamino)pyrimidine-5-carboxamide; 4-(3-fluorobenzylamino)-2-(3-(isonicotinamido)-phenylamino)pyrimidine-5-carboxamide; 4-(2-fluorobenzylamino)-2-(3-(picolinamido)-phenylamino)pyrimidine-5-carboxamide; 4-(2-fluorobenzylamino)-2-(3-(nicotinamido)-phenylamino)pyrimidine-5-carboxamide; 4-(2-fluorobenzylamino)-2-(3-(2-(pyridin-3-yl)acetamido)-phenylamino)pyrimidine-5-carboxamide; 4-(2-fluorobenzylamino)-2-(3-(6-hydroxypicolinamido)-phenylamino)pyrimidine-5-carboxamide; 4-(2-fluorobenzylamino)-2-(3-(2-(pyridin-4-yl)acetamido)-phenylamino)pyrimidine-5-carboxamide; 4-(2-fluorobenzylamino)-2-(3-(2-(pyridin-2-yl)acetamido)-phenylamino)pyrimidine-5-carboxamide; 2-(3-acetamidophenylamino)-4-(4-(2-cyanoacetamido)-phenylamino)pyrimidine-5-carboxamide; 2-(3-acetamidophenylamino)-4-(4-(1-cyanocyclopropane-carboxamido)phenylamino)pyrimidine-5-carboxamide; 2-(3-acetamidophenylamino)-4-(4-(3,3,3-trifluoro-propanamido)phenylamino)pyrimidine-5-carboxamide; 2-(3-acetamido-4-(2-(pyrrolidin-1-yl)ethoxy)phenylamino)-4-(1-methyl-1H-indazol-4-ylamino)pyrimidine-5-carboxamide; 4-(benzylamino)-2-(3-(2-(dimethylamino)acetamido)phenylamino)pyrimidine-5-carboxamide; 2-(3-(2-(dimethylamino)acetamido)phenylamino)-4-(1-methyl-1H-indazol-4-ylamino)pyrimidine-5-carboxamide; 2-(3-acetamidophenylamino)-4-(1-phenylcyclopropylamino)pyrimidine-5-carboxamide; 2-(3-(2-(dimethylamino)acetamido)phenylamino)-4-(1-phenylcyclopropylamino)pyrimidine-5-carboxamide; 2-(3-acetamido-4-methylphenylamino)-4-(1-phenylcyclopropylamino)pyrimidine-5-carboxamide; 4-(benzylamino)-2-(2,2-dimethyl-3-oxo-3,4-dihydro-2H-benzo[b][1,4]oxazin-6-ylamino)-pyrimidine-5-carboxamide; 2-(2,2-dimethyl-3-oxo-3,4-dihydro-2H-benzo[b][1,4]oxazin-6-ylamino)-4-(1-phenylcyclopropylamino)pyrimidine-5-carboxamide; 4-(benzylamino)-2-(3-isobutyraminophenylamino)pyrimidine-5-carboxamide; 4-(benzylamino)-2-(3-pivalaminophenylamino)pyrimidine-5-carboxamide; (S)-4-(benzylamino)-2-(3-(1-methylpyrrolidine-2-carboxamido)phenylamino)pyrimidine-5-carboxamide; 2-(3-acetamidophenylamino)-4-((1-methyl-1H-pyrazol-4-yl)methylamino)pyrimidine-5-carboxamide; 4-((1-methyl-1H-pyrazol-4-yl)methylamino)-2-(2-oxo-2,3-dihydrobenzo[d]oxazol-5-ylamino)-pyrimidine-5-carboxamide; 2-(2,2-dimethyl-3-oxo-3,4-dihydro-2H-benzo[b][1,4]oxazin-6-ylamino)-4-((1-methyl-1H-pyrazol-4-yl)methylamino)pyrimidine-5-carboxamide; 2-(2,2-dimethyl-3-oxo-3,4-dihydro-2H-benzo[b][1,4]oxazin-6-ylamino)-4-(pyridine-2-ylmethylamino)pyrimidine-5-carboxamide; 2-(3-acetamidophenylamino)-4-(cyclopentylmethylamino)pyrimidine-5-carboxamide; 4-(cyclopentylmethylamino)-2-(3-(pyrrolidine-1-carboxamido)phenylamino)pyrimidine-5-carboxamide; (R)-4-(benzylamino)-2-(3-(3-hydroxypyrrolidine-1-carboxamido)phenylamino)pyrimidine-5-carboxamide; (R)-4-(benzylamino)-2-(3-(3-fluoropyrrolidine-1-carboxamido)phenylamino)pyrimidine-5-carboxamide; (S)-4-(benzylamino)-2-(3-(3-fluoropyrrolidine-1-carboxamido)phenylamino)pyrimidine-5-carboxamide; and 6-(4-fluoro-3-(pyrrolidine-1-carboxamido)phenylamino)-4-(pyridin-3-ylmethylamino)nicotinamide; 6-(3-(azetidine-1-carboxamido)-4-fluorophenylamino)-4-(3-fluorobenzylamino)nicotinamide; (R)-6-(3-(3-(dimethylamino)pyrrolidine-1-carboxamido)phenylamino)-4-(3-fluorobenzylamino)nicotinamide; (6-(4-fluoro-3-(pyrrolidine-1-carboxamido)phenylamino)-4-(3-fluorobenzylamino)nicotinamide; N-(3-(5-carbamoyl-4-(3-fluorobenzylamino)pyridin-2-ylamino)phenyl)morpholine-4-carboxamide; 4-(3-fluorobenzylamino)-6-(3-(pyrrolidine-1-carboxamido)phenylamino)nicotinamide; 6-(3-acetamidophenylamino)-4-(3-fluorobenzylamino)nicotinamide; (S)-6-(3-(azetidine-1-carboxamido)-4-fluorophenylamino)-4-(2-hydroxy-1-phenylethylamino)nicotinamide; 6-(3-((R)-3-(dimethylamino)pyrrolidine-1-carboxamido)phenylamino)-4-((S)-2-hydroxy-1-phenylethylamino)nicotinamide; (S)-6-(4-fluoro-3-(pyrrolidine-1-carboxamido)phenylamino)-4-(2-hydroxy-1-phenylethylamino)nicotinamide; (S)-N-(3-(5-carbamoyl-4-(2-hydroxy-1-phenylethylamino)pyridin-2-ylamino)phenyl)morpholine-4-carboxamide; (S)-4-(2-hydroxy-1-phenylethylamino)-6-(3-(pyrrolidine-1-carboxamido)phenylamino)nicotinamide; (S)-6-(3-acetamidophenylamino)-4-(2-hydroxy-1-phenylethylamino)nicotinamide; 6-(3-(azetidine-1-carboxamido)-4-fluorophenylamino)-4-(pyridin-3-ylmethylamino)nicotinamide; (R)-6-(3-(3-(dimethylamino)pyrrolidine-1-carboxamido)phenylamino)-4-(pyridin-3-ylmethylamino)nicotinamide; N-(3-(5-carbamoyl-4-(pyridin-3-ylmethylamino)pyridin-2-ylamino)phenyl)morpholine-4-carboxamide; 4-(pyridin-3-ylmethylamino)-6-(3-(pyrrolidine-1-carboxamido)phenylamino)nicotinamide; 6-(3-acetamidophenylamino)-4-(pyridin-3-ylmethylamino)nicotinamide; (R)-6-(3-acetamidophenylamino)-4-(1-phenylethylamino)nicotinamide; 6-(3-acetamidophenylamino)-4-(isobutylamino)nicotinamide; 4-(isobutylamino)-6-(3-(pyrrolidine-1-carboxamido)phenylamino)nicotinamide; (R)-4-(1-phenylethylamino)-6-(3-(pyrrolidine-1-carboxamido)phenylamino)nicotinamide; 4-(benzylamino)-6-(3-(pyrrolidine-1-carboxamido)phenylamino)nicotinamide; 6-(3-acetamidophenylamino)-4-(isopentylamino)nicotinamide; 4-(isopentylamino)-6-(3-(pyrrolidine-1-carboxamido)phenylamino)nicotinamide; 6-(3-acetamidophenylamino)-4-(cyclopropylmethylamino)nicotinamide; 6-(3-acetamidophenylamino)-4-(cyclopentylamino)nicotinamide; 6-(3-acetamidophenylamino)-4-(cyclobutylmethylamino)nicotinamide; 6-(3-acetamidophenylamino)-4-(4-fluorobenzylamino)nicotinamide; 6-(3-acetamidophenylamino)-4-(2,3-dihydro-1H-inden-2-ylamino)nicotinamide; 6-(3-acetamidophenylamino)-4-(benzo[d][1,3]dioxol-5-ylmethylamino)nicotinamide; (S)-6-(3-acetamidophenylamino)-4-(2,3-dihydro-1H-inden-1-ylamino)nicotinamide; 6-(3-acetamidophenylamino)-4-(2,3-difluorobenzylamino)nicotinamide; 6-(3-acetamidophenylamino)-4-(3-chlorobenzylamino)nicotinamide; 6-(3-acetamidophenylamino)-4-(phenethylamino)nicotinamide; 6-(3-acetamidophenylamino)-4-(benzylamino)-N-methylnicotinamide; 6-(3-acetamidophenylamino)-4-(2-fluorobenzylamino)nicotinamide; and 4-(3,5-difluorobenzylamino)-6-(3-(pyrrolidine-1-carboxamido)phenylamino)nicotinamide In any of the embodiments, the present invention provides that the compound is not a compound selected from the group consisting of:

31

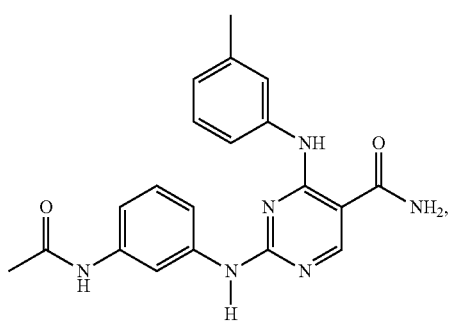

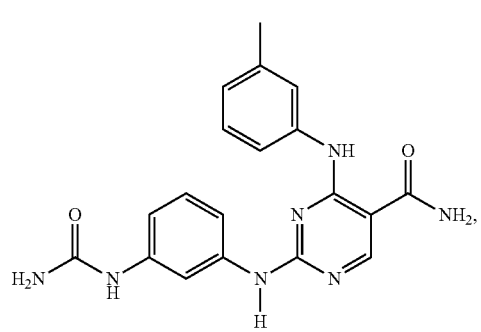

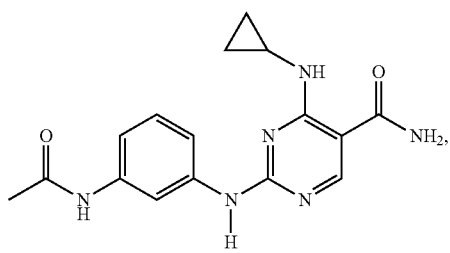

32

-continued

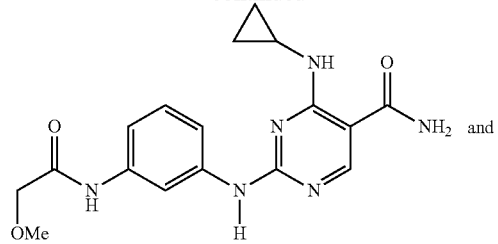

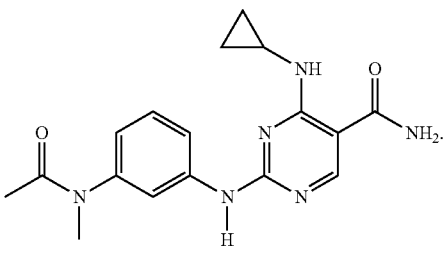

It is understood that in another group of embodiments, any of the above embodiments may also be combined with other embodiments listed herein, to form other embodiments of the invention. Similarly, it is understood that in other embodiments, listing of groups includes embodiments wherein one or more of the elements of those groups is not included.

b. Methods of Synthesis

The compounds of the present invention may be prepared by known organic synthesis techniques, including the methods described in more detail in the Examples. In general, the compounds of formula (I) above may be made by the following Figure 1, wherein all substituents are as defined above unless indicated otherwise.

Compounds having formula I may be prepared according to Figure 1:

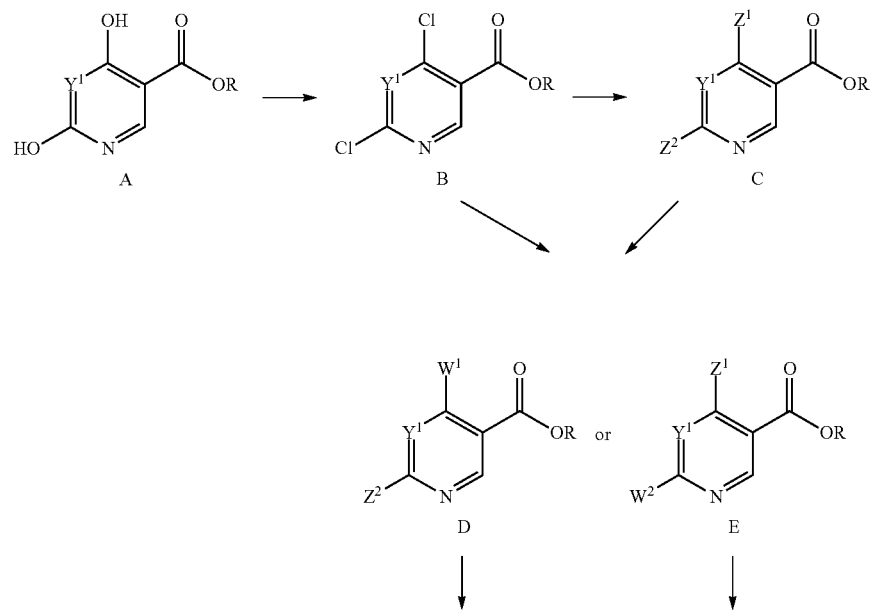

FIG. 1:

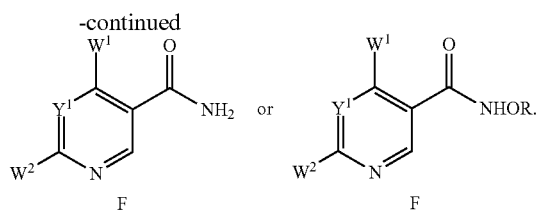

Dihydroxy compound, A, is dichlorinated with a chlorinating agent, such as phosphorous oxychloride. Other activated compounds, B or C, wherein one of $Z^1$ or $Z^2$ is e.g. a —S-alkyl or a benzotriazolyl ether, may also be prepared through a linear route. Selective displacement of the one of the activated groups by an appropriate amine, such as $R^1$ or $R^2$, (available commercially or synthesized using methods known to those skilled in the art), under basic conditions, such as with diisopropylamine (DIA), provides compounds of formula D or E. Displacement of the other activated group with an appropriate amine, such as $R^2$ (available commercially or synthesized using methods known to those skilled in the art), gives the desired product F, wherein $R^1$ and $R^2$ are represented herein in Formula I.

One skilled in the art will recognize that in certain embodiments of formulas (I) when $W^1$ or $W^2$ comprises a terminal heteroatom, it may be advantageous to use a protecting group strategy. The protecting group can be removed using methods known to those skilled in the art to yield compounds of structure F.

The compounds of the present invention may generally be utilized as the free base. Alternatively, the compounds of this invention may be used in the form of acid addition salts as described below.

c. Inhibition of Kinases

The activity of a specified compound as an inhibitor of a JAK may be assessed in vitro or in vivo. In some embodiments, the activity of a specified compound can be tested in a cellular assay. Selectivity could also be ascertained in biochemical assays with isolated kinases.

Similar types of assays can be used to assess JAK inhibitory activity and to determine the degree of selectivity of the particular compound as compared to syk. One means of assaying for such inhibition is detection of the effect of the compounds of the present invention on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (e.g., the 2,4-substituted pyrimidinediamine compounds described herein) on the JAK1 and JAK3, human Ramos B-cells are stimulated with human IL-4. 10' post-stimulation, cells are subjected to intracellular flow cytometry to measure the extent of STAT-6 phosphorylation. 20 to 24 hours post-stimulation, cells are stained for upregulation of CD23 and analyzed using flow cytometry. A reduction of the amount of phospohorylated STAT-6 and/or cell surface CD23 present compared to control conditions indicates that the test compound actively inhibits the JAK pathway.

Additionally, IL-6 stimulation of Ramos B-cells induces JAKs 1, 2, and Tyk2, leading to Stat-3 and Erk phosphorylation. 10' post-stimulation, cells are subjected to intracellular flow cytometry to measure the ability of compound to inhibit these phosphorylation events. To specifically measure the activity of JAK2, the CellSensor irf1-bla HEL cell line expressing the beta-lactamase reporter gene controlled by Stat5 will be used (Invitrogen, Carlsbad, Calif.). These cells express a constituitively active JAK2 mutant (JAK2V617F), found naturally in myeloproliferative neoplasms (Constantinescu, S., et.al, *Trends Biochem Sci.*, 2008; 33:122-31). A reduction in the amount of beta-lactamase reporter gene expression is used a measure of the JAK2 inhibitory activity of compounds.

Stimulation with IL-1β through the IL-1 β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$ values are calculated. Exemplary assays of this type are described in greater detail in the Examples.

Active compounds as described herein generally inhibit the JAK pathway with an $IC_{50}$ in the range of about 1 mM or less, as measured in the assays described herein. Of course, skilled artisans will appreciate that compounds which exhibit lower $IC_{50}$s, (on the order, for example, of 100 μM, 75 μM, 50 μM, 40 μM, 30 μM, 20 μM, 15 μM, 10 μM, 5 μM, 1 μM, 500 nM, 100 nM, 10 nM, 1 nM, or even lower) can be particularly useful in therapeutic applications. In instances where activity specific to a particular cell type is desired, the compound can be assayed for activity with the desired cell type and counter-screened for a lack of activity against other cell types. The desired degree of "inactivity" in such counter screens, or the desired ratio of activity vs. inactivity, may vary for different situations and can be selected by the user.

The active compounds also typically inhibit IL-4 stimulated expression of CD23 in B-cells with an $IC_{50}$ in the range of about 20 μM or less, typically in the range of about 10 μM, 1 μM, 500 nM, 100 nM, 10 nM, 1 nM, or even lower. A suitable assay that can be used is the assay described in the Examples, "Assay for Ramos B-cell Line Stimulated with IL-4." In certain embodiments, the active compounds of the present invention have an $IC_{50}$ of less than or equal to 5 μM, greater than 5 μM but less than 20 μM, greater than 20 μM, or greater than 20 μM but less than 50 μM in the assay described in the Examples.

The active compounds also typically inhibit expression of ICAM1 (CD54) induced by IFNγ exposure in A549 cells with an $IC_{50}$ in the range of about 20 μM or less, typically in the range of about 10 μM, 1 μM, 500 nM, 100 nM, 10 nM, 1 nM, or even lower. The $IC_{50}$ against expression of ICAM (CD54) in IFNγ stimulated cells can be determined in a functional cellular assay with an isolated A549 cell line. Suitable assays that can be used are the assays described in the Examples, "A549 Epithelial Line Stimulated with IFNγ". In certain embodiments, the active compounds of the present invention have an $IC_{50}$ of less than or equal to 20 µM, greater than 20 µM, or greater than 20 µM but less than 50 µM in the assays described in the Examples.

d. Compositions and Methods of Administration

The present invention further provides compositions comprising one or more compounds of formula (I) or a pharmaceutically acceptable salt, ester or prodrug thereof, and a pharmaceutically acceptable carrier or diluent. It will be appreciated that the compounds of formula (I)) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), similar to metabolically labile esters or carbamates, which are capable of producing the parent compounds of formula (I) in vivo, are within the scope of this invention.

As used herein, the term "pharmaceutically acceptable salts" refers to any acid or base addition salt whose counterions are non-toxic to the patient in pharmaceutical doses of the salts. A host of pharmaceutically acceptable salts are well known in the pharmaceutical field. If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

The term "unit dosage form" refers to physically discrete units suitable as unitary dosages for human subjects and other mammals, each unit containing a predetermined quantity of drug calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of one or more JAK inhibitors.

Methods for preparing such dosage forms are known to those skilled in the art (see, for example, REMINGTON'S PHARMACEUTICAL SCIENCES, 18TH ED., Mack Publishing Co., Easton, Pa. (1990)). In addition, pharmaceutically acceptable salts of the JAK inhibitors of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of one or more JAK inhibitors, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

Administration of a composition comprising one or more JAK inhibitors with one or more suitable pharmaceutical excipients as advantageous can be carried out via any of the accepted modes of administration. Thus, administration can be, for example, oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation. According to a representative embodiment, the compositions of this invention are formulated for pharmaceutical administration to a mammal, preferably a human being.

The compositions of the present invention containing one or more JAK inhibitors can be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical compositions of this invention may be in any orally acceptable dosage form, including tablets, capsules, cachets, emulsions, suspensions, solutions, syrups, elixirs, sprays, boluses, lozenges, powders, granules, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, the compositions take the form of a pill, tablet, or capsule, and thus, the composition can contain, along with one or more JAK inhibitors, a diluent such as lactose, sucrose, dicalcium phosphate, and the like; a disintegrant such as starch or derivatives thereof; a lubricant such as magnesium stearate and the like; and/or a binder such a starch, gum acacia, polyvinylpyrrolidone, gelatin, cellulose and derivatives thereof. A tablet can be made by any compression or molding process known to those of skill in the art. Compressed tablets may be prepared by compressing in a suitable machine the JAK inhibitors in a free-flowing form, e.g., a powder or granules, optionally mixed with accessory ingredients, e.g., binders, lubricants, diluents, disintegrants, or dispersing agents. Molded tablets can be made by molding in a suitable machine a mixture of the powdered JAK inhibitors with any suitable carrier.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax, polyethylene glycol (PEG), hard fat, and/or hydrogenated cocoglyceride. Compositions suitable for rectal administration may also comprise a rectal enema unit containing one or more JAK inhibitors and pharmaceutically-acceptable vehicles (e.g., 50% aqueous ethanol or an aqueous salt solution) that are physiologically compatible with the rectum and/or colon. The rectal enema unit contains an applicator tip protected by an inert cover, preferably comprised of polyethylene, lubricated with a lubricant such as white petrolatum, and preferably protected by a one-way valve to prevent back-flow of the dispensed formula. The rectal enema unit is also of sufficient length, preferably two inches, to be inserted into the colon via the anus.

Liquid compositions can be prepared by dissolving or dispersing one or more JAK inhibitors and optionally one or more pharmaceutically acceptable adjuvants in a carrier such as, for example, aqueous saline, aqueous dextrose, glycerol, ethanol, and the like, to form a solution or suspension, e.g., for oral, topical, or intravenous administration. Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs. For topical administration, the composition containing one or more JAK inhibitors can be in the form of emulsions, lotions, gels, foams, creams, jellies, solutions, suspensions, ointments, and transdermal patches.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

The pharmaceutical compositions of this invention may also be administered by nasal aerosol or inhalation. For delivery by inhalation, the compositions can be delivered as a dry powder or in liquid form via a nebulizer. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

For parenteral administration, the compositions can be in the form of sterile injectable solutions and sterile packaged powders. Preferably, injectable solutions are formulated at a pH of about 4.5 to about 7.5.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Any of the above dosage forms containing effective amounts are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

e. Methods of Use

The invention provides methods of inhibiting or decreasing JAK activity as well as treating or ameliorating a JAK associated state, symptom, condition, disorder or disease in a patient in need thereof (e.g., human or non-human). In one embodiment, the JAK associated state, symptom, condition, disorder or disease is mediated, at least in part by JAK activity. In more specific embodiments, the present invention provides a method for treating a condition or disorder mediated at least in part by JAK activity is cardiovascular disease, inflammatory disease or autoimmune disease.

The compounds described herein are also potent and/or selective inhibitors of JAKs. As a consequence of this activity, the compounds can be used in a variety of in vitro, in vivo, and ex vivo contexts to regulate or inhibit JAK activity, signaling cascades in which JAKs play a role, and the biological responses effected by such signaling cascades. For example, in one embodiment, the compounds can be used to inhibit JAK, either in vitro or in vivo, in virtually any cell type expressing the JAK, such as in hematopoietic cells in which, for example, JAK3 is predominantly expressed. They may also be used to regulate signal transduction cascades in which JAKs, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds may also be used in vitro or in vivo to regulate, and in particular to inhibit, cellular or biological responses affected by such JAK-dependent signal transduction cascades. Such cellular or biological responses include, but are not limited to, IL-4/Ramos CD23 upregulation and IL-2 mediated T-cell proliferation. Importantly, the compounds can be used to inhibit JAKs in vivo as a therapeutic approach towards the treatment or prevention of diseases mediated, either wholly or in part, by a JAK activity (referred to herein as "JAK mediated diseases"). Non-limiting examples of JAK mediated diseases that can be treated or prevented with the compounds include, but are not limited to, the following: allergies; asthma; autoimmune diseases such as transplant rejection (e.g., kidney, heart, lung, liver, pancreas, skin, small intestine, large intestine, host versus graft reaction (HVGR), and graft versus host reaction (GVHR)), rheumatoid arthritis, and amyotrophic lateral sclerosis; T-cell mediated autoimmune diseases such as multiple sclerosis, psoraiasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliteraus and primary pulmonary hypertension; solid, delayed Type IV hypersensitivity reactions; and hematologic malignancies such as leukemia and lymphomas.

Examples of diseases that are mediated, at least in part, by JAKs that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoraiasis and Sjogren's syndrome, Type II inflammatory disease such as vascular inflammation (including vasculitis, ateritis, atherosclerosis and coronary artery disease) or other inflammatory diseases such as osteoarthritis, inflammatory bowel disease, ulcerative colitis, Crohn's disease, idiopathic inflammatory bowel disease, irritable bowel syndrome, spastic colon, low grade scarring (e.g., scleroderma, increased fibrosis, keloids, post-surgical scars, pulmonary fibrosis, vascular spasms, migraine, reperfusion injury and post myocardial infarction), and sicca complex or syndrome, diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lyphomas.

In another embodiment, this invention provides a method of inhibiting an activity of a JAK, comprising contacting the JAK with an amount of a compound effective to inhibit an activity of the JAK, wherein the compound is selected from the compounds of this invention. In certain embodiments of the methods described herein, the method is carried out in vivo.

In another embodiment, this invention provides a method of inhibiting an activity of a JAK, comprising contacting in vitro a JAK3 with an amount of a compound effective to inhibit an activity of the JAK, wherein the compound is selected from the compounds of this invention.

In a specific embodiment, the compounds can be used to treat and/or prevent rejection in organ and/or tissue transplant recipients (i.e., treat and/or prevent allorgraft rejection). Allografts can be rejected through either a cell-mediated or humoral immune reaction of the recipient against transplant (histocompability) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophapges and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAKs play a critical role in the activation of T-cells, the compounds described herein can be used to treat and/or prevent many aspects of transplant rejection, and are particularly useful in the treatment and/or prevention of rejection reactions that are mediated, at least in part, by T-cells, such as HVGR or GVHR. The compounds can also be used to treat and/or prevent chronic rejection in transplant recipients and, in particular, in renal transplant recipients. The compound can also be administered to a tissue or an organ prior to transplanting the tissue or organ in the transplant recipient.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention. In certain embodiments of the methods the autoimmune disease is multiple sclerosis (MS), psoraisis, or Sjogran's syndrome. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be .beta.-cell (humoral) based or T-cell based, include Cogan's syndrome, ankylosing spondylitis, Wegener's granulomatosis, autoimmune alopecia, Type I or juvenile onset diabetes, and thyroiditis.

The types of autoimmune diseases that may be treated or prevented with such prodrugs generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the prodrugs according to structural formula (I). In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated.

Therapy using the compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth under the brand name RAPAMUNE; tacrolimus is currently available from Fujisawa under the brand name PROGRAF; cyclosporine is current available from Novartis under the brand name SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the compounds could be administered either in combination or adjunctively with an inhibitor of a syk. Syk is a tyrosine kinase known to play a critical role in Fcγ receptor signaling, as well as in other signaling cascades, such as those involving B-cell receptor signaling (Turner et al., (2000), Immunology Today 21:148-154) and integrins beta (1), beta (2), and beta (3) in neutrophils (Mocsai et al., (2002), Immunity 16:547-558). For example, syk plays a pivotal role in high affinity IgE receptor signaling in mast cells that leads to activation and subsequent release of multiple chemical mediators that trigger allergic attacks. However, unlike the JAKs, which help regulate the pathways involved in delayed or cell-mediated Type IV hypersensitivity reactions, syk helps regulate the pathways involved in immediate IgE-mediated, Type I hypersensitivity reactions. Certain compounds that affect the syk pathway may or may not also affect the JAK pathways.

Suitable syk inhibitory compounds are described, for example, in Ser. No. 10/355,543 filed Jan. 31, 2003 (publication no. 2004/0029902); WO 03/063794; Ser. No. 10/631,029 filed Jul. 29, 2003; WO 2004/014382; Ser. No. 10/903,263 filed Jul. 30, 2004; PCT/US2004/24716 filed Jul. 30, 2004 (WO005/016893); Ser. No. 10/903,870 filed Jul. 30, 2004; PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The compounds described herein and syk inhibitory compounds could be used alone or in combination with one or more conventional transplant rejection treatments, as described above.

In a specific embodiment, the compounds can be used to treat or prevent these diseases in patients that are either initially non-responsive (resistant) to or that become non-responsive to treatment with a JAK inhibitory compound or one of the other current treatments for the particular disease. The compounds could also be used in combination with syk inhibitory compounds in patients that are JAK-compound resistant or non-responsive. Suitable JAK-inhibitory compounds with which the compounds can be administered are provided infra In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits JAK with an $IC_{50}$ in the range of at least 10 µM.

In another embodiment, this invention provides a method of treating or preventing allograft transplant rejection in a transplant recipient, comprising administering to the transplant recipient an amount of a compound effective to treat or prevent the rejection wherein the compound is selected from the compounds of the invention, as described herein. In a further embodiment, the compound is administered to a tissue or an organ prior to transplanting the tissue or organ in the transplant recipient.

In another embodiment, this invention provides a method of treating or preventing allograft transplant rejection in a transplant recipient, in which the rejection is acute rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is chronic rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection wherein the compound is selected from the compounds of the invention, as described herein, in which the compound is administered in combination with or adjunctively to another immunosuppressant.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of the invention, as described herein, in which the compound is administered in combination with or adjunctively to another immunosuppressant, in which the immunosuppressant is selected from cyclosporine, tacrolimus, sirolimus, an inhibitor of IMPDH, mycophenolate, mycophanolate mofetil, an anti-T-Cell antibody, and OKT3.

The compounds described herein are cytokine moderators of IL-4 signaling. As a consequence, the compounds could slow the response of Type I hypersensitivity reactions. Thus, in a specific embodiment, the compounds could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the compounds can be administered singly, as mixtures of one or more compounds, or in mixture or combination with other agents useful for treating such diseases and/or the symptoms associated with such diseases. The compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, beta.-agonists, tryptase inhibitors, aspirin, cyclooxygenase (COX) inhibitors, methotrexate, anti-TNF drugs, anti CD20 antibody, PD4 inhibitors, p38 inhibitors, PDE4 inhibitors, and antihistamines, to name a few. The compounds can be administered per se in the form of prodrugs or as pharmaceutical compositions, comprising an active compound or prodrug.

In another embodiment, this invention provides a method of treating or preventing a Type IV hypersensitivity reaction, comprising administering to a subject an amount of a compound effective to treat or prevent the hypersensitivity reaction, wherein the compound is selected from the compounds of this invention, as described herein.

In another embodiment, this invention provides a method of treating or preventing a Type IV hypersensitivity reaction, which is practical prophylactically, comprising administering to a subject an amount of a compound effective to treat or prevent the hypersensitivity reaction, wherein the compound is selected from the compounds of this invention, as described herein, and is administered prior to exposure to an allergen.

In another embodiment, this invention provides a method of inhibiting a signal transduction cascade in which JAK3 plays a role, comprising contacting a cell expressing a receptor involved in such a signaling cascade with a compound wherein the compound is selected from the compounds of this invention, as described herein.

In another embodiment, this invention provides a method of treating or preventing a JAK-mediated disease, comprising administering to a subject an amount of compound effective to treat or prevent the JAK-mediated disease, wherein the compound is selected from the compounds of this invention, as described herein.

In another embodiment, this invention provides a method of treating or preventing a JAK-mediated disease, in which the JAK-disease is HVGR or GVHR, comprising administering to a subject an amount of compound effective to treat or prevent the JAK-mediated disease, wherein the compound is selected from the compounds of the invention, as described herein.

In another embodiment, this invention provides a method of treating or preventing a JAK-mediated disease, in which the JAK-disease is acute allograft rejection, comprising administering to a subject an amount of compound effective to treat or prevent the JAK-mediated disease, wherein the compound is selected from the compounds of the invention, as described herein.

In another embodiment, this invention provides a method of treating or preventing a JAK-mediated disease, in which the JAK-mediated disease is chronic allograft rejection, comprising administering to a subject an amount of compound effective to treat or prevent the JAK-mediated disease, wherein the compound is selected from the compounds of the invention, as described herein.

Active compounds of the invention typically inhibit the JAK/Stat pathway. The activity of a specified compound as an inhibitor of a JAK can be assessed in vitro or in vivo. In some embodiments, the activity of a specified compound can be tested in a cellular assay.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the JAK inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant JAK activity can be treated with the JAK inhibitory compounds.

In some embodiments, the compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

"Treating" within the context of the invention means an alleviation of symptoms associated with a disorder or disease, or halt of further progression or worsening of those symptoms, or prevention or prophylaxis of the disease or disorder.

The term "mammal" includes organisms which express JAK. Examples of mammals include mice, rats, cows, sheep, pigs, goats, horses, bears, monkeys, dogs, cats and, preferably, humans. Transgenic organisms which express JAK are also included in this definition.

The inventive methods comprise administering an effective amount of a compound or composition described herein to a mammal or non-human animal. As used herein, "effective amount" of a compound or composition of the invention includes those amounts that antagonize or inhibit JAK. An amount which antagonizes or inhibits JAK is detectable, for example, by any assay capable of determining JAK activity, including the one described below as an illustrative testing method. Effective amounts may also include those amounts which alleviate symptoms of a JAK associated disorder treatable by inhibiting JAK. Accordingly, "antagonists of JAK" include compounds which interact with the JAK, respectively, and modulate, e g., inhibit or decrease, the ability of a second compound, e.g., another JAK ligand, to interact with the JAK, respectively. The JAK binding compounds are preferably antagonists of JAK, respectively. The language "JAK-binding compound" (e.g., exhibits binding affinity to the receptor) includes those compounds which interact with JAK resulting in modulation of the activity of JAK, respectively. JAK binding compounds may be identified using an in vitro (e.g., cell and non-cell based) or in vivo method. A description of in vitro methods are provided below.

The amount of compound present in the methods and compositions described herein should be sufficient to cause a detectable decrease in the severity of the disorder, as measured by any of the assays described in the examples. The amount of JAK modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula (I), another therapeutic agent (e.g., methotrexate) or a pharmaceutically acceptable salt, ester or prodrug thereof, and a pharmaceutically acceptable excipient or carrier.

The invention comprises a compound having the formula (I), a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

All of the compounds of the present invention are either potent inhibitors of JAK kinases, exhibiting $IC_{50}$s in the respective assay in the range of less than 5 µM, with most being in the nanomolar, and several in the sub-nanomolar, range. In some embodiments, the compounds of the present invention may be "dual" syk/JAK inhibitors in that they inhibit both syk and JAK kinase to some degree. In other embodiments, the compounds of the present invention may selectively inhibit JAK kinase, but not appreciably inhibit one or more syk kinases.

f. Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where JAK plays a role.

EXAMPLES

The following examples are offered to illustrate, but not to limit, the claimed invention.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates may be characterized by high performance liquid chromatography (HPLC) using a Waters Alliance chromatography system with a 2695 Separation Module (Milford, Mass.). The analytical columns may be C-18 SpeedROD RP-18E Columns from Merck KGaA (Darmstadt, Germany). Alternately, characterization may be performed using a Waters Unity (UPLC) system with Waters Acquity UPLC BEH C-18 2.1 mm×15 mm columns. A gradient elution may be used, typically starting with 5% acetonitrile/95% water and progressing to 95% acetonitrile over a period of 5 minutes for the Alliance system and 1 minute for the Acquity system. All solvents may contain 0.1% trifluoroacetic acid (TFA). Compounds may be detected by ultraviolet light (UV) absorption at either 220 nm or 254 nm or by mass spectrometry in the case of the Acuity system by using a Waters SQD detector. HPLC solvents may be from EMD Chemicals, Inc. (Gibbstown, N.J.). In some instances, purity may be assessed by thin layer chromatography (TLC) using glass backed silica gel plates, such as, for example, EMD Silica Gel 60 2.5 cm×7.5 cm plates. TLC results may be readily detected visually under ultraviolet light, or by employing well known iodine vapor and other various staining techniques.

Nuclear magnetic resonance (NMR) analysis may be performed on some of the compounds with a Varian 400 MHz NMR (Palo Alto, Calif.). The spectral reference may be either TMS or the known chemical shift of the solvent.

The purity of some of the invention compounds may be assessed by elemental analysis (Robertson Microlit, Madison, N.J.).

Melting points may be determined on a Laboratory Devices Mel-Temp apparatus (Holliston, Mass.).

Preparative separations may be carried out as needed, using either a Sq16x or a Sg100c or a CombiPrep Rf chromatography system and prepackaged silica gel columns all purchased from Teledyne Isco, (Lincoln, Nebr.). Alternately, compounds and intermediates may be purified by flash column chromatography using silica gel (230-400 mesh) packing material, or by HPLC using a C-18 reversed phase column. Typical solvents employed for the Isco systems and flash column chromatography may be dichloromethane, methanol, ethyl acetate, hexane, acetone, aqueous hydroxyamine and triethyl amine. Typical solvents employed for the reverse phase HPLC may be varying concentrations of acetonitrile and water with 0.1% trifluoroacetic acid.

General Methods

The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

Example 1

2-(3-acetamidophenylamino)-4-(cyclobutylamino)pyrimidine-5-carboxamide

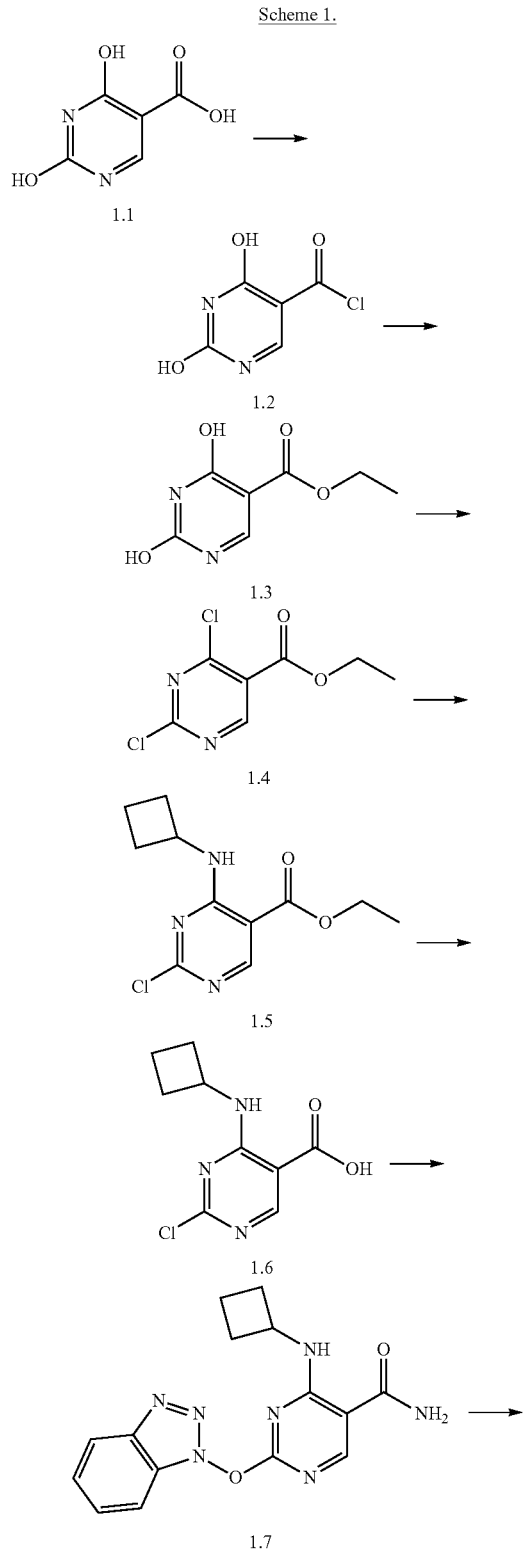

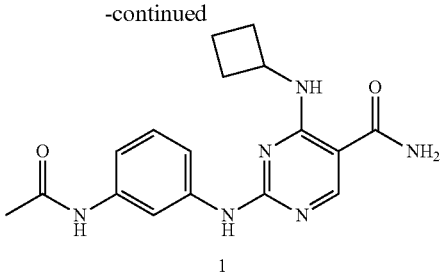

Step 1: To a stirring solution of carboxylic acid 1.1 (85 g, 540 mmol) in thionyl chloride (425 mL) was added pyridine (8.5 mL, 0.11 mmol), slowly. The reaction was stirred at 75° C. overnight at which time it was concentrated and dried under vacuum to a light yellow powder which was used immediately for the next step.

Step 2: The yellow solid from the previous page was slowly diluted with 750 mL of ethanol and refluxed overnight. The next day the reaction was determined to be complete by HPLC and then cooled in an ice bath and the solid filtered and washed with diethyl ether affording the desired ethyl ester 1.3 as an off-white powder (91 g, 87% for two steps). MS found for $C_7H_8N_2O_4$ as $(M+H)^+$ 185.0.

Step 3: Ester 1.3 (22 g, 120 mmol) was dissolved in phosphorous oxychloride (60 mL, 600 mmol) and the mixture treated with N,N-diethylaniline (27 mL, 167 mmol) and the mixture heated to 105° C. until the reaction was determined to be complete by HPLC. It was then cooled to rt and slowly added to 1 L of crushed ice resulting in the formation of a beige precipitate which was collected by filtration and dried under vacuum affording the desired dichloride (1.4) as a light yellow powder (22.5 g, 85%). $^1$H NMR (DMSO-$d_6$, 400 MHz): δ 9.13 (s, 1H), 4.37 (q, 2H), 1.32 (t, 3H).

Step 4: Dichloropyrimidine 1.4 (5.9 g, 27 mmol) was dissolved in acetonitrile (50 mL) and treated sequentially with diisopropylamine (5.2 mL, 30 mmol) followed by cyclobutyl amine (1.9 g, 27 mmol) and stirred at rt until all starting material had been consumed. The reaction mixture was then diluted with water to a total volume of 150 mL and the precipitate collected by filtration affording the desired product as a light yellow solid (6.02 g, 87%). $^1$H NMR (DMSO-$d_6$, 400 MHz): δ 8.60 (S, 1H), 8.48 (d, 1H), 4.52 (m, 1H), 4.29 (q, 2 H), 2.30 (m, 2H), 2.04 (m, 2H), 1.73 (m, 2H), 1.30 (t, 3H).

Step 5: Ethyl ester 1.5 (6.02 g, 24 mmol) was diluted with 1,4-dioxane (26 mL) followed by aqueous lithium hydroxide (1.0 M, 26 mL, 26 mmol) and stirred at rt until all starting material had been converted to the carboxylic acid. The reaction was then diluted with water to a total volume of 100 mL and acidified to pH=2 with 6 M HCl. The resulting suspension was then filtered and dried by aspiration giving 3.51 g of the carboxylic acid (64%). $^1$H NMR (DMSO-$d_6$, 400 MHz): δ 8.64 (d, 1H), 8.74 (s, 1H), 4.50 (m, 1H), 2.31 (m, 2H), 2.03 (m, 2H), 1.72 (m, 2H).

Step 6: Carboxylic acid 1.6 (3.15 g, 15 mmol) was dissolved in N,N-dimethylformamide (70 mL) and treated with HOBt (3.13 g, 23 mmol) and EDC (4.4 g, 23 mmol). After stirring ca. 25 min ammonia (0.5 M in 1,4-dioxane, 72 mL, 36 mmol) was added and the reaction stirred overnight. The following morning the reaction was diluted with water to a total volume of 500 mL and the desired product collected by filtration affording 3.62 g (74%) of a light-beige solid. $^1$H NMR (DMSO-$d_6$, 400 MHz): δ 9.30 (d, 1H), 8.54 (s, 1H), 8.15 (d, 1H), 8.09 (s, 1H), 7.74 (d, 1H), 7.64 (m, 2H), 7.51 (t, 1H), 3.77 (m, 1H), 1.79 (m, 2H), 1.74 (m, 2H), 1.53 (m, 1H), 1.41 (m, 1H).

Step 7: Benzotriazolyl ether 1.7 (50 mg, 0.17 mmol), 3-aminiacetanilide (40 mg) and p-toluenesulfonic acid (30 mg, 0.17 mmol) were diluted with 1,4-dioxane (5 mL) or NMP (5 mL) and stirred at 100° C. until all starting material had been consumed. The reaction was cooled to rt, diluted with water and directly purified by preparative HPLC affording the desired product after lyophilization. The above compound was prepared using the procedure described in Scheme 1. MS found for $C_{17}H_{20}N_6O_2$ as $(M+H)^+$ 341. UV: $\lambda$=251.

Example 2

2-(3-acetamido-4-chlorophenylamino)-4-(benzylamino)pyrimidine-5-carboxamide

Scheme 2:

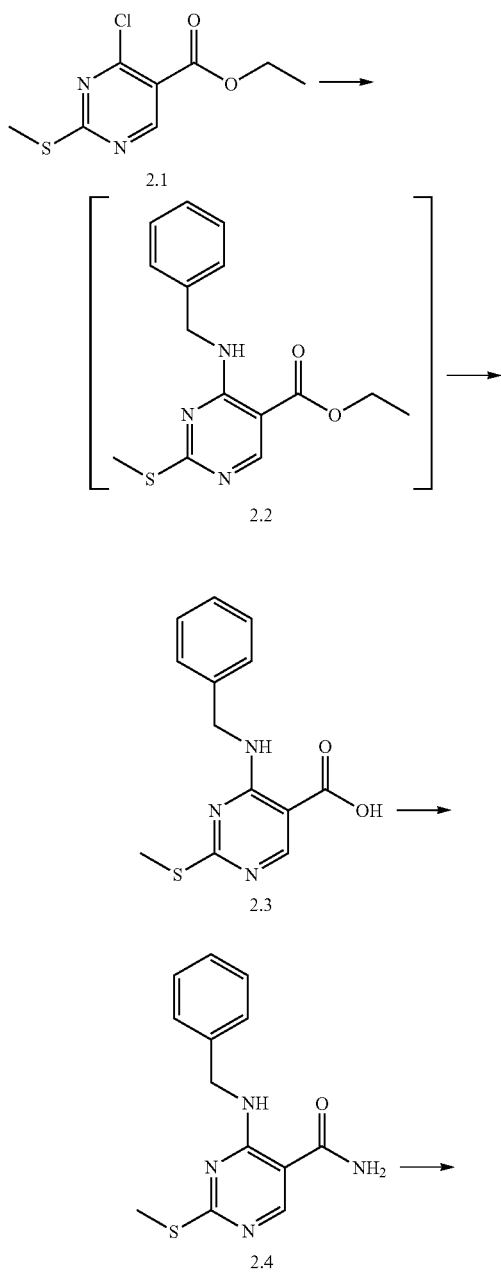

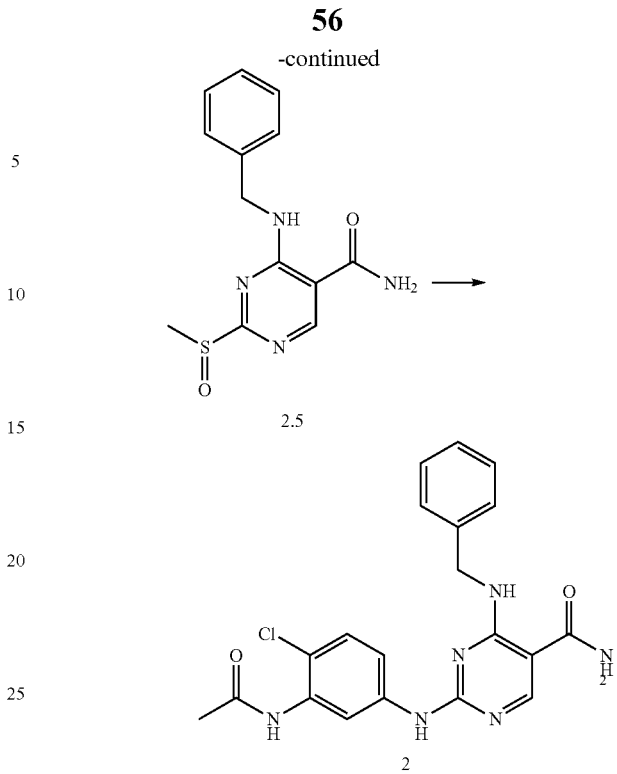

Step 1: Chloropyrimidine 2.1 (6.2 g, 27 mmol) was dissolved in dioxane (30 mL) and treated sequentially with diisopropylamine (5.0 mL, 29 mmol) followed by benzylamine (3.2 mL, 29 mmol) and stirred at rt until all starting material had been consumed and converted to the desired product $(C_{15}H_{17}N_3O_2S$ as $(M+H)^+$ 304.2; UV: $\lambda$=203, 257). The reaction mixture was then diluted with 45 mL of 1.0 M aqueous LiOH and stirred overnight. The following morning the reaction had not gone to completion, and was treated with ca. 1.0 g of solid LiOH and stirred at rt overnight. The following day all material had been converted to the carboxylic acid $(C_{13}H_{13}N_3O_2S$ as $(M+H)^+$ 276.2; UV: $\lambda$=202, 257). The reaction mixture was concentrated by rotary evaporation to remove a majority of the dioxane, then acidifed with 3M HCl to pH=2 (250 mL total volume) resulting in the formation of a white precipitate. The solid was isolated by filtration and dried by aspiration, then used for the next step. (7.2 g, 97%)

Step 2: Carboxylic acid 2.3 (7.2 g, 26 mmol) was dissolved in N,N-dimethylformamide (30 mL) and treated with HOBt (4.8 g, 31 mmol) and EDC (6.0 31 mmol). After stirring ca. 40 min aq ammonia (17 M, 3.1 mL, 52 mmol) was added and the reaction stirred at rt. After 30 min the reaction was determined to be complete by UPLC $(C_{13}H_{14}N_4OS$ as $(M+H)^+$ 275.2; UV: $\lambda$=200, 258. It was then diluted with water 150 mL total volume and stirred until a filterable precipitate formed. The solid was then isolated by filtration and dried by aspiration affording the desired amide as a white solid (3.87 g, 54%).

Step 3: Sulfide 2.4 (3.87 g, 14 mmol) was suspended in 40 mL of dioxane and treated with peroxyacetic acid in acetic acid (5.9 M, 2.9 mL, 17 mmol) and stirred at rt for 1 hr at which time the reaction was found to be incomplete. It was treated with 1 mL of peroxyacetic acid/acetic acid and stirred at rt. Later, the reaction was checked and found to contain sulfoxide with small amounts of 2.4 and sulfone. It was then diluted with water until precipitate formation ceased, filtered, and the solid dried by aspiration affording the desired product as a white solid $C_{13}H_{14}N_4O_2S$ as $(M+H)^+$ 291.2; UV: $\lambda$=203, 254, 316.

Step 4: Sulfoxide 2.5 (50 mg, 0.14 mmol) and TsOH (30 mg, 0.16 mmol) was dissolved in 1 mL of NMP, then treated with approximately 40 mg of 2-chloro-5-aminoacetanilide and stirred at 100° C. for 1 hr. The reaction was then checked by HPLC and found to be incomplete, but with some impurities present. The reaction solution was cooled, purified by preparative HPLC, and the desired product lyophilized affording a fluffy solid. MS found for $C_{20}H_{19}ClN_6O_2$ as $(M+H)^+$ 411.3, 413.3. UV: $\lambda$=206, 250.

Example 3

(S)-2-(3-acetamidophenylamino)-4-(2-phenylpropylamino)pyrimidine-5-carboxamide

Scheme 3:

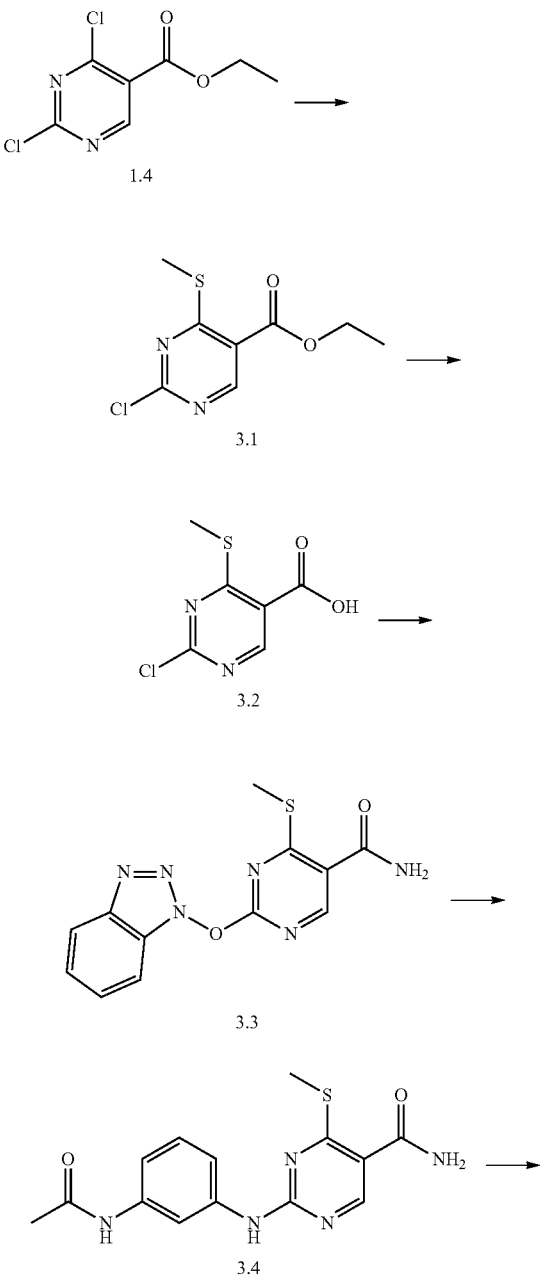

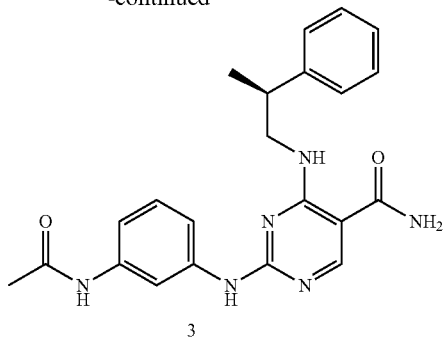

Step 1: Dichloropyrimidine 1.4 (3.39 g, 15 mmol) was diluted with toluene (8 mL) and treated with benzyltriethylammonium chloride (0.68 g, 3 mmol) then sodium thiomethoxide (1.2 g, 17 mmol). The resulting suspension was then diluted with 8 mL of water and stirred vigorously for one hr at which time the starting material was found to be consumed by UPLC. The mixture was then diluted with water and ethyl acetate and the layers separated. The organic phase was extracted once with ethyl acetate and the combined organic layers concentrated in vacuo. The resulting solid was then triturated with ca. 15 mL of diethyl ether and the solid isolated by filtration and washed with a small amount of diethyl ether resulting in a light beige solid (0.66 g, 19%). MS found for $C_8H_9ClN_2O_2S$ as $(M+H)^+$ 233.0, 235.1.

Step 2: Ethyl ester 3.1 (0.66 g, 2.8 mmol) was diluted with dioxane (8 mL), then treated with aqueous LiOH (1 M, 4.2 mL, 4.2 mmol) and stirred until all starting material had been consumed. The reaction mixture was then acidified to pH=2 with 1 M HCl and stirred until a filterable solid formed. The solid was isolated by filtration, washed with water, then aspirated to dryness afording the desired carboxylic acid as a light pink solid (0.50 g, 88%). found for $C_{12}H_{10}N_6O_2S$ as $(M+H)^-$ 205.0, 207.0.3. UV: $\lambda$=224, 277.

Step 3: Carboxylic acid 3.2 (0.50 g, 2.5 mmol) was dissolved in 10 mL of DMF, then treated with hydroxybenzotriazole-hydrate (0.44 g, 2.9 mmol) and EDC (0.56 g, 2.9 mmol) and stirred at rt. After stirring 10 min the reaction was checked by UPLC which showed complete conversion to the activated species. The reaction was then treated with ammonia/dioxane (0.5 M, 10 mL, 10 mmol) and stirred overnight. The following morning the reaction was checked by UPLC which showed the desired product (MS found for $C_{12}H_{10}N_6O_2S$ as $(M+H)^+$ 303.2). The reaction was concentrated by rotary evaporation to remove the dioxane, then diluted with water slowly until precipitation ceased. The solid was then isolated by filtration and aspirated to dryness affording amide 3.3 as a light pink solid (0.57 g, 75%).

Step 4: Amide 3.3 (1.4 gm 4.6 mmol) was diluted with 10 mL of NMP, then treated with 3-aminoacetanilide (0.83 g, 5.6 mmol) and TsOH (1.1 g, 5.6 mmol). The reaction was heated to 100° C. and stirred until only a trace of 3.3 remained. The reaction was then cooled to rt and diluted with water to 100 mL total volume. After stirring vigorously for 30 min the desired product (3.4) was isolated by filtration as a light beige solid (MS found for $C_{14}H_{15}N_5O_2S$ as $(M+H)^+$ 318.2).

Step 5: Sulfide 3.4 (0.35 g, 1.1 mmol) was dissolved in NMP (10 mL) then treated with mCPBA (65%, 0.35 g, 1.3 mmol) and stirred at rt until all starting material had been oxidized to the sulfoxide (MS found for $C_{14}H_{15}N_5O_3S$ as $(M+H)^+$ 334.2). DIEA (1.0 mL, 5.5 mmol) was then added and then 1/10$^{th}$ of the solution aliquotted into a scintillation vial and treated with 100 microliters of (S)-2-phenyl-1-propylamine. The reaction was then heated to 100° C. until complete, then purified by preparative HPLC affording the desired product as a fluffy solid after lyophilization. MS found for $C_{22}H_{24}N_6O_2$ as $(M+H)^+$ 405.4.

Example 4

Methyl 3-(5-carbamoyl-4-(2,2,2-trifluoroethylamino) pyrimidin-2-ylamino)phenylcarbamate

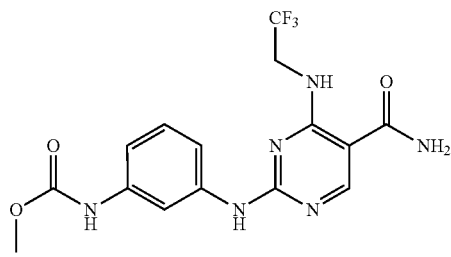 [SMILES: COC(=O)Nc1cccc(Nc2ncc(C(N)=O)c(NCC(F)(F)F)n2)c1]

The above compound was prepared using a procedure similar to that described in Scheme 1 using trifluoroethylamine in place of cyclobutylamine and using an aniline prepared from 3-nitroaniline and methyl chloroformate followed by reduction using hydrogen gas and Pd/C. MS found for $C_{15}H_{15}F_3N_6O_3$ as $(M+H)^+$ 385.3.

Example 5

2-(3-(cyclopropanecarboxamido)phenylamino)-4-(2,2,2-trifluoroethylamino)pyrimidine-5-carboxamide

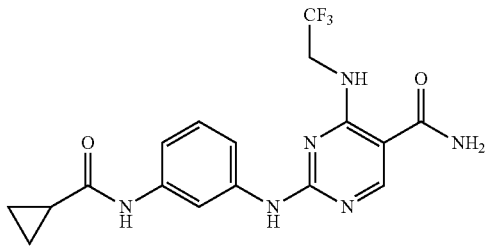 [SMILES: NC(=O)c1cnc(Nc2cccc(NC(=O)C3CC3)c2)nc1NCC(F)(F)F]

The above compound was prepared using a procedure similar to that described in Scheme 1 using trifluoroethylamine in place of cyclobutylamine and an aniline prepared from 3-nitro aniline and cyclopropylcarbonyl chloride followed by reduction using hydrogen gas and Pd/C. MS found for $C_{17}H_{17}F_3N_6O_2$ as $(M+H)^+$ 395.3.

Example 6

2-(3-(2-methoxyacetamido)phenylamino)-4-(2,2,2-trifluoroethylamino)pyrimidine-5-carboxamide

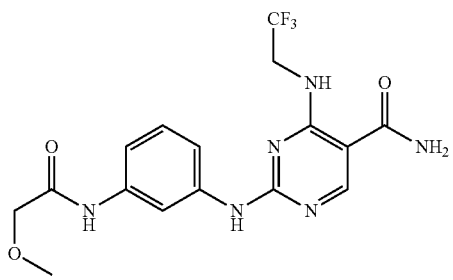 [SMILES: COCC(=O)Nc1cccc(Nc2ncc(C(N)=O)c(NCC(F)(F)F)n2)c1]

The above compound was prepared using a procedure similar to that described in Scheme 1 using trifluoroethylamine in place of cyclobutylamine and an aniline prepared from 3-nitro aniline and methoxyacetyl achloride chloride followed by reduction using hydrogen gas and Pd/C. MS found for $C_{16}H_{17}F_3N_6O_3$ as $(M+H)^+$ 399.3.

Example 7

2-(3-acetamidophenylamino)-4-(2,2,2-trifluoroethylamino)pyrimidine-5-carboxamide

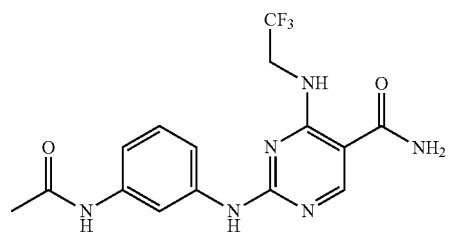 [SMILES: CC(=O)Nc1cccc(Nc2ncc(C(N)=O)c(NCC(F)(F)F)n2)c1]

The above compound was prepared using a procedure similar to that described in Scheme 1 using trifluoroethylamine in place of cyclobutylamine and 3-aminoacetanilide. MS found for $C_{15}H_{15}F_3N_6O_2$ as $(M+H)^+$ 369.2. UV: λ=209, 246.

Example 8

2-(3-acetamidophenylamino)-4-(methylamino)pyrimidine-5-carboxamide

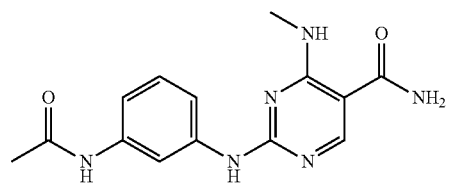 [SMILES: CNc1nc(Nc2cccc(NC(C)=O)c2)ncc1C(N)=O]

The above compound was prepared using a procedure similar to that described in Scheme 1 using methylamine in place of cyclobutylamine and 3-aminoacetanilide. MS found for $C_{14}H_{16}N_6O_2$ as $(M+H)^+$ 301.3. UV: $\lambda$=201, 249.

Example 9

2-(3-acetamidophenylamino)-4-(ethylamino)pyrimidine-5-carboxamide

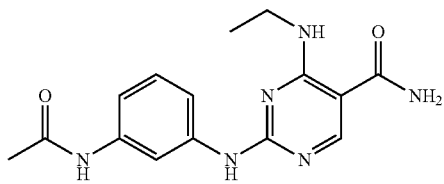 [SMILES: CCNc1nc(Nc2cccc(NC(C)=O)c2)ncc1C(N)=O]

The above compound was prepared using a procedure similar to that described in Scheme 1 using ethylamine in place of cyclobutylamine and 3-aminoacetanilide. MS found for $C_{15}H_{18}N_6O_2$ as $(M+H)^+$ 315.3.

Example 10

2-(3-acetamidophenylamino)-4-(prop-2-ynylamino)pyrimidine-5-carboxamide

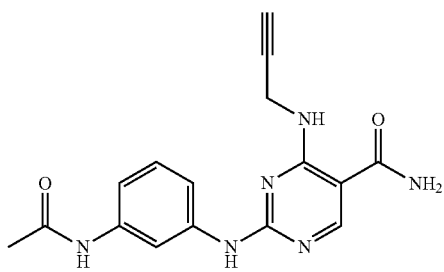 [SMILES: C#CCNc1nc(Nc2cccc(NC(C)=O)c2)ncc1C(N)=O]

The above compound was prepared using a procedure similar to that described in Scheme 1 using propargylamine in place of cyclobutylamine and 3-aminoacetanilide. MS found for $C_{16}H_{16}N_6O_2$ as $(M+H)^-$ 325.3.

Example 11

2-(3-acetamidophenylamino)-4-(isopropylamino)pyrimidine-5-carboxamide

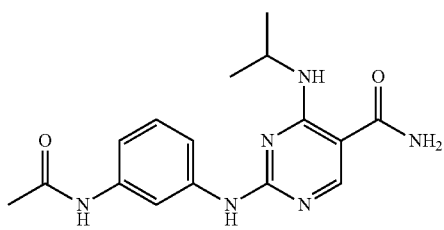 [SMILES: CC(=O)Nc1cccc(Nc2ncc(C(N)=O)c(NC(C)C)n2)c1]

The above compound was prepared using a procedure similar to that described in Scheme 1 using isopropylamine in place of cyclobutylamine and 3-aminoacetanilide. MS found for $C_{16}H_{20}N_6O_2$ as $(M+H)^-$ 329.3.

Example 12

2-(3-acetamidophenylamino)-4-(cyclopropylmethylamino)pyrimidine-5-carboxamide

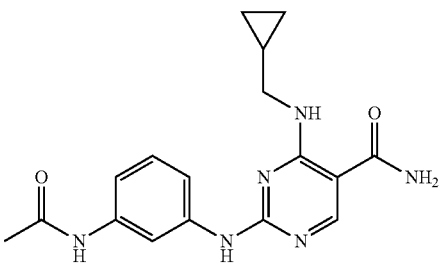

The above compound was prepared using a procedure similar to that described in Scheme 1 using cyclopropylmethylamine in place of cyclobutylamine and 3-aminoacetanilide. MS found for $C_{17}H_{20}N_6O_2$ as $(M+H)^-$ 341.3.

Example 13

2-(3-acetamidophenylamino)-4-(tert-butylamino)pyrimidine-5-carboxamide

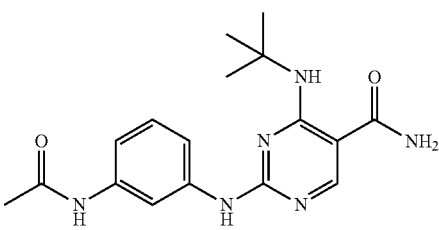 [SMILES: CC(=O)Nc1cccc(Nc2ncc(C(N)=O)c(NC(C)(C)C)n2)c1]

The above compound was prepared using a procedure similar to that described in Scheme 1 using tert-butylamine in place of cyclobutylamine and 3-aminoacetanilide. MS found for $C_{17}H_{20}N_6O_2$ as $(M+H)^+$ 343.3. UV: $\lambda$=200, 248.

Example 14

2-(3-acetamidophenylamino)-4-(2-methoxyethylamino)pyrimidine-5-carboxamide

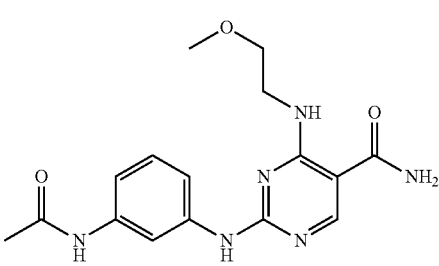 [SMILES: COCCNc1nc(Nc2cccc(NC(C)=O)c2)ncc1C(N)=O]

The above compound was prepared using a procedure similar to that described in Scheme 1 using methoxyethylamine in place of cyclobutylamine and 3-aminoacetanilide. MS found for $C_{16}H_{20}N_6O_3$ as $(M+H)^+$ 345.3.

Example 15

2-(3-acetamidophenylamino)-4-(cyclopentylamino)pyrimidine-5-carboxamide

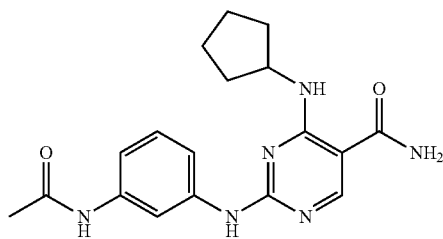 [SMILES: CC(=O)Nc1cccc(Nc2ncc(C(N)=O)c(NC3CCCC3)n2)c1]

The above compound was prepared using a procedure similar to that described in Scheme 1 using cyclopentylamine in place of cyclobutylamine and 3-aminoacetanilide. MS found for $C_{18}H_{22}N_6O_2$ as $(M+H)^+$ 355.3.

Example 16

2-(3-acetamidophenylamino)-4-(3-methoxypropylamino)pyrimidine-5-carboxamide

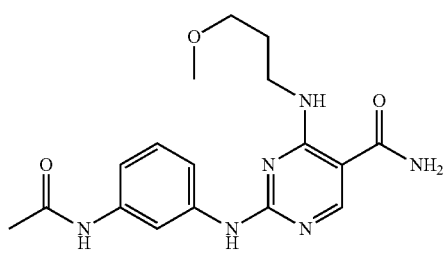 [SMILES: COCCCNc1nc(Nc2cccc(NC(C)=O)c2)ncc1C(N)=O]

The above compound was prepared using a procedure similar to that described in Scheme 1 using 3-methoxypropylamine in place of cyclobutylamine and 3-aminoacetanilide. MS found for $C_{17}H_{22}N_6O_3$ as $(M+H)^+$ 359.3.

Example 17

2-(3-acetamidophenylamino)-4-(benzylamino)pyrimidine-5-carboxamide

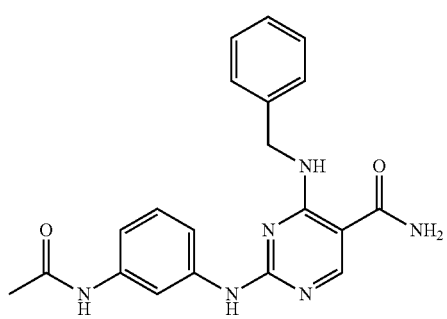

The above compound was prepared using a procedure similar to that described in Scheme 1 using benzylamine in place of cyclobutylamine and 3-aminoacetanilide. MS found for $C_{20}H_{20}N_6O_2$ as $(M+H)^+$ 377.3.

Example 18

Methyl 5-(5-carbamoyl-4-(2,2,2-trifluoroethylamino)pyrimidin-2-ylamino)-2-chlorophenylcarbamate

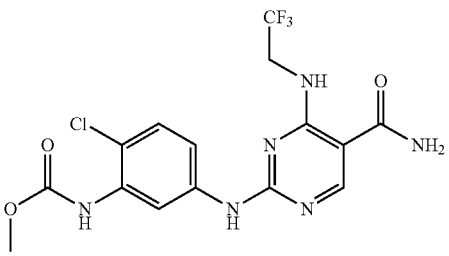 [SMILES: COC(=O)Nc1cc(Nc2ncc(C(N)=O)c(NCC(F)(F)F)n2)ccc1Cl]

The above compound was prepared using a procedure similar to that described Scheme 1 using trifluoroethylamine in place of cyclobutylamine and an aniline prepared from methylchloroformate and 2-chloro-5-nitroaniline. MS found for $C_{15}H_{14}ClF_3N_6O_3$ as $(M+H)^+$ 419.2, 421.2. UV: $\lambda$=206, 241, 276.

Example 19

4-(cyclopentylamino)-2-(3-(cyclopropanecarboxamido)phenylamino)pyrimidine-5-carboxamide

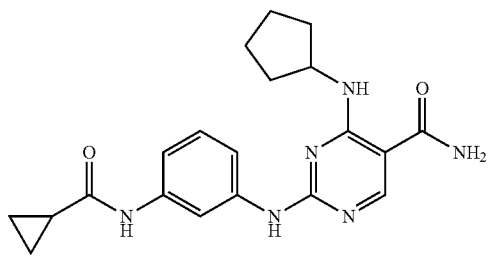 [SMILES: NC(=O)c1cnc(Nc2cccc(NC(=O)C3CC3)c2)nc1NC1CCCC1]

The above compound was prepared using a procedure similar to that described in Scheme 1, using cyclopentylamine in place of cyclobutylamine and an aniline prepared from 3-nitroaniline and cyclopropanecarbonyl chloride. MS found for $C_{20}H_{24}N_6O_2$ as $(M+H)^+$ 381.4. UV: $\lambda$=202, 250.

Example 20

2-(3-(cyclobutanecarboxamido)phenylamino)-4-(cyclopentylamino)pyrimidine-5-carboxamide

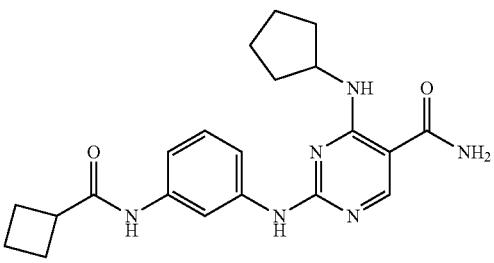 [SMILES: NC(=O)c1cnc(Nc2cccc(NC(=O)C3CCC3)c2)nc1NC1CCCC1]

The above compound was prepared using a procedure similar to that described in Scheme 1, using cyclopentylamine in place of cyclobutylamine and an aniline prepared from 3-nitroaniline and cyclobutanecarbonyl chloride. MS found for $C_{21}H_{26}N_6O_2$ as $(M+H)^+$ 395.4. UV: $\lambda$=205, 252.

Example 21

4-(cyclopentylamino)-2-(3-propionamidophenylamino)pyrimidine-5-carboxamide

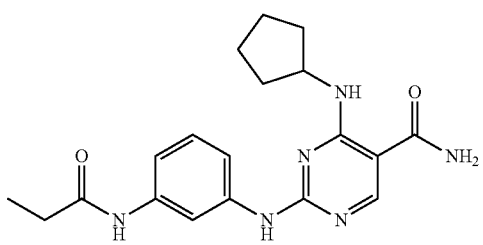 [SMILES: CCC(=O)Nc1cccc(Nc2ncc(C(N)=O)c(NC3CCCC3)n2)c1]

The above compound was prepared using a procedure similar to that described in Scheme 1, using cyclopentylamine in place of cyclobutylamine and an aniline prepared from 3-nitroaniline and propionyl chloride. MS found for $C_{19}H_{24}N_6O_2$ as $(M+H)^+$ 369.4. UV: $\lambda$=210, 249.

Example 22

4-(cyclopentylamino)-2-(3-(2-methoxyacetamido)phenylamino)pyrimidine-5-carboxamide

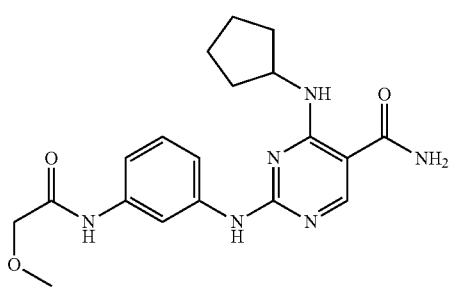 [SMILES: COCC(=O)Nc1cccc(Nc2ncc(C(N)=O)c(NC3CCCC3)n2)c1]

The above compound was prepared using a procedure similar to that described in Scheme 1, using cyclopentylamine in place of cyclobutylamine and an aniline prepared from 3-nitroaniline and methoxyacetyl chloride. MS found for $C_{19}H_{24}N_6O_3$ as $(M+H)^-$ 385.3. UV: $\lambda$=204, 251.

Example 23

Methyl 3-(5-carbamoyl-4-(cyclopentylamino)pyrimidin-2-ylamino)phenylcarbamate

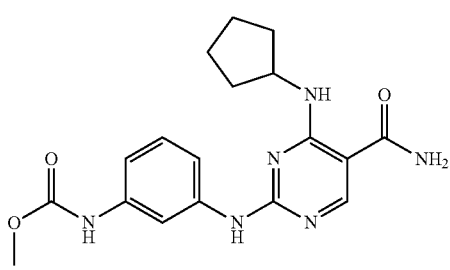 [SMILES: COC(=O)Nc1cccc(Nc2ncc(C(N)=O)c(NC3CCCC3)n2)c1]

The above compound was prepared using a procedure similar to that described in Scheme 1, using cyclopentylamine in place of cyclobutylamine and an aniline prepared from 3-nitroaniline and methyl chloroformate. MS found for $C_{18}H_{22}N_6O_3$ as $(M+H)^+$ 371.3. UV: $\lambda$=204, 243.

Example 24

Ethyl 3-(5-carbamoyl-4-(cyclopentylamino)pyrimidin-2-ylamino)phenylcarbamate

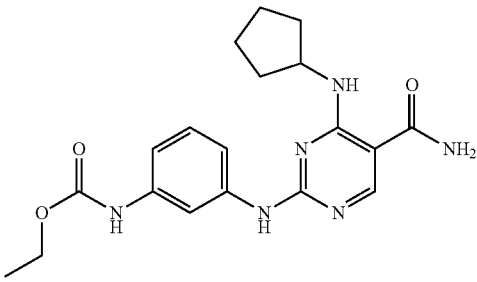 [SMILES: CCOC(=O)Nc1cccc(Nc2ncc(C(N)=O)c(NC3CCCC3)n2)c1]

The above compound was prepared using a procedure similar to that described in Scheme 1, using cyclopentylamine in place of cyclobutylamine and an aniline prepared from 3-nitroaniline and ethyl chloroformate chloride. MS found for $C_{19}H_{24}N_6O_3$ as $(M+H)^+$ 385.4. UV: $\lambda$=203, 244.

Example 25

Methyl 5-(5-carbamoyl-4-(cyclopentylamino)pyrimidin-2-ylamino)-2-chlorophenylcarbamate

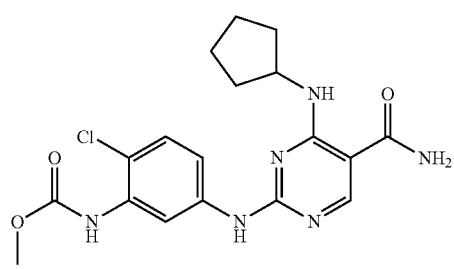 [SMILES: COC(=O)Nc1cc(Nc2ncc(C(N)=O)c(NC3CCCC3)n2)ccc1Cl]

The above compound was prepared using a procedure similar to that described in Scheme 1, using cyclopentylamine in place of cyclobutylamine and an aniline prepared from 2-chloro-5-nitroaniline and methyl chloroformate. MS found for $C_{18}H_{21}ClN_6O_3$ as $(M+H)^+$ 405.4, 407.4. UV: $\lambda$=205, 244.

Example 26

4-(benzylamino)-2-(3-(cyclopropanecarboxamido)phenylamino)pyrimidine-5-carboxamide

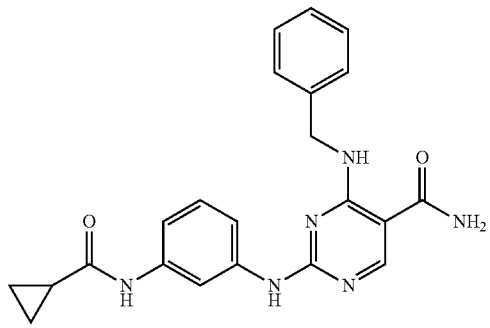 [SMILES: NC(=O)c1cnc(Nc2cccc(NC(=O)C3CC3)c2)nc1NCc1ccccc1]

The above compound was prepared using a procedure similar to that described in Scheme 1, using benzylamine in place of cyclobutylamine and an aniline prepared from 3-nitroaniline and cyclopropanecarbonyl chloride. MS found for $C_{22}H_{22}N_6O_2$ as $(M+H)^+$ 403.4. UV: $\lambda$=205, 250.

Example 27

4-(benzylamino)-2-(3-(cyclobutanecarboxamido)phenylamino)pyrimidine-5-carboxamide

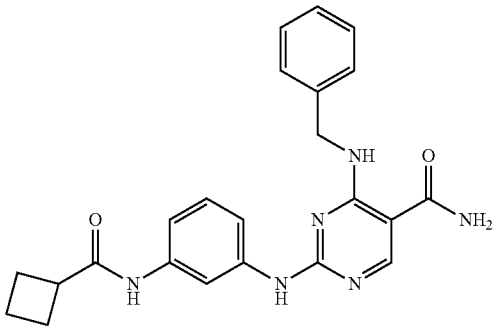 [SMILES: NC(=O)c1cnc(Nc2cccc(NC(=O)C3CCC3)c2)nc1NCc1ccccc1]

The above compound was prepared using a procedure similar to that described in Scheme 1, using benzylamine in place of cyclobutylamine and an aniline prepared from 3-nitroaniline and cyclobutanecarbonyl chloride. MS found for $C_{23}H_{24}N_6O_2$ as $(M+H)^+$ 417.4. UV: $\lambda=250$.

Example 28

4-(benzylamino)-2-(3-propionamidophenylamino)pyrimidine-5-carboxamide

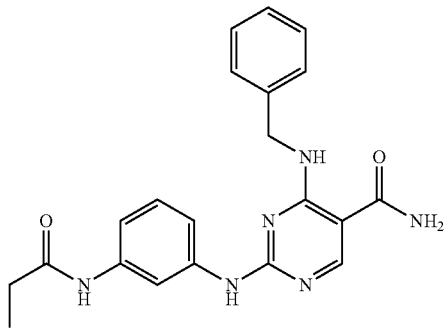 [SMILES: CCC(=O)Nc1cccc(Nc2ncc(C(N)=O)c(NCc3ccccc3)n2)c1]

The above compound was prepared using a procedure similar to that described in Scheme 1, using benzylamine in place of cyclobutylamine and an aniline prepared from 3-nitroaniline and cyclopropanecarbonyl chloride. MS found for $C_{21}H_{22}N_6O_2$ as $(M+H)^+$ 391.3. UV: $\lambda=200, 249$.

Example 29

4-(benzylamino)-2-(3-(2-methoxyacetamido)phenylamino)pyrimidine-5-carboxamide

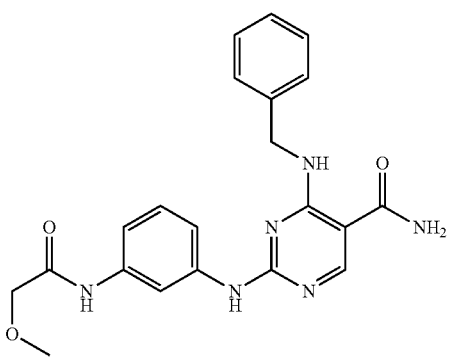 [SMILES: COCC(=O)Nc1cccc(Nc2ncc(C(N)=O)c(NCc3ccccc3)n2)c1]

The above compound was prepared using a procedure similar to that described in Scheme 1, using benzylamine in place of cyclobutylamine and an aniline prepared from 3-nitroaniline and methoxyacetyl chloride. MS found for $C_{21}H_{22}N_6O_3$ as $(M+H)^-$ 407.3. UV: $\lambda=202, 249$.

Example 30

Methyl 3-(4-(benzylamino)-5-carbamoylpyrimidin-2-ylamino)phenylcarbamate

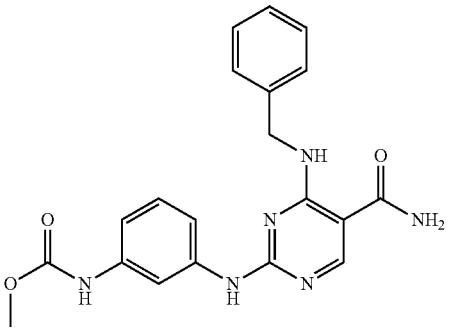 [SMILES: COC(=O)Nc1cccc(Nc2ncc(C(N)=O)c(NCc3ccccc3)n2)c1]

The above compound was prepared using a procedure similar to that described in Scheme 1, using benzylamine in place of cyclobutylamine and an aniline prepared from 3-nitroaniline and methyl chloroformate. MS found for $C_{20}H_{20}N_6O_3$ as $(M+H)^+$ 393.4. UV: $\lambda=200, 244$.

Example 31

Ethyl 3-(4-(benzylamino)-5-carbamoylpyrimidin-2-ylamino)phenylcarbamate

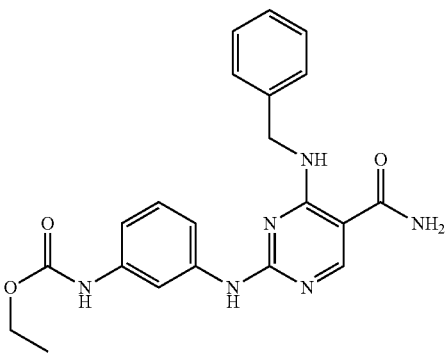 [SMILES: CCOC(=O)Nc1cccc(Nc2ncc(C(N)=O)c(NCc3ccccc3)n2)c1]

The above compound was prepared using a procedure similar to that described in Scheme 1, using benzylamine in place of cyclobutylamine and an aniline prepared from 3-nitroaniline and ethyl chloroformate. MS found for $C_{21}H_{22}N_6O_3$ as $(M+H)^+$ 407.3. UV: $\lambda=202, 249$.

Example 32

Methyl 5-(4-(benzylamino)-5-carbamoylpyrimidin-2-ylamino)-2-chlorophenylcarbamate

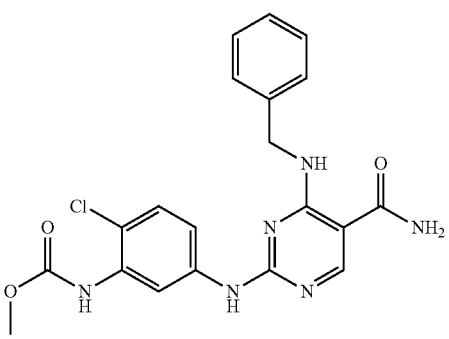 [SMILES: COC(=O)Nc1cc(Nc2ncc(C(N)=O)c(NCc3ccccc3)n2)ccc1Cl]

The above compound was prepared using a procedure similar to that described in Scheme 1, using benzylamine in place of cyclobutylamine and an aniline prepared from 2-chloro-5-nitroaniline and methyl chloroformate. MS found for $C_{20}H_{19}ClN_6O_3$ as $(M+H)^+$ 427.3, 429.3. UV: $\lambda=201, 244$.

Example 33

4-(cyclopentylamino)-2-(3-ureidophenylamino)pyrimidine-5-carboxamide

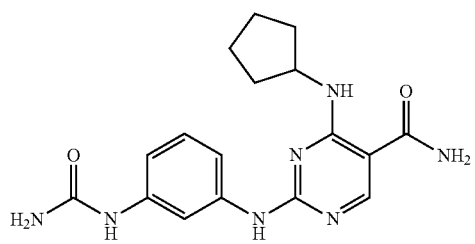 [SMILES: NC(=O)Nc1cccc(Nc2ncc(C(N)=O)c(NC3CCCC3)n2)c1]

The above compound was prepared using a procedure similar to that described in Scheme 1, using cyclopentyl amine in place of cyclobutylamine and an aniline prepared from 3-nitroaniline and sodium isocyanate. MS found for $C_{17}H_{21}N_7O_2$ as $(M+H)^+$ 356.4. UV: $\lambda$=205, 246.

Example 34

4-(cyclopentylamino)-2-(3-(3-methylureido)phenylamino)pyrimidine-5-carboxamide

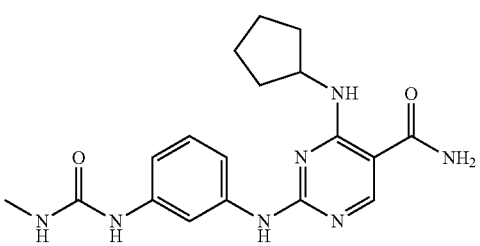

The above compound was prepared using a procedure similar to that described in Scheme 1, using cyclopentylamine in place of cyclobutylamine and an aniline prepared from 3-nitroaniline, phosgene, and methylamine. MS found for $C_{18}H_{23}N_7O_2$ as $(M+H)^+$ 370.4. UV: $\lambda$=208, 252.

Example 35

4-(cyclopentylamino)-2-(3-(3,3-dimethylureido)phenylamino)pyrimidine-5-carboxamide

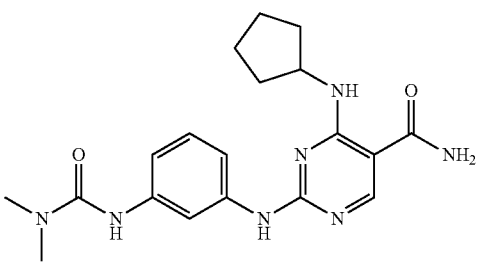 [SMILES: CN(C)C(=O)Nc1cccc(Nc2ncc(C(N)=O)c(NC3CCCC3)n2)c1]

The above compound was prepared using a procedure similar to that described in Scheme 1, using cyclopentylamine in place of cyclobutylamine and an aniline prepared from 3-nitroaniline, phosgene, and dimethylamine. MS found for $C_{19}H_{25}N_7O_2$ as $(M+H)^+$ 384.4. UV: $\lambda$=206, 248.

Example 36

4-(cyclopentylamino)-2-(3-(3-ethylureido)phenylamino)pyrimidine-5-carboxamide

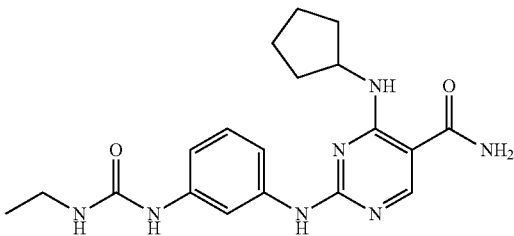 [SMILES: CCNC(=O)Nc1cccc(Nc2ncc(C(N)=O)c(NC3CCCC3)n2)c1]

The above compound was prepared using a procedure similar to that described in Scheme 1, using cyclopentylamine in place of cyclobutylamine and an aniline prepared from 3-nitroaniline, phosgene, and ethylamine. MS found for $C_{19}H_{25}N_7O_2$ as $(M+H)^+$ 384.4. UV: $\lambda$=206, 247.

Example 37

4-(cyclopentylamino)-2-(3-(pyrrolidine-1-carboxamido)phenylamino)pyrimidine-5-carboxamide

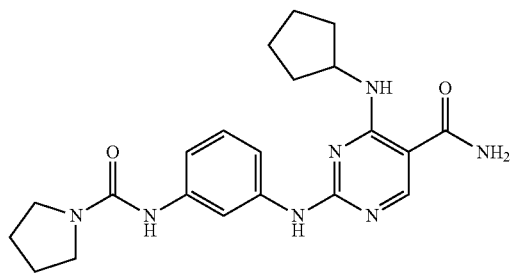 [SMILES: NC(=O)c1cnc(Nc2cccc(NC(=O)N3CCCC3)c2)nc1NC1CCCC1]

The above compound was prepared using a procedure similar to that described in Scheme 1, using cyclopentylamine in place of cyclobutylamine and an aniline prepared from 3-nitroaniline, phosgene, and pyrrolidine. MS found for $C_{21}H_{27}N_7O_2$ as $(M+H)^+$ 410.5. UV: $\lambda$=207, 249.

Example 38

4-(benzylamino)-2-(3-ureidophenylamino)pyrimidine-5-carboxamide

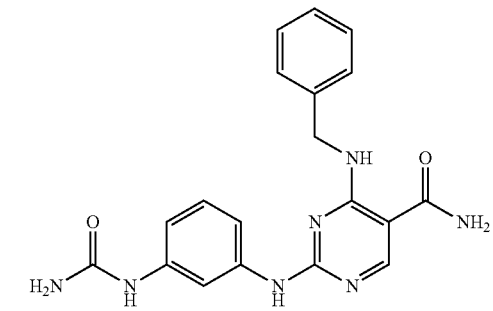 [SMILES: NC(=O)Nc1cccc(Nc2ncc(C(N)=O)c(NCc3ccccc3)n2)c1]

The above compound was prepared using a procedure similar to that described in Scheme 1, using benzylamine in place of cyclobutylamine and an aniline prepared from 3-nitroaniline and sodium isocyanate. MS found for $C_{19}H_{19}N_7O_2$ as $(M+H)^+$ 378.4. UV: $\lambda$=205, 246.

Example 39

4-(benzylamino)-2-(3-(3-methylureido)phenylamino)pyrimidine-5-carboxamide

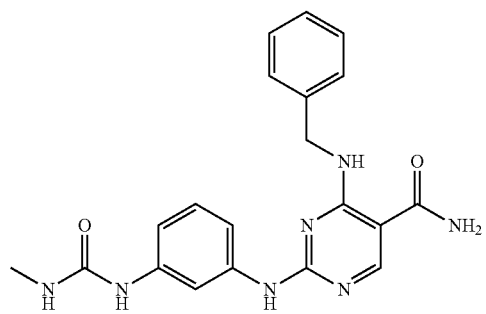 [SMILES: CNC(=O)Nc1cccc(Nc2ncc(C(N)=O)c(NCc3ccccc3)n2)c1]

The above compound was prepared using a procedure similar to that described in Scheme 1, using benzylamine in place of cyclobutylamine and an aniline prepared from 3-nitroaniline, phosgene, and methylamine. MS found for $C_{20}H_{21}N_7O_2$ as (M+H)$^+$ 392.5. UV: λ=207, 247.

Example 40

4-(benzylamino)-2-(3-(pyrrolidine-1-carboxamido)phenylamino)pyrimidine-5-carboxamide

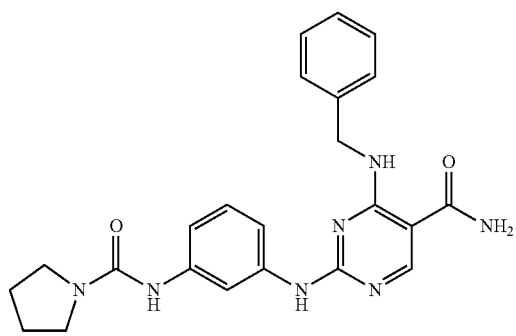 [SMILES: NC(=O)c1cnc(Nc2cccc(NC(=O)N3CCCC3)c2)nc1NCc1ccccc1]

The above compound was prepared using a procedure similar to that described in Scheme 1, using benzylamine in place of cyclobutylamine and an aniline prepared from 3-nitroaniline, phosgene, and pyrrolidine. MS found for $C_{23}H_{25}N_7O_2$ as (M+H)$^+$ 432.5. UV: λ=206, 249.

Example 41

Isopropyl 3-(4-(benzylamino)-5-carbamoylpyrimidin-2-ylamino)phenylcarbamate

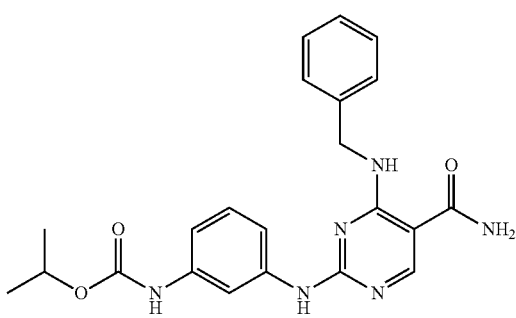 [SMILES: CC(C)OC(=O)Nc1cccc(Nc2ncc(C(N)=O)c(NCc3ccccc3)n2)c1]

The above compound was prepared using a procedure similar to that described in Scheme 1, using benzylamine in place of cyclobutylamine and an aniline prepared from 3-nitroaniline and isopropylchloroformate. MS found for $C_{22}H_{24}N_6O_3$ as (M+H)$^+$ 421.5. UV: λ=244.

Example 42

(S)-2-(3-(2-methoxyacetamido)phenylamino)-4-(1-phenylethylamino)pyrimidine-5-carboxamide

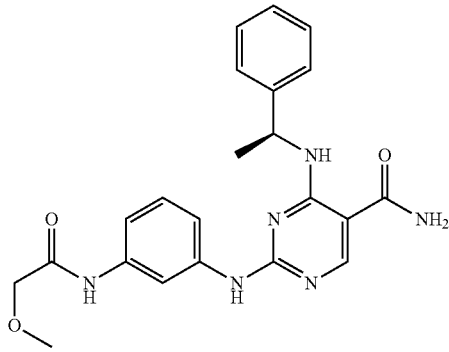 [SMILES: COCC(=O)Nc1cccc(Nc2ncc(C(N)=O)c(N[C@@H](C)c3ccccc3)n2)c1]

The above compound was prepared using a procedure similar to that described in Scheme 1, using (S)-1-phenylethylamine in place of cyclobutylamine and an aniline prepared from 3-nitroaniline and methoxyacetyl chloride. MS found for $C_{22}H_{24}N_6O_3$ as (M+H)$^+$ 421.0. UV: λ=250.

Example 43

2-(3-(2-methoxyacetamido)phenylamino)-4-(4-methylbenzylamino)pyrimidine-5-carboxamide

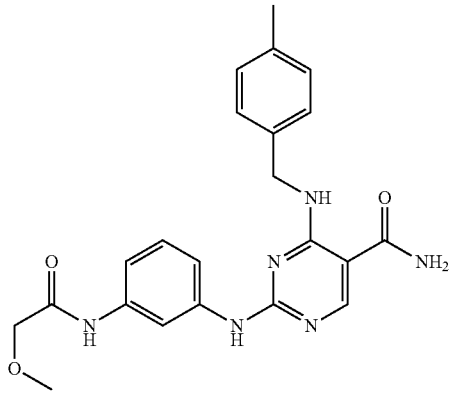 [SMILES: COCC(=O)Nc1cccc(Nc2ncc(C(N)=O)c(NCc3ccc(C)cc3)n2)c1]

The above compound was prepared using a procedure similar to that described in Scheme 1, using 4-methylbenzylamine in place of cyclobutylamine and an aniline prepared from 3-nitroaniline and methoxyacetyl chloride. MS found for $C_{22}H_{24}N_6O_3$ as (M+H)$^+$ 421.0. UV: λ=247.

Example 44

2-(3-(2-methoxyacetamido)phenylamino)-4-(4-methoxybenzylamino)pyrimidine-5-carboxamide

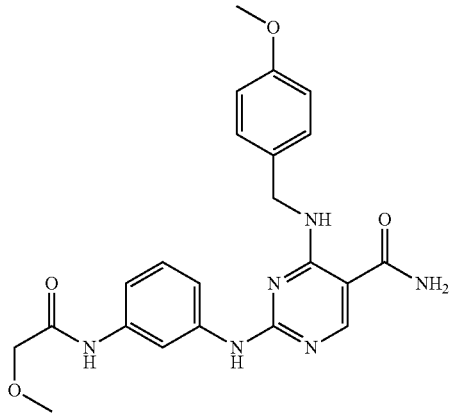 [SMILES: COCC(=O)Nc1cccc(Nc2ncc(C(N)=O)c(NCc3ccc(OC)cc3)n2)c1]

The above compound was prepared using a procedure similar to that described in Scheme 1, using 4-methoxybenzylamine in place of cyclobutylamine and an aniline prepared from 3-nitroaniline and methoxyacetyl chloride. MS found for $C_{22}H_{24}N_6O_4$ as (M+H)$^+$ 437.0. UV: λ=246.

Example 45

4-(4-chlorobenzylamino)-2-(3-(2-methoxyacetamido)phenylamino)pyrimidine-5-carboxamide

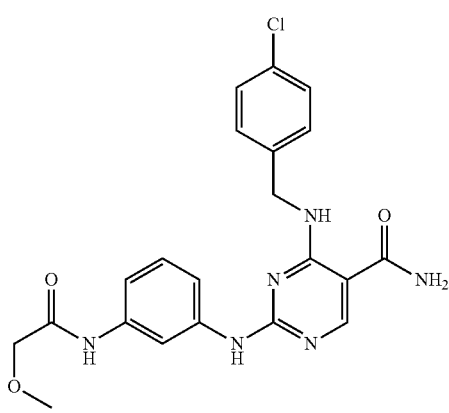

The above compound was prepared using a procedure similar to that described in Scheme 1, using 4-chlorobenzylamine in place of cyclobutylamine and an aniline prepared from 3-nitroaniline and methoxyacetyl chloride. MS found for $C_{21}H_{21}ClN_6O_3$ as (M+H)$^+$ 441. UV: λ=250.

Example 46

4-(3,4-dichlorobenzylamino)-2-(3-(2-methoxyacetamido)phenylamino)pyrimidine-5-carboxamide

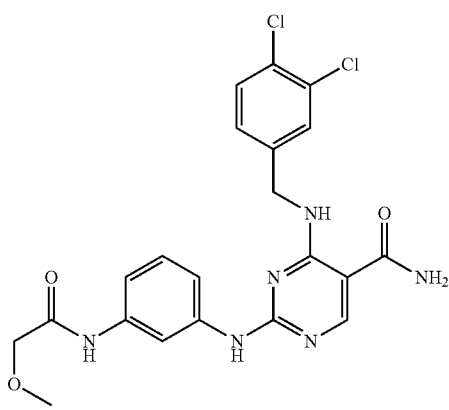 [SMILES: COCC(=O)Nc1cccc(Nc2ncc(C(N)=O)c(NCc3ccc(Cl)c(Cl)c3)n2)c1]

The above compound was prepared using a procedure similar to that described in Scheme 1, using 3,4-dichlorobenzylamine in place of cyclobutylamine and an aniline prepared from 3-nitroaniline and methoxyacetyl chloride. MS found for $C_{21}H_{20}Cl_2N_6O_3$ as (M+H)$^+$ 475, 477. UV: λ=249.

Example 47

(R)-2-(3-(2-methoxyacetamido)phenylamino)-4-(1-phenylethylamino)pyrimidine-5-carboxamide

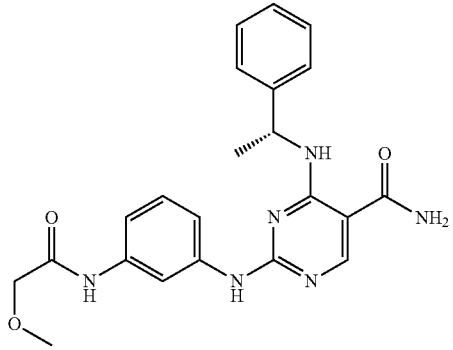 [SMILES: COCC(=O)Nc1cccc(Nc2ncc(C(N)=O)c(N[C@H](C)c3ccccc3)n2)c1]

The above compound was prepared using a procedure similar to that described in Scheme 1, using (R)-1-phenylethylamine in place of cyclobutylamine and an aniline prepared from 3-nitroaniline and methoxyacetyl chloride. MS found for $C_{22}H_{24}N_6O_3$ as (M+H)$^+$ 421. UV: λ=249.

Example 48

(S)-2-(3-acetamidophenylamino)-4-(2-hydroxy-2-phenylethylamino)pyrimidine-5-carboxamide

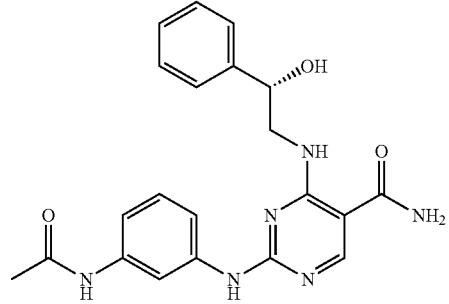 [SMILES: CC(=O)Nc1cccc(Nc2ncc(C(N)=O)c(NC[C@@H](O)c3ccccc3)n2)c1]

The above compound was prepared using a procedure similar to that described in Scheme 3, using (S)-2-hydroxy-2-phenylethylamine in place of (S)-2-phenyl-1-propylamine. MS found for $C_{21}H_{22}N_6O_3$ as (M+H)$^+$ 407.4. UV: λ=203, 250.

Example 49

(R)-2-(3-acetamidophenylamino)-4-(2-hydroxy-2-phenylethylamino)pyrimidine-5-carboxamide

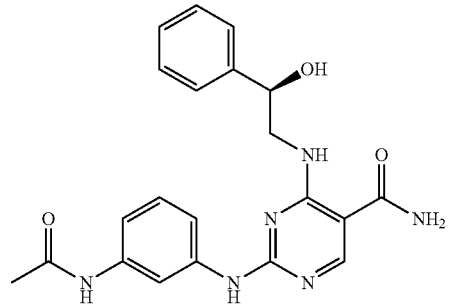 [SMILES: CC(=O)Nc1cccc(Nc2ncc(C(N)=O)c(NC[C@H](O)c3ccccc3)n2)c1]

The above compound was prepared using a procedure similar to that described in Scheme 3, using (R)-2-hydroxy-2-phenylethylamine in place of (S)-2-phenyl-1-propylamine. MS found for $C_{21}H_{22}N_6O_3$ as (M+H)$^+$ 407.4. UV: λ=250.

Example 50

2-(3-acetamidophenylamino)-4-(2-amino-2-oxoethylamino)pyrimidine-5-carboxamide

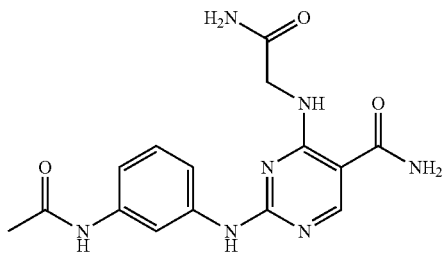 [SMILES: CC(=O)Nc1cccc(Nc2ncc(C(N)=O)c(NCC(N)=O)n2)c1]

The above compound was prepared using a procedure similar to that described in Scheme 3, using glycinamide in place of (S)-2-phenyl-1-propylamine. MS found for $C_{15}H_{17}N_7O_3$ as $(M+H)^+$ 344.3.

Example 51

2-(3-acetamidophenylamino)-4-(2-phenylcyclopropylamino)pyrimidine-5-carboxamide

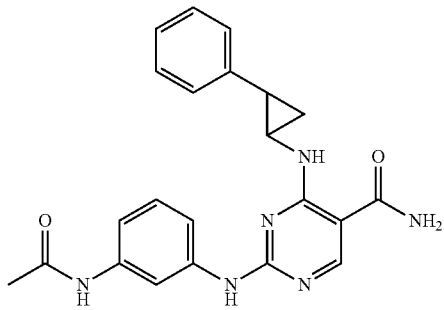 [SMILES: CC(=O)Nc1cccc(Nc2ncc(C(N)=O)c(NC3CC3c3ccccc3)n2)c1]

The above compound was prepared using a procedure similar to that described in Scheme 3, using trans-2-phenylcyclopropylamine in place of (S)-2-phenyl-1-propylamine. MS found for $C_{22}H_{22}N_6O_2$ as $(M+H)^+$ 403.4.

Example 52

2-(3-acetamidophenylamino)-4-(cyclohexylamino)pyrimidine-5-carboxamide

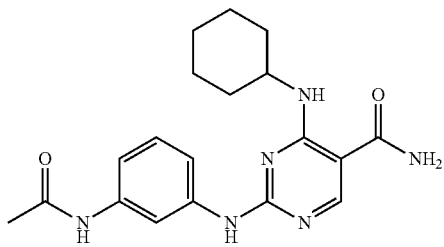

The above compound was prepared using a procedure similar to that described in Scheme 3, using cyclopentylamine in place of (S)-2-phenyl-1-propylamine. MS found for $C_{19}H_{24}N_6O_2$ as $(M+H)^+$ 369.4.

Example 53

2-(3-acetamidophenylamino)-4-((trans)-2-hydroxycyclopentylamino)pyrimidine-5-carboxamide

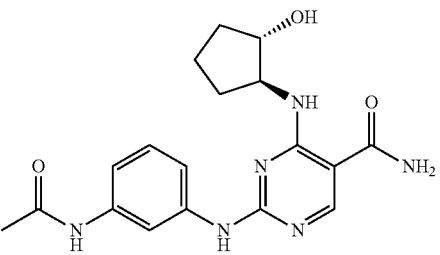 [SMILES: CC(=O)Nc1cccc(Nc2ncc(C(N)=O)c(N[C@H]3CCC[C@@H]3O)n2)c1]

The above compound was prepared using a procedure similar to that described in Scheme 3, using trans-2-aminopentanol in place of (S)-2-phenyl-1-propylamine. MS found for $C_{18}H_{22}N_6O_3$ as $(M+H)^+$ 371.4. UV: $\lambda=250$.

Example 54

2-(3-acetamidophenylamino)-4-(benzyl(methyl)amino)pyrimidine-5-carboxamide

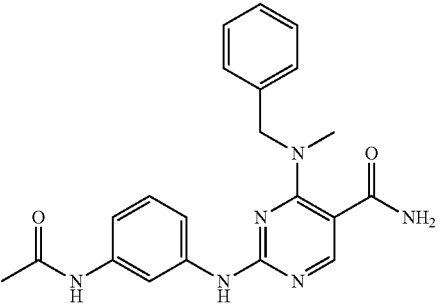 [SMILES: CC(=O)Nc1cccc(Nc2ncc(C(N)=O)c(N(C)Cc3ccccc3)n2)c1]

The above compound was prepared using a procedure similar to that described in Scheme 3, using N-methylbenzylamine in place of (S)-2-phenyl-1-propylamine. MS found for $C_{21}H_{22}N_6O_2$ as $(M+H)^+$ 391.4. UV: $\lambda=207, 252$.

Example 55

4-(cyclobutylamino)-2-(3-(2-methoxyacetamido)phenylamino)pyrimidine-5-carboxamide

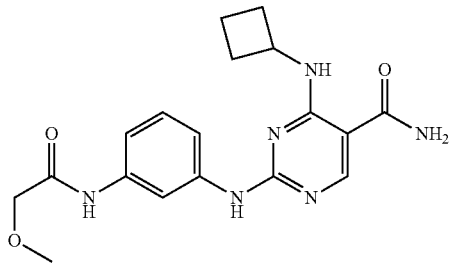 [SMILES: COCC(=O)Nc1cccc(Nc2ncc(C(N)=O)c(NC3CCC3)n2)c1]

The above compound was prepared using a procedure similar to that described in Scheme 1, using an aniline prepared from 3-nitroaniline and methoxyacetyl chloride. MS found for $C_{18}H_{22}N_6O_3$ as $(M+H)^-$ 371. UV: $\lambda=252$.

Example 56

2-(3-acetamidophenylamino)-4-(phenethylamino)pyrimidine-5-carboxamide

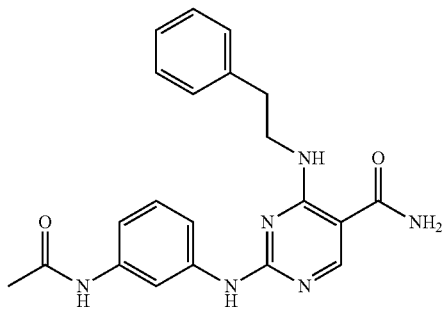 [SMILES: CC(=O)Nc1cccc(Nc2ncc(C(N)=O)c(NCCc3ccccc3)n2)c1]

The above compound was prepared using a procedure similar to that described in Scheme 3, using phenethylamine in place of (S)-2-phenyl-1-propylamine. MS found for $C_{21}H_{22}N_6O_2$ as $(M+H)^+$ 391.4.

Example 57

4-(isopropylamino)-2-(3-(2-methoxyacetamido)phenylamino)pyrimidine-5-carboxamide

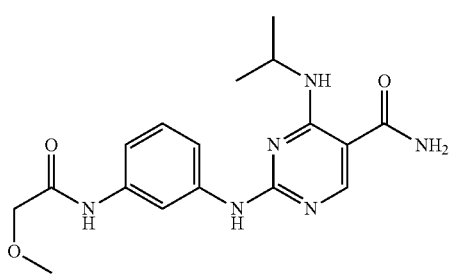 [SMILES: COCC(=O)Nc1cccc(Nc2ncc(C(N)=O)c(NC(C)C)n2)c1]

The above compound was prepared using a procedure similar to that described in Scheme 1, using isopropylamine in place of cyclobutylamine and an aniline prepared from 3-nitroaniline and methoxyacetyl chloride. MS found for $C_{17}H_{22}N_6O_3$ as $(M+H)^-$ 359. UV: $\lambda$=247.

Example 58

2-(3-(2-methoxyacetamido)phenylamino)-4-(2,3,6-trifluorobenzylamino)pyrimidine-5-carboxamide

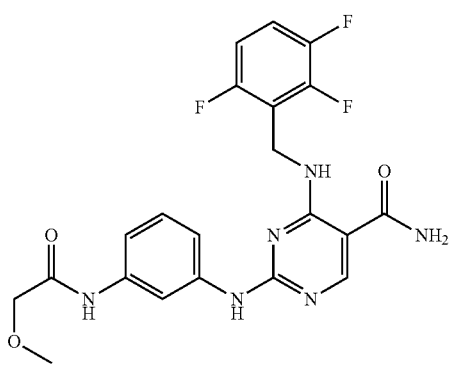 [SMILES: COCC(=O)Nc1cccc(Nc2ncc(C(N)=O)c(NCc3c(F)ccc(F)c3F)n2)c1]

The above compound was prepared using a procedure similar to that described in Scheme 1, using 2,3,6-trifluorobenzylamine in place of cyclobutylamine and an aniline prepared from 3-nitroaniline and methoxyacetyl chloride. MS found for $C_{21}H_{19}F_3N_6O_3$ as $(M+H)^+$ 461. UV: $\lambda$=204, 247.

Example 59

2-(3-acetamidophenylamino)-4-(2,3,6-trifluorobenzylamino)pyrimidine-5-carboxamide

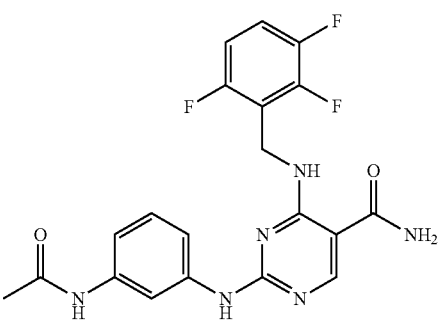 [SMILES: CC(=O)Nc1cccc(Nc2ncc(C(N)=O)c(NCc3c(F)ccc(F)c3F)n2)c1]

The above compound was prepared using a procedure similar to that described in Scheme 1, using benzylamine in place of cyclobutylamine and 3-aminoacetanilide. MS found for $C_{21}H_{19}F_3N_6O_3$ as $(M+H)^+$ 461. UV: $\lambda$=204, 247.

Example 60

(S)-2-(3-acetamidophenylamino)-4-(1-hydroxy-3-(1H-imidazol-5-yl)propan-2-ylamino)pyrimidine-5-carboxamide

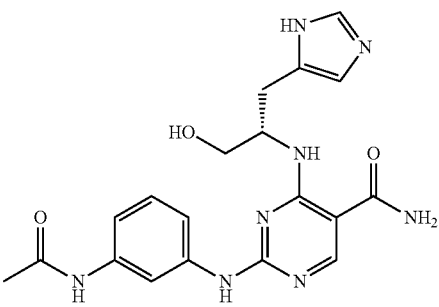 [SMILES: CC(=O)Nc1cccc(Nc2ncc(C(N)=O)c(N[C@H](CO)Cc3cnc[nH]3)n2)c1]

The above compound was prepared using a procedure similar to that described in Scheme 3, using (S)-histidinol in place of (S)-2-phenyl-1-propylamine. MS found for $C_{19}H_{22}N_8O_3$ as $(M+H)^+$ 411.3. UV: $\lambda$=249.

Example 61

2-(3-acetamidophenylamino)-4-(3-amino-3-oxopropylamino)pyrimidine-5-carboxamide

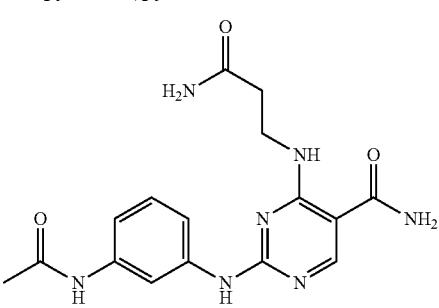

The above compound was prepared using a procedure similar to that described in Scheme 3, using 3-aminobutylamine in place of (S)-2-phenyl-1-propylamine. MS found for $C_{16}H_{19}N_7O_3$ as $(M+H)^+$ 358.3. UV: $\lambda$=204, 277.

Example 62

(R)-2-(3-acetamidophenylamino)-4-(1-hydroxy-4-methylpentan-2-ylamino)pyrimidine-5-carboxamide

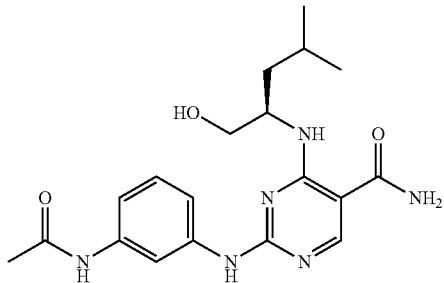 [SMILES: CC(=O)Nc1cccc(Nc2ncc(C(N)=O)c(N[C@@H](CO)CC(C)C)n2)c1]

The above compound was prepared using a procedure similar to that described in Scheme 3, using (R)-leucinol in place of (S)-2-phenyl-1-propylamine. MS found for $C_{19}H_{26}N_6O_3$ as $(M+H)^+$ 387.4. UV: $\lambda$=250.

Example 63

2-(3-acetamidophenylamino)-4-(2-(pyrrolidin-1-yl)ethylamino)pyrimidine-5-carboxamide

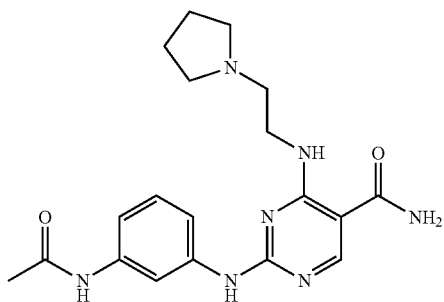 [SMILES: CC(=O)Nc1cccc(Nc2ncc(C(N)=O)c(NCCN3CCCC3)n2)c1]

The above compound was prepared using a procedure similar to that described in Scheme 3, using 2-(pyrrolidin-1-yl)ethylamine in place of (S)-2-phenyl-1-propylamine. MS found for $C_{19}H_{25}N_7O_2$ as $(M+H)^+$ 384.4. UV: $\lambda$=204, 246.

Example 64

(S)-2-(3-acetamidophenylamino)-4-(1-phenylethylamino)pyrimidine-5-carboxamide

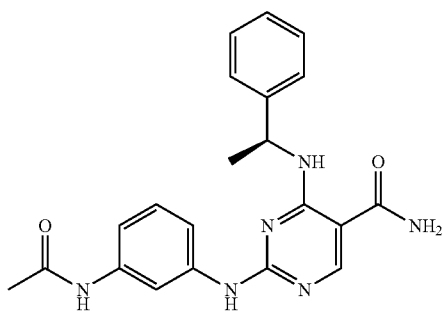 [SMILES: CC(=O)Nc1cccc(Nc2ncc(C(N)=O)c(N[C@@H](C)c3ccccc3)n2)c1]

The above compound was prepared using a procedure similar to that described in Scheme 1, using (S)-1-phenylethylamine in place of cyclobutylamine and 3-aminoacetanilide. MS found for $C_{22}H_{24}N_6O_2$ as $(M+H)^+$ 405.4. UV: $\lambda$=204, 250.

Example 65

2-(3-acetamidophenylamino)-4-(2-oxo-2-(pyrrolidin-1-yl)ethylamino)pyrimidine-5-carboxamide

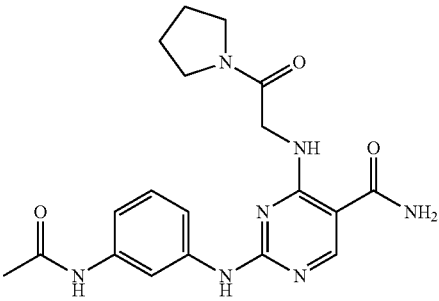 [SMILES: CC(=O)Nc1cccc(Nc2ncc(C(N)=O)c(NCC(=O)N3CCCC3)n2)c1]

The above compound was prepared using a procedure similar to that described in Scheme 2, using 2-amino-1-(pyrrolidin-1-yl)ethanone in place of benzylamine and 3-aminoacetanilide. MS found for $C_{19}H_{23}N_7O_3$ as $(M+H)^+$ 398.4.

Example 66

(R)-2-(3-acetamidophenylamino)-4-(piperidin-3-ylamino)pyrimidine-5-carboxamide

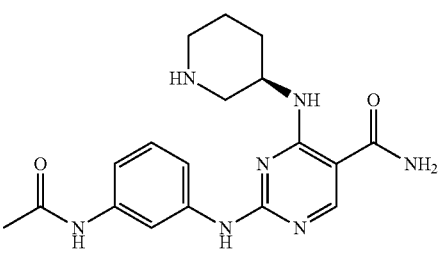 [SMILES: CC(=O)Nc1cccc(Nc2ncc(C(N)=O)c(N[C@@H]3CCCNC3)n2)c1]

The above compound was prepared using a procedure similar to that described in Scheme 1, using (R)-tert-butyl 3-aminopiperidine-1-carboxylate in place of cyclobutylamine and acetanilide. MS found for $C_{18}H_{23}N_7O_2$ as $(M+H)^+$ 370.3.

Example 67

2-(3-acetamidophenylamino)-4-(4-methylbenzylamino)pyrimidine-5-carboxamide

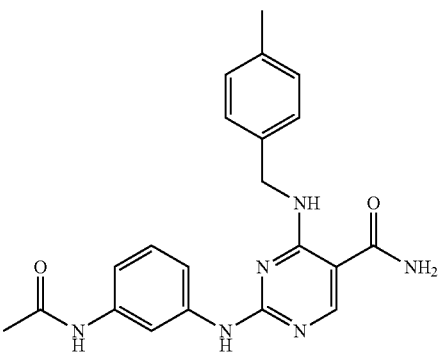 [SMILES: CC(=O)Nc1cccc(Nc2ncc(C(N)=O)c(NCc3ccc(C)cc3)n2)c1]

The above compound was prepared using a procedure similar to that described in Scheme 1, using 4-methylbenzylamine in place of cyclobutylamine and acetanilide. MS found for $C_{21}H_{22}N_6O_2$ as $(M+H)^-$ 391. UV: $\lambda$=249.

Example 68

2-(3-acetamidophenylamino)-4-(4-methoxybenzy-lamino)pyrimidine-5-carboxamide

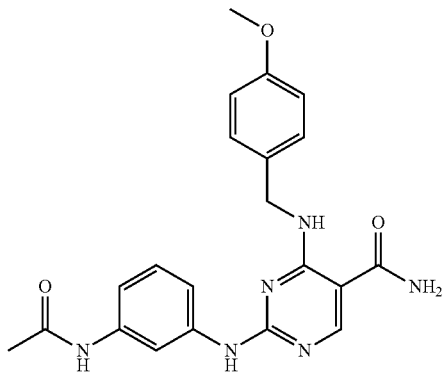 [SMILES: COc1ccc(CNc2nc(Nc3cccc(NC(C)=O)c3)ncc2C(N)=O)cc1]

The above compound was prepared using a procedure similar to that described in Scheme 1, using 4-methoxybenzylamine in place of cyclobutylamine and acetanilide. MS found for $C_{21}H_{22}N_6O_3$ as $(M+H)^-$ 407. UV: $\lambda=249$.

Example 69

2-(3-acetamidophenylamino)-4-(4-chlorobenzy-lamino)pyrimidine-5-carboxamide

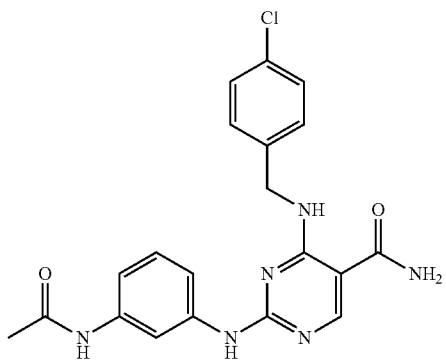

The above compound was prepared using a procedure similar to that described in Scheme 1, using 4-chlorobenzylamine in place of cyclobutylamine and acetanilide. MS found for $C_{20}H_{19}ClN_6O_2$ as $(M+H)^+$ 411. UV: $\lambda=249$.

Example 70

2-(3-acetamidophenylamino)-4-(3,4-dichlorobenzy-lamino)pyrimidine-5-carboxamide

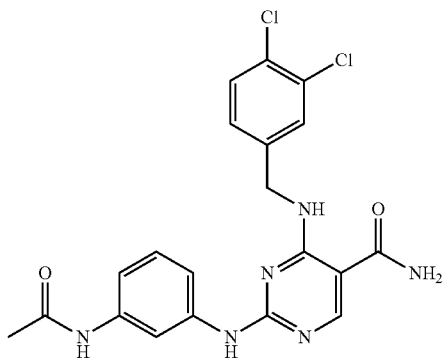 [SMILES: CC(=O)Nc1cccc(Nc2ncc(C(N)=O)c(NCc3ccc(Cl)c(Cl)c3)n2)c1]

The above compound was prepared using a procedure similar to that described in Scheme 1, using 3,4-dichlorobenzylamine in place of cyclobutylamine and acetanilide. MS found for $C_{20}H_{18}Cl_2N_6O_2$ as $(M+H)^+$ 445, 447. UV: $\lambda=203$, 243, 292.

Example 71

(R)-2-(3-acetamidophenylamino)-4-(1-phenylethy-lamino)pyrimidine-5-carboxamide

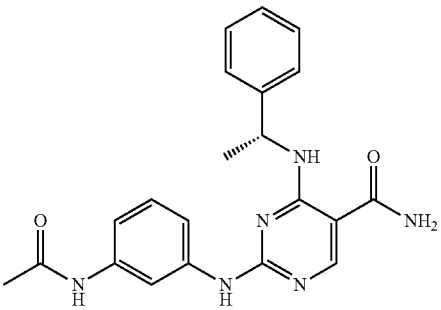 [SMILES: CC(=O)Nc1cccc(Nc2ncc(C(N)=O)c(N[C@H](C)c3ccccc3)n2)c1]

The above compound was prepared using a procedure similar to that described in Scheme 1, using 3,4-dichlorobenzylamine in place of cyclobutylamine and acetanilide. MS found for $C_{21}H_{22}N_6O_2$ as $(M+H)^+$ 391. UV: $\lambda=213, 256$.

Example 72

2-(3-acetamidophenylamino)-4-(2-(methylamino)-2-oxoethylamino)pyrimidine-5-carboxamide

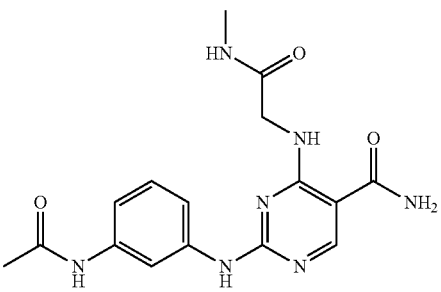 [SMILES: CNC(=O)CNc1nc(Nc2cccc(NC(C)=O)c2)ncc1C(N)=O]

The above compound was prepared using a procedure similar to that described in Scheme 3, using 2-amino-N-methylacetamide in place of (S)-2-phenyl-1-propylamine. MS found for $C_{16}H_{19}N_7O_3$ as $(M+H)^+$ 358.3.

Example 73

2-(3-acetamidophenylamino)-4-((2S,3S)-1-hydroxy-3-methylpentan-2-ylamino)pyrimidine-5-carboxamide

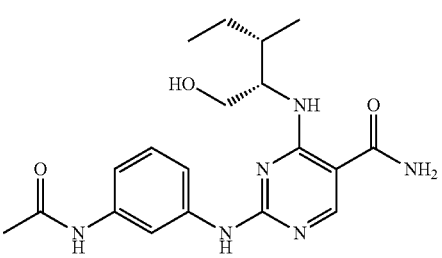 [SMILES: CC[C@H](C)[C@@H](CO)Nc1nc(Nc2cccc(NC(C)=O)c2)ncc1C(N)=O]

The above compound was prepared using a procedure similar to that described in Scheme 3, using (2S,3S)-1-hydroxy-3-methylpentan-2-ylamine in place of (S)-2-phenyl-1-propylamine. MS found for $C_{19}H_{26}N_6O_3$ as $(M+H)^+$ 387.4. UV: $\lambda=249$.

Example 74

2-(3-acetamidophenylamino)-4-(cyanomethylamino)pyrimidine-5-carboxamide

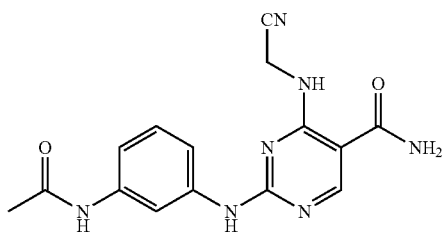

The above compound was prepared using a procedure similar to that described in Scheme 3, using aminoacetonitrile in place of (S)-2-phenyl-1-propylamine. MS found for $C_{15}H_{15}N_7O_2$ as $(M+H)^+$ 326.2. UV: $\lambda=245$.

Example 75

2-(3-acetamidophenylamino)-4-(tetrahydro-2H-pyran-4-ylamino)pyrimidine-5-carboxamide

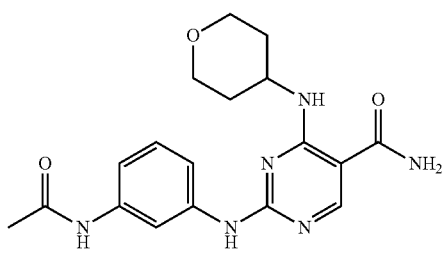

The above compound was prepared using a procedure similar to that described in Scheme 3, using 4-aminotetrahydropyran in place of (S)-2-phenyl-1-propylamine. MS found for $C_{18}H_{22}N_6O_3$ as $(M+H)^-$ 371.3.

Example 76

(S)-2-(3-acetamidophenylamino)-4-(1-hydroxy-3-phenylpropan-2-ylamino)pyrimidine-5-carboxamide

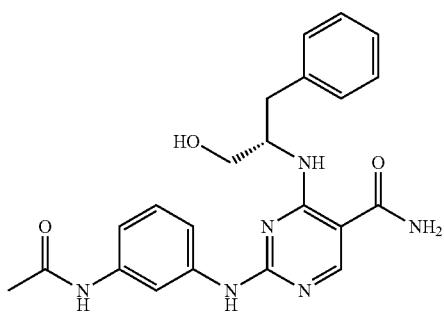 [SMILES: CC(=O)Nc1cccc(Nc2ncc(C(N)=O)c(N[C@H](CO)Cc3ccccc3)n2)c1]

The above compound was prepared using a procedure similar to that described in Scheme 3, using (S)-alaninol in place of (S)-2-phenyl-1-propylamine. MS found for $C_{22}H_{24}N_6O_3$ as $(M+H)^+$ 421.4.

Example 77

4-(isopropylamino)-2-(3-(N-methylacetamido)phenylamino)pyrimidine-5-carboxamide

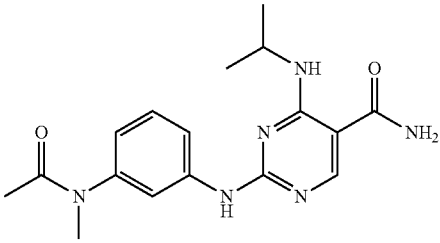 [SMILES: CC(=O)N(C)c1cccc(Nc2ncc(C(N)=O)c(NC(C)C)n2)c1]

The above compound was prepared using a procedure similar to that described in Scheme 1 using isopropylamine in place of cyclobutylamine and an aniline prepared from 3-nitroaniline, acetyl chloride, and iodomethane. MS found for $C_{17}H_{22}N_6O_2$ as $(M+H)^+$ 343. UV: $\lambda=219, 255$.

Example 78

4-(cyclopentylamino)-2-(3-(N-methylacetamido)phenylamino)pyrimidine-5-carboxamide

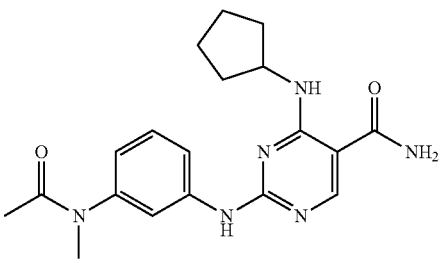 [SMILES: CC(=O)N(C)c1cccc(Nc2ncc(C(N)=O)c(NC3CCCC3)n2)c1]

The above compound was prepared using a procedure similar to that described in Scheme 1 using cyclopentylamine in place of cyclobutylamine and an aniline prepared from 3-nitroaniline, acetyl chloride, and iodomethane. MS found for $C_{19}H_{24}N_6O_2$ as $(M+H)^+$ 369. UV: $\lambda=204, 259$.

Example 79

4-(benzylamino)-2-(3-(N-methylacetamido)phenylamino)pyrimidine-5-carboxamide

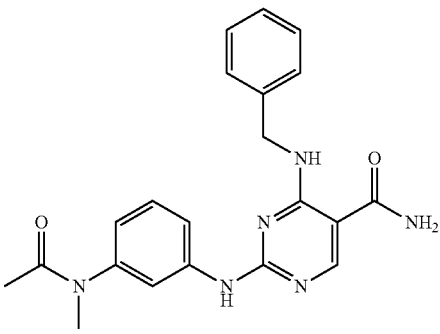 [SMILES: CC(=O)N(C)c1cccc(Nc2ncc(C(N)=O)c(NCc3ccccc3)n2)c1]

The above compound was prepared using a procedure similar to that described in Scheme 1 using benzylamine in place of cyclobutylamine and an aniline prepared from 3-nitroaniline, acetyl chloride, and iodomethane. MS found for $C_{21}H_{22}N_6O_2$ as $(M+H)^+$ 391. UV: $\lambda=255$.

Example 80

2-(3-acetamidophenylamino)-4-(2-morpholinoethylamino)pyrimidine-5-carboxamide

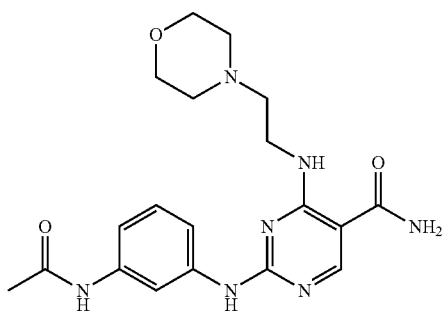 [SMILES: CC(=O)Nc1cccc(Nc2ncc(C(N)=O)c(NCCN3CCOCC3)n2)c1]

The above compound was prepared using a procedure similar to that described in Scheme 3, using 2-(1-morpholinyl)ethylamine in place of (S)-2-phenyl-1-propylamine. MS found for $C_{19}H_{25}N_7O_3$ as $(M+H)^+$ 400.3.

Example 81

(R)-2-(3-acetamidophenylamino)-4-(2-phenylpropylamino)pyrimidine-5-carboxamide

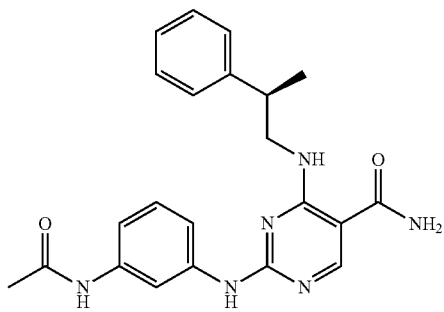 [SMILES: CC(=O)Nc1cccc(Nc2ncc(C(N)=O)c(NC[C@H](C)c3ccccc3)n2)c1]

The above compound was prepared using a procedure similar to that described in Scheme 3, using (R)-2-phenylpropylamine in place of (S)-2-phenyl-1-propylamine. MS found for $C_{22}H_{24}N_6O_2$ as $(M+H)^+$ 405.3.

Example 82

(S)-2-(3-acetamidophenylamino)-4-(2-hydroxypropylamino)pyrimidine-5-carboxamide

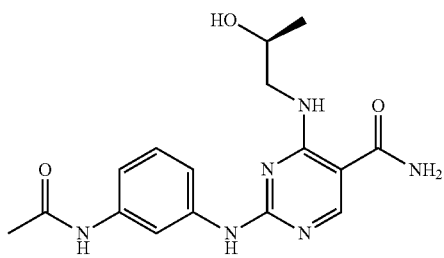 [SMILES: CC(=O)Nc1cccc(Nc2ncc(C(N)=O)c(NC[C@H](C)O)n2)c1]

The above compound was prepared using a procedure similar to that described in Scheme 3, using (S)-2-hydroxy-1-propylamine in place of (S)-2-phenyl-1-propylamine. MS found for $C_{16}H_{20}N_6O_3$ as $(M+H)^+$ 405.3.

Example 83

(R)-2-(3-acetamidophenylamino)-4-(2,3-dihydroxypropylamino)pyrimidine-5-carboxamide

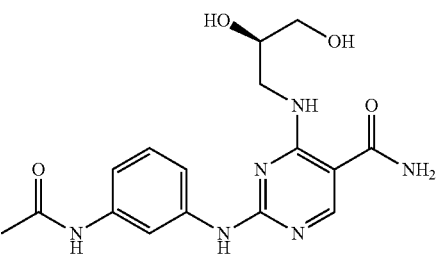 [SMILES: CC(=O)Nc1cccc(Nc2ncc(C(N)=O)c(NC[C@@H](O)CO)n2)c1]

The above compound was prepared using a procedure similar to that described in Scheme 3, using (R)-2,3-dihydroxypropylamine in place of (S)-2-phenyl-1-propylamine. MS found for $C_{16}H_{20}N_6O_3$ as $(M+H)^+$ 361.2.

Example 84

2-(3-acetamidophenylamino)-4-(2-methoxy-2-phenylethylamino)pyrimidine-5-carboxamide

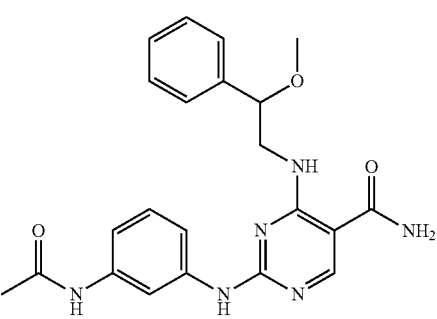 [SMILES: COC(CNc1nc(Nc2cccc(NC(C)=O)c2)ncc1C(N)=O)c1ccccc1]

The above compound was prepared using a procedure similar to that described in Scheme 3, using 2-methoxy-2-phenylethylamine in place of (S)-2-phenyl-1-propylamine. MS found for $C_{22}H_{24}N_6O_3$ as $(M+H)^+$ 421.3.

Example 85

(S)-2-(3-acetamidophenylamino)-4-(1-amino-1-oxopropan-2-ylamino)pyrimidine-5-carboxamide

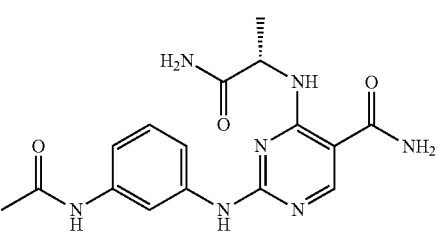 [SMILES: CC(=O)Nc1cccc(Nc2ncc(C(N)=O)c(N[C@@H](C)C(N)=O)n2)c1]

The above compound was prepared using a procedure similar to that described in Scheme 3, using (S)-alaninamide in place of (S)-2-phenyl-1-propylamine. MS found for $C_{16}H_{19}N_7O_3$ as $(M+H)^+$ 358.3.

Example 86

(R)-2-(3-(2-methoxy-N-methylacetamido)phenylamino)-4-(1-phenylethylamino)pyrimidine-5-carboxamide

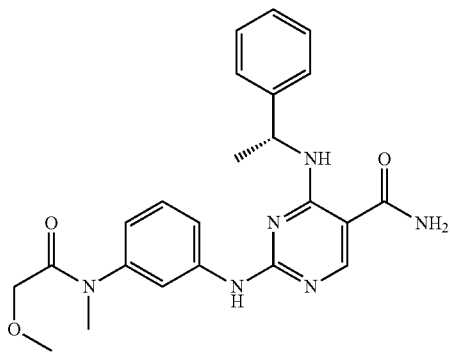 [SMILES: COCC(=O)N(C)c1cccc(Nc2ncc(C(N)=O)c(N[C@H](C)c3ccccc3)n2)c1]

The above compound was prepared using a procedure similar to that described in Scheme 1, using (R)-1-phenylethylamine in place of cyclobutylamine and an aniline prepared from 3-nitroaniline, methoxyacetyl chloride, and iodomethane. MS found for $C_{23}H_{26}N_6O_3$ as $(M+H)^+$ 435. UV: $\lambda$=208, 252, 292.

Example 87

(R)-2-(3-(N-methylacetamido)phenylamino)-4-(1-phenylethylamino)pyrimidine-5-carboxamide

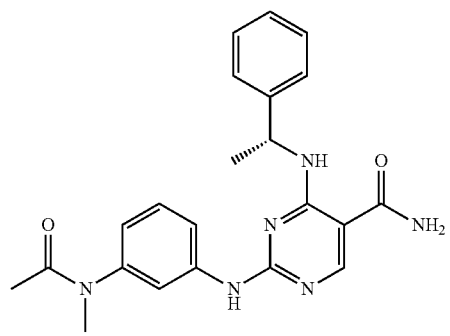 [SMILES: CC(=O)N(C)c1cccc(Nc2ncc(C(N)=O)c(N[C@H](C)c3ccccc3)n2)c1]

The above compound was prepared using a procedure similar to that described in Scheme 1, using (R)-1-phenylethylamine in place of cyclobutylamine and an aniline prepared from 3-nitroaniline, acetyl chloride, and iodomethane. MS found for $C_{22}H_{24}N_6O_2$ as $(M+H)^-$ 405. UV: $\lambda$=207, 246.

Example 88

4-(isopropylamino)-2-(3-(2-methoxy-N-methylacetamido)phenylamino)pyrimidine-5-carboxamide

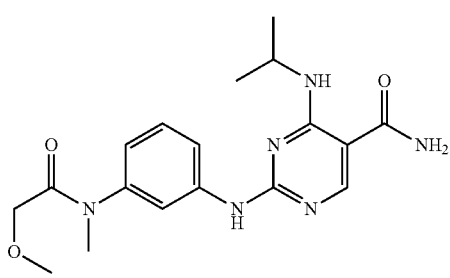

The above compound was prepared using a procedure similar to that described in Scheme 1, using isopropylamine in place of cyclobutylamine and an aniline prepared from 3-nitroaniline, methoxyacetyl chloride, and iodomethane. MS found for $C_{18}H_{24}N_6O_3$ as $(M+H)^+$ 373. UV: $\lambda$=217, 246.

Example 89

4-(cyclopentylamino)-2-(3-(2-methoxy-N-methylacetamido)phenylamino)pyrimidine-5-carboxamide

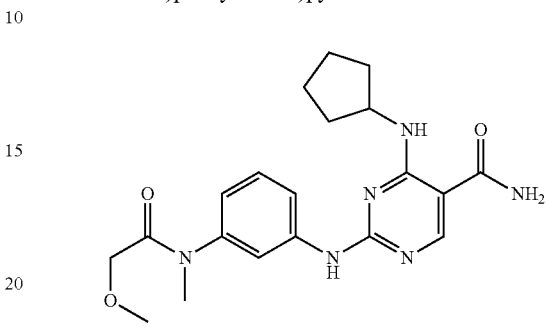

The above compound was prepared using a procedure similar to that described in Scheme 1, using cyclopentylamine in place of cyclobutylamine and an aniline prepared from 3-nitroaniline, methoxyacetyl chloride, and iodomethane. MS found for $C_{20}H_{26}N_6O_3$ as $(M+H)^+$ 399. UV: $\lambda$=204, 256.

Example 90

4-(benzylamino)-2-(3-(2-methoxy-N-methylacetamido)phenylamino)pyrimidine-5-carboxamide

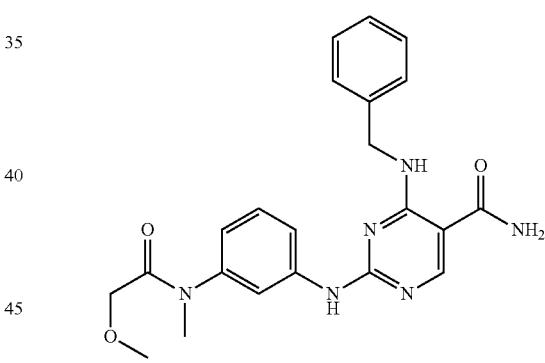

The above compound was prepared using a procedure similar to that described in Scheme 1, using benzylamine in place of cyclobutylamine and an aniline prepared from 3-nitroaniline, methoxyacetyl chloride, and iodomethane. MS found for $C_{22}H_{24}N_6O_3$ as $(M+H)^+$ 421. UV: $\lambda$=204, 255.

Example 91

(R)-2-(3-acetamidophenylamino)-4-(1-amino-1-oxopropan-2-ylamino)pyrimidine-5-carboxamide

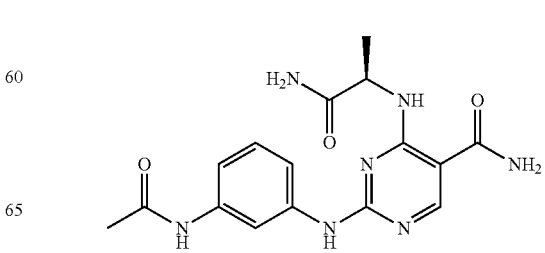

The above compound was prepared using a procedure similar to that described in Scheme 3, using (R)-alaninamide in place of (S)-2-phenyl-1-propylamine. MS found for $C_{16}H_{19}N_7O_3$ as $(M+H)^+$ 358.3.

Example 92

2-(3-acetamidophenylamino)-4-(2,3-dihydro-1H-inden-2-ylamino)pyrimidine-5-carboxamide

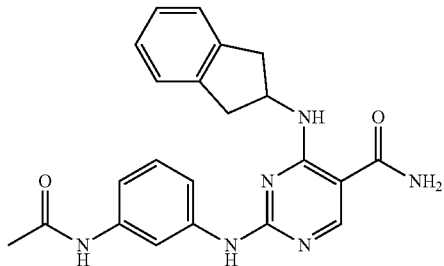 [SMILES: CC(=O)Nc1cccc(Nc2ncc(C(N)=O)c(NC3Cc4ccccc4C3)n2)c1]

The above compound was prepared using a procedure similar to that described in Scheme 3, using 2-aminoindan in place of (S)-2-phenyl-1-propylamine. MS found for $C_{22}H_{22}N_6O_2$ as $(M+H)^+$ 403.3. UV: $\lambda$=204, 250.

Example 93

(S)-2-(3-acetamidophenylamino)-4-(2-hydroxy-1-phenylethylamino)pyrimidine-5-carboxamide

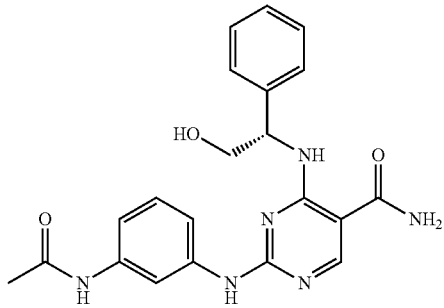 [SMILES: CC(=O)Nc1cccc(Nc2ncc(C(N)=O)c(N[C@H](CO)c3ccccc3)n2)c1]

The above compound was prepared using a procedure similar to that described in Scheme 3, using (S)-phenylglycinol in place of (S)-2-phenyl-1-propylamine. MS found for $C_{21}H_{22}N_6O_3$ as $(M+H)^+$ 407.3. UV: $\lambda$=249.

Example 94

2-(3-acetamidophenylamino)-4-(3-fluorobenzylamino)pyrimidine-5-carboxamide

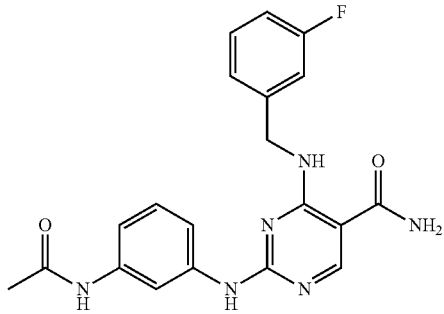 [SMILES: CC(=O)Nc1cccc(Nc2ncc(C(N)=O)c(NCc3cccc(F)c3)n2)c1]

The above compound was prepared using a procedure similar to that described in Scheme 3, using 3-fluorobenzylamine in place of (S)-2-phenyl-1-propylamine. MS found for $C_{20}H_{19}FN_6O_2$ as $(M+H)^+$ 395.3. UV: $\lambda$=204, 249.

Example 95

2-(3-acetamidophenylamino)-4-(2,3-difluorobenzylamino)pyrimidine-5-carboxamide

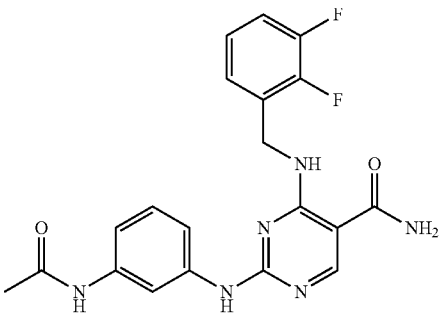 [SMILES: CC(=O)Nc1cccc(Nc2ncc(C(N)=O)c(NCc3cccc(F)c3F)n2)c1]

The above compound was prepared using a procedure similar to that described in Scheme 3, using 2,3-difluorobenzylamine in place of (S)-2-phenyl-1-propylamine. MS found for $C_{20}H_{18}F_2N_6O_2$ as $(M+H)^+$ 413.3.

Example 96

(S)-2-(3-acetamidophenylamino)-4-(2,3-dihydro-1H-inden-1-ylamino)pyrimidine-5-carboxamide

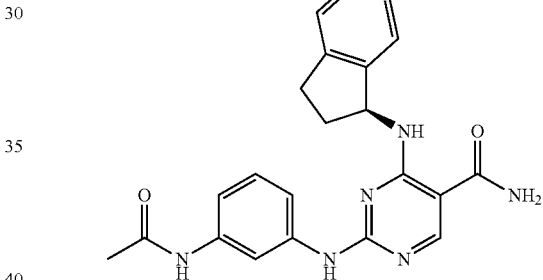

The above compound was prepared using a procedure similar to that described in Scheme 3, using (S)-1-aminoindan in place of (S)-2-phenyl-1-propylamine. MS found for $C_{22}H_{22}N_6O_2$ as $(M+H)^+$ 403.3.

Example 97

(R)-2-(3-acetamidophenylamino)-4-(2,3-dihydro-1H-inden-1-ylamino)pyrimidine-5-carboxamide

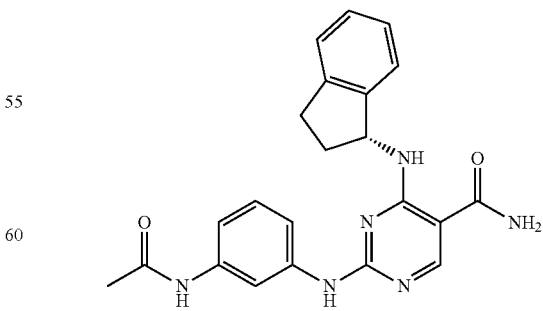

The above compound was prepared using a procedure similar to that described in Scheme 3, using (R)-1-aminoindan in place of (S)-2-phenyl-1-propylamine. MS found for $C_{22}H_{22}N_6O_2$ as $(M+H)^+$ 403.3. UV: $\lambda$=205, 250.

Example 98

(R)-2-(3-acetamidophenylamino)-4-(2-hydroxy-1-phenylethylamino)pyrimidine-5-carboxamide

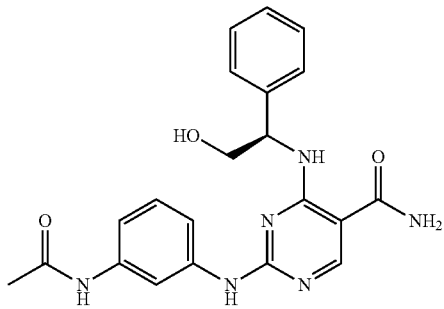 [SMILES: CC(=O)Nc1cccc(Nc2ncc(C(N)=O)c(N[C@@H](CO)c3ccccc3)n2)c1]

The above compound was prepared using a procedure similar to that described in Scheme 3, using (R)-phenylglycinol in place of (S)-2-phenyl-1-propylamine. MS found for $C_{21}H_{22}N_6O_3$ as $(M+H)^+$ 407.3. UV: $\lambda$=205, 249.

Example 99

2-(3-acetamidophenylamino)-4-(benzo[d][1,3]dioxol-5-ylmethylamino)pyrimidine-5-carboxamide

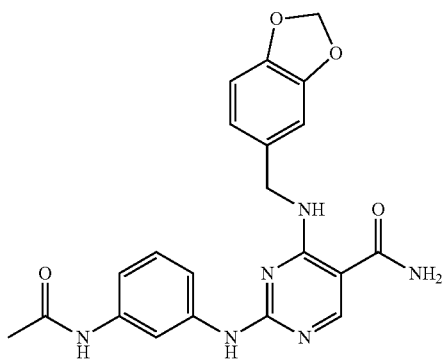 [SMILES: CC(=O)Nc1cccc(Nc2ncc(C(N)=O)c(NCc3ccc4c(c3)OCO4)n2)c1]

The above compound was prepared using a procedure similar to that described in Scheme 3, using benzo[d][1,3]dioxol-5-ylmethylamine in place of (S)-2-phenyl-1-propylamine. MS found for $C_{21}H_{20}N_6O_4$ as $(M+H)^+$ 421.3. UV: $\lambda$=205, 250.

Example 100

2-(3-acetamidophenylamino)-4-(2-fluorobenzylamino)pyrimidine-5-carboxamide

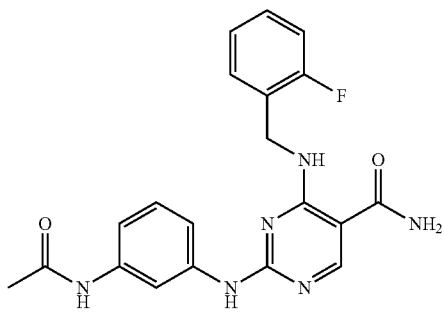 [SMILES: CC(=O)Nc1cccc(Nc2ncc(C(N)=O)c(NCc3ccccc3F)n2)c1]

The above compound was prepared using a procedure similar to that described in Scheme 3, using 2-fluorobenzylamine in place of (S)-2-phenyl-1-propylamine. MS found for $C_{20}H_{19}FN_6O_2$ as $(M+H)^+$ 395.3.

Example 101

2-(3-acetamidophenylamino)-4-(3-chlorobenzylamino)pyrimidine-5-carboxamide

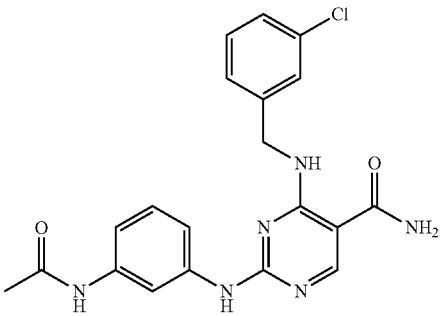

The above compound was prepared using a procedure similar to that described in Scheme 3, using 3-chlorobenzylamine in place of (S)-2-phenyl-1-propylamine. MS found for $C_{20}H_{19}ClN_6O_2$ as $(M+H)^+$ 411.3, 413.3.

Example 102

2-(3-acetamidophenylamino)-4-(2,5-difluorobenzylamino)pyrimidine-5-carboxamide

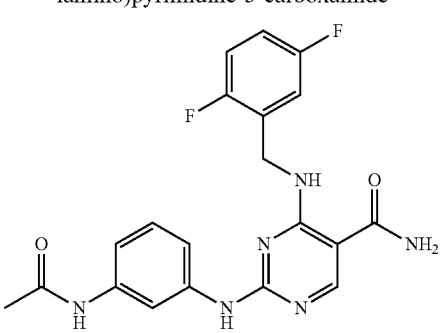

The above compound was prepared using a procedure similar to that described in Scheme 3, using 2,5-difluorobenzylamine in place of (S)-2-phenyl-1-propylamine. MS found for $C_{20}H_{18}F_2N_6O_2$ as $(M+H)^+$ 413.3. UV: $\lambda$=204, 250.

Example 103

2-(3-acetamidophenylamino)-4-(4-fluorobenzylamino)pyrimidine-5-carboxamide

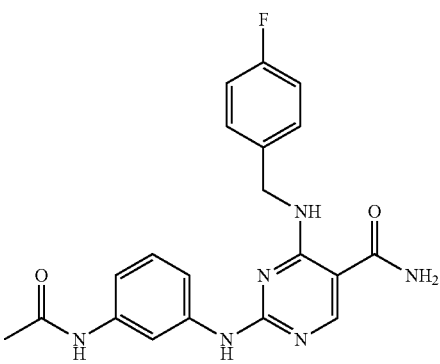 [SMILES: CC(=O)Nc1cccc(Nc2ncc(C(N)=O)c(NCc3ccc(F)cc3)n2)c1]

The above compound was prepared using a procedure similar to that described in Scheme 2, using 4-fluorobenzylamine in place of benzylamine and acetanilide. MS found for $C_{20}H_{19}FN_6O_2$ as $(M+H)^+$ 395. UV: $\lambda$=201, 249.

Example 104
4-(4-fluorobenzylamino)-2-(3-(2-methoxyacetamido)phenylamino)pyrimidine-5-carboxamide

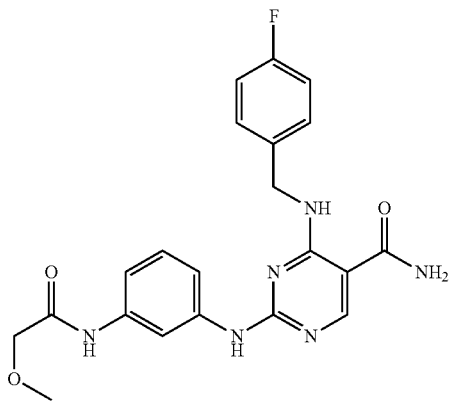 [SMILES: COCC(=O)Nc1cccc(Nc2ncc(C(N)=O)c(NCc3ccc(F)cc3)n2)c1]

The above compound was prepared using a procedure similar to that described in Scheme 2, using 4-fluorobenzylamine in place of benzylamine and an aniline prepared from 3-nitroaniline and methoxyacetyl chloride. MS found for $C_{21}H_{21}FN_6O_3$ as $(M+H)^+$ 425. UV: $\lambda$=201, 250.

Example 105
(R)-4-(1-phenylethylamino)-2-(3-(pyrrolidine-1-carboxamido)phenylamino)pyrimidine-5-carboxamide

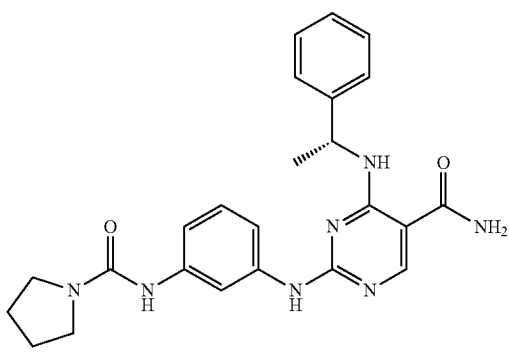 [SMILES: C[C@@H](Nc1nc(Nc2cccc(NC(=O)N3CCCC3)c2)ncc1C(N)=O)c1ccccc1]

The above compound was prepared using a procedure similar to that described in Scheme 1, using (R)-1-phenylethylamine in place of cyclobutylamine and an aniline prepared from 3-nitroaniline, phosgene, and pyrrolidine. MS found for $C_{24}H_{27}N_7O_2$ as $(M+H)^+$ 446. UV: $\lambda$=250.

Example 106
4-(benzylamino)-2-(4-chloro-3-(2-methoxyacetamido)phenylamino)pyrimidine-5-carboxamide

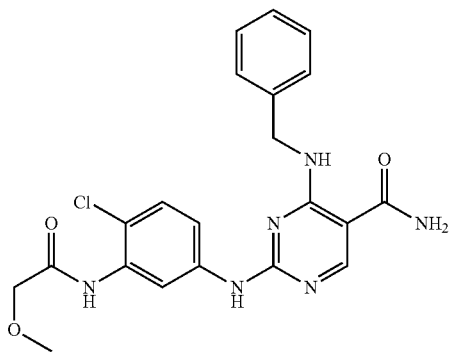 [SMILES: COCC(=O)Nc1cc(Nc2ncc(C(N)=O)c(NCc3ccccc3)n2)ccc1Cl]

The above compound was prepared using a procedure similar to that described in Scheme 2, using an aniline prepared from 2-chloro-5-nitroaniline and methoxyacetyl chloride. MS found for $C_{21}H_{21}ClN_6O_3$ as $(M+H)^+$ 441.4, 443.3. UV: $\lambda$=207, 250.

Example 107
4-(benzylamino)-2-(4-chloro-3-(3-cyclobutylureido)phenylamino)pyrimidine-5-carboxamide

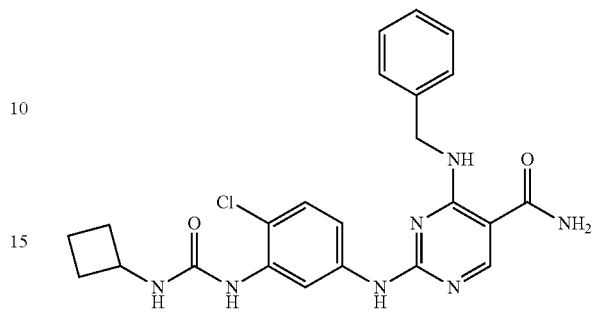

The above compound was prepared using a procedure similar to that described in Scheme 2, using an aniline prepared from 2-chloro-5-nitroaniline, phosgene, and cyclobutylamine. MS found for $C_{23}H_{24}ClN_7O_2$ as $(M+H)^+$ 466.4, 468.4. UV: $\lambda$=208, 249.

Example 108
(R)-2-(3-acetamido-4-chlorophenylamino)-4-(1-phenylethylamino)pyrimidine-5-carboxamide

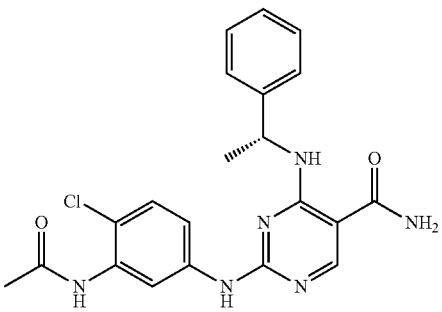 [SMILES: CC(=O)Nc1cc(Nc2ncc(C(N)=O)c(N[C@H](C)c3ccccc3)n2)ccc1Cl]

The above compound was prepared using a procedure similar to that described in Scheme 2, using (R)-1-phenylethylamine in place of benzylamine an aniline prepared from 2-chloro-5-nitroaniline and acetyl chloride. MS found for $C_{21}H_{21}ClN_6O_2$ as $(M+H)^+$ 425.3, 427.4,

Example 109
(R)-2-(4-chloro-3-(2-methoxyacetamido)phenylamino)-4-(1-phenylethylamino)pyrimidine-5-carboxamide

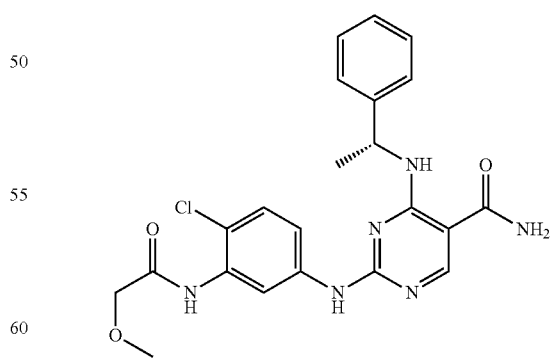

The above compound was prepared using a procedure similar to that described in Scheme 2, using (R)-1-phenylethylamine in place of benzylamine an aniline prepared from 2-chloro-5-nitroaniline and methoxyacetyl chloride. MS found for $C_{22}H_{23}ClN_6O_3$ as $(M+H)^+$ 455.3, 457.3. UV: $\lambda$=206, 250.

Example 110

(R)-2-(4-chloro-3-(cyclopropanecarboxamido)phenylamino)-4-(1-phenylethylamino)pyrimidine-5-carboxamide

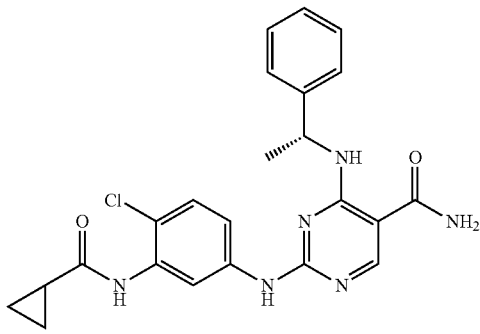 [SMILES: C[C@@H](Nc1nc(Nc2ccc(Cl)c(NC(=O)C3CC3)c2)ncc1C(N)=O)c1ccccc1]

The above compound was prepared using a procedure similar to that described in Scheme 2, using (R)-1-phenylethylamine in place of benzylamine an aniline prepared from 2-chloro-5-nitroaniline and cyclopropylcarbonyl chloride. MS found for $C_{23}H_{23}ClN_6O_2$ as $(M+H)^+$ 451.3, 453.3. UV: $\lambda$=206, 250.

Example 111

(R)-2-(4-chloro-3-(3-cyclobutylureido)phenylamino)-4-(1-phenylethylamino)pyrimidine-5-carboxamide

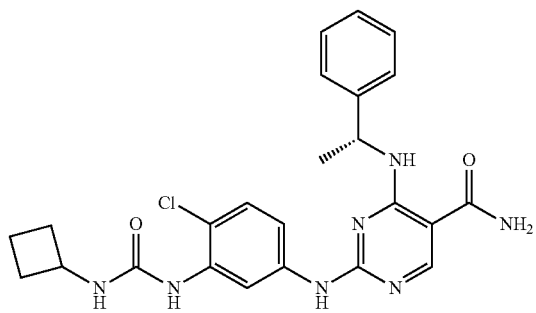 [SMILES: C[C@@H](Nc1nc(Nc2ccc(Cl)c(NC(=O)NC3CCC3)c2)ncc1C(N)=O)c1ccccc1]

The above compound was prepared using a procedure similar to that described in Scheme 2, using (R)-1-phenylethylamine in place of benzylamine an aniline prepared from 2-chloro-5-nitroaniline, phosgene, and cyclobutylamine. MS found for $C_{24}H_{26}ClN_7O_2$ as $(M+H)^-$ 480.4, 482.5. UV: $\lambda$=208, 250.

Example 112

2-(3-acetamidophenylamino)-4-(benzylamino)-N-methylpyrimidine-5-carboxamide

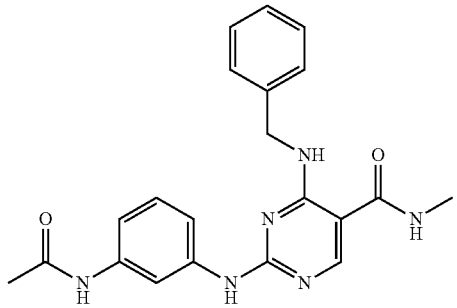 [SMILES: CNC(=O)c1cnc(Nc2cccc(NC(C)=O)c2)nc1NCc1ccccc1]

The above compound was prepared using a procedure similar to that described in Scheme 1, using benzylamine in place of cyclobutylamine, methylamine in place of ammonia, and acetanilide. MS found for $C_{21}H_{22}N_6O_2$ as $(M+H)^+$ 391. UV: $\lambda$=203, 250.

Example 113

4-(benzylamino)-2-(3-(2-methoxyacetamido)phenylamino)-N-methylpyrimidine-5-carboxamide

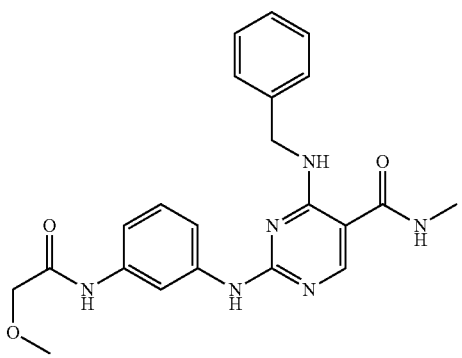 [SMILES: CNC(=O)c1cnc(Nc2cccc(NC(=O)COC)c2)nc1NCc1ccccc1]

The above compound was prepared using a procedure similar to that described in Scheme 1, using benzylamine in place of cyclobutylamine, methylamine in place of ammonia, and an aniline prepared from 3-nitroaniline and methoxyacetyl chloride. MS found for $C_{22}H_{24}N_6O_3$ as $(M+H)^+$ 421. UV: $\lambda$=250.

Example 114

4-(2,3-dihydro-1H-inden-2-ylamino)-2-(3-(2-methoxyacetamido)phenylamino)-N-methylpyrimidine-5-carboxamide

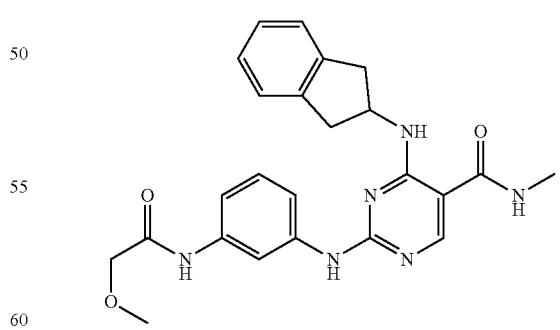

The above compound was prepared using a procedure similar to that described in Scheme 1, using 2-aminoindane in place of cyclobutylamine and an aniline prepared from 2-chloro-5-nitroaniline and methoxyacetyl chloride. MS found for $C_{23}H_{24}N_6O_3$ as $(M+H)^-$ 433. UV: $\lambda$=201, 250.

Example 115

Benzyl 3-((2-(3-acetamidophenylamino)-5-carbamoylpyrimidin-4-ylamino)methyl)piperidine-1-carboxylate

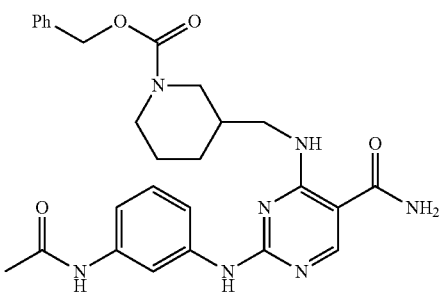 [SMILES: CC(=O)Nc1cccc(Nc2ncc(C(N)=O)c(NCC3CCCN(C(=O)OCc4ccccc4)C3)n2)c1]

Scheme 4

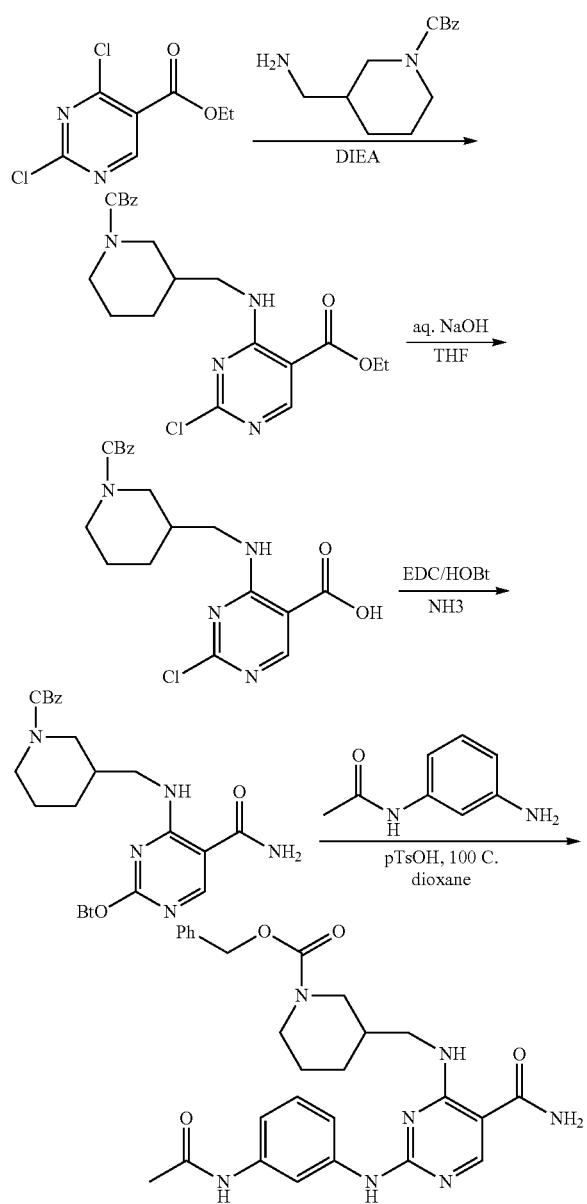

The mixture of ethyl 2,4-dichloropyrimidine-5-carboxylate (442 mg, 2.00 mmol), 3-aminomethyl-1-N-CBz-piperidine (496 mg, 2.00 mmol) and DIEA (0.700 mL, 4.02 mmol) in CH₃CN (12 mL) was stirred at room temperature for 5 h. Water and EtOAc were added. The organic phase was separated, washed with 1N HCl, then with 5% NaHCO₃, dried over Na₂SO₄, concentrated in vacuo to give ethyl 4-((1-(benzyloxycarbonyl)piperidin-3-yl)methylamino)-2-chloropyrimidine-5-carboxylate (808 mg).

To a solution of ethyl 4-((1-(benzyloxycarbonyl)piperidin-3-yl)methylamino)-2-chloropyrimidine-5-carboxylate (808 mg, 1.86 mmol) in THF (10 mL), aq. 1N NaOH (10 mL, 10.0 mmol) was added. The mixture was stirred at room temperature for 18 h. It was acidified to pH 1-2 with 6N HCl. Water and EtOAc were added. The organic phase was separated, washed with brine, dried over Na₂SO₄, concentrated in vacuo to give 4-((1-(benzyloxycarbonyl)piperidin-3-yl)methylamino)-2-chloropyrimidine-5-carboxylic acid (745 mg).

To a solution of 4-((1-(benzyloxycarbonyl)piperidin-3-yl)methylamino)-2-chloropyrimidine-5-carboxylic acid (745 mg, 1.84 mmol) and HOBt monohydrate (422 mg, 2.76 mmol) in DMF (10 mL), EDC (529 mg, 2.76 mmol) was added. After 1 h of stirring, NH₃ (0.5 M in dioxane, 11.0 mL, 5.50 mmol) was added. The mixture was stirred at room temperature for 18 h. Water and EtOAc were added. The organic phase was separated, washed with 5% NaHCO₃, dried over Na₂SO₄, concentrated in vacuo to give benzyl 3-((2-(1H-benzo[d][1,2,3]triazol-1-yloxy)-5-carbamoylpyrimidin-4-ylamino)methyl)piperidine-1-carboxylate (779 mg).

A mixture of benzyl 3-((2-(1H-benzo[d][1,2,3]triazol-1-yloxy)-5-carbamoylpyrimidin-4-ylamino)methyl)piperidine-1-carboxylate (582 mg, 1.16 mmol), 3'-amino-acetanilide (210 mg, 1.40 mmol) and pTsOH (220 mg, 1.16 mmol) in dioxane (10 mL) was stirred at 100 C for 4 h. Water and EtOAc were added. The organic phase was separated, washed with 1N HCl. During the washing white solids precipitated out, which were collected to give the titled compound (412 mg). MS 518.5 (M+H); UV 201.6, 249.8 nm.

Example 116

2-(3-acetamidophenylamino)-4-(piperidin-3-ylmethylamino)pyrimidine-5-carboxamide

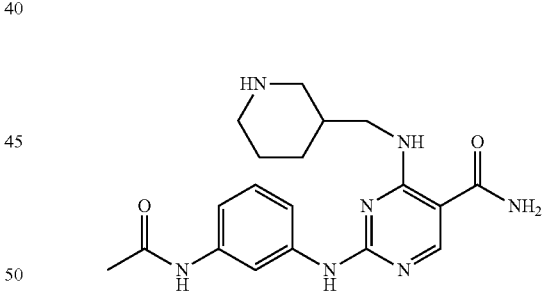

Scheme 5

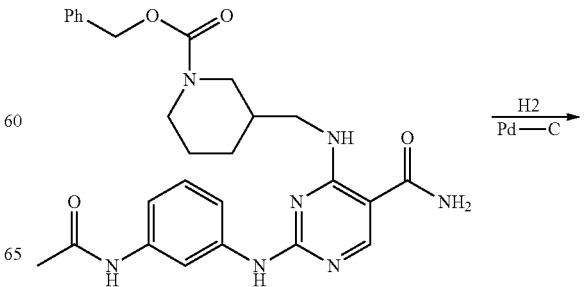

-continued

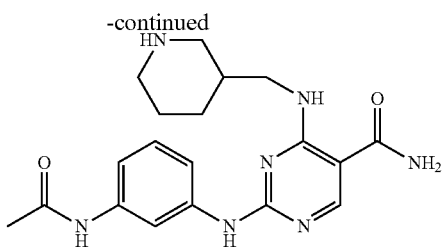

A mixture of benzyl 3-((2-(3-acetamidophenylamino)-5-carbamoylpyrimidin-4-ylamino)methyl)piperidine-1-carboxylate (340 mg, 0.657 mmol) and Pd—C (10%, 52 mg) in MeOH (10 mL) containing 5 drops of aq. 6N HCl was hydrogenated under balloon H2 for 18 h. It was then filtered through celite. The filtrate was concentrated in vacuo to give the titled compound (219 mg). MS 384.4 (M+H); UV 246.7 nm.

Example 117

2-(3-acetamidophenylamino)-4-((1-carbamoylpiperidin-3-yl)methylamino)pyrimidine-5-carboxamide

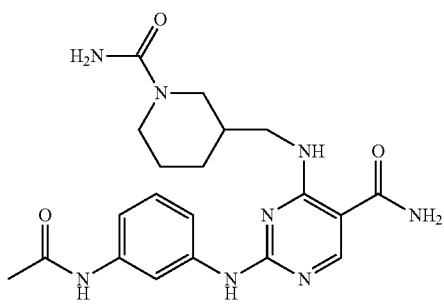 [SMILES: CC(=O)Nc1cccc(Nc2ncc(C(N)=O)c(NCC3CCCN(C(N)=O)C3)n2)c1]

Scheme 6

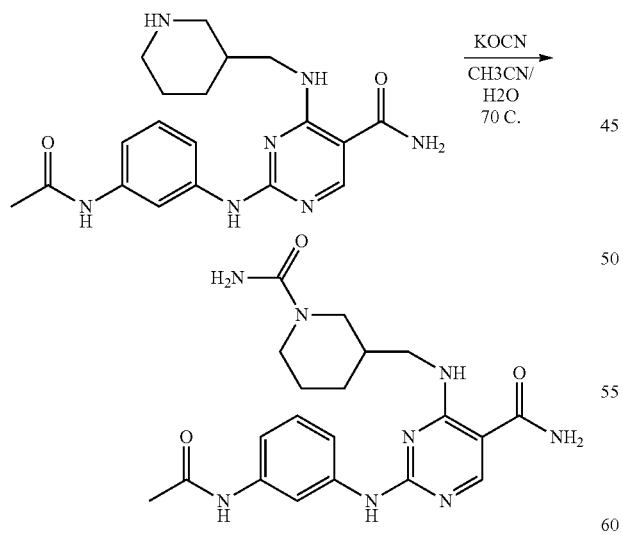

To a mixture of 2-(3-acetamidophenylamino)-4-(piperidin-3-ylmethylamino)pyrimidine-5-carboxamide (40 mg, 0.104 mmol) in CH$_3$CN (2 mL), a solution of KOCN (50 mg, 0.617 mmol) in H2O (1 mL) was added. The mixture was stirred at 70 C for 4 h. It was then purified by HPLC to give the titled compound (3 mg). MS 427.4 (M+H); UV 202.2, 248.6 nm.

Example 118

2-(3-acetamidophenylamino)-4-((1-(4-fluorophenylcarbamoyl)piperidin-3-yl)methylamino)pyrimidine-5-carboxamide

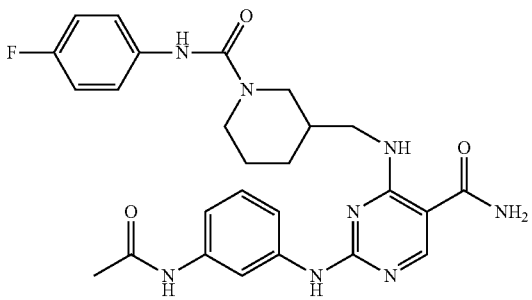 [SMILES: CC(=O)Nc1cccc(Nc2ncc(C(N)=O)c(NCC3CCCN(C(=O)Nc4ccc(F)cc4)C3)n2)c1]

Scheme 7

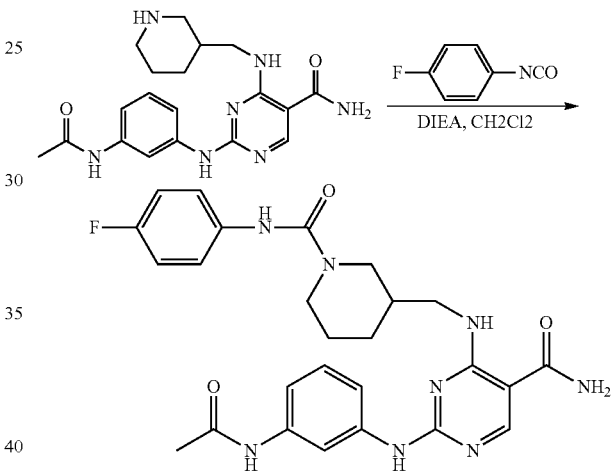

To a mixture of 2-(3-acetamidophenylamino)-4-(piperidin-3-ylmethylamino)pyrimidine-5-carboxamide (40 mg, 0.104 mmol) and DIEA (0.100 mL, 0.575 mmol) in CH$_2$Cl$_2$ (2 mL), 4-fluorophenyl isocyanate (0.023 mL, 0.205 mmol) was added. The mixture was stirred at room temperature for 4 h. It was then purified by HPLC to give the titled compound (32 mg). MS 521.5 (M+H); UV 204.1, 243.1 nm.

Example 119

2-(3-acetamidophenylamino)-4-((1-acetylpiperidin-3-yl)methylamino)pyrimidine-5-carboxamide

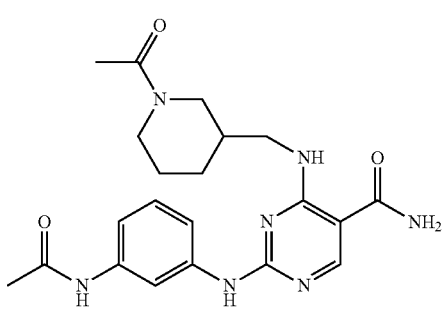 [SMILES: CC(=O)Nc1cccc(Nc2ncc(C(N)=O)c(NCC3CCCN(C(C)=O)C3)n2)c1]

Scheme 8

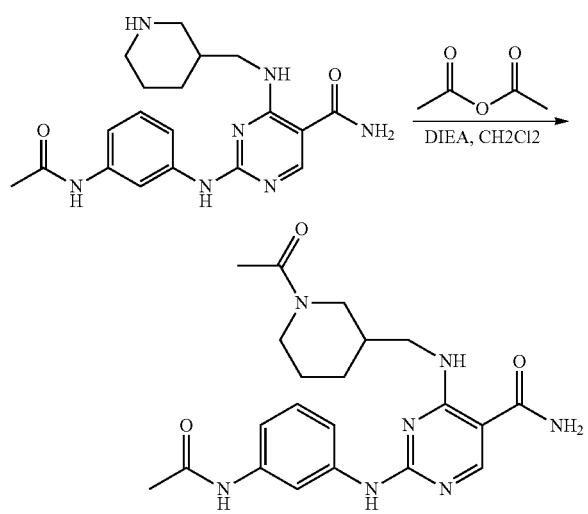

To a mixture of 2-(3-acetamidophenylamino)-4-(piperidin-3-ylmethylamino)pyrimidine-5-carboxamide (40 mg, 0.104 mmol) and DIEA (0.100 mL, 0.575 mmol) in $CH_2Cl_2$ (2 mL), acetic anhydride (0.040 mL, 0.423 mmol) was added. The mixture was stirred at room temperature for 4 h. It was then purified by HPLC to give the titled compound (5 mg). MS 426.5 (M+H); UV 248.6 nm.

Example 120

2-(3-acetamidophenylamino)-4-((1-(methylsulfonyl)piperidin-3-yl)methylamino)pyrimidine-5-carboxamide

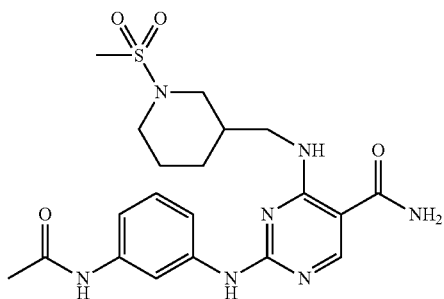

Scheme 9

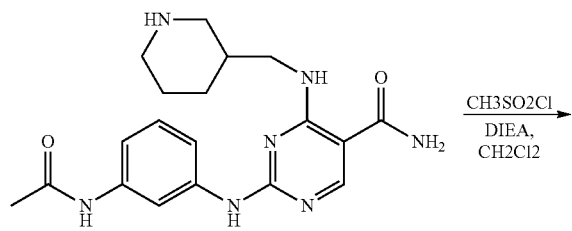

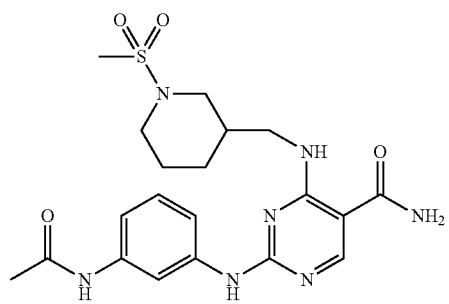 [SMILES: CC(=O)Nc1cccc(Nc2ncc(C(N)=O)c(NCC3CCCN(S(C)(=O)=O)C3)n2)c1]

To a mixture of 2-(3-acetamidophenylamino)-4-(piperidin-3-lmethylamino)pyrimidine-5-carboxamide (40 mg, 0.104 mmol) and DIEA (0.100 mL, 0.575 mmol) in $CH_2Cl_2$ (2 mL), methanesulfonyl chloride (0.032 mL, 0.413 mmol) was added. The mixture was stirred at room temperature for 18 h. It was then purified by HPLC to give the titled compound (6 mg). MS 462.4 (M+H); UV 204.7, 248.6 nm.

Example 121

(R)-2-(3-(2,5-dihydro-1H-pyrrole-1-carboxamido)phenylamino)-4-(1-phenylethylamino)pyrimidine-5-carboxamide

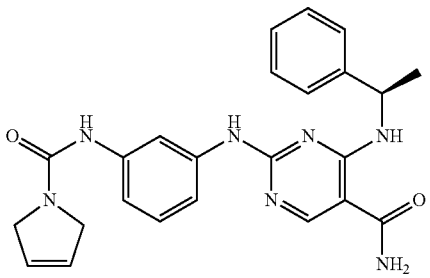 [SMILES: C[C@@H](Nc1nc(Nc2cccc(NC(=O)N3CC=CC3)c2)ncc1C(N)=O)c1ccccc1]

The title compound was synthesized as in scheme 10 and as described in following procedures.

Scheme 10

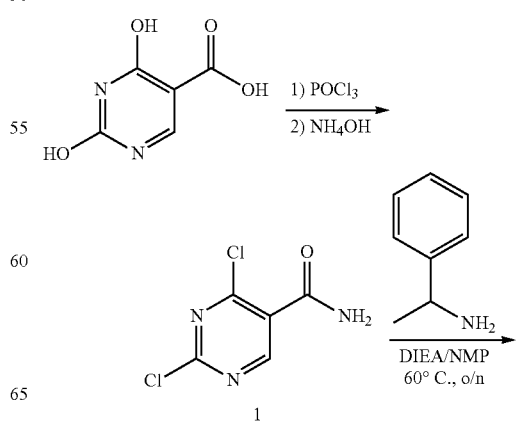

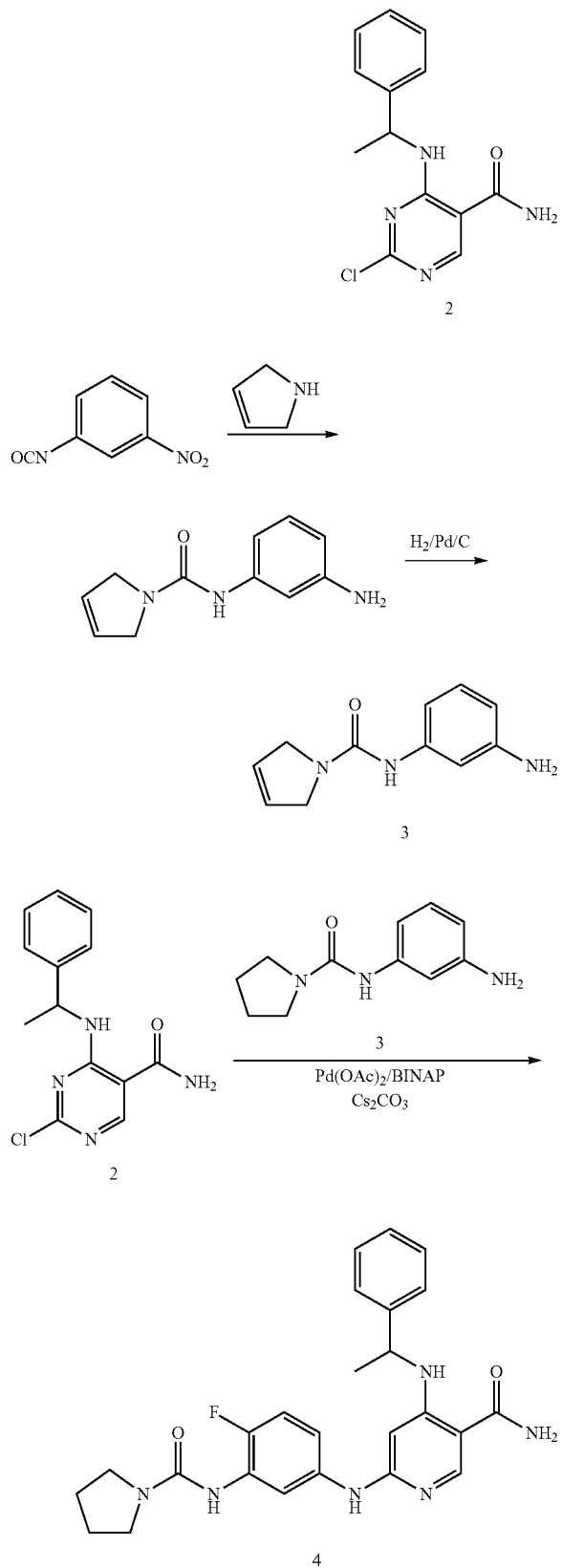

The title compound was synthesized as scheme 10 described in following procedures.

Step I, 2,4-dichloropyrimidine-5-carboxamide (1)

A suspension of 2,4-dihydroxypyrimidine-5-carboxylic acid (3.10 g, 20 mmoles) in phosphoryl trichloride (50 mL) was stirred at 100° C. for 4 hrs. After cooled to room temperature, the reaction solution was poured into a cold ammonium hydroxide solution (27-30%) in several portions and kept the mixture basic. The first portion of desired product as precipitate was collected by filtration. The second portion of desired product was obtained by extraction of mother aqueous liquid with DCM. The total amount of 2,4-dichloropyrimidine-5-carboxamide (1) was 2.78 g. MS+: 191.0, UV: λ=201.0; 269.2 nm, $^1$H NMR: (CDCl$_3$) δ8.77 (s, 1H), δ7.45 (s, 1H), δ6.34 (b, 1H), δ6.21 (b, 1H).

Step II, 2-chloro-4-(1-phenylethylamino)pyrimidine-5-carboxamide (2)

A mixture of 2,4-dichloropyrimidine-5-carboxamide (1, 950 mg, 5 mmoles), 3-1-phenylethanamine (756 mg, 7 mmoles) and DIEA (12 mmoles) in NMP (5 mL) was stirred at 60° C. for 20 hrs. The reaction mixture was concentrated under an oil pump. The residue was washed with water and dried under an oil pump. The desired 2-chloro-4-(1-phenylethylamino)pyrimidine-5-carboxamide (2, 1.085 g) was obtained. MS+: 263.1, UV: λ=220.9; 260.9 nm. $^1$H NMR: (CDCl$_3$) δ8.96 (s, 1H), δ8.60 (s, 1H), δ8.57 (d, J=3.2 Hz, 1H), δ8.30 (s, 1H), δ7.64 (d, J=7.6 Hz, 1H), δ7.31 (dd, J1=7.6 Hz, J2=3.2 Hz, 1H), δ6.51 (s, 1H), δ5.80 (b, 2H), δ4.47 (s, 1H), δ4.45 (s, 1H).

Step III, N-(3-aminophenyl)-2,5-dihydro-1H-pyrrole-1-carboxamide (3)

A mixture of 1-isocyanato-3-nitrobenzene (1.125 g, 6.18 mmoles) and pyrrolidine (485 mg, 6.8 mmoles) in DCM (20 mL) was stirred at r.t. for 14 hrs. After concentrated, the mixture was extracted with ethyl acetate. The organic layer was washed with aqueous citric acid solution and dried over MgSO$_4$, followed by hydrogenation with Pd/C (wet, 10%, 0.15 g) under a hydrogen balloon overnight. After filtration and concentration, the reasonable pure N-(3-aminophenyl)-2,5-dihydro-1H-pyrrole-1-carboxamide (3, 1.44 g) was used for the next reactions. MS+: 224.2, UV: λ=271.6 nm. $^1$H NMR: (DMSO) δ7.44 (s, 1H), δ6.78 (m, 1H), δ6.20 (m, 1H), δ3.32 (m, 4H), δ1.83 (m, 4H).

Step IV, (R)-2-(3-(2,5-dihydro-1H-pyrrole-1-carboxamido)phenylamino)-4-(1-phenylethylamino)pyrimidine-5-carboxamide (4)

A mixture of 2-chloro-4-(1-phenylethylamino)pyrimidine-5-carboxamide (2, 27 mg, 0.1 mmoles), N-(3-aminophenyl)-2,5-dihydro-1H-pyrrole-1-carboxamide (3, 34 mg, 0.15 mmoles), Pd(OAc)$_2$ (2 mg). BINAP (15 mg), Cs$_2$CO$_3$ (100 mg) in dioxane (1 mL) was heated at 120° C. under microwave for 60 min. Purification with reversed phase HPLC, (R)-2-(3-(2,5-dihydro-1H-pyrrole-1-carboxamido) phenylamino)-4-(1-phenylethylamino)pyrimidine-5-carboxamide (4, 10 mg) was obtained. MS found for C$_{24}$H$_{25}$N7O$_2$ as (M+H)$^+$ 444. UV: λ=248 nm. $^1$H NMR: (CD$_3$OD) δ 8.35 (s, 1H), 7.85 (s, 1H), 7.3 (m, 4H), 7.2 (m, 3H), 7.05 (d, 1H), 5.95 (s, 2H), 5.4 (dd, 1H), 4.25 (s, 4H), 1.48 (d, 3H).

Example 122

(R)-2-(3-(N-methylpyrrolidine-1-carboxamido)phenylamino)-4-(1-phenylethylamino)pyrimidine-5-carboxamide

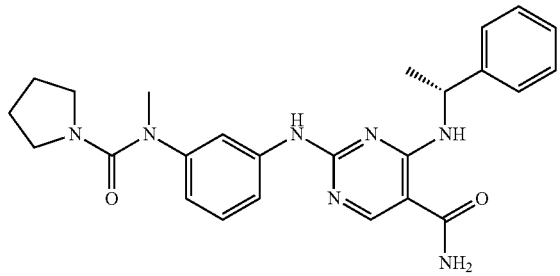 [SMILES: C[C@@H](Nc1nc(Nc2cccc(N(C)C(=O)N3CCCC3)c2)ncc1C(N)=O)c1ccccc1]

The title compound was synthesized similar to step IV in Scheme 10 for Example 121. MS found for $C_{25}H_{29}N_7O_2$ as (M+H)⁺ 460. UV: λ=206, 259 nm. ¹H NMR: (CD₃OD) δ 8.4 (s, 1H), 7.38 (m, 6H), 7.25 (t, 2H), 7.05 (d, 1H), 5.25 (dd, 1H), 3.25 (s, 3H), 3.10 (t, 4H), 1.75 (t, 3H), 1.6 (d, 3H).

Example 123

4-(cyclopropylmethylamino)-2-(3-(pyrrolidine-1-carboxamido)phenylamino)pyrimidine-5-carboxamide

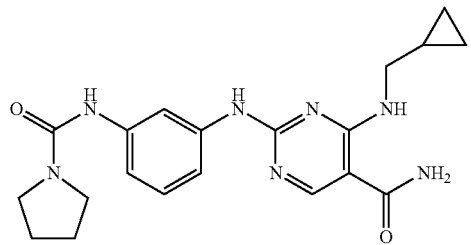 [SMILES: NC(=O)c1cnc(Nc2cccc(NC(=O)N3CCCC3)c2)nc1NCC1CC1]

The title compound was synthesized similar to step IV in Scheme 10 for Example 121. MS found for $C_{20}H_{25}N_7O_2$ as (M+H)⁺ 396.4. UV: λ=206, 247 nm. ¹H NMR: (D-DMSO) δ 8.2 (s, 1H), 7.9 (s, 1H), 7.8 (s, 2H), 6.9 (m, 3H), 3.15 (m, 4H), 1.65 (t, 4H), 0.85 (t, 1H), 0.25 (d, 2H), 0.15 (d, 2H).

Example 124

4-(cyclopropylmethylamino)-2-(3-(2-methoxyacetamido)phenylamino)pyrimidine-5-carboxamide

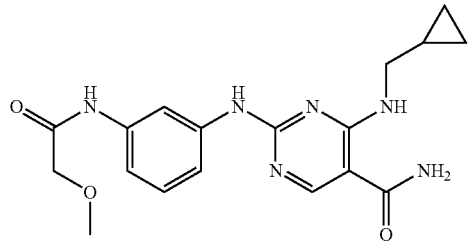 [SMILES: COCC(=O)Nc1cccc(Nc2ncc(C(N)=O)c(NCC3CC3)n2)c1]

The title compound was synthesized similar to step IV in Scheme 10 for Example 121. MS found for $C_{19}H_{24}N_6O_3$ as (M+H)⁺ 371.3. UV: λ=248 nm. ¹H NMR: (CD₃OD) δ 8.35 (s, 1H), 8.15 (s, 1H), 7.38 (t, 1H), 7.35 (d, 1H), 7.28 (s, 1H), 4.05 (s, 2H), 3.5 (s, 3H), 3.05 (d, 2H), 1.15 (t, 1H), 0.55 (d, 2H), 0.35 (d, 2H).

Example 125

4-(cyclopropylmethylamino)-2-(3-(2-methoxy-N-methylacetamido)phenylamino)pyrimidine-5-carboxamide

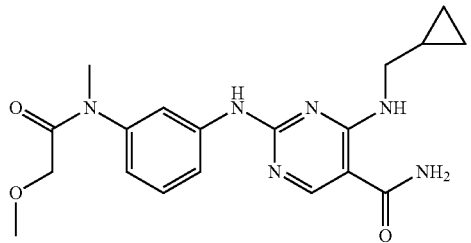 [SMILES: COCC(=O)N(C)c1cccc(Nc2ncc(C(N)=O)c(NCC3CC3)n2)c1]

The title compound was synthesized similar to step IV in Scheme 10 for Example 121. MS found for $C_{19}H_{24}N_6O_3$ as (M+H)⁺ 385.3. UV: λ=257 nm. ¹H NMR: (CD₃OD) δ 8.4 (s, 1H), 7.8 (s, 1H), 7.5 (t, 2H), 7.15 (d, 1H), 3.9 (s, 2H), 3.45 (d, 2H), 3.4 (t, 1H), 1.2 (t, 1H), 0.6 (d, 2H), 0.3 (d, 2H).

Example 126

4-(cyclopropylmethylamino)-2-(3-(N-methylacetamido)phenylamino)pyrimidine-5-carboxamide

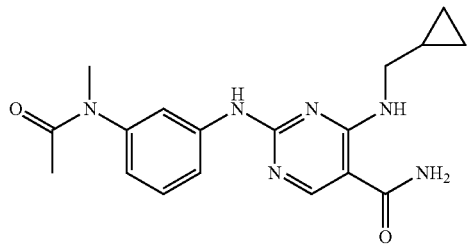 [SMILES: CC(=O)N(C)c1cccc(Nc2ncc(C(N)=O)c(NCC3CC3)n2)c1]

The title compound was synthesized similar to step IV in Scheme 10 for Example 121. MS found for $C_{18}H_{22}N_6O_2$ as (M+H)⁺ 355.3. UV: λ=258 nm. ¹H NMR: (CD₃OD) δ 8.4 (s, 1H), 7.8 (s, 1H), 7.5 (d, 2H), 7.19 (t, 1H), 3.45 (s, 3H), 1.9 (s, 3H), 1.15 (t, 1H), 0.6 (d, 2H), 0.3 (d, 2H).

Example 127

4-(cyclopropylmethylamino)-2-(3-(N-methylpyrrolidine-1-carboxamido)phenylamino)pyrimidine-5-carboxamide

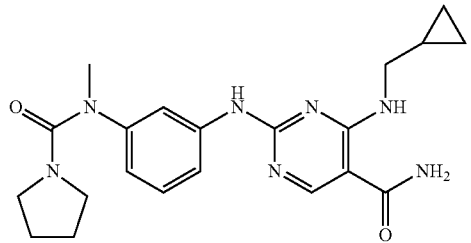 [SMILES: CN(C(=O)N1CCCC1)c1cccc(Nc2ncc(C(N)=O)c(NCC3CC3)n2)c1]

The title compound was synthesized similar to step IV in Scheme 10 for Example 121. MS found for $C_{21}H_{27}N_7O_2$ as (M+H)⁺ 410. UV: λ=205, 248 nm. ¹H NMR: (CD₃OD) δ 8.35 (s, 1H), 7.55 (s, 1H), 7.4 (t, 1H), 7.3 (d, 1H), 7.0 (d, 1H), 3.35 (t, 4H), 3.2 (s, 3H), 3.1 (d, 2H), 1.75 (t, 4H), 1.15 (t, 1H), 0.6 (d, 2H), 0.3 (d, 2H).

Example 128

2-(3-((S)-3-hydroxypyrrolidine-1-carboxamido)phenylamino)-4-((R)-1-phenylethylamino)pyrimidine-5-carboxamide

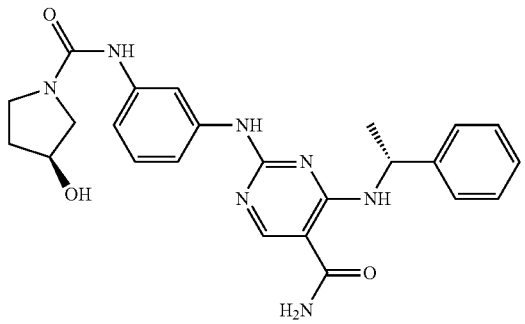 [SMILES: C[C@@H](Nc1nc(Nc2cccc(NC(=O)N3CC[C@H](O)C3)c2)ncc1C(N)=O)c1ccccc1]

The title compound was synthesized similar to step IV in Scheme 10 for Example 121. MS found for $C_{24}H_{27}N_7O_3$ as (M+H)+ 462.4. UV: λ=208, 250 nm.

Example 129

(R)-methyl 5-(5-carbamoyl-4-(1-phenylethylamino)pyrimidin-2-ylamino)-2-chlorophenylcarbamate

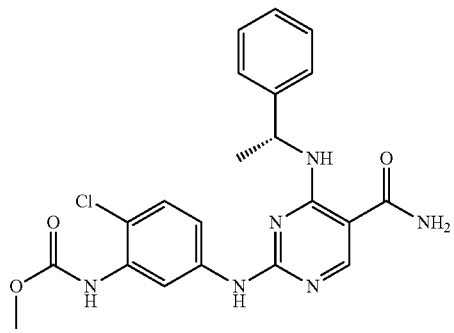 [SMILES: COC(=O)Nc1cc(Nc2ncc(C(N)=O)c(N[C@H](C)c3ccccc3)n2)ccc1Cl]

The title compound was synthesized similar Example 121. MS found for $C_{21}H_{21}ClN_6O_3$ as (M+H)+ UV: λ=8.41 nm. ¹H NMR: (CD$_3$OD) δ 8.42 (s, 1H), 8.26 (s, 1H), 7.38 (d, 1H), 7.30 (m, 5H), 7.22 (d, 1H), 4.83 (s, 2H).5.42 (q, 1H), 3.78 (s, 3H), 1.58 (d, 3H).

Example 130

4-(benzylamino)-2-(4-chloro-3-(pyrrolidine-1-carboxamido)phenylamino)pyrimidine-5-carboxamide

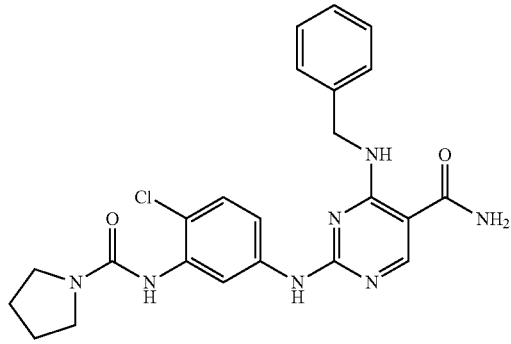

The title compound was synthesized similar to Example 121. MS found for $C_{23}H_{24}ClN_7O_2$ as (M+H)+ 466.4, 468.2. UV: λ=249 nm. ¹H NMR: (CD$_3$OD) δ 8.42 (s, 1H), 8.23 (s, 1H), 7.39 (d, 1H), 7.35 (m, 6H), 7.20 (d, 1H), 4.82 (s, 2H), 3.46 (m, 4H), 1.99 (m, 4H).

Example 131

4-(benzylamino)-2-(4-chloro-3-(3-methylureido)phenylamino)pyrimidine-5-carboxamide

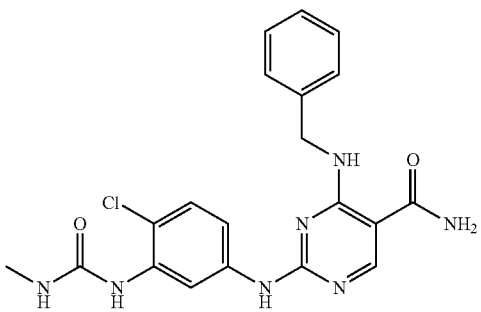

The title compound was synthesized similar to Example 121. MS found for $C_{20}H_{20}ClN_7O_2$ as (M+H)+ 426.2, 428.5. UV: λ=248 nm. ¹H NMR: (CD$_3$OD) δ 8.49 (s, 1H), 8.42 (s, 1H), 7.38 (m, 5H), 7.29 (m, 1H), 7.11 (d, 1H), 4.82 (s, 2H), 2.77 (s, 3H).

Example 132

(R)-2-(4-chloro-3-(3-methylureido)phenylamino)-4-(1-phenylethylamino)pyrimidine-5-carboxamide

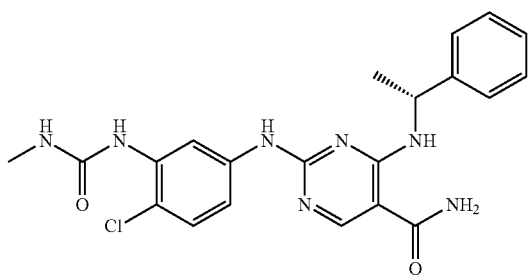

The title compound was synthesized similar to step IV in Scheme 10 for Example 121. MS found for $C_{21}H_{22}ClN_7O_2$ as (M+H)+ 440.4. UV: λ=206, 250 nm. ¹H NMR: (D-DMSO) δ 8.4 (s, 1H), 7.9 (s, 1H), 7.1-7.3 (m, 5H), 7.0 (d, 1H), 6.8 (d, 1H), 5.4 (t, 1H), 2.6 (d, 3H), 1.4 (d, 3H).

Example 133

4-(methylamino)-2-(3-(pyrrolidine-1-carboxamido)phenylamino)pyrimidine-5-carboxamide

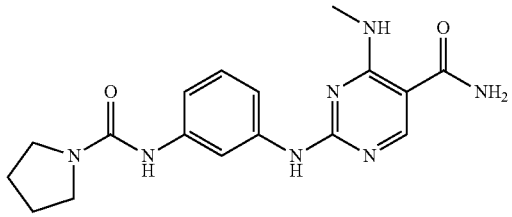 [SMILES: CNc1nc(Nc2cccc(NC(=O)N3CCCC3)c2)ncc1C(N)=O]

The title compound was synthesized similar to Example 121. MS found for C₁₇H₂₁N₇O₂ as (M+H)+ 356.3. UV: λ=202, 250 nm. ¹H NMR: (CD3OD) δ 8.39 (s, 1H), 7.94 (s, 1H), 7.34 (m, 3H), 7.24 (d, 1H), 3.51 (m, 4H), 3.14 (s, 3H), 2.01 (m, 4H). 3, 442, 3. UV: λ=249 nm.

Example 34

4-(ethylamino)-2-(3-(pyrrolidine-1-carboxamido)phenylamino)pyrimidine-5-carboxamide

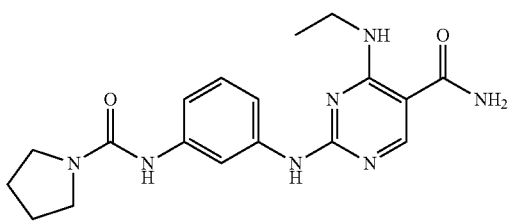 [SMILES: CCNc1nc(Nc2cccc(NC(=O)N3CCCC3)c2)ncc1C(N)=O]

The title compound was synthesized similar to Example 121. MS found for C₁₈H₂₃N₇O₂ as (M+H)+ 370.3. UV: λ=247 nm. ¹H NMR: (CD₃OD) δ 8.33 (s, 1H), 7.82 (s, 1H), 7.33 (t, 1H), 7.19 (m, 3H), 3.63 (q, 2H), 3.46 (m, 4H), 1.98 (m, 4H), 1.27 (t, 3H).

Example 135

4-(butylamino)-2-(3-(pyrrolidine-1-carboxamido)phenylamino)pyrimidine-5-carboxamide

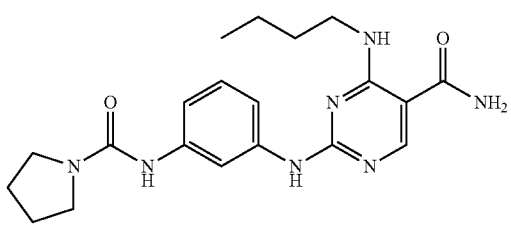 [SMILES: CCCCNc1nc(Nc2cccc(NC(=O)N3CCCC3)c2)ncc1C(N)=O]

The title compound was synthesized Example 121. MS found for C₂₀H₂₇N₇O₂ as (M+H)⁻ 398.3. UV: λ=248 nm. ¹H NMR: (CD₃OD) δ 8.38 (s, 1H), 7.91 (s, 1H), 7.31 (t, 1H), 7.22 (m, 2H), 3.61 (t, 2H), 3.49 (m, 4H), 1.99 (m, 4H), 1.64 (m, 2H), 1.42 (m, 2H), 0.98 (t, 3H).

Example 136

2-(3-(pyrrolidine-1-carboxamido)phenylamino)-4-(2,2,2-trifluoroethylamino)pyrimidine-5-carboxamide

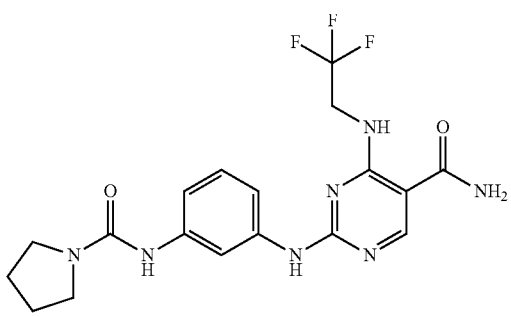 [SMILES: NC(=O)c1cnc(Nc2cccc(NC(=O)N3CCCC3)c2)nc1NCC(F)(F)F]

The title compound was synthesized similar to Example 121. MS found for C₁₈H₂₀F₃N₇O₂ as (M+H)⁺ 424.3. UV: λ=246 nm. ¹H NMR: (CD₃OD) δ 8.52 (s, 1H), 8.01 (s, 1H), 7.29 (t, 1H), 7.18 (m, 2H), 4.47 (q, 2H), 3.48 (m, 4H), 1.97 (m, 4H).

Example 137

2-(3-((S)-2-methylpyrrolidine-1-carboxamido)phenylamino)-4-((R)-1-phenylethylamino)pyrimidine-5-carboxamide

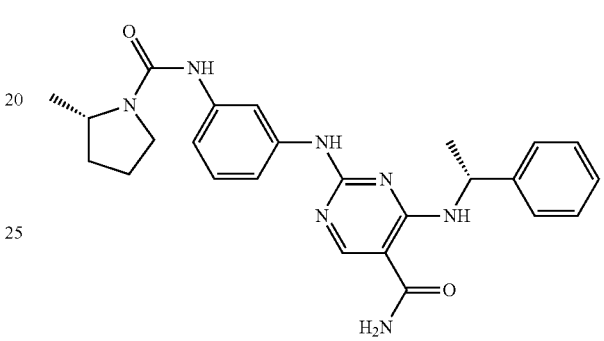

The title compound was synthesized similar to step IV in Scheme 10 for Example 121. MS found for C₂₅H₂₉N₇O₂ as (M+H)⁺ 460.5. UV: λ=205, 251 nm. ¹H NMR: (D-DMSO) δ 8.1 (s, 1H), 7.3 (m, 5H), 7.2 (d, 1H), 7.1 (1H), 7.05 (d, 1H), 5.4 (t, 1H), 4.0 (t, 1H), 3.5 (m, 1H), 3.3 (d, 1H), 2 (s, 3H), 1.9 (m, 4H), 1.5 (d, 4H), 1.1 (d, 3H).

Example 138

2-(3-((S)-2-(methoxymethyl)pyrrolidine-1-carboxamido) phenylamino)-4-((R)-1-phenylethylamino)pyrimidine-5-carboxamide

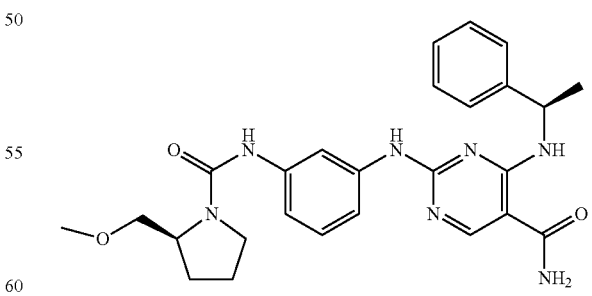

The title compound was synthesized similar to step IV in Scheme 10 for Example 121. MS found for C₂₆H₃₁N₇O₃ as (M+H)⁺ 490.5. UV: λ=207, 251 nm. ¹H NMR: (D-DMSO) δ 8.0 (s, 1H), 7.0-7.4 (m, 8H), 5.4 (t, 1H), 4.05 (d, 1H), 3.4 (t, 2H), 3.35 (s, 1H), 3.3 (s, 3H), 1.7-1.9 (m, 4H), 1.5 (d, 3H).

Example 139

(S)-4-(benzylamino)-2-(3-(2-methylpyrrolidine-1-carboxamido)phenylamino)pyrimidine-5-carboxamide

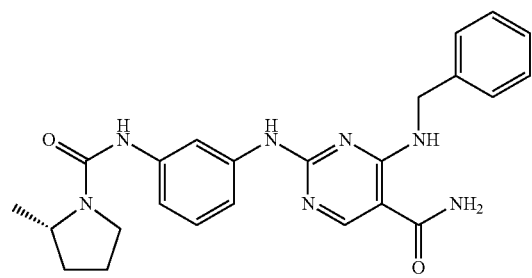 [SMILES: C[C@H]1CCCN1C(=O)Nc1cccc(Nc2ncc(C(N)=O)c(NCc3ccccc3)n2)c1]

The title compound was synthesized similar to step IV in Scheme 10 for Example 121. MS found for $C_{24}H_{27}N_7O_2$ as $(M+H)^+$ 446.4. UV: $\lambda=248$ nm. $^1$H NMR: (D-DMSO) δ 8.4 (s, 1H), 8.0 (s, 2H), 7.3 (m, 4H), 7.2 (m, 1H), 7.1 (t, 2H), 4.7 (d, 2H), 3.5 (t, 1H), 3.3 (dd, 2H), 1.7-1.9 (m, 3H), 1.5 (d, 1H), 1.1 (d, 3H).

Example 140

(S)-4-(benzylamino)-2-(3-(2-(methoxymethyl)pyrrolidine-1-carboxamido)phenylamino)pyrimidine-5-carboxamide

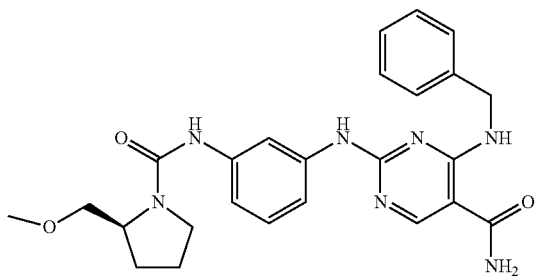 [SMILES: COC[C@@H]1CCCN1C(=O)Nc1cccc(Nc2ncc(C(N)=O)c(NCc3ccccc3)n2)c1]

The title compound was synthesized similar to step IV in Scheme 10 for Example 121. MS found for $C_{25}H_{29}N_7O_3$ as $(M+H)^+$ 476. UV: $\lambda=250$ nm. $^1$H NMR: (D-DMSO) δ 8.3 (s, 1H), 7.1 (d, 2H), 6.9 (t, 2H), 6.7-6.85 (m, 5H), 4.5 (d, 2H), 3.7 (d, 1H), 3.1 (m, 2H), 2.9 (s, 3H), 1.5 (m, 2H), 1.4 (m, 2H).

Example 141

4-(benzylamino)-2-(3-(N-methylpyrrolidine-1-carboxamido)phenylamino)pyrimidine-5-carboxamide

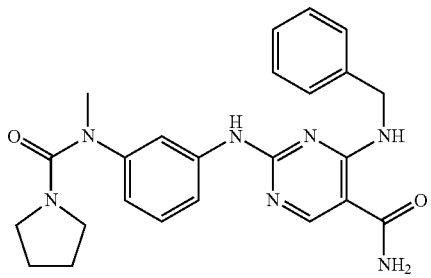 [SMILES: CN(C(=O)N1CCCC1)c1cccc(Nc2ncc(C(N)=O)c(NCc3ccccc3)n2)c1]

The title compound was synthesized similar to step IV in Scheme 10 for Example 121. MS found for $C_{24}H_{27}N_7O_2$ as $(M+H)^+$ 446.4. UV: $\lambda=207, 257$ nm. $^1$H NMR: (D-DMSO) δ 8.25 (s, 1H), 7.35 (t, 1H), 7.1 (d, 1H), 7.0 (d, 2H), 6.95 (t, 2H), 6.9 (t, 2H) 6.4 (d, 1H), 4.4 (d, 2H), 2.7 (s, 3H), 2.65 (t, 2H), 1.3 (t, 2H).

Example 142

4-(benzylamino)-2-(3-(2,5-dihydro-1H-pyrrole-1-carboxamido)phenylamino)pyrimidine-5-carboxamide

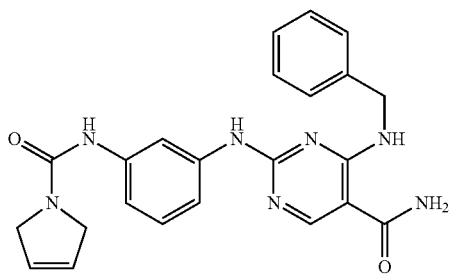 [SMILES: NC(=O)c1cnc(Nc2cccc(NC(=O)N3CC=CC3)c2)nc1NCc1ccccc1]

The title compound was synthesized similar to step IV in Scheme 10 for Example 121. MS found for $C_{23}H_{23}N_7O_2$ as $(M+H)^+$ 430.4. UV: $\lambda=201, 248$ nm. $^1$H NMR: (D-DMSO) δ 8.3 (s, 1H), 7.0 (d, 2H), 6.95, (t, 2H), 6.9 (t, 2H), 6.8, (d, 2H), 5.5 (s, 2 H), 4.5 (d, 2H) 3.8 (s, 4H).

Example 143

(S)-4-(benzylamino)-2-(3-(3-hydroxypyrrolidine-1-carboxamido)phenylamino)pyrimidine-5-carboxamide

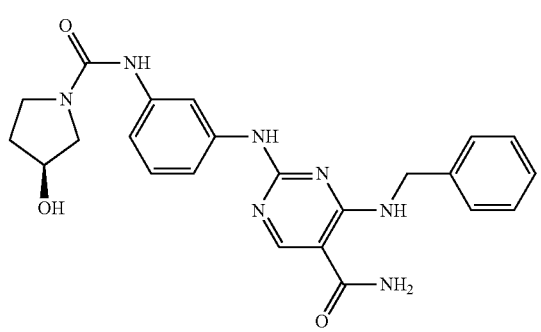 [SMILES: NC(=O)c1cnc(Nc2cccc(NC(=O)N3CC[C@H](O)C3)c2)nc1NCc1ccccc1]

The title compound was synthesized similar to step IV in Scheme 10 for Example 121. MS found for $C_{23}H_{25}N_7O_3$ as $(M+H)^+$ 448.4. UV: $\lambda=206, 247$ nm. $^1$H NMR: (D-DMSO) δ 8.3 (s, 1H), 7.1 (d, 2H), 6.95 (t, 2H), 6.9 (d, 3H), 6.8 (d, 2H), 4.45 (d, 2H), 3.15 (m, 2H), 3.05 (d, 1H).

Example 144

(S)-4-(sec-butylamino)-2-(3-(2-methoxyacetamido)phenylamino)pyrimidine-5-carboxamide

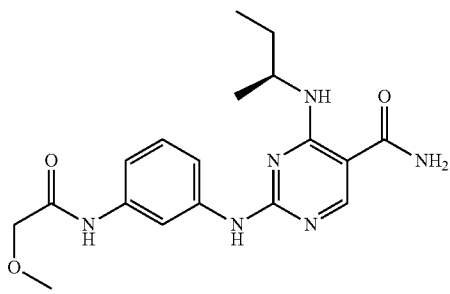 [SMILES: CC[C@H](C)Nc1nc(Nc2cccc(NC(=O)COC)c2)ncc1C(N)=O]

The title compound was synthesized similar to step Example 121. MS found for $C_{18}H_{24}N_6O_3$ as $(M+H)^+$ 373.4. UV: λ=204, 247 nm. $^1$H NMR: ($CD_3OD$) δ 8.35 (s, 1H), 8.08 (s, 1H), 7.30 (m, 3H), 4.23 (m, 1H), 4.03 (s, 2H), 3.48 (s, 3H), 1.63 (m, 2H), 1.26 (d, 3H), 0.97 (t, 3H).

Example 146

(R)-4-(benzylamino)-2-(3-(2-methylpyrrolidine-1-carboxamido) phenylamino)pyrimidine-5-carboxamide

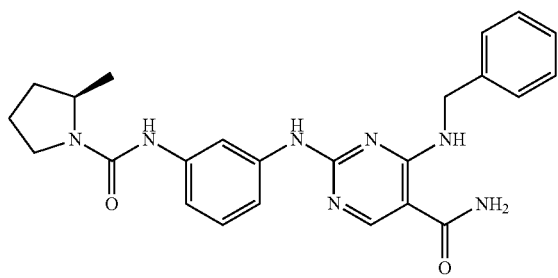 [SMILES: C[C@@H]1CCCN1C(=O)Nc1cccc(Nc2ncc(C(N)=O)c(NCc3ccccc3)n2)c1]

The title compound was synthesized similar to step IV in Scheme 10 for Example 121. MS found for $C_{24}H_{27}N_7O_2$ as $(M+H)^+$ 446.4. UV: λ=201, 247 nm. $^1$H NMR: (D-DMSO) δ 8.5 (s, 1H), 7.3 (d, 5H), 7.2 (m, 2H), 7.1 (bs, 3H), 4.7 (d, 2H), 4.0 (t, 1H), 3.45 (t, 1H), 3.25 (d, 1H), 1.9 (d, 2H), 1.8 (t, 1H), 1.5 (1H).

Example 147

(R)-4-(benzylamino)-2-(3-(2-(methoxymethyl)pyrrolidine-1-carboxamido)phenylamino)pyrimidine-5-carboxamide

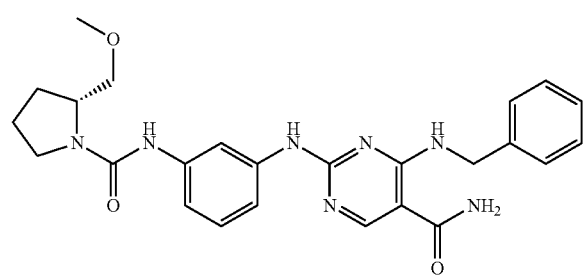 [SMILES: COC[C@H]1CCCN1C(=O)Nc1cccc(Nc2ncc(C(N)=O)c(NCc3ccccc3)n2)c1]

The title compound was synthesized similar to step IV in Scheme 10 for Example 121. MS found for $C_{25}H_{29}N_7O_3$ as $(M+H)^+$ 476.4. UV: λ=205, 245 nm. $^1$H NMR: (D-DMSO) δ 8.5 (s, 1H), 7.3 (d, 4H), 7.2 (d, 1H), 7.1 (d, 2H), 4.7 (d, 2H), 4.0 (d, 2H), 3.3 (m, 4H), 3.2 (t, 3H), 1.7-2.9 (m, 4H).

Example 148

2-(3-((R)-2-methylpyrrolidine-1-carboxamido)phenylamino)-4-((R)-1-phenylethylamino)pyrimidine-5-carboxamide

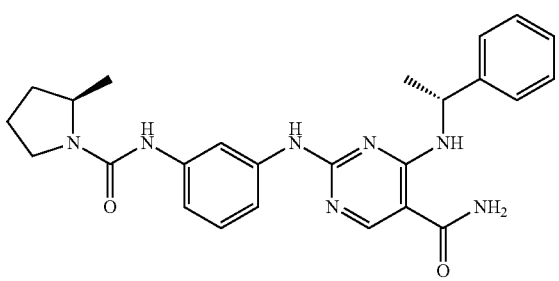 [SMILES: C[C@@H]1CCCN1C(=O)Nc1cccc(Nc2ncc(C(N)=O)c(N[C@H](C)c3ccccc3)n2)c1]

The title compound was synthesized similar to step IV in Scheme 10 for Example 121. MS found for $C_{25}H_{29}N_7O_2$ as $(M+H)^+$ 460.5. UV: λ=208, 248 nm. $^1$H NMR: (D-DMSO) δ 8.4 (s, 1H), 7.25 dd, 4H), 7.2 (t, 1H), 7.0 (d, 1H), 6.9 (m, 3H). 5.3 (t, 1H), 4.0 (t, 1H), 1.7-1.9 (m, 3H), 1.45 (d, 1H), 1.4 (d, 3H), 1.1 (d, 3H).

Example 149

2-(3-((R)-2-(methoxymethyl)pyrrolidine-1-carboxamido)phenylamino)-4-((R)-1-phenylethylamino)pyrimidine-5-carboxamide

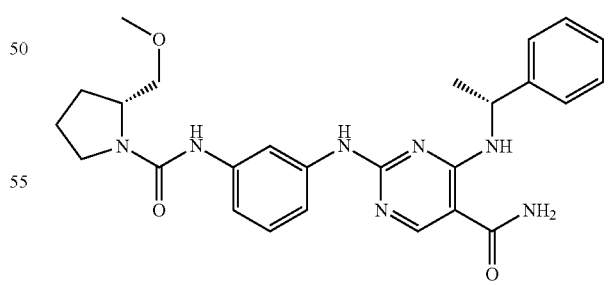

The title compound was synthesized similar to step IV in Scheme 10 for Example 121. MS found for $C_{26}H_{31}N_7O_3$ as $(M+H)^+$ 490.5. UV: λ=208, 250 nm. $^1$H NMR: (D-DMSO) δ 8.5 (s, 1H), 8.3 (s, 1H), 7.3 (d, 5H), 7.25 (t, 1H), 7.1 (d, 1H), 7.05 (t, 1H), 5.04 (t, 1H), 4.05 (d, 1H), 3.4 (t, 3H), 1.9 (t, 2H), 1.8 (d, 1H), 1.5 (d, 3H).

Example 150

4-(benzylamino)-2-(3-(N-cyclopropyl-2-methoxyacetamido)phenylamino)pyrimidine-5-carboxamide

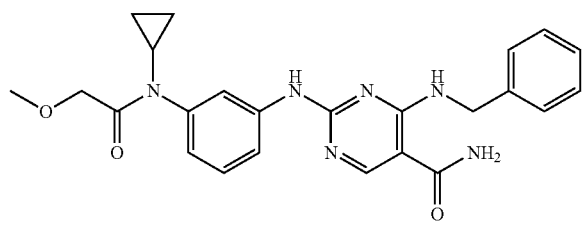 [SMILES: COCC(=O)N(c1cccc(Nc2ncc(C(N)=O)c(NCc3ccccc3)n2)c1)C1CC1]

The title compound was synthesized similar to step IV in Scheme 10 for Example 121. MS found for $C_{24}H_{26}N_6O_3$ as $(M+H)^+$ 447.4. UV: $\lambda$=247 nm. $^1$H NMR: (CD$_3$OD) $\delta$ 8.5 (s, 1H), 7.7 (s, 1H), 7.3 (m, 7H). 7.0 (d, 1H). 4.6 (s, 2H), 2.9 (s, 1H), 0.8 (d, 2H), 0.6 (d, 2H).

Example 151

4-(benzylamino)-2-(3-(N-cyclopropylcyclopropanecarboxamido) phenylamino)pyrimidine-5-carboxamide

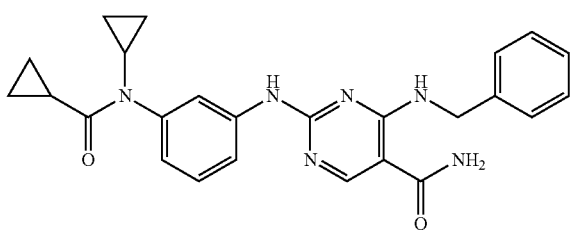 [SMILES: NC(=O)c1cnc(Nc2cccc(N(C(=O)C3CC3)C3CC3)c2)nc1NCc1ccccc1]

The title compound was synthesized similar to step IV in Scheme 10 for Example 121. MS found for $C_{25}H_{26}N_6O_2$ as $(M+H)^+$ 443.5. UV: $\lambda$=247 nm. $^1$H NMR: (CD$_3$OD) $\delta$ 8.5 (s, 1H), 7.8 (s, 1H), 7.4 (m, 7H), 7.0 (d, 1H), 4.6 (s, 2H), 3.0 (s, 1H), 0.9 (s, 3H), 0.8 (s, 4H), 0.5 (s, 2H).

Example 152

(R)-2-(3-acetamidophenylamino)-4-(cyclopropyl(phenyl)methylamino)pyrimidine-5-carboxamide

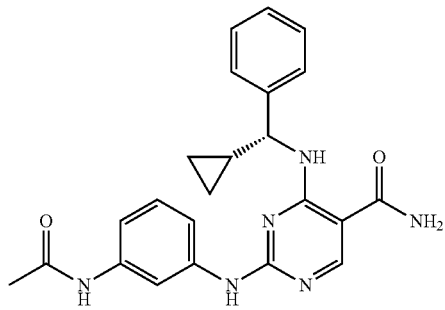 [SMILES: CC(=O)Nc1cccc(Nc2ncc(C(N)=O)c(N[C@@H](c3ccccc3)C3CC3)n2)c1]

The title compound was synthesized similar to step Example 121 using the 2-methylsulfoxide and an amine synthesized using a procedure similar to that described in Eleveld, M. B.; Hogeveen, H.; Schudde, E. P. J. Org. Chem., 1986, 51 (19), pp 3635-3642. MS found for $C_{23}H_{24}N_6O_2$ as $(M+H)^+$ 417.4. UV: $\lambda$=205, 212 nm. $^1$H NMR: (CD$_3$OD) $\delta$ 8.37 (s, 1H), 8.00 (s, 1H), 7.10-7.32 (m, 6H), 7.02 (d, 1H), 4.67 (d, 1H), 2.18 (s, 3H), 1.33 (m, 1H), 0.61 (m, 2H), 0.43 (m, 2H).

Example 154

4-(benzylamino)-2-(4-chloro-3-(3-cyclopropylureido)phenylamino)pyrimidine-5-carboxamide

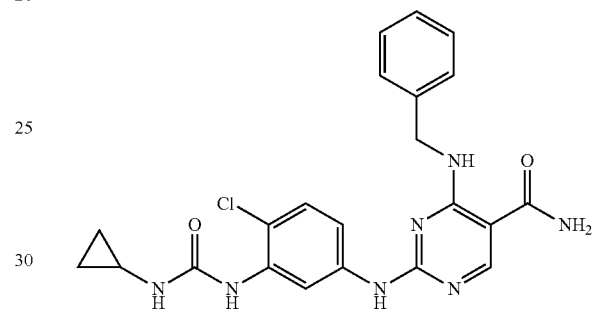

The title compound was synthesized similar to Example 121. MS found for $C_{22}H_{22}ClN_7O_2$ as $(M+H)^+$ 452.4, 454.2. UV: $\lambda$=206, 246 nm. $^1$H NMR: (CD$_3$OD) $\delta$ 8.57 (s, 1H), 8.43 (s, 1H), 7.34 (m, 6H), 7.18 (d, 1H), 4.81 (s, 2H), 2.61 (m, 1H), 0.73 (m, 2H), 0.52 (m, 2H).

Example 155

2-(3-acetamido-4-methylphenylamino)-4-(benzylamino)pyrimidine-5-carboxamide

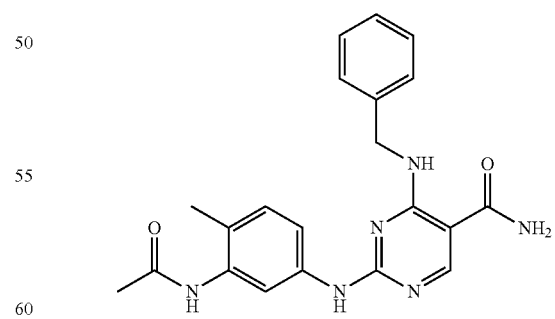

The title compound was synthesized similar to Example 121. MS found for $C_{21}H_{22}N_6O_2$ as $(M+H)^+$ 391.4. UV: $\lambda$=207, 248 nm. $^1$H NMR: (CD$_3$OD) $\delta$ 8.49 (s, 1H), 7.84 (s, 1H), 7.21-7.40 (m, 7H), 4.82 (s, 2H), 2.28 (s, 3H), 2.13 (s, 3H).

Example 156

2-(3-acetamido-4-fluorophenylamino)-4-(benzylamino)pyrimidine-5-carboxamide

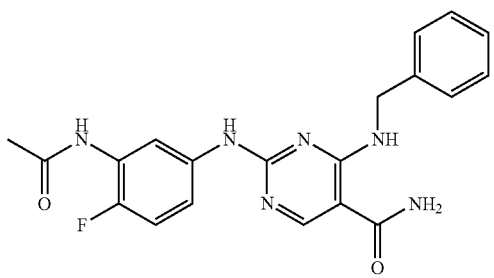 [SMILES: CC(=O)Nc1cc(Nc2ncc(C(N)=O)c(NCc3ccccc3)n2)ccc1F]

The title compound was synthesized similar to step IV in Scheme 10 for Example 121. MS found for $C_{20}H_{19}FN_6O_2$ as $(M+H)^+$ 395.2. UV: $\lambda$=208, 250 nm.

Example 157

4-(benzylamino)-2-(4-methyl-3-(3-methylureido)phenylamino)pyrimidine-5-carboxamide

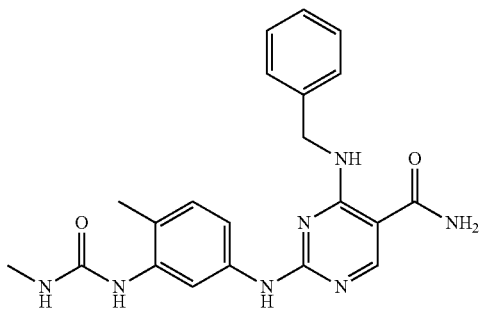 [SMILES: CNC(=O)Nc1cc(Nc2ncc(C(N)=O)c(NCc3ccccc3)n2)ccc1C]

The title compound was synthesized similar to Example 121. MS found for $C_{21}H_{23}N_7O_2$ as $(M+H)^+$ 406.4. UV: $\lambda$=209, 246 nm. $^1$H NMR: (CD$_3$OD) δ 8.31 (s, 1H), 7.88 (s, 1H), 7.30 (m, 5H), 7.20 (d, 1H), 7.03 (d, 1H), 4.77 (s, 2H), 2.74 (s, 3H), 2.24 (s, 3H).

Example 158

4-(benzylamino)-2-(4-fluoro-3-(3-methylureido)phenylamino)pyrimidine-5-carboxamide

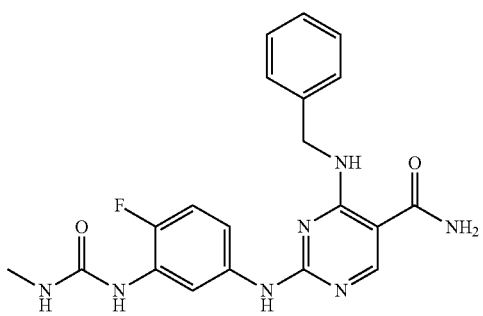 [SMILES: CNC(=O)Nc1cc(Nc2ncc(C(N)=O)c(NCc3ccccc3)n2)ccc1F]

The title compound was synthesized similar to Example 121. MS found for $C_{20}H_{20}FN_7O_2$ as $(M+H)^+$ 410.3. UV: $\lambda$=206, 244 nm. $^1$H NMR: (CD$_3$OD) δ 8.33 (s, 1H), 8.28 (m, 1H), 7.26 (m, 5H), 7.02 (m, 2H), 4.77 (s, 2H), 2.76 (s, 3H).

Example 159

4-(benzylamino)-2-(4-(pyrrolidin-1-yl)-3-(pyrrolidine-1-carboxamido)phenylamino)pyrimidine-5-carboxamide

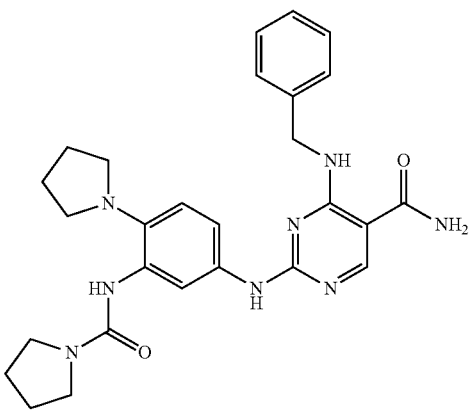 [SMILES: NC(=O)c1cnc(Nc2ccc(N3CCCC3)c(NC(=O)N3CCCC3)c2)nc1NCc1ccccc1]

The title compound was synthesized similar to Example 121, using an aniline derived from 2-fluoro-5-nitroisocyanate and excess pyrrolidine. MS found for $C_{27}H_{32}N_8O_2$ as $(M+H)^+$ 501.5 UV: $\lambda$=202, 256 nm. $^1$H NMR: (CD$_3$OD) δ 8.37 (s, 1H), 7.79 (broad s, 1H), 7.30 (m, 7H), 4.77 (s, 2H), 3.59 (m, 4H), 3.43 (m, 4H), 2.11 (m, 4H), 1.92 (m, 4H).

Example 161

(R)-2-(3-(N-cyclopropylacetamido)phenylamino)-4-(1-phenylethylamino)pyrimidine-5-carboxamide

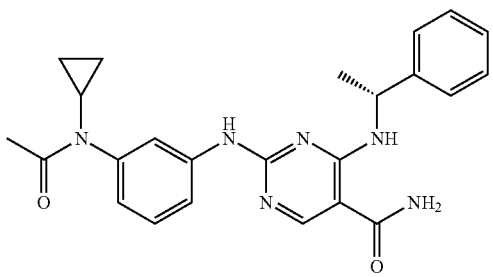 [SMILES: CC(=O)N(c1cccc(Nc2ncc(C(N)=O)c(N[C@H](C)c3ccccc3)n2)c1)C1CC1]

The title compound was synthesized similar to step IV in Scheme 10 for Example 121. MS found for $C_{24}H_{26}N_6O_2$ as $(M+H)^+$ 431.4. UV: $\lambda$=252 nm. $^1$H NMR: (CD$_3$OD) δ 8.4 (s, 1H), 7.5 (s, 1H), 7.4 (d, 2H), 7.3 (m, 4H), 7.2 (d, 1H), 7.0 (s, 1H), 5.3 (d, 1H), 3.2 (d, 1H), 1.6 (d, 3H), 0.9 (s, 2H), 0.6 (s, 2H).

Example 162

(R)-2-(3-(N-cyclopropyl-2-methoxyacetamido)phenylamino)-4-(1-phenylethylamino)pyrimidine-5-carboxamide

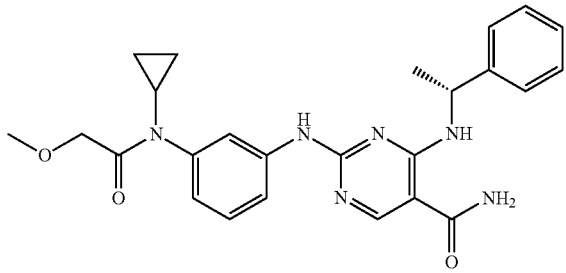 [SMILES: COCC(=O)N(c1cccc(Nc2ncc(C(N)=O)c(N[C@H](C)c3ccccc3)n2)c1)C1CC1]

The title compound was synthesized similar to step IV in Scheme 10 for Example 121. MS found for $C_{25}H_{28}N_6O_3$ as (M+H)$^+$ 461.4. UV: λ=254 nm. $^1$H NMR: (CD$_3$OD) δ 8.4 (s, 1H), 7.5 (s, 1H), 7.4 (d, 2H), 7.3 (m, 4H), 7.2 (d, 1H), 7.0 (d, 1H), 5.4 (d, 1H), 3.4 (s, 3H), 3.2 (d, 2H), 1.6 (s, 3H), 0.9 (s, 2H), 0.6 (s, 2H).

Example 163

4-(benzylamino)-2-(4-methoxy-3-(pyrrolidine-1-carboxamido)phenylamino)pyrimidine-5-carboxamide

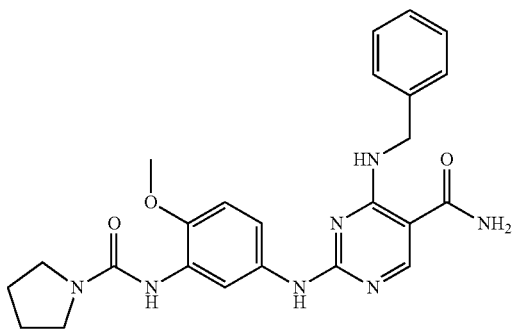 [SMILES: COc1ccc(Nc2ncc(C(N)=O)c(NCc3ccccc3)n2)cc1NC(=O)N1CCCC1]

The title compound was synthesized similar to Example 121. MS found for $C_{24}H_{27}N_7O_3$ as (M+H)$^+$ 462.5. UV: λ=213, 247 nm. $^1$H NMR: (DMSO) δ 8.42 (s, 1H), 8.23 (broad s, 1H), 7.51 (broad s, 1H), 4.31 (m, 4H), 7.23 (m, 1H), 7.13 (s, 1H), 7.08 (dd, 1H), 6.92 (d, 1H), 4.70 (d, 2H), 3.81 (s, 3H), 3.32 (m, 4H), 1.82 (m, 4H).

Example 164

4-(benzylamino)-2-(4-methoxy-3-(3-methylureido)phenylamino)pyrimidine-5-carboxamide

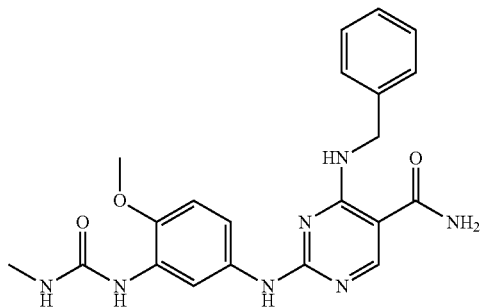 [SMILES: CNC(=O)Nc1cc(Nc2ncc(C(N)=O)c(NCc3ccccc3)n2)ccc1OC]

The title compound was synthesized similar to Example 121. MS found for $C_{21}H_{23}N_7O_3$ as (M+H)$^+$ 422.4. UV: λ=245, 293 nm. $^1$H NMR: (DMSO) δ 8.42 (s, 1H), 8.40 (s, 1H), 8.07 (s, 1H), 7.95 (s, 1H0, 7.52 (s, 1H), 7.30 (m, 4H), 7.23 (m, 1H), 6.98 (dd, 1H), 6.89 (d, 1H), 6.73 (m, 1H), 4.70 (d, 2H), 3.80 (s, 3H), 2.60 (d, 3H).

Example 165

2-(4-chloro-3-(3-methylureido)phenylamino)-4-(3-chlorobenzylamino)pyrimidine-5-carboxamide

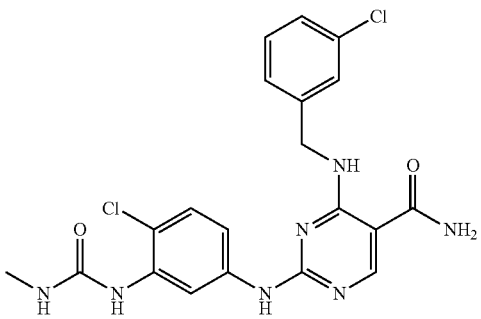 [SMILES: CNC(=O)Nc1cc(Nc2ncc(C(N)=O)c(NCc3cccc(Cl)c3)n2)ccc1Cl]

The title compound was synthesized similar to Example 121. MS found for $C_{20}H_{19}Cl_2N_7O_2$ as (M+H)$^+$ 460.2, 462.3. UV: λ=211, 247 nm. $^1$H NMR: (CD$_3$OD) δ 8.54 (s, 1H0, 8.46 (s, 1H), 7.20-7.36 (m, 6H), 4.73 (s, 2H), 2.62 (s, 3H).

Example 166

2-(4-chloro-3-(3-methylureido)phenylamino)-4-(cyclopentylamino)pyrimidine-5-carboxamide

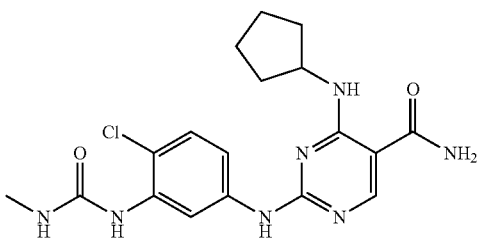 [SMILES: CNC(=O)Nc1cc(Nc2ncc(C(N)=O)c(NC3CCCC3)n2)ccc1Cl]

The title compound was synthesized similar to Example 121. MS found for $C_{18}H_{22}ClN_7O_2$ as (M+H)$^+$ 404.3. UV: λ=258 nm. $^1$H NMR: (DMSO) δ 8.57 (s, 1H0, 8.38 (s, 1H), 7.90 (s, 1H), 7.88 (s, 1H), 7.24 (d, 1H), 7.12 (dd, 1H), 6.77 (m, 1H), 4.41 (q, 1H), 2.58 (d, 3H), 1.92 (m, 1H), 1.59 (m, 2H), 1.52 (m, 2H), 1.39 (m, 2H).

Example 167

2-(4-chloro-3-(pyrrolidine-1-carboxamido)phenylamino)-4-(cyclopentylamino)pyrimidine-5-carboxamide

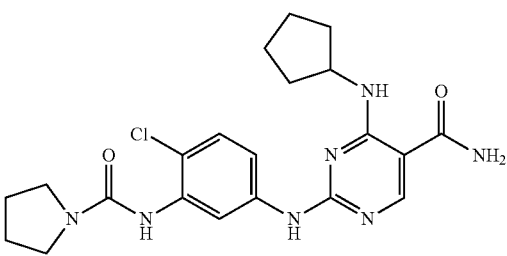 [SMILES: NC(=O)c1cnc(Nc2ccc(Cl)c(NC(=O)N3CCCC3)c2)nc1NC1CCCC1]

The title compound was synthesized similar to Example 121. MS found for $C_{21}H_{26}ClN_7O_2$ as $(M+H)^+$ 444.5. UV: $\lambda$=214, 253 nm. $^1$H NMR: (CD$_3$OD) δ 8.42 (s, 1H0, 8.79 (s, 1H0, 7.33 (d, 1H), 7.27 (d, 1H0, 4.52 (m, 1H), 3.38 (m, 4H), 1.99 (m, 2H), 1.89 (m, 4H), 1.58 (m, 2H0, 1.50 (m, 2H0, 1.39 (m, 2H).

Example 168

4-(2-fluorobenzylamino)-2-(3-(pyrrolidine-1-carboxamido)phenylamino)pyrimidine-5-carboxamide

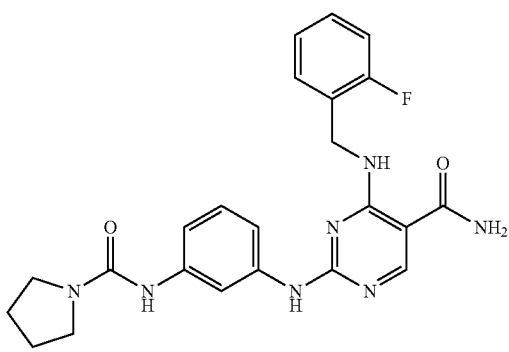 [SMILES: NC(=O)c1cnc(Nc2cccc(NC(=O)N3CCCC3)c2)nc1NCc1ccccc1F]

The title compound was synthesized similar to Example 121. MS found for $C_{23}H_{24}FN_7O_2$ as $(M+H)^+$ 450.4. UV: $\lambda$=207, 248 nm. $^1$H NMR: (CD$_3$OD) δ 8.43 (s, 1H), 7.92 (s, 1H), 7.38 (m, 2H), 7.23 (m, 1H), 7.18 (m, 5H), 4.7 (s, 2H), 3.45 (m, 4H), 1.97 (m, 4H).

Example 169

2-(4-chloro-3-(3-methylureido)phenylamino)-4-(2-fluorobenzylamino)pyrimidine-5-carboxamide

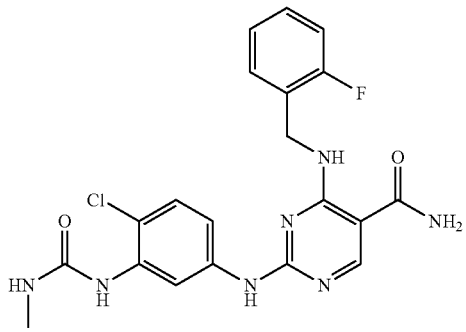 [SMILES: CNC(=O)Nc1cc(Nc2ncc(C(N)=O)c(NCc3ccccc3F)n2)ccc1Cl]

The title compound was synthesized similar to Example 121. MS found for $C_{20}H_{19}ClFN_7O_2$ as $(M+H)^+$ 444.4, 446.4. $^1$H NMR: (CD$_3$OD) δ 8.45 (s, 1H), 8.42 (s, 1H), 7.37 (m, 3H), 7.13 (m, 3H), 4.87 (s, 2H), 2.78 (s, 3H).

Example 170

2-(4-chloro-3-(pyrrolidine-1-carboxamido)phenylamino)-4-(2-fluorobenzylamino)pyrimidine-5-carboxamide

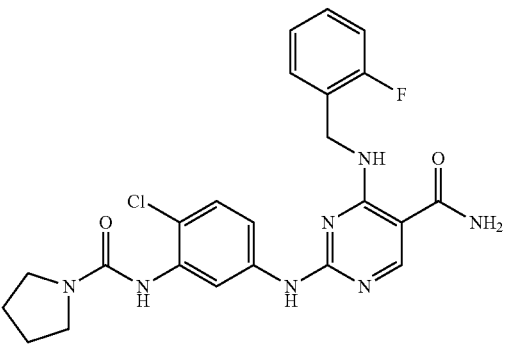 [SMILES: NC(=O)c1cnc(Nc2ccc(Cl)c(NC(=O)N3CCCC3)c2)nc1NCc1ccccc1F]

The title compound was synthesized similar to Example 121. MS found for $C_{23}H_{23}ClFN_7O_2$ as $(M+H)^+$ 484.5, 486.5. UV: $\lambda$=207, 249 nm. $^1$H NMR: (CD$_3$OD) δ 8.42 (s, 1H), 8.22 (s, 1H), 7.38 (d, 1H), 7.35 (m, 2H), 7.20 (d, 1H), 7.14 (m, 2H), 4.83 (s, 2H), 3.45 (m, 4H), 1.99 (m, 4H).

Example 171

2-(5-acetamido-2-fluorophenylamino)-4-(benzylamino)pyrimidine-5-carboxamide

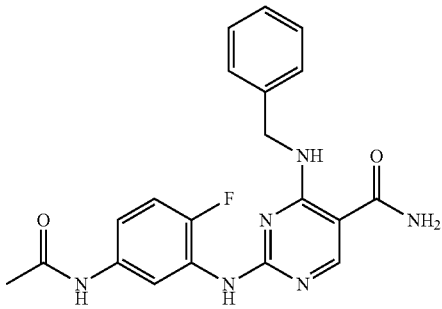 [SMILES: CC(=O)Nc1ccc(F)c(Nc2ncc(C(N)=O)c(NCc3ccccc3)n2)c1]

The title compound was synthesized similar to Example 121. MS found for $C_{20}H_{19}FN_6O_2$ as $(M+H)^+$ 395.4. UV: $\lambda$=204, 246 nm. $^1$H NMR: (CD$_3$OD) δ 8.51 (s, 1H), 8.37 (s, 1H), 7.68 (d, 1H), 7.29 (m, 7H), 4.78 (s, 2H), 2.18 (s, 3H).

Example 172

4-(benzylamino)-2-(2-fluoro-5-(2-methoxyacetamido)phenylamino)pyrimidine-5-carboxamide

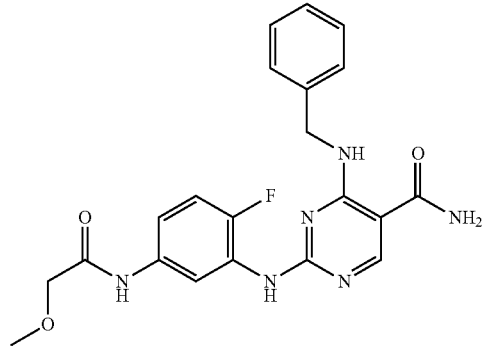 [SMILES: COCC(=O)Nc1ccc(F)c(Nc2ncc(C(N)=O)c(NCc3ccccc3)n2)c1]

The title compound was synthesized similar to Example 121. MS found for C$_{21}$H$_{21}$FN$_6$O$_3$ as (M+H)$^+$ 425.4. $^1$H NMR: (CD$_3$OD) δ 8.47 (s, 1H), 8.43 (s, 1H), 7.41 (s, 1H), 7.29 (6H), 4.77 (s, 2H), 4.05 (s, 2H), 3.48 (s, 3H).

Example 173

2-(4-chloro-3-(pyrrolidine-1-carboxamido)phenylamino)-4-(3-chlorobenzylamino)pyrimidine-5-carboxamide

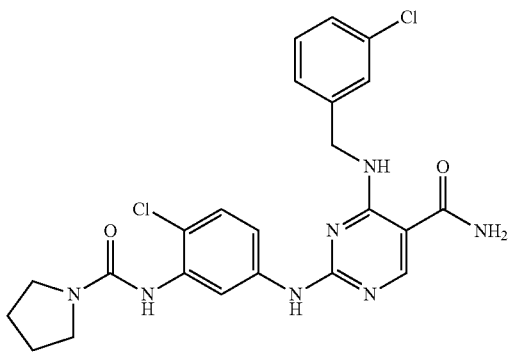 [SMILES: NC(=O)c1cnc(Nc2ccc(Cl)c(NC(=O)N3CCCC3)c2)nc1NCc1cccc(Cl)c1]

The title compound was synthesized similar to Example 121. MS found for C$_{23}$H$_{23}$Cl$_2$N$_7$O$_2$ as (M+H$^+$ 500.4. $^1$H NMR: (CD$_3$OD) δ 8.43 (s, 1H), 8.23 (d, 1H0, 7.20-7.32 (m, 5H), 7.12 (dd, 1H), 4.76 (s, 2H0, 3.37 (m, 4H0, 1.82 (m, 4H).

Example 174

2-(4-chloro-3-(pyrrolidine-1-carboxamido)phenylamino)-4-(cyclopropylmethylamino)pyrimidine-5-carboxamide

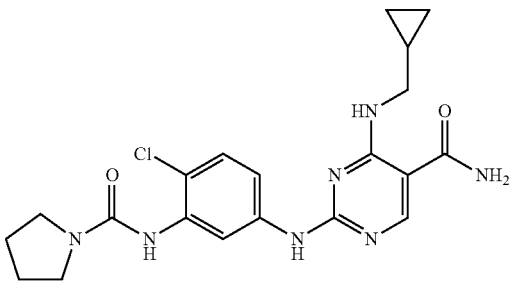 [SMILES: NC(=O)c1cnc(Nc2ccc(Cl)c(NC(=O)N3CCCC3)c2)nc1NCC1CC1]

The title compound was synthesized similar to Example 121. MS found for C$_{20}$H$_{24}$ClN$_7$O$_2$ as (M+H)$^+$ 430.4. UV: λ=212, 246, 290 nm. $^1$H NMR: (CD$_3$OD) δ 8.43 (s, 1H0, 8.33 (s, 1H0, 7.33 (d, 1H), 7.29 (dd, 1H), 3.38 (m, 6H), 1.84 (m, 4H0, 1.08 (m, 1H0, 0.43 (m, 2H0, 0.22 (m, 2H).

Example 175

(S)-4-(sec-butylamino)-2-(4-chloro-3-(3-methylureido)phenylamino)pyrimidine-5-carboxamide

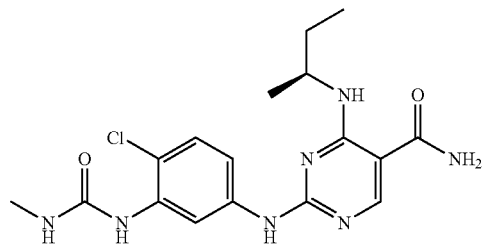 [SMILES: CC[C@H](C)Nc1nc(Nc2ccc(Cl)c(NC(=O)NC)c2)ncc1C(N)=O]

The title compound was synthesized similar to Example 121. MS found for C$_{17}$H$_{22}$ClN$_7$O$_2$ as (M+H)$^+$ 292.3. UV: λ=210, 246, 288 nm. $^1$H NMR: (CD$_3$OD) δ 8.52 (s, 1H), 8.38 (s, 1H0, 7.28 (d, 1H), 7.18 (dd, 1H0, 4.21 (m, 1H), 3.63 (s, 3H), 1.51 (m, 2H), 1.13 (d, 3H), 0.83 (t, 3H).

Example 176

(S)-4-(sec-butylamino)-2-(4-chloro-3-(pyrrolidine-1-carboxamido)phenylamino)pyrimidine-5-carboxamide

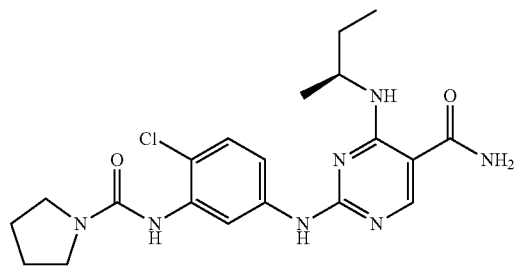 [SMILES: CC[C@H](C)Nc1nc(Nc2ccc(Cl)c(NC(=O)N3CCCC3)c2)ncc1C(N)=O]

The title compound was synthesized similar to Example 121. MS found for C$_{20}$H$_{26}$ClN$_7$O2 as (M+H)$^+$ 432.2. UV: λ=214, 258 nm. $^1$H NMR: (CD$_3$OD) δ 8.41 (s, 1H), 8.26 (d, 1H0, 7.32 (d, 1H), 7.27 (dd, 1H), 4.18 (m, 1H), 3.38 (m, 4H), 1.85 (m, 4H), 1.52 (m, 2H), 1.17 (d, 3H), 0.84 (t, 3H).

Example 177

2-(4-chloro-3-(pyrrolidine-1-carboxamido)phenylamino)-4-(3-fluorobenzylamino)pyrimidine-5-carboxamide

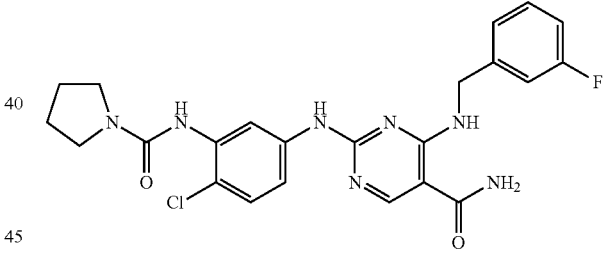

The title compound was synthesized similar to step IV in Scheme 10 for Example 121. MS found for C$_{23}$H$_{23}$ClFN$_7$O$_2$ as (M+H)$^+$ 484.4. UV: λ=250 nm.

Example 178

2-(4-chloro-3-(3-methylureido)phenylamino)-4-(cyclopropylmethylamino)pyrimidine-5-carboxamide

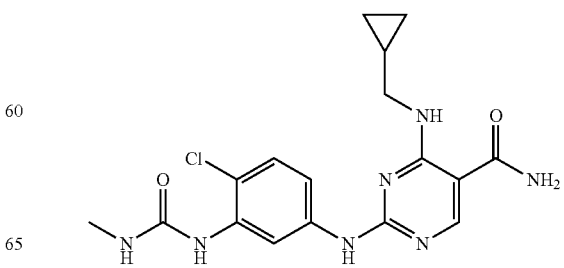

The title compound was synthesized similar to Example 121. MS found for C₁₇H₂₀ClN₇O2 as (M+H)⁺ 390.4. UV: λ=210, 249 nm. ¹H NMR: (CD₃OD) δ 8.57 (s, 1H), 8.39 (s, 1H), 7.29 (d, 1H), 7.17 (d, 1H), 3.37 (d, 2H), 3.63 (s, 3H), 1.07 (m, 1H), 0.43 (m, 2H), 0.22 (m, 2H).

Example 179

4-(3-fluorobenzylamino)-2-(3-(pyrrolidine-1-carboxamido)phenylamino)pyrimidine-5-carboxamide

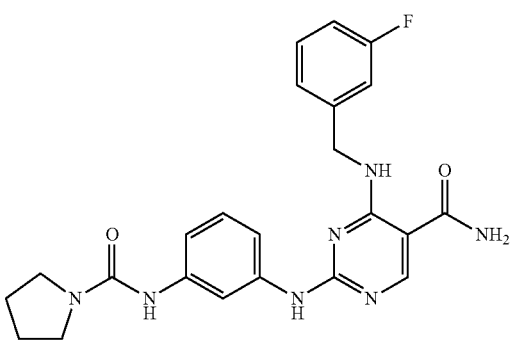 [SMILES: NC(=O)c1cnc(Nc2cccc(NC(=O)N3CCCC3)c2)nc1NCc1cccc(F)c1]

The title compound was synthesized similar to Example 121. MS found for C₂₃H₂₄FN₇O₂ as (M+H)⁺ 450.5. UV: λ=256 nm. ¹H NMR: (CD₃OD) δ 8.41 (s, 1H), 7.92 (s, 1H), 7.27 (m, 1H), 6.93-7.12 (m, 6H), 4.68 (s, 2H), 3.31 (m, 4H), 1.81 (m, 4H).

Example 180

4-(3-chlorobenzylamino)-2-(3-(pyrrolidine-1-carboxamido)phenylamino)pyrimidine-5-carboxamide

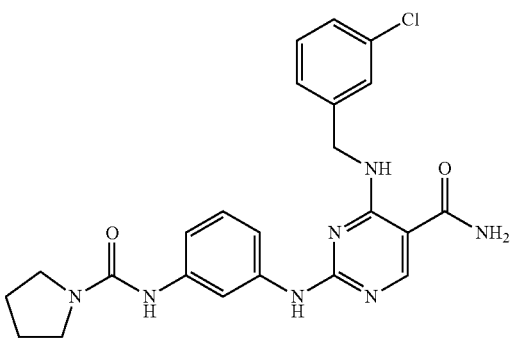 [SMILES: NC(=O)c1cnc(Nc2cccc(NC(=O)N3CCCC3)c2)nc1NCc1cccc(Cl)c1]

The title compound was synthesized similar to Example 121. MS found for C₂₃H₂₄ClN₇O₂ as (M+H)⁺ 466.5. UV: λ=202, 249 nm. ¹H NMR: (CD₃OD) δ 8.40 (s, 1H), 7.94 (s, 1H), 7.30 (s, 1H), 7.22 (m, 3H), 7.08 (m, 2H), 6.98 (dd, 1H), 4.72 (s, 2H), 3.30 (m, 4H), 1.82 (m, 4H).

Example 181

4-(2-fluorobenzylamino)-2-(3-(3-methylureido)phenylamino)pyrimidine-5-carboxamide

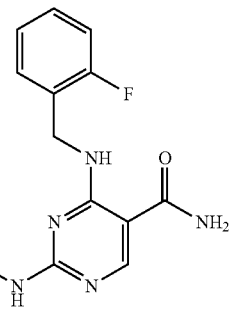

The title compound was synthesized similar to Example 121. MS found for C₂₀H₂₀FN₇O₂ as (M+H)⁺ 394.5. UV: λ=205, 249 8.42 (s, 1H), 7.97 (s, 1H), 7.22 (m, 4H), 7.03 (m, 4H), nm. ¹H NMR: (CD₃OD) δ 8.42 (s, 1H), 7.97 (s, 1H), 7.22 (m, 4H), 7.03 (m, 4H), 4.76 (s, 2H).

Example 182

N-(5-(4-(benzylamino)-5-carbamoylpyrimidin-2-ylamino)-2-chlorophenyl)morpholine-4-carboxamide

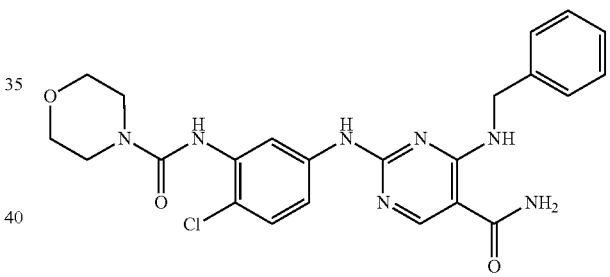

The title compound was synthesized similar to step IV in Scheme 10 for Example 121. MS found for C₂₃H₂₄ClN₇O₃ as (M+H)⁺ 482.4. UV: λ=250 nm. ¹H NMR: (D-DMSO) δ 8.5 (s, 1H), 7.3 (m, 8H), 4.7 (d, 2H), 3.5 (d, 4H), 3.4 (d, 4H).

Example 183

(R)-N-(5-(5-carbamoyl-4-(1-phenylethylamino)pyrimidin-2-ylamino)-2-chlorophenyl)morpholine-4-carboxamide

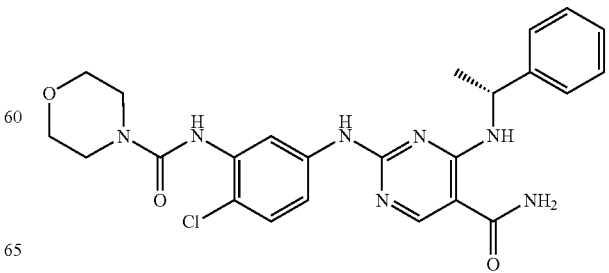

The title compound was synthesized similar to step IV in Scheme 10 for Example 121. MS found for $C_{24}H_{26}ClN_7O_3$ as $(M+H)^+$ 496.5. UV: $\lambda=250$ nm. $^1H$ NMR: (D-DMSO) δ 8.5 (s, 1H), 7.3 (m, 5H), 7.2 (dd, 2H), 5.4 (t, 1H), 3.5 (t, 4H), 3.4 (t, 4H), 1.5 (d, 3H).

Example 184

Preparation of 2-(3-acetamidophenylamino)-4-(1-methyl-1H-indol-4-ylamino)pyrimidine-5-carboxamide Scheme 11

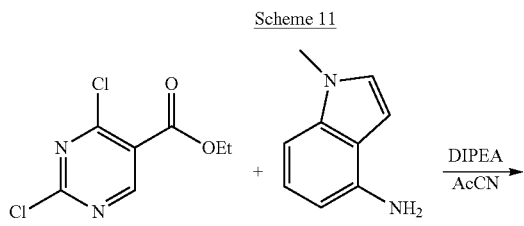

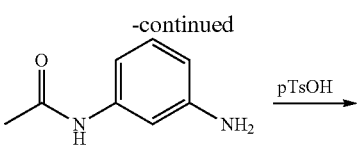

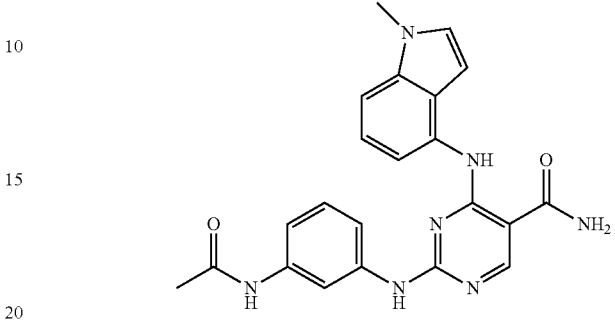

Step 1: To a solution of ethyl 2,4-dichloropyrimidine-5-carboxylate (328 mg, 1.48 mmol) and 1-methyl-1H-indol-4-amine (260 mg, 1.78 mmol) in $CH_3CN$ (6 mL) at room temperature, DIEA (0.4 mL, 2.22 mmol) was added. The mixture was stirred at room temperature for 24 h. Water (15 mL) was added to induce precipitation. The precipitate was collected, dried on vacuum to give ethyl 2-chloro-4-(1-methyl-1H-indol-4-ylamino) pyrimidine-5-carboxylate as a solid.

Step 2: To a solution of ethyl 2-chloro-4-(1-methyl-1H-indol-4-ylamino) pyrimidine-5-carboxylate (crude from step 1) in THF (4 mL), aq. 1N LiOH (2.25 mL, 2.25 mmol) was added. The mixture was stirred at room temperature overnight. Upon acidification of the mixture with 1N HCl, white solids precipitated out, which were collected, and dried on vacuum to give 2-chloro-4-(1-methyl-1H-indol-4-ylamino) pyrimidine-5-carboxylic acid (325 mg). MS 303.3, 305.3 (M+H, Cl pattern)

Step 3: To a solution of 2-chloro-4-(1-methyl-1H-indol-4-ylamino)pyrimidine-5-carboxylic acid (325 mg, 1.08 mmol) and $HOBt \cdot H_2O$ (198 mg, 1.29 mmol) in DMF (4 mL), EDC (248 mg, 1.29 mmol) was added. The mixture was stirred at room temperature for 1.5 h. Ammonia (0.5 M in dioxane, 8.00 mL, and 4.00 mmol) was added. It was stirred at room temperature overnight. Water and EtOAc were added. The organic phase was separated, washed with 1 N HCl, then with 5% $NaHCO_3$, dried over $Na_2SO_4$, concentrated in vacuo to give 2-(1H-benzo[d][1,2,3]triazol-1-yloxy)-4-(1-methyl-1H-indol-4-ylamino)pyrimidine-5-carboxamide (378 mg). MS 401.4 (M+H)

Step 4: To a solution of 2-(1H-benzo[d][1,2,3]triazol-1-yloxy)-4-(1-methyl-1H-indol-4-ylamino)pyrimidine-5-carboxamide (60 mg, 0.15 mmol) in NMP (0.6 mL) was added 3-acetamidoaniline (25 mg, 0.165 mmol) and $pTsOH \cdot H_2O$ (28 mg, 0.15 mmol). The mixture was heated at 100° C. for 2 h, cooled to room temperature, purified by preparative HPLC to give 2-(3-acetamidophenylamino)-4-(1-methyl-1H-indol-4-ylamino)pyrimidine-5-carboxamide (20 mg). MS found for $C_{22}H_{21}N_7O_2$ as $(M+H)^+$ 416.3. $\lambda=211.3, 250.9$.

Example 185

Preparation of 2-(3-acetamidophenylamino)-4-(1-ethyl-1H-indol-4-ylamino)pyrimidine-5-carboxamide

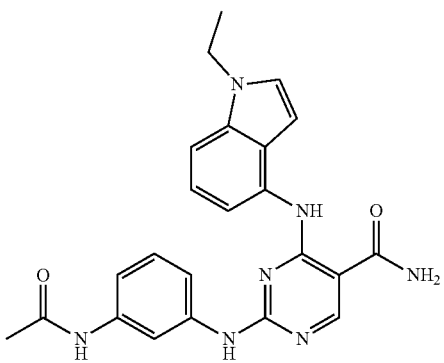 [SMILES: CCn1ccc2c(Nc3nc(Nc4cccc(NC(C)=O)c4)ncc3C(N)=O)cccc21]

The title compound was prepared using the same synthetic scheme demonstrated in Example 184 with 1-ethyl-1H-indol-4-ylamine to replace 1-methyl-1H-indol-4-ylamine. MS found for $C_{23}H_{23}N_7O_2$ as $(M+H)^+$ 430.3. $\lambda$=215.7, 249.9.

Example 186

Preparation of 2-(3-acetamidophenylamino)-4-(2-methyl-2H-indazol-4-ylamino)pyrimidine-5-carboxamide

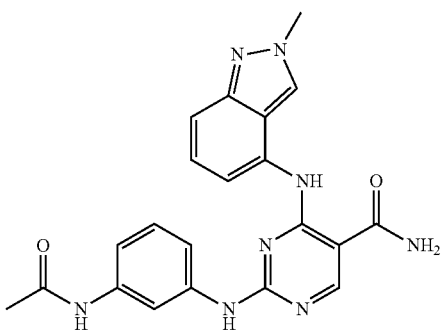 [SMILES: CC(=O)Nc1cccc(Nc2ncc(C(N)=O)c(Nc3cccc4nn(C)cc34)n2)c1]

The title compound was prepared using the same synthetic scheme demonstrated in Example 184 with 2-methyl-2H-indazol-4-ylamine to replace 1-methyl-1H-indol-4-ylamine. MS found for $C_{21}H_{20}N_8O_2$ as $(M+H)^+$ 417.3. $\lambda$=208.6, 251.1.

Example 187

2-(3-acetamidophenylamino)-4-(pyridin-2-ylmethylamino)pyrimidine-5-carboxamide

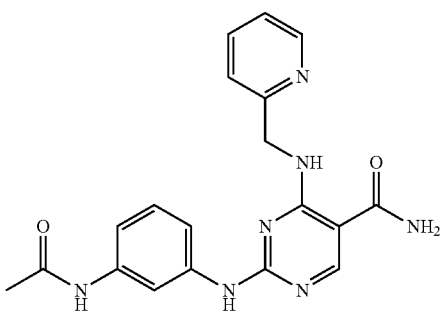

The title compound was synthesized similar to Example 184, using the 4-sulfoxide intermediate. MS found for $C_{19}H_{19}N_7O_2$ as $(M+H)^+$ 378.4. UV: $\lambda$=204, 250 nm. $^1$H NMR: $(CD_3OD)$ $\delta$ 8.32 (d, 1H), 8.22 (s, 1H), 8.03 (s, 1H), 7.94 (t, 1H), 7.50 (d, 1H), 7.43 (m, 1H), 7.24 (t, 1H), 7.13 (d, 1H), 7.04 (d, 1H), 4.95 (s, 2H), 2.16 (s, 3H).

Example 188

2-(3-acetamidophenylamino)-4-(pyridin-3-ylmethylamino)pyrimidine-5-carboxamide

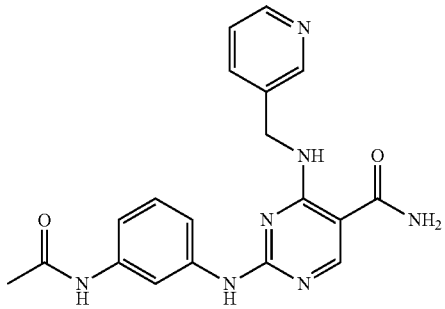

The title compound was synthesized similar to Example 184 using the 4-methylsulfoxide intermediate. MS found for $C_{19}H_{19}N_7O_2$ as $(M+H)^+$ 378.4. UV: $\lambda$=204, 252 nm. $^1$H NMR: $(CD_3OD)$ $\delta$ 8.59 (s, 1H), 8.55 (d, 1H), 3.39 (s, 1H), 8.23 (d, 1H), 8.08 (s, 1H), 7.64 (dd, 1H), 7.28 (t, 1H), 7.12 (d, 1H), 7.08 (d, 1H), 4.83 (s, 2H), 2.11 (s, 3H).

Example 189

2-(3-acetamidophenylamino)-4-(pyridin-4-ylmethylamino)pyrimidine-5-carboxamide

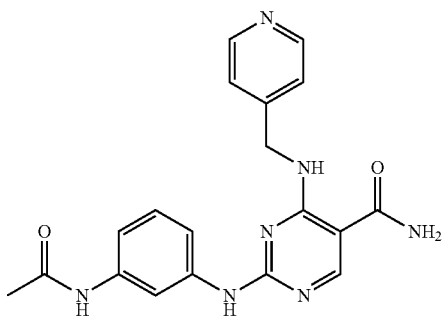 [SMILES: CC(=O)Nc1cccc(Nc2ncc(C(N)=O)c(NCc3ccncc3)n2)c1]

The title compound was synthesized similar to Example 184 using the 4-methylsulfoxide intermediate. MS found for $C_{19}H_{19}N_7O_2$ as $(M+H)^+$ 378.4. $^1$H NMR: $(CD_3OD)$ $\delta$ 8.57 (d, 2H), 8.43 (s, 1H), 7.98 (s, 1H), 7.72 (d, 2H), 7.20 (t, 1H), 7.07 (d, 1H), 7.02 (d, 1H), 4.98 (s, 2H), 2.13 (s, 3H).

Example 190

2-(3-acetamidophenylamino)-4-(piperidin-4-ylmethylamino)pyrimidine-5-carboxamide

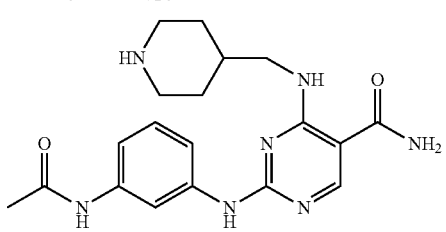 [SMILES: CC(=O)Nc1cccc(Nc2ncc(C(N)=O)c(NCC3CCNCC3)n2)c1]

Scheme 12

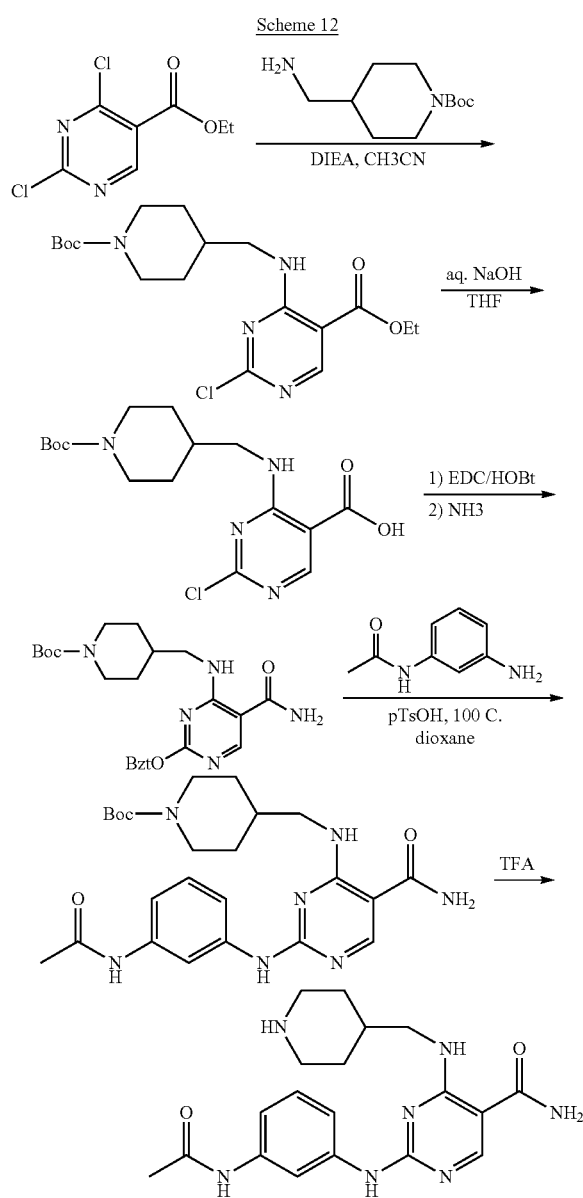

The mixture of ethyl 2,4-dichloropyrimidine-5-carboxylate (442 mg, 2.00 mmol), 1-Boc-4-aminomethylpiperidine hydrochloride (502 mg, 2.00 mmol) and DIEA (1.00 mL, 5.75 mmol) in CH$_3$CN (12 mL) was stirred at room temperature for 3 h. Water and EtOAc were added. The organic phase was separated, washed with 1N HCl, then with 5% NaHCO$_3$, dried over Na$_2$SO$_4$, concentrated in vacuo to give ethyl 4-((1-(tert-butoxycarbonyl)piperidin-4-yl)methylamino)-2-chloropyrimidine-5-carboxylate (797 mg).

To a solution of ethyl 4-((1-(tert-butoxycarbonyl)piperidin-4-yl)methylamino)-2-chloropyrimidine-5-carboxylate (797 mg, 2.00 mmol) in THF (10 mL), aq. 1N NaOH (10 mL, 10.0 mmol) was added. The mixture was stirred at room temperature for 18 h. It was acidified to pH 1-2 with 6N HCl. Water and EtOAc were added. The organic phase was separated, washed with brine, dried over Na$_2$SO$_4$, concentrated in vacuo to give 4-((1-(tert-butoxycarbonyl)piperidin-4-yl)methylamino)-2-chloropyrimidine-5-carboxylic acid (720 mg).

To a solution of 4-((1-(tert-butoxycarbonyl)piperidin-4-yl)methylamino)-2-chloropyrimidine-5-carboxylic acid (720 mg, 1.94 mmol) and HOBt monohydrate (386 mg, 2.52 mmol) in DMF (10 mL), EDC (484 mg, 2.52 mmol) was added. After 1 h of stirring, conc. NH4OH (0.600 mL, ca. 8.40 mmol) was added. The mixture was stirred at room temperature for 18 h. Water and EtOAc were added. The organic phase was separated, washed with 5% NaHCO$_3$, dried over Na$_2$SO$_4$, concentrated in vacuo to give tert-butyl 4-((2-((1H-benzo[d][1,2,3]triazol-1-yloxy)-5-carbamoylpyrimidin-4-ylamino)methyl)piperidine-1-carboxylate (722 mg).

A mixture of tert-butyl 4-((2-((1H-benzo[d][1,2,3]triazol-1-yloxy)-5-carbamoylpyrimidin-4-ylamino)methyl)piperidine-1-carboxylate (107 mg, 0.228 mmol), 3'-amino-acetanilide (41 mg, 0.273 mmol) and pTsOH (50 mg, 0.263 mmol) in dioxane (2 mL) was stirred at 100 C for 5 h. After standing at room temperature overnight, white solids precipitated out, which were collected to give tert-butyl 4-((2-(3-acetamidophenylamino)-5-carbamoylpyrimidin-4-ylamino)methyl)piperidine-1-carboxylate (100 mg).

A solution of tert-butyl 4-((2-(3-acetamidophenylamino)-5-carbamoylpyrimidin-4-ylamino)methyl)piperidine-1-carboxylate (100 mg, 0.207 mmol) in TFA (3 mL) was stirred at room temperature for 30 min. TFA was removed in vacuo. The residue was purified by HPLC to give the titled compound (47 mg). MS 384.4 (M+H); UV 200.0, 248.6 nm.

Example 191

Preparation of 2-(3-acetamidophenylamino)-4-(1-methyl-1H-indazol-4-ylamino)pyrimidine-5-carboxamide

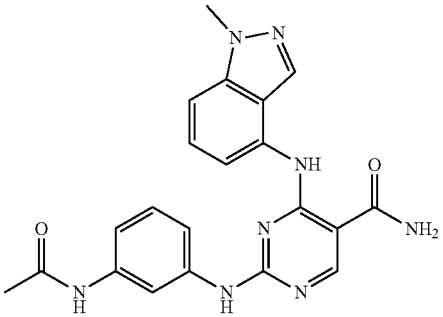 [SMILES: CC(=O)Nc1cccc(Nc2ncc(C(N)=O)c(Nc3cccc4c3cnn4C)n2)c1]

The title compound was prepared using the same synthetic scheme demonstrated in Example 184 with 1-methyl-1H-indazol-4-ylamine to replace 1-methyl-1H-indol-4-ylamine. MS found for C$_{21}$H$_{20}$N$_8$O$_2$ as (M+H)$^+$ 417.3. λ=211.9, 251.5.

Example 192

Preparation of 2-(3-acetamidophenylamino)-4-(benzo[c][1,2,5]thiadiazo-4-ylamino)pyrimidine-5-carboxamide

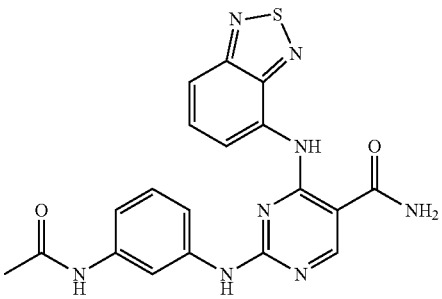 [SMILES: CC(=O)Nc1cccc(Nc2ncc(C(N)=O)c(Nc3cccc4nsnc34)n2)c1]

The title compound was prepared using the same synthetic scheme demonstrated in Example 184 with benzo[c][1,2,5]thiadiazo-4-amine to replace 1-methyl-1H-indol-4-ylamine. MS found for C$_{19}$H$_{16}$N$_8$O$_2$S as (M+H)$^+$ 421.2. λ=243.0, 282.8, 301.9.

Example 193

(R)-2-(4-chloro-3-ureidophenylamino)-4-(1-phenyl-ethylamino)pyrimidine-5-carboxamide

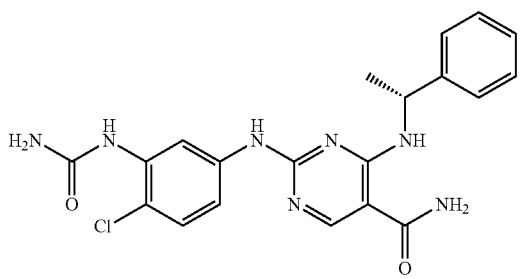 [SMILES: C[C@@H](Nc1nc(Nc2ccc(Cl)c(NC(N)=O)c2)ncc1C(N)=O)c1ccccc1]

The title compound was synthesized similar to step IV in Scheme 10 for Example 121. MS found for $C_{20}H_{20}ClN_7O_2$ as $(M+H)^+$ 412.3. UV: $\lambda$=208, 247 nm. $^1$H NMR: (D-DMSO) $\delta$ 8.5 (s, 1H), 7.3 (m, 5H), 7.1 (d, 1H), 6.4 (bs, 2H), 5.4 (t, 1H), 1.5 (t, 3H).

Example 194

4-(benzylamino)-2-(4-chloro-3-ureidophenylamino) pyrimidine-5-carboxamide

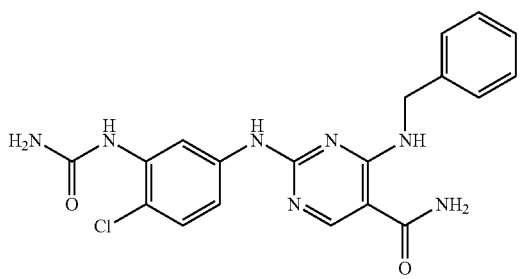 [SMILES: NC(=O)Nc1cc(Nc2ncc(C(N)=O)c(NCc3ccccc3)n2)ccc1Cl]

The title compound was synthesized similar to step IV in Scheme 10 for Example 121. MS found for $C_{19}H_{18}ClN_7O_2$ as $(M+H)^+$ 412.3. UV: $\lambda$=207, 244 nm. $^1$H NMR: (D-DMSO) $\delta$ 8.5 (s, 1H), 7.3 (m, 4H), 7.2 (t, 2H), 7.1 (d, 1H), 4.7 (d, 2H).

Example 195

(R)-2-(4-chloro-3-(3,3-dimethylureido)phenylamino)-4-(1-phenylethylamino) pyrimidine-5-carboxamide

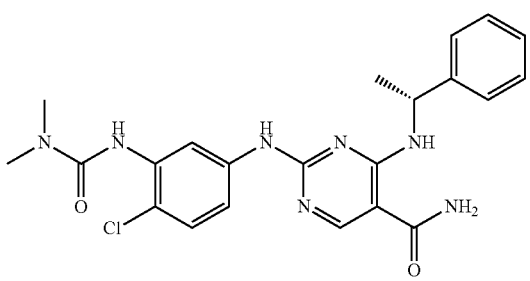 [SMILES: C[C@@H](Nc1nc(Nc2ccc(Cl)c(NC(=O)N(C)C)c2)ncc1C(N)=O)c1ccccc1]

The title compound was synthesized similar to step IV in Scheme 10 for Example 121. MS found for $C_{22}H_{24}ClN_7O_2$ as $(M+H)^+$ 454.4. UV: $\lambda$=208, 248 nm. $^1$H NMR: (D-DMSO) $\delta$ 8.5 (s, 1H (, 8.1 (s, 1H), 7.8 (s, 1H), 7.3 (m, 5H), 7.2 (t, 2H), 5.4 (t, 1H), 2.9 (s, 6H), 1.5 (d, 3H).

Example 196

4-(benzylamino)-2-(4-chloro-3-(3,3-dimethylureido) phenylamino) pyrimidine-5-carboxamide

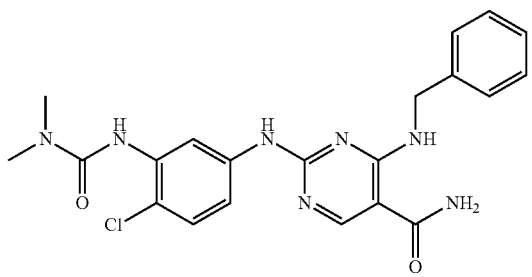 [SMILES: CN(C)C(=O)Nc1cc(Nc2ncc(C(N)=O)c(NCc3ccccc3)n2)ccc1Cl]

The title compound was synthesized similar to step IV in Scheme 10 for Example 121. MS found for $C_{21}H_{22}ClN_7O_2$ as $(M+H)^+$ 440.4. UV: $\lambda$=204, 249 nm. $^1$H NMR: (D-DMSO) $\delta$ 8.5 (s, 1H), 7.8 (s, 1H), 7.2-7.3 (m, 7H), 4.7 (d, 2H), 2.9 (s, 6H).

Example 200

4-(benzylamino)-2-(2-fluoro-5-(3-methylureido) phenylamino)pyrimidine-5-carboxamide

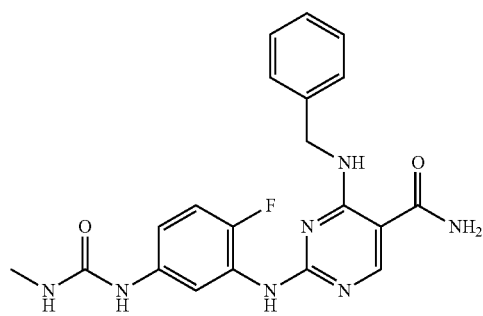 [SMILES: CNC(=O)Nc1ccc(F)c(Nc2ncc(C(N)=O)c(NCc3ccccc3)n2)c1]

The title compound was synthesized similar to Example 121. MS found for $C_{20}H_{20}FN_7O_2$ as $(M+H)^+$ 410.4. UV: $\lambda$=239 nm. $^1$H NMR: (CD$_3$OD) $\delta$ 8.18 (s, 1H), 8.03 (broad s, 1H), 7.18 (m, 6H), 7.09 (m, 1H), 7.00 (m, 1H), 7.62 (s, 2H), 2.61 (s, 3H).

Example 201

4-(benzylamino)-2-(5-(3,3-dimethylureido)-2-fluorophenylamino)pyrimidine-5-carboxamide

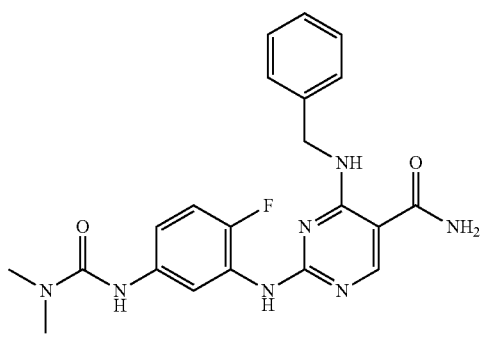 [SMILES: CN(C)C(=O)Nc1ccc(F)c(Nc2ncc(C(N)=O)c(NCc3ccccc3)n2)c1]

The title compound was synthesized similar to Example 121. MS found for $C_{21}H_{22}FN_7O_2$ as $(M+H)^+$ 424.4. UV: λ=210, 244 nm. $^1$H NMR: (CD$_3$OD) δ 8.39 (s, 1H), 8.03 (s, 1H). 7.03-7.22 (m, 7H), 4.63 (s, 2H), 2.84 (s, 6H).

Example 202

(R)-4-(benzylamino)-2-(3-(tetrahydrofuran-2-carboxamido)phenylamino)pyrimidine-5-carboxamide

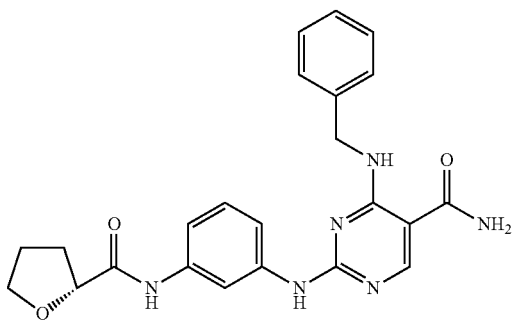 [SMILES: NC(=O)c1cnc(Nc2cccc(NC(=O)[C@H]3CCCO3)c2)nc1NCc1ccccc1]

The title compound was synthesized similar to Example 121. MS found for $C_{23}H_{24}N_6O_3$ as $(M+H)^+$ 433.4. UV: λ=202, 246 nm. $^1$H NMR: (CD$_3$OD) δ 9.51 (s, 1 H), 8.40 (s, 1H), 8.13 (s, 1H), 7.13-7.22 (m, 8H), 4.71 (s, 1H), 4.31 (dd, 1H), 3.92 (dd, 1H), 3.78 (dd, 1H), 2.14 (m, 1H), 1.90 (m, 1H), 1.79 (m, 2H).

Example 203

4-(benzylamino)-2-(3-(tetrahydrofuran-3-carboxamido)phenylamino)pyrimidine-5-carboxamide

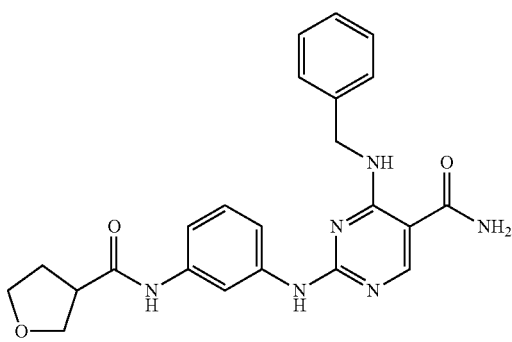 [SMILES: NC(=O)c1cnc(Nc2cccc(NC(=O)C3CCOC3)c2)nc1NCc1ccccc1]

The title compound was synthesized similar to Example 121. MS found for $C_{23}H_{24}N_6O_3$ as $(M+H)^+$ 433.4. UV: λ=205, 251 nm. $^1$H NMR: (CD$_3$OD) δ 9.90 (s, 1H), 8.40 (s, 1H), 8.13 (s, 1H), 7.23 (d, 4H), 7.18 (m, 4H), 7.08 (d, 1H), 4.71 (s, 2H), 3.87 (s, 1H), 3.67 (m, 3H), 3.08 (m, 1H), 2.01 (ddd, 1H).

Example 204

4-(benzylamino)-2-(2-fluoro-5-(pyrrolidine-1-carboxamido)phenylamino)pyrimidine-5-carboxamide

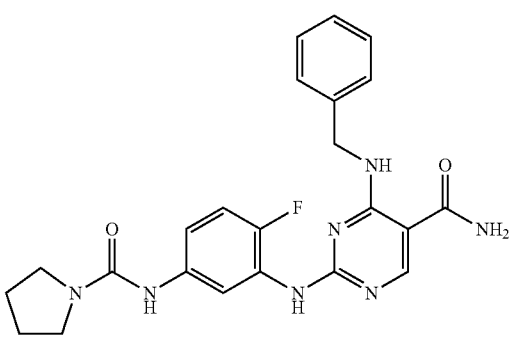 [SMILES: NC(=O)c1cnc(Nc2cc(NC(=O)N3CCCC3)ccc2F)nc1NCc1ccccc1]

The title compound was synthesized similar to Example 121. MS found for $C_{23}H_{24}FN_7O_2$ as $(M+H)^+$ 450.5. UV: λ=239 nm. $^1$H NMR: (CD$_3$OD) δ 8.40 (s, 1H0, 8.08 (s, 1H), 7.18 (m, 6H), 7.09 (t, 1H), 4.62 (s, 2H), 3.30 (m, 4H), 1.80 (m, 4H).

Example 205

(R)-2-(4-chloro-3-(piperidine-1-carboxamido)phenylamino)-4-(1-phenylethylamino)pyrimidine-5-carboxamide

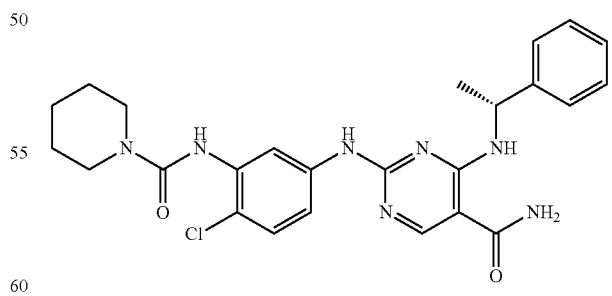

The title compound was synthesized similar to step IV in Scheme 10 for Example 121. MS found for $C_{25}H_{28}ClN_7O_2$ as $(M+H)^+$ 494.5. UV: λ=249 nm. $^1$H NMR: (D-DMSO) δ 8.5 (s, 1H), 8.1 (s, 1H), 7.1-7.5 (m, 7H), 5.4 (t, 1H), 3.4 (t, 4H), 1.6 (d, 2H), 1.5 (m, 9H).

Example 206

(S)-4-(benzylamino)-2-(3-(tetrahydrofuran-2-carboxamido) phenylamino)pyrimidine-5-carboxamide

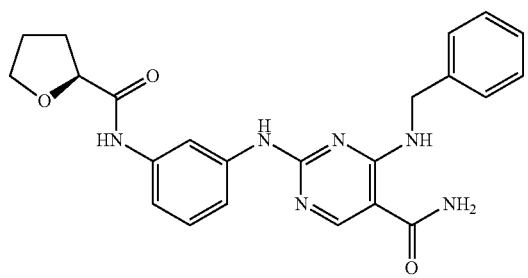 [SMILES: NC(=O)c1cnc(Nc2cccc(NC(=O)[C@@H]3CCCO3)c2)nc1NCc1ccccc1]

The title compound was synthesized similar to step IV in Scheme 10 for Example 121. MS found for C₂₃H₂₄N₆O₃ as (M+H)⁺ 433.4. UV: λ=249 nm. ¹H NMR: (D-DMSO) δ 8.5 (s, 1H), 8.2 (s, 1H), 7.3 (dd, 4H), 7.05-7.15 (m, 4H), 4.7 (d, 2H), 4.35 (t, 1H), 2.15 (m, 2H), 1.9 (m, 2H), 1.8 (m, 2H).

Example 207

4-((R)-1-phenylethylamino)-2-(3-((S)-tetrahydrofuran-2-carboxamido)phenylamino)pyrimidine-5-carboxamide

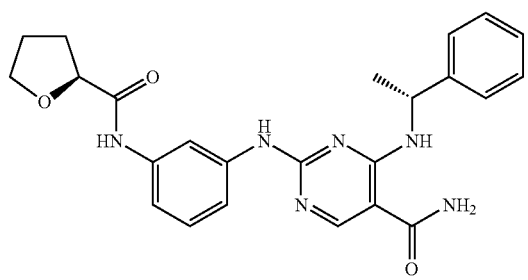 [SMILES: C[C@@H](Nc1nc(Nc2cccc(NC(=O)[C@@H]3CCCO3)c2)ncc1C(N)=O)c1ccccc1]

The title compound was synthesized similar to step IV in Scheme 10 for Example 121. MS found for C₂₄H₂₆N₆O₃ as (M+H)⁺ 447.5. UV: λ=249 nm. ¹H NMR: (D-DMSO) δ 8.5 (s, 1H0, 8.2 (s, 1H), 7.3 (dd, 4H), 7.2 (m, 4H), 5.4 (t, 1H), 4.4 (t, 1H), 2.2, (m, 2H), 1.8 (m, 2H), 1.8 (m, 2H), 1.5 (d, 3H).

Example 208

(S)-4-(3-fluorobenzylamino)-2-(3-(tetrahydrofuran-2-carboxamido) phenylamino)pyrimidine-5-carboxamide

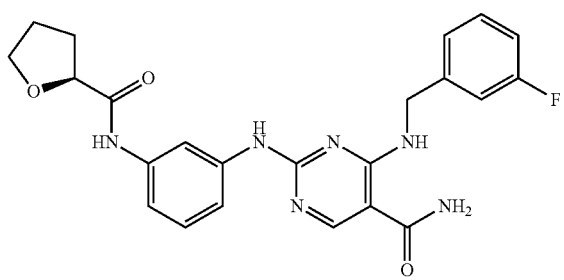 [SMILES: NC(=O)c1cnc(Nc2cccc(NC(=O)[C@@H]3CCCO3)c2)nc1NCc1cccc(F)c1]

The title compound was synthesized similar to step IV in Scheme 10 for Example 121. MS found for C₂₃H₂₃FN₆O₃ as (M+H)⁺ 451.4. UV: λ=207, 240 nm. ¹H NMR: (D-DMSO) δ 8.5 (s, 1H), 7.0-7.2 (m, 8H), 4.7 (d, 2H), 4.5 (t, 1H), 3.9 (d, 1H), 3.8 (d, 1H), 2.1 (m, 1H), 1.9 (m, 1H), 1.8 (d, 2H).

Example 209

4-(benzylamino)-2-(4-chloro-3-(piperidine-1-carboxamido) phenylamino)pyrimidine-5-carboxamide

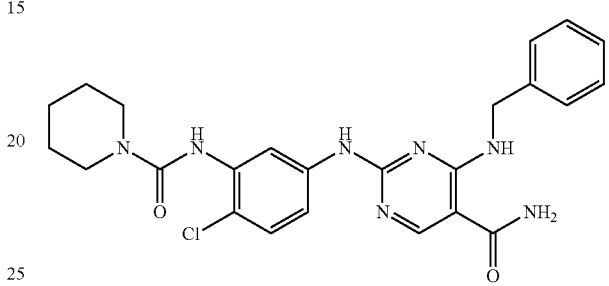

The title compound was synthesized similar to step IV in Scheme 10 for Example 121. MS found for C₂₄H₂₆ClN₇O₂ as (M+H)⁺ 480.5. UV: λ=207, 249 nm. ¹H NMR: (D-DMSO) δ 8.5 (s, 1H), 8.0 (s, 2H), 7.2-7.3 (m, 7H), 4.7 (d, 2H), 3.4 (t, 4H), 1.5 (d, 2H), 1.4 (d, 4H).

Example 210

(R)-4-(benzylamino)-2-(3-(3-(dimethylamino)pyrrolidine-1-carboxamido)phenylamino)pyrimidine-5-carboxamide

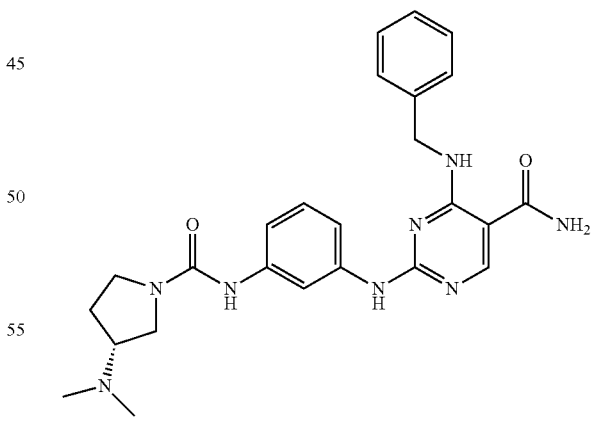

The title compound was synthesized similar to Example 121. MS found for C₂₅H₃₀N₈O₂ as (M+H)⁺ 475.6. UV: λ=205, 246 nm. ¹H NMR: (CD₃OD) δ 8.43 (s, 1H), 7.92 (s, 1H), 7.50 (d, 1H), 7.27 (d, 3H), 7.20 (m, 1H), 7.12 (m, 2H), 7.04 (m, 1H), 4.71 (s, 2H), 3.77 (m, 2H), 3.59 (m, 1H), 3.45 (m, 1H), 3.38 (m, 1H), 3.31 (m, 1H), 2.79, s, 6H), 2.31 (m, 1H), 2.08 (m, 1H).

Example 212

(R)-4-(benzylamino)-2-(3-(3-hydroxypiperidine-1-carboxamido)phenylamino)pyrimidine-5-carboxamide

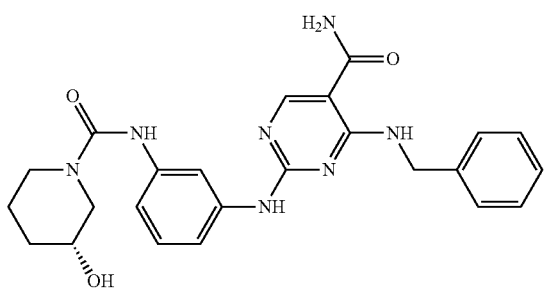 [SMILES: NC(=O)c1cnc(Nc2cccc(NC(=O)N3CCC[C@@H](O)C3)c2)nc1NCc1ccccc1]

The title compound was synthesized similar to Example 121. MS found for $C_{24}H_{27}N_7O_3$ as $(M+H)^+$ 462.5. UV: $\lambda$=249 nm.

Example 213

6-(3-acetamidophenylamino)-4-(benzylamino)nicotinamide

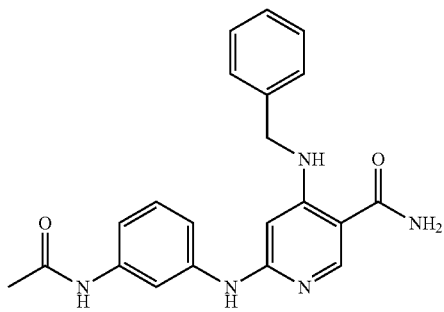 [SMILES: CC(=O)Nc1cccc(Nc2cc(NCc3ccccc3)c(C(N)=O)cn2)c1]

The title compound was synthesized similar Scheme 11 for Example 184, however the final step was accomplished thermally without the use of palladium catalysis. MS found for $C_{21}H_{21}N_5O_2$ as $(M+H^+$ 376.4. UV: $\lambda$=207, 254 nm. $^1$H NMR: (CD$_3$OD) δ 8.20 (s, 1H), 7.78 (s, 1H), 7.33 (m, 7H), 6.84 (d, 1H), 6.03 (s, 1H), 4.52 (s, 2H), 2.17 (s, 3H).

Example 215

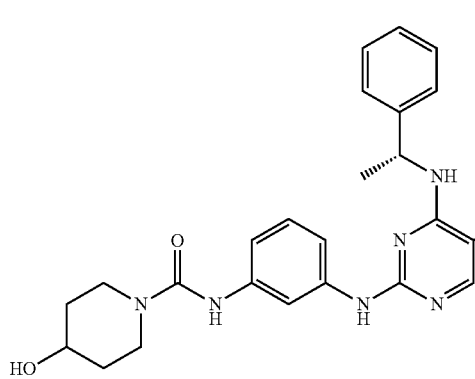

The title compound was synthesized similar to Example 121. MS found for $C_{25}H_{29}N_7O_3$ as $(M+H)^+$ 476.6.

Example 216

4-(benzylamino)-2-(3-(4-methylpiperazine-1-carboxamido)phenylamino) pyrimidine-5-carboxamide

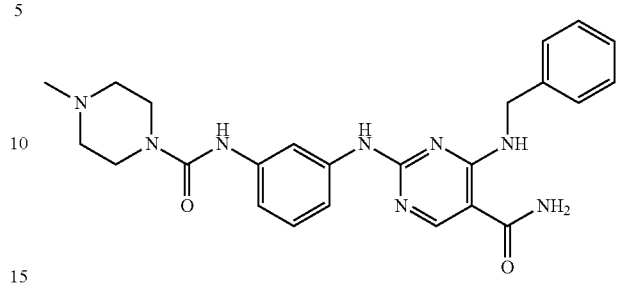

The title compound was synthesized similar to step IV in Scheme 10 for Example 121. MS found for $C_{24}H_{28}N_8O_2$ as $(M+H)^+$ 460.4. UV: $\lambda$=212, 246 nm. $^1$H NMR: (D-DMSO) δ 8.7 (s, 1H), 8.7 (s, 1H), 7.9 (s, 1H), 7.3 (d, 4H), 7.2 (dd, 3H), 7.1 (t, 1H), 7.0 (d, 1H), 4.7 (d, 2H), 4.2 (d, 2H), 3.1 (t, 3H), 2.9 (t, 2H), 2.8 (s, 3H).

Example 217

N-(3-(4-(benzylamino)-5-carbamoylpyrimidin-2-ylamino)phenyl)morpholine-4-carboxamide

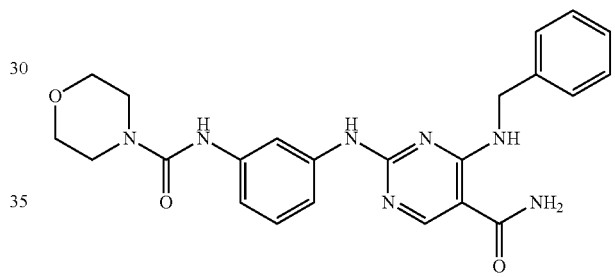

The title compound was synthesized similar to step IV in Scheme 10 for Example 121. MS found for $C_{23}H_{25}N_7O_3$ as $(M+H)^+$ 448.5. UV: $\lambda$=211, 245 nm. $^1$H NMR: (D-DMSO) δ 10 (bs, 1H), 8.6 (s, 1H), 8.5 (s, 1H), 7.0 (bs, 1H), 7.9 (s, 1H), 7.4 (bs, 1H), 7.3 (d, 4H), 7.2 (d, 1H), 7.1 d, 2H), 7.0 (d, 1H), 4.7 (d, 2H), 3.5 (t, 4H), 3.4 (t, 4H).

Example 218

4-(benzylamino)-2-(3-(piperidine-1-carboxamido)phenylamino)pyrimidine-5-carboxamide

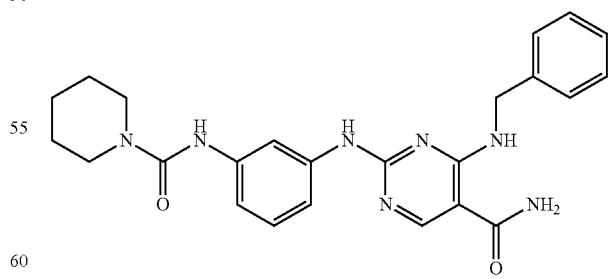

The title compound was synthesized similar to step IV in Scheme 10 for Example 121. MS found for $C_{24}H_{27}N_7O_2$ as $(M+H)^+$ 446.5. UV: $\lambda$=249 nm. $^1$H NMR: (D-DMSO) δ 8.5 (d, 2H), 8.0 (bs, 1H), 7.9 (s, 1H), 7.5 (bs, 1H), 7.3 (d, 4H), 7.25 (dd, 1H), 7.0-7.1 (m, 3H), 4.7 (d, 2H), 3.4 (t, 4H), 1.5 (d, 2H), 1.4 (d, 4H).

Example 219

2-(3-(azetidine-1-carboxamido)phenylamino)-4-(benzylamino) pyrimidine-5-carboxamide

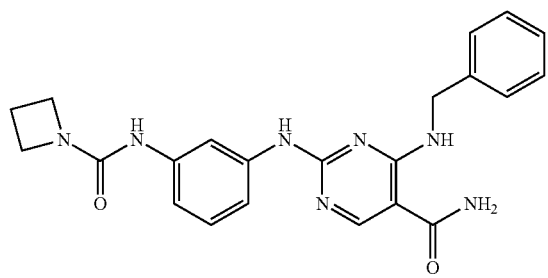 [SMILES: NC(=O)c1cnc(Nc2cccc(NC(=O)N3CCC3)c2)nc1NCc1ccccc1]

The title compound was synthesized similar to step IV in Scheme 10 for Example 121. MS found for $C_{24}H_{26}FN_7O_2$ as $(M+H)^+$ 464.5. UV: λ=249 nm. $^1$H NMR: (D-DMSO) δ 8.5 (s, 1H), 8.45 (s, 1H), 8.0 (s, 1H), 7.3 (t, 1H), 7.1 (m, 6H), 4.7 (d, 2H), 3.4 (t, 4H), 1.5 (d, 2H), 1.4 (d, 4H).

Example 220

(R)-4-(1-phenylethylamino)-2-(3-(piperidine-1-carboxamido) phenylamino)pyrimidine-5-carboxamide

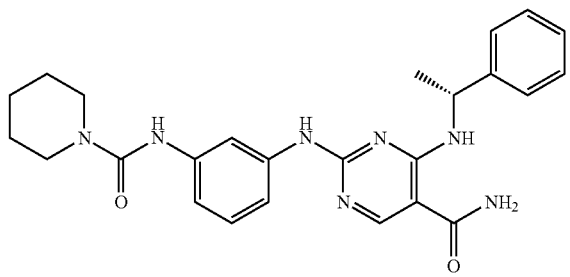 [SMILES: C[C@@H](Nc1nc(Nc2cccc(NC(=O)N3CCCCC3)c2)ncc1C(N)=O)c1ccccc1]

The title compound was synthesized similar to step IV in Scheme 10 for Example 121. MS found for $C_{25}H_{29}N_7O_2$ as $(M+H)^+$ 460. UV: λ=249 nm. $^1$H NMR: (D-DMSO) δ 8.5 (d, 2H), 8.0 (s, 1H), 7.3 (m, 4H), 7.2 (d, 1H), 7.1 (d, 1H), 7.05 (d, 1H), 6.95 (s, 1H), 5.4 (t, 1H),1.5 (d, 2H), 1.4 (dd, 7H).

Example 221

(R)-2-(4-chloro-3-(pyrrolidine-1-carboxamido)phenylamino)-4-(1-phenylethylamino)pyrimidine-5-carboxamide

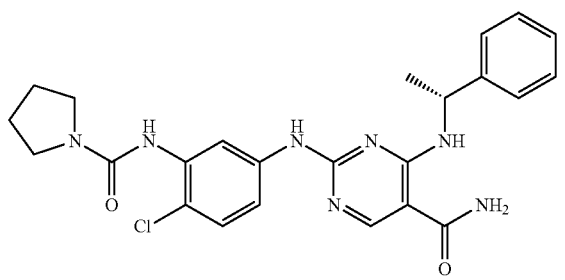 [SMILES: C[C@@H](Nc1nc(Nc2ccc(Cl)c(NC(=O)N3CCCC3)c2)ncc1C(N)=O)c1ccccc1]

The title compound was synthesized similar to step IV in Scheme 10 for Example 121. MS found for $C_{24}H_{26}ClN_7O_2$ as $(M+H)^+$ 480.5. UV: λ=205, 249 nm. $^1$H NMR: (D-DMSO) δ 8.5 (s, 1H), 8.2 (s, 1H), 7.4 (s, 1H), 7.3 (m 5H), 7.2 (d, 1H), 5.4 (t, 1H), 3.3 (t, 4H), 1.9 (s, 4H), 1.4 (d, 3H).

Example 222

2-(3-(azetidine-1-carboxamido)phenylamino)-4-(benzylamino) pyrimidine-5-carboxamide

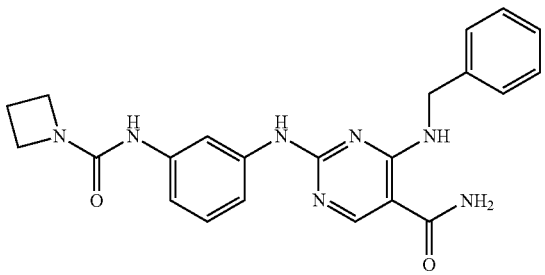 [SMILES: NC(=O)c1cnc(Nc2cccc(NC(=O)N3CCC3)c2)nc1NCc1ccccc1]

The title compound was synthesized similar to step IV in Scheme 10 for Example 121. MS found for $C_{22}H_{23}N_7O_2$ as $(M+H)^+$ 418.5. UV: λ=249 nm. $^1$H NMR: (D-DMSO) δ 8.5 (s, 1H), 8.3 (s, 1H), 7.9 (s, 1H), 7.3 (d, 4H), 7.2 (t, 1H), 7.1 (d, 1H), 7.05 (t, 1H), 4.7 (d, 2H), 3.9 (t, 4H), 2.2 (dd, 2H).

Example 223

Preparation of 2-(3-acetamido-4-(2-(pyrrolidin-1-yl)ethoxy)phenylamino)-4-(3-fluorobenzylamino)pyrimidine-5-carboxamide Scheme 13

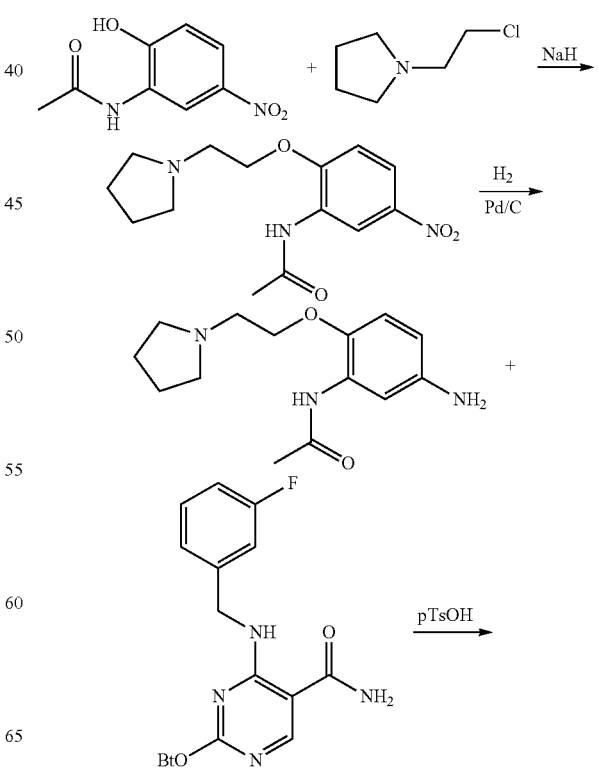

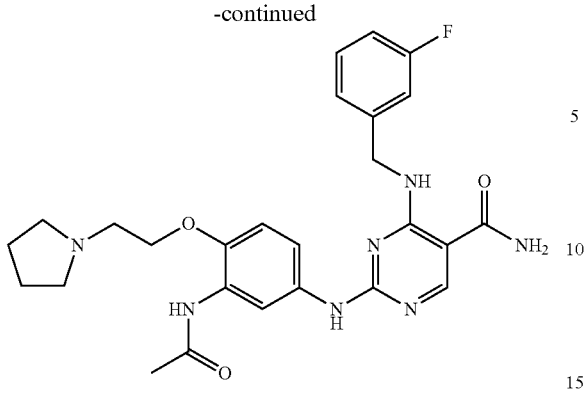

Step 1: To a solution of N-(2-hydroxy-5-nitrophenyl)acetamide (870 mg, 4.44 mmol) in DMF (5 mL) was added NaH (196 mg, 5.32 mmol) and $K_2CO_3$ (2.11 g, 13.32 mmol), followed by 1-(2-chloroethyl)pyrrolidine hydrochloride (905 mg, 5.32 mmol). After heating at 100° C. for 20 h, the solution was poured to ice, and was extracted with EtOAc, organic layer was washed with Sat. $NaHCO_3$, brine, dried and concentrated to give N-(5-nitro-2-(2-(pyrrolidin-1-yl)ethoxy)phenyl)acetamide (430 mg).

Step 2: To a solution of N-(5-nitro-2-(2-(pyrrolidin-1-yl)ethoxy)phenyl)acetamide (430 mg) in EtOH (10 mL) was added Pd/C (200 mg) and was charged with $H_2$ (1 atm). After stirring for 3 h, Pd/C was removed by filtration and the filtrate was concentrated to give N-(5-amino-2-(2-(pyrrolidin-1-yl)ethoxy)phenyl)acetamide (380 mg).

Step 3: To a solution of 2-(1H-benzo[d][1,2,3]triazol-1-yloxy)-4-(3-fluorobenzylamino)pyrimidine-5-carboxamide (57 mg, 0.15 mmol) in NMP (0.6 mL) was added N-(5-amino-2-(2-(pyrrolidin-1-yl)ethoxy)phenyl)acetamide (47 mg, 0.18 mmol) and pTsOH.H2O (28 mg, 0.15 mmol). The mixture was heated at 100° C. for 2 h, cooled to room temperature, and purified by preparative HPLC to give 2-(3-acetamido-4-(2-(pyrrolidin-1-yl)ethoxy)phenylamino)-4-(3-fluorobenzylamino)pyrimidine-5-carboxamide (46 mg). MS found for $C_{26}H_{30}FN_7O_3$ as $(M+H)^+$ 508.5. λ 248.5.

Example 224

Preparation of 2-(3-acetamido-4-(2-(pyrrolidin-1-yl)ethoxy)phenylamino)-4-(2-methyl-2H-indazol-4-ylamino)pyrimidine-5-carboxamide

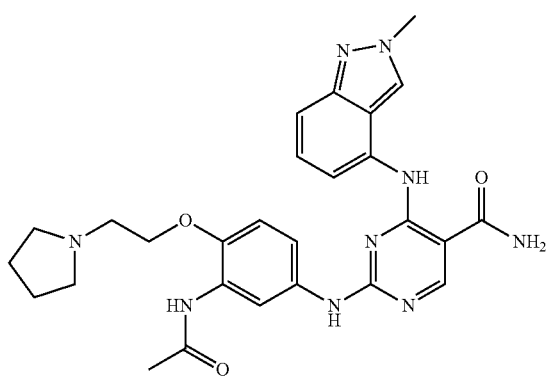 [SMILES: CC(=O)Nc1cc(Nc2ncc(C(N)=O)c(Nc3cccc4nn(C)cc34)n2)ccc1OCCN1CCCC1]

The title compound was prepared using the same synthetic scheme demonstrated in Example 223. MS found for $C_{27}H_{31}N_9O_3$ as (M+H) 530.5. λ=250.9, 286.5.

Example 225 tert-butyl 3-((2-(3-acetamidophenylamino)-5-carbamoylpyrimidin-4-ylamino)methyl)pyrrolidine-1-carboxylate

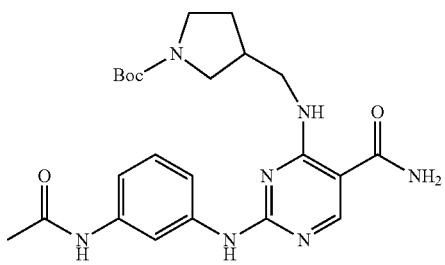 [SMILES: CC(=O)Nc1cccc(Nc2ncc(C(N)=O)c(NCC3CCN(C(=O)OC(C)(C)C)C3)n2)c1]

Scheme 14

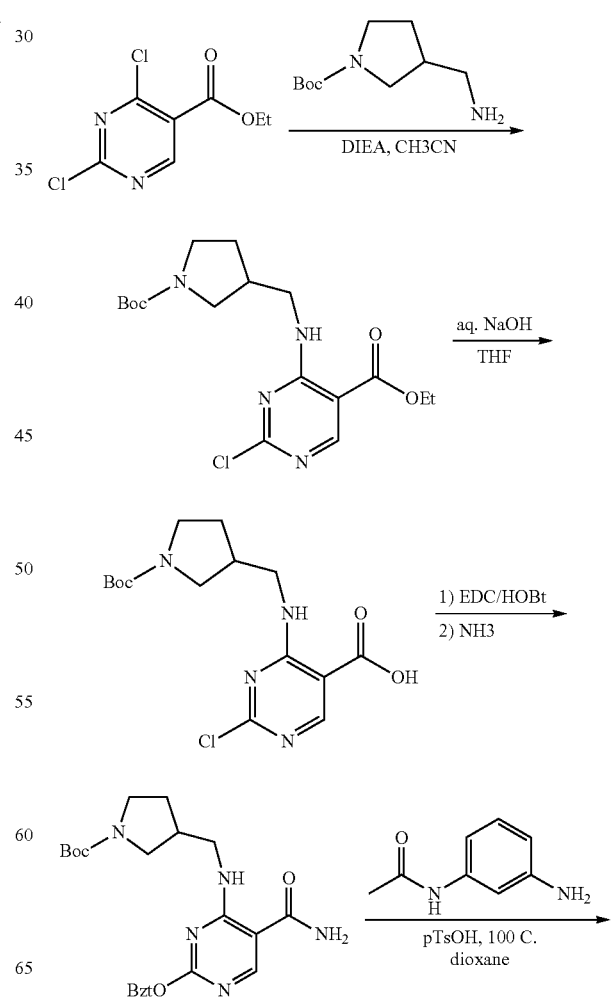

-continued

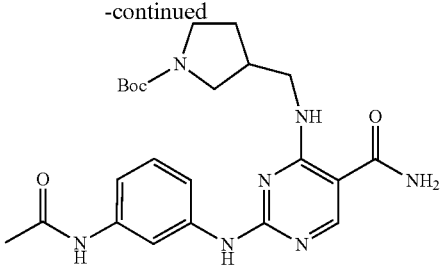

The mixture of ethyl 2,4-dichloropyrimidine-5-carboxylate (332 mg, 1.50 mmol), 1-Boc-3-aminomethylpyrrolidine (300 mg, 1.50 mmol) and DIEA (0.650 mL, 3.73 mmol) in $CH_3CN$ (6 mL) was stirred at room temperature for 18 h. Water and EtOAc were added. The organic phase was separated, washed with 1N HCl, then with 5% $NaHCO_3$, dried over $Na_2SO_4$, concentrated in vacuo to give ethyl 4-((1-(tert-butoxycarbonyl)pyrrolidin-3-yl)methylamino)-2-chloropyrimidine-5-carboxylate (544 mg).

To a solution of ethyl 4-((1-(tert-butoxycarbonyl)pyrrolidin-3-yl)methylamino)-2-chloropyrimidine-5-carboxylate (544 mg, 1.41 mmol) in THF (8 mL), aq. 1N NaOH (8 mL, 8.0 mmol) was added. The mixture was stirred at room temperature for 18 h. It was acidified to pH 1-2 with 6N HCl. Water and EtOAc were added. The organic phase was separated, washed with brine, dried over $Na_2SO_4$, concentrated in vacuo to give 4-((1-(tert-butoxycarbonyl)pyrrolidin-3-yl)methylamino)-2-chloropyrimidine-5-carboxylic acid (503 mg).

To a solution of 4-((1-(tert-butoxycarbonyl)pyrrolidin-3-yl)methylamino)-2-chloropyrimidine-5-carboxylic acid (503 mg, 1.41 mmol) and HOBt monohydrate (280 mg, 1.83 mmol) in DMF (8 mL), EDC (352 mg, 1.83 mmol) was added. After 1 h of stirring, conc. NH4OH (0.400 mL, ca. 5.60 mmol) was added. The mixture was stirred at room temperature for 18 h. Water and EtOAc were added. The organic phase was separated, washed with 5% $NaHCO_3$, dried over $Na_2SO_4$, concentrated in vacuo to give tert-butyl 3-((2-(1H-benzo[d][1,2,3]triazol-1-yloxy)-5-carbamoylpyrimidin-4-ylamino)methyl)pyrrolidine-1-carboxylate (472 mg).

A mixture of tert-butyl 3-((2-(1H-benzo[d][1,2,3]triazol-1-yloxy)-5-carbamoylpyrimidin-4-ylamino)methyl)pyrrolidine-1-carboxylate (118 mg, 0.260 mmol), 3'-amino-acetamide (47 mg, 0.31 mmol) and pTsOH (57 mg, 0.30 mmol) in dioxane (2 mL) was stirred at 100 C for 18 h, during which time white solids precipitated out, which were collected and purified by HPLC to give the titled compound (69 mg). MS 470.6 (M+H); UV 202.2, 248.6 nm.

Example 226

2-(3-acetamidophenylamino)-4-(pyrrolidin-3-ylmethylamino)pyrimidine-5-carboxylic acid

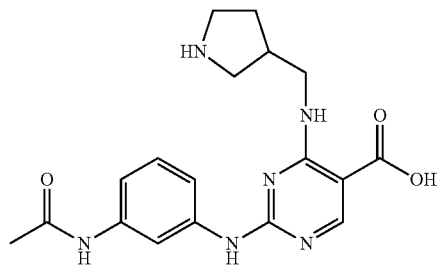 [SMILES: CC(=O)Nc1cccc(Nc2ncc(C(=O)O)c(NCC3CCNC3)n2)c1]

Scheme 15

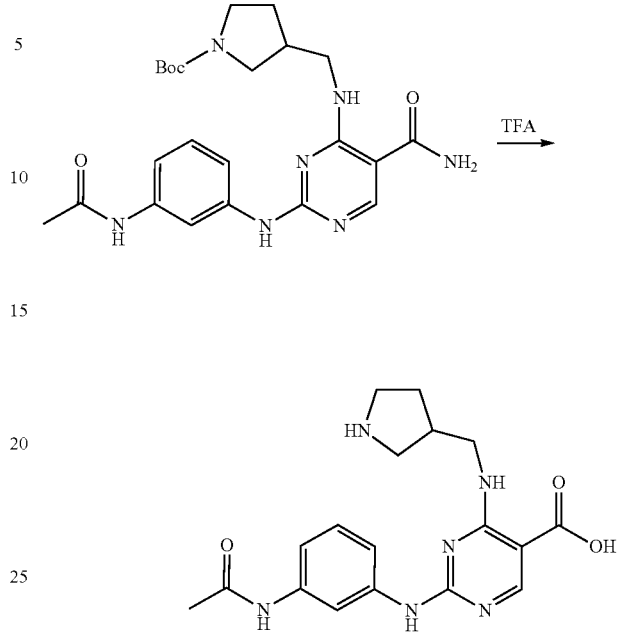

A solution of tert-butyl 3-((2-(3-acetamidophenylamino)-5-carbamoylpyrimidin-4-ylamino)methyl)pyrrolidine-1-carboxylate (65 mg, 0.138 mmol) in TFA (1 mL) and $CH_2Cl_2$ mL) was stirred at room temperature for 2 h. TFA and $CH_2Cl_2$ were removed in vacuo. The residue was purified by HPLC to give the titled compound (25 mg). MS 370.3 (M+H); UV 206.4, 244.2 nm.

Example 227

Preparation of 2-(3-acetamido-4-(2-(pyrrolidin-1-yl)ethoxy)phenylamino)-4-(benzo[c][1,2,5]thiadiazo-4-ylamino)pyrimidine-5-carboxamide

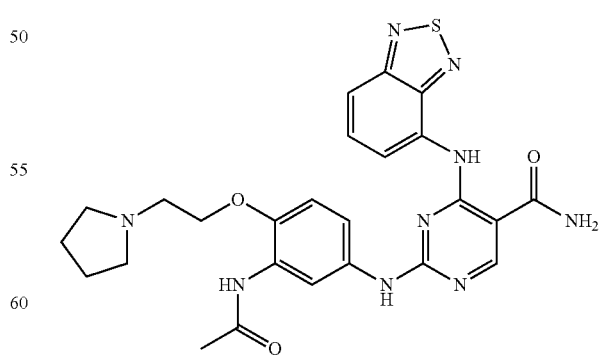

The title compound was prepared using the same synthetic scheme demonstrated in Example 223. MS found for $C_{25}H_{27}N_9O_3S$ as $(M+H)^+$ 534.3. $\lambda$=203.4, 238.1, 289.0.

Example 228

Preparation of 2-(3-acetamido-4-(2-(dimethylamino)ethoxy)phenylamino)-4-(3-fluorobenzylamino)pyrimidine-5-carboxamide

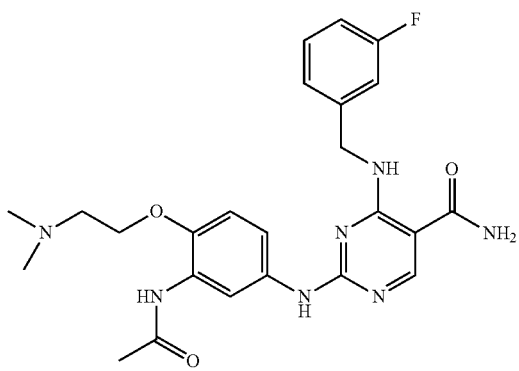 [SMILES: CC(=O)Nc1cc(Nc2ncc(C(N)=O)c(NCc3cccc(F)c3)n2)ccc1OCCN(C)C]

The title compound was prepared using the same synthetic scheme demonstrated in Example 223. MS found for $C_{24}H_{28}FN_7O_3$ as (M+H)$^+$ 482.4. λ=208.2, 248.5.

Example 229

Preparation of 2-(3-acetamido-4-(2-(dimethylamino)ethoxy)phenylamino)-4-(2-methyl-2H-indazol-4-ylamino)pyrimidine-5-carboxamide

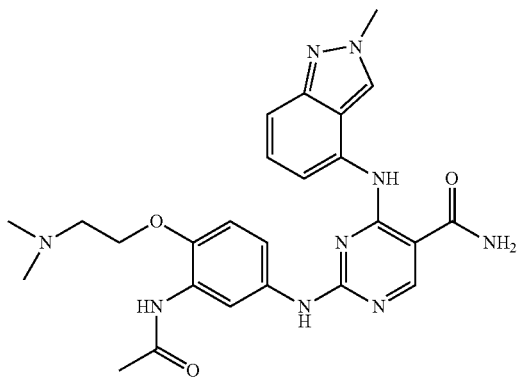 [SMILES: CC(=O)Nc1cc(Nc2ncc(C(N)=O)c(Nc3cccc4nn(C)cc34)n2)ccc1OCCN(C)C]

The title compound was prepared using the same synthetic scheme demonstrated in Example 223. MS found for $C_{25}H_{29}N_9O_3$ as (M+H)$^+$ 504.4. λ=250.9, 285.9.

Example 230

Preparation of 2-(3-acetamido-4-(2-(dimethylamino)ethoxy)phenylamino)-4-(benzo[c][1,2,5]thiadiazo-4-ylamino)pyrimidine-5-carboxamide

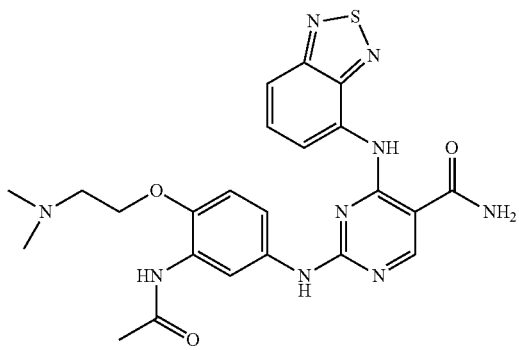 [SMILES: CC(=O)Nc1cc(Nc2ncc(C(N)=O)c(Nc3cccc4nsnc34)n2)ccc1OCCN(C)C]

The title compound was prepared using the same synthetic scheme demonstrated in Example 223. MS found for $C_{23}H_{25}N_9O_3S$ as (M+H)$^+$ 508.4. λ=241.1, 300.7.

Example 231

Preparation of 2-(3-acetamido-4-(2-(piperidin-1-yl)propoxy)phenylamino)-4-(3-fluorobenzylamino)pyrimidine-5-carboxamide

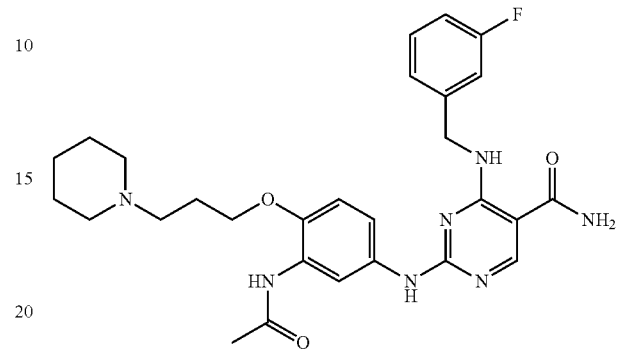

The title compound was prepared using the same synthetic scheme demonstrated in Example 223. MS found for $C_{28}H_{34}FN_7O_3$ as (M+H)$^+$ 536.4. λ=209.8, 247.5.

Example 232

Preparation of 2-(3-acetamido-4-(2-(piperidin-1-yl)propoxy)phenylamino)-4-(2-methyl-2H-indazol-4-ylamino)pyrimidine-5-carboxamide

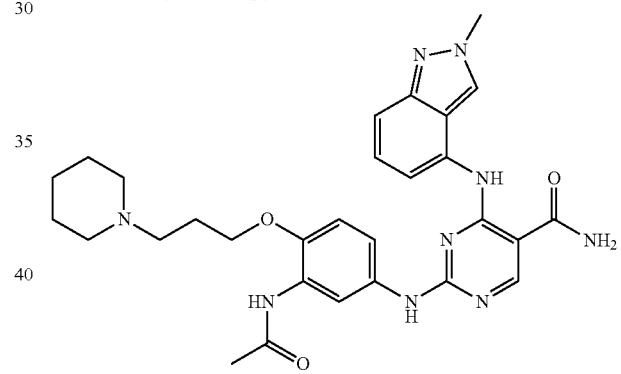

The title compound was prepared using the same synthetic scheme demonstrated in Example 223. MS found for $C_{29}H_{35}N_9O_3$ as (M+H)$^+$ 558.6. λ=247.5, 286.6.

Example 233

2-(3-(azetidine-1-carboxamido)-4-chlorophenylamino)-4-(benzylamino)pyrimidine-5-carboxamide

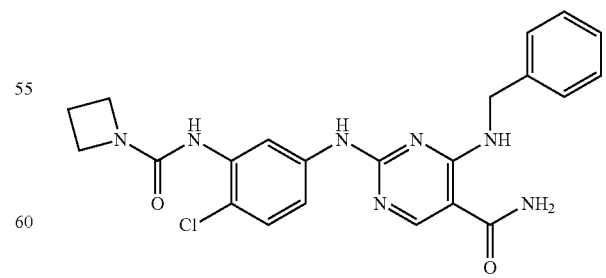

The title compound was synthesized similar to step IV in Scheme 10 for Example 121. MS found for $C_{22}H_{22}ClN_7O_2$ as (M+H)$^+$ 452.4. UV: λ=207, 249 nm. $^1$H NMR: (D-DMSO) δ 8.5 (s, 1H), 8.2 (s, 1H), 7.7m (s, 1H), 7.3 (d, 4H), 7.2 (dd, 2H), 4.7 (d, 2H), 3.9 (t, 4H), 2.1 (dd, 2H).

Example 234

2-(3-(azetidine-1-carboxamido)-4-fluorophenylamino)-4-(benzylamino)pyrimidine-5-carboxamide

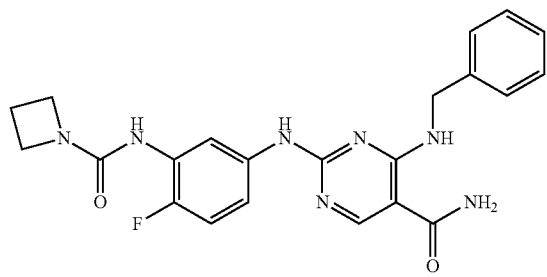 [SMILES: NC(=O)c1cnc(Nc2ccc(F)c(NC(=O)N3CCC3)c2)nc1NCc1ccccc1]

The title compound was synthesized similar to step IV in Scheme 10 for Example 121. MS found for $C_{22}H_{22}FN_7O_2$ as $(M+H)^+$ 436.4. UV: $\lambda=207, 244$ nm. $^1$H NMR: (D-DMSO) δ 8.5 (s, 1H), 8.0 (s, 1H), 7.3 (s, 4H), 7.2 (m, 2H), 7.0 (t, 1H), 4.7 (d, 2H), 3.9 (t, 4H), 2.1 (t, 2H).

Example 235

2-(3-acetamidophenylamino)-4-(isobutylamino)pyrimidine-5-carboxamide

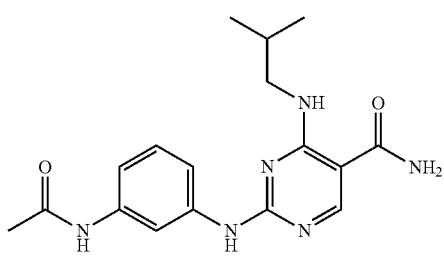 [SMILES: CC(=O)Nc1cccc(Nc2ncc(C(N)=O)c(NCC(C)C)n2)c1]

The title compound was synthesized similar to Example 121. MS found for $C_{17}H_{22}N_6O_2$ as $(M+H)^+$ 343.3. $^1$H NMR: (CD$_3$OD) δ 8.38 (s, 1H), 8.17 *s, 1H), 7.38 (m, 2H), 7.20 (d, 1H), 3.44 (d, 2H), 2.16 (s, 3H), 1.98 (m, 1H), 1.99 (d, 6H).

Example 236

2-(4-chloro-3-(pyrrolidine-1-carboxamido)phenylamino)-4-(isobutylamino)pyrimidine-5-carboxamide

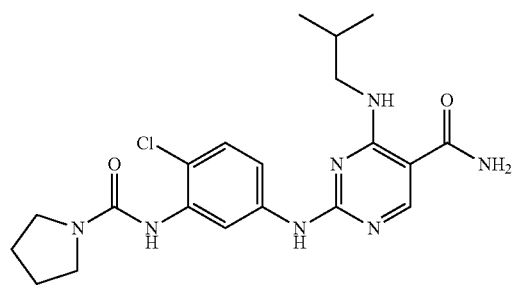 [SMILES: CC(C)CNc1nc(Nc2ccc(Cl)c(NC(=O)N3CCCC3)c2)ncc1C(N)=O]

The title compound was synthesized similar to Example 121. MS found for $C_{20}H_{26}ClN_7O_2$ as $(M+H)^+$ 432.5. $^1$H NMR: (CD$_3$OD) δ

Example 237

(R)-4-(sec-butylamino)-2-(4-chloro-3-(pyrrolidine-1-carboxamido)phenylamino)pyrimidine-5-carboxamide

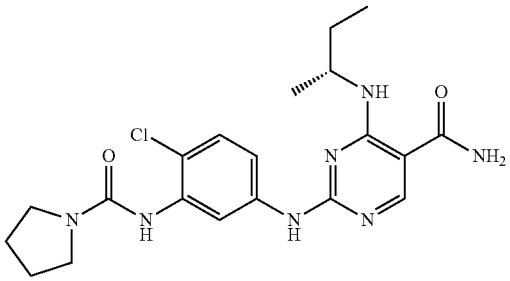 [SMILES: CC[C@@H](C)Nc1nc(Nc2ccc(Cl)c(NC(=O)N3CCCC3)c2)ncc1C(N)=O]

The title compound was synthesized similar to Example 121. MS found for $C_{20}H_{26}ClN_7O_2$ as $(M+H)^+$ 434.5. UV: $\lambda=202, 247$ nm.

Example 238

(R)-2-(3-acetamidophenylamino)-4-(sec-butylamino)pyrimidine-5-carboxamide

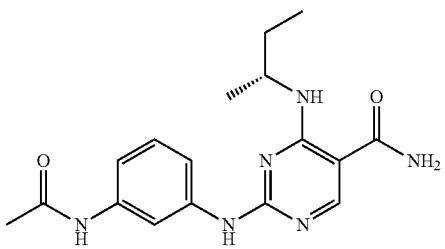 [SMILES: CC[C@@H](C)Nc1nc(Nc2cccc(NC(C)=O)c2)ncc1C(N)=O]

The title compound was synthesized similar to Example 121. MS found for $C_{17}H_{22}N_6O_2$ as $(M+H)^+$ 343.4. UV: $\lambda=202, 248$ nm. $^1$H NMR: (CD$_3$OD) δ 8.43 (s, 1H), 8.13 (s, 1H), 7.37 (d, 2H), 7.23 (m, 1H), 4.28 (q, 1H), 2.17 (s, 3H), 1.66 (m, 2H), 1.30 (d, 3H), 0.8 (t, 3H).

Example 239

4-(benzylamino)-2-(4-methoxy-3-(N-methylpyrrolidine-1-carboxamido)phenylamino)pyrimidine-5-carboxamide

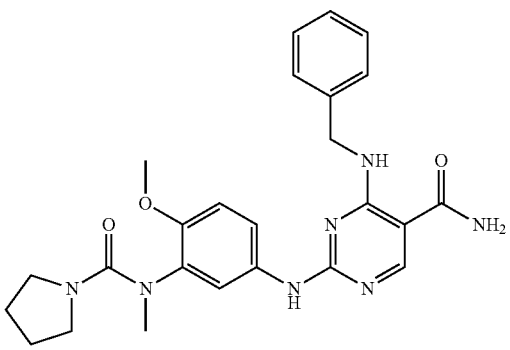 [SMILES: COc1ccc(Nc2ncc(C(N)=O)c(NCc3ccccc3)n2)cc1N(C)C(=O)N1CCCC1]

The title compound was synthesized similar to Example 121. MS found for $C_{25}H_{29}N_7O_3$ as $(M+H)^+$ 476.5. UV: $\lambda=205, 251$ nm. $^1$H NMR: (CD$_3$OD) δ

Example 240

4-(3-fluorobenzylamino)-2-(4-methoxy-3-(N-methylpyrrolidine-1-carboxamido)phenylamino)pyrimidine-5-carboxamide

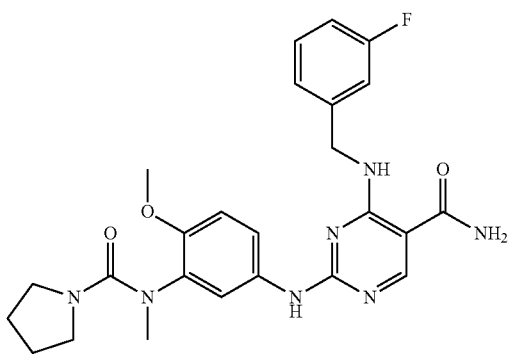 [SMILES: COc1ccc(Nc2ncc(C(N)=O)c(NCc3cccc(F)c3)n2)cc1N(C)C(=O)N1CCCC1]

The title compound was synthesized similar to Example 121. MS found for $C_{25}H_{28}FN_7O_3$ as $(M+H)^+$ 494.5. UV: $\lambda$=205, 251 nm. $^1$H NMR: (CD$_3$OD) δ 8.44 8.55 (s, 1H), 7.76 (s, 1H), 7.43 (m, 3H), 7.24 (d, 1H), 7.17 (d, 1H), 7.03 (t, 1H), 4.80 (s, 2H), 4.67 (s, 3H), 3.08 (s, 3H), 3.02 (m, 4H), 1.73 (m, 4H).

Example 241

4-(benzylamino)-2-(4-chloro-3-(N-methylpyrrolidine-1-carboxamido)phenylamino)pyrimidine-5-carboxamide

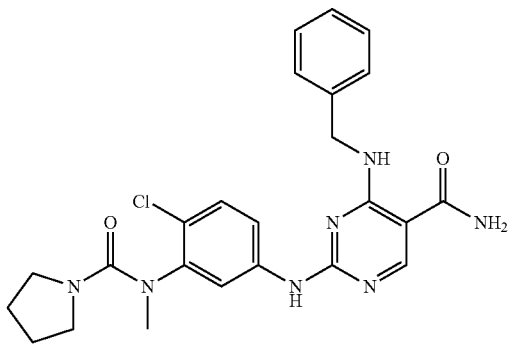 [SMILES: CN(C(=O)N1CCCC1)c1cc(Nc2ncc(C(N)=O)c(NCc3ccccc3)n2)ccc1Cl]

The title compound was synthesized similar to Example 121. MS found for $C_{24}H_{26}ClN_7O_2$ as $(M+H)^+$ 480.5. UV: $\lambda$=204, 256 nm. $^1$H NMR: (CD$_3$OD) δ 8.52 (s, 1H), 7.79 (s, 1H), 7.46 (d, 2H), 7.38 (d, 4H), 7.35 (m, 1H), 4.80 (s, 2H), 3.07 (s, 3H), 3.02 (m, 4H), 1.71 (m, 4H).

Example 242

2-(4-chloro-3-(N-methylpyrrolidine-1-carboxamido)phenylamino)-4-(3-fluorobenzylamino)pyrimidine-5-carboxamide

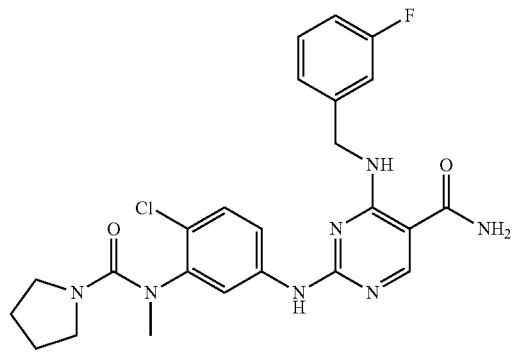 [SMILES: CN(C(=O)N1CCCC1)c1cc(Nc2ncc(C(N)=O)c(NCc3cccc(F)c3)n2)ccc1Cl]

The title compound was synthesized similar to Example 121. MS found for $C_{24}H_{25}ClFN_7O_2$ as $(M+H)^+$ 498.5, 500.5. UV: $\lambda$=204, 257 nm.

Example 243

Preparation of 2-(3-acetamido-4-(2-(piperidin-1-yl)propoxy)phenylamino)-4-(benzo[c][1,2,5]thiadiazo-4-ylamino)pyrimidine-5-carboxamide

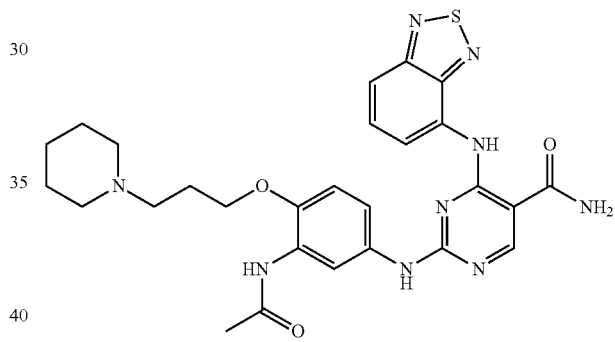

The title compound was prepared using the same synthetic scheme demonstrated in Example 223. MS found for $C_{27}H_{31}N_9O_3S$ as $(M+H)^+$ 562.4. $\lambda$=235.7, 289.0, 300.9.

Example 244

Preparation of 2-(3-acetamido-4-(2-(pyrrolidin-1-yl)ethoxy)phenylamino)-4-(benzylamino)pyrimidine-5-carboxamide

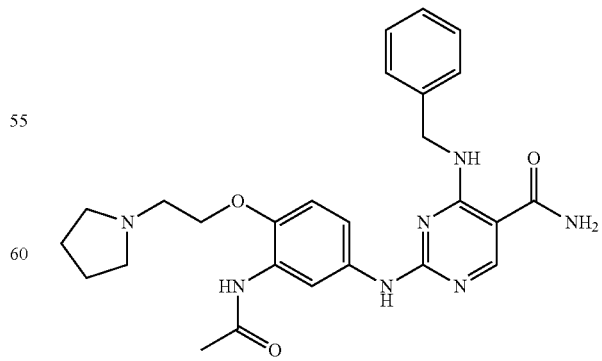

The title compound was prepared using the same synthetic scheme demonstrated in Example 223. MS found for $C_{26}H_{31}N_7O_3$ as $(M+H)^+$ 490.4. $\lambda$=249.9.

Example 245

Preparation of 2-(3-acetamido-4-(2-(piperidin-1-yl)propoxy)phenylamino)-4-(benzylamino)pyrimidine-5-carboxamide

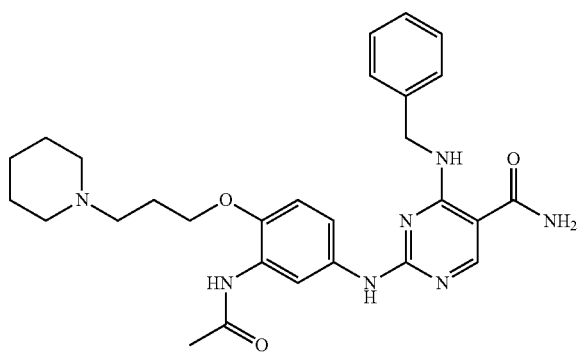 [SMILES: CC(=O)Nc1cc(Nc2ncc(C(N)=O)c(NCc3ccccc3)n2)ccc1OCCCN1CCCCC1]

The title compound was prepared using the same synthetic scheme demonstrated in Example 223. MS found for $C_{28}H_{35}N_7O_3$ as $(M+H)^+$ 518.4. λ=248.7, 279.5.

Example 246

Preparation of 2-(3-acetamido-4-(2-(piperidin-1-yl)propoxy)phenylamino)-4-(1-methyl-1H-indazol-4-ylamino)pyrimidine-5-carboxamide

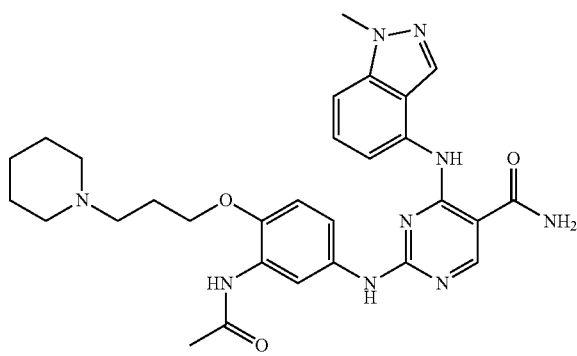 [SMILES: CC(=O)Nc1cc(Nc2ncc(C(N)=O)c(Nc3cccc4c3cnn4C)n2)ccc1OCCCN1CCCCC1]

The title compound was prepared using the same synthetic scheme demonstrated in Example 223. MS found for $C_{29}H_{35}N_9O_3$ as $(M+H)^+$ 558.5. λ=246.3, 287.8.

Example 247

(S)-2-(3-acetamidophenylamino)-4-(3-methylbutan-2-ylamino)pyrimidine-5-carboxamide

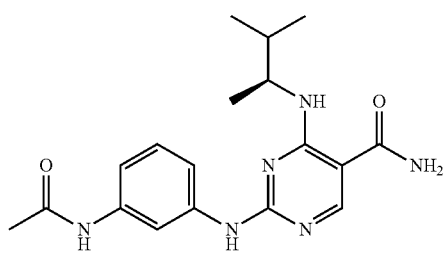 [SMILES: CC(=O)Nc1cccc(Nc2ncc(C(N)=O)c(N[C@@H](C)C(C)C)n2)c1]

The title compound was synthesized similar to Example 121. MS found for $C_{18}H_{24}N_6O_2$ as $(M+H)^+$ 357.4. UV: λ=208, 150 nm. $^1$H NMR: (CD$_3$OD) δ 8.40 (s, 1H), 8.13 (s, 1H), 7.35 (m, 2H), 7.19 (d, 1H), 4.24 (m, 1H), 2.16 (s, 3H), 1.93 (m, 1H), 1.23 (d, 3H), 0.97 (t, 3H).

Example 248

(S)-2-(4-chloro-3-(pyrrolidine-1-carboxamido)phenylamino)-4-(3-methylbutan-2-ylamino)pyrimidine-5-carboxamide

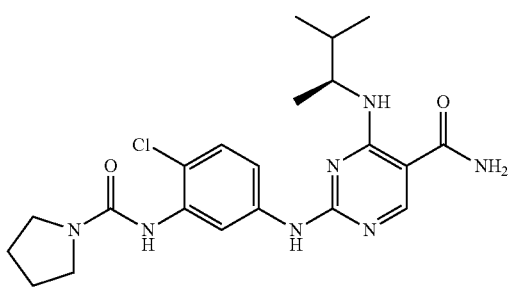 [SMILES: CC(C)[C@H](C)Nc1nc(Nc2ccc(Cl)c(NC(=O)N3CCCC3)c2)ncc1C(N)=O]

The title compound was synthesized similar to Example 121. MS found for $C_{21}H_{28}ClN_7O_2$ as $(M+H)^+$ 446.5, 448.5. UV: λ=209, 248 nm. $^1$H NMR: (CD$_3$OD) δ 8.39 (s, 1H), 8.28 (s, 1H), 7.43 (d, 1H), 7.23 (dd, 1H), 4.24 (m, 1H), 3.52 (m, 4H), 2.12 (m, 4H), 1.91 (m, 1H), 1.22 (d, 3H), 0.98 (t, 3H).

Example 249

2-(3-acetamidophenylamino)-4-(2-methylbutylamino)pyrimidine-5-carboxamide

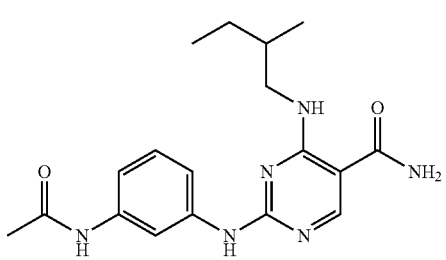 [SMILES: CCC(C)CNc1nc(Nc2cccc(NC(C)=O)c2)ncc1C(N)=O]

The title compound was synthesized similar to Example 121. MS found for $C_{18}H_{24}N_6O_2$ as $(M+H)^+$ 357.5. UV: λ=205, 249 nm. $^1$H NMR: (CD$_3$OD) δ 8.39 (s, 1H), 8.14 (s, 1H), 7.36 (m, 2H), 7.20 (d, 1H), 3.58 (dd, 1H), 3.42 (dd, 1H), 2.17 (s, 3H), 1.78 (m, 1H), 1.46 (m, 1H), 1.23 (m, 1), 0.98 (d, 3H), 0.96 (t, 3H).

Example 250

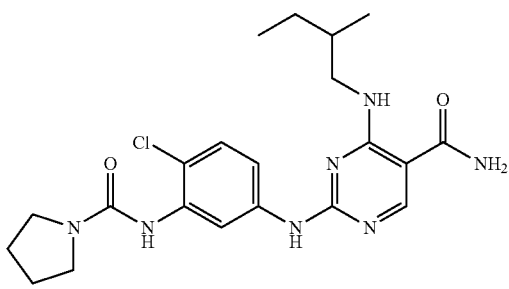 [SMILES: CCC(C)CNc1nc(Nc2ccc(Cl)c(NC(=O)N3CCCC3)c2)ncc1C(N)=O]

The title compound was synthesized similar to Example 121. MS found for C₂₁H₂₈ClN₇O₂ as (M+H)⁺ 446.5, 448.5. UV: λ=210, 249 nm. ¹H NMR: (CD₃OD) δ 8.42 (s, 1H), 8.29 (s, 1H), 7.47 (d, 1H), 7.30 (dd, 1H), 3.57 (dd, 1H), 3.51 (m, 4H), 3.44 (dd, 1H), 2.03 (m, 4H), 1.78 (m, 1H), 1.49 (m, 1H), 1.25 (m, 1H), 1.00 (d, 3H), 0.97 (t, 3H).

Example 251

2-(3-acetamidophenylamino)-4-(isopentylamino)pyrimidine-5-carboxamide

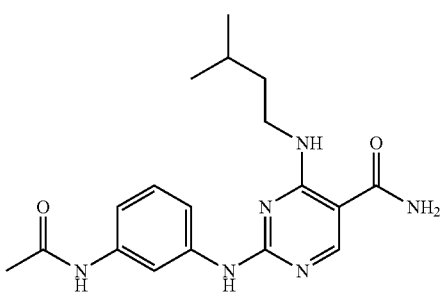 [SMILES: CC(=O)Nc1cccc(Nc2ncc(C(N)=O)c(NCCC(C)C)n2)c1]

The title compound was synthesized similar to Example 121. MS found for C₁₈H₂₄N₆O₂ as (M+H)⁺ 357.4. UV: λ=206, 249 nm. ¹H NMR: (CD₃OD) δ 8.37 (s, 1H), 8.20 (s, 1H), 7.35 (m, 2H), 7.18 (d, 1H), 3.61 (t, 2H), 2.12 (s, 3H), 1.67 (m, 1H), 1.55 (q, 2H), 0.94 (d, 6H).

Example 252

(R)-2-(3-acetamidophenylamino)-4-(3-methylbutan-2-ylamino)pyrimidine-5-carboxamide

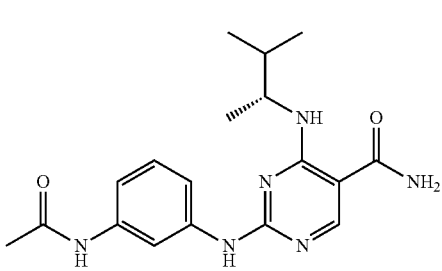

The title compound was synthesized similar to Example 121. MS found for C₁₈H₂₄N₆O₂ as (M+H)⁺ 357.4. UV: λ=207, 249 nm. ¹H NMR: (CD₃OD) δ 8.3.7 (s, 1H), 8.09 (s, 1H), 7.34 (m, 2H), 7.09 (d, 1H), 4.22 (m, 1H), 2.13 (s, 3H), 1.91 (m, 1H), 1.22 (d, 3H), 0.98 (t, 3H).

Example 253

(R)-2-(4-chloro-3-(pyrrolidine-1-carboxamido)phenylamino)-4-(3-methylbutan-2-ylamino)pyrimidine-5-carboxamide

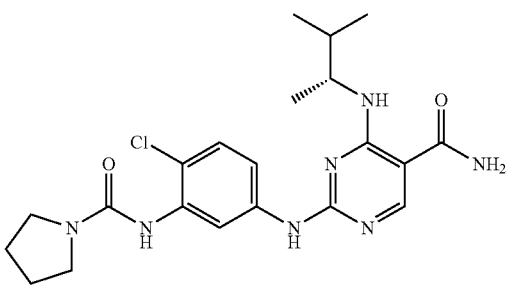 [SMILES: CC(C)[C@@H](C)Nc1nc(Nc2ccc(Cl)c(NC(=O)N3CCCC3)c2)ncc1C(N)=O]

The title compound was synthesized similar to Example 121. MS found for C₂₁H₂₈ClN₇O₂ as (M+H)⁺ 446.5, 448.5. UV: λ=212, 251 nm. ¹H NMR: (CD₃OD) δ 8.39 (s, 1H), 8.29 (s, 1H), 7.45 (d, 1H), 7.24 (dd, 1H), 4.28 (m, 1H), 3.52 (m, 4H), 2.03 (m, 4H), 1.91 (m, 1H), 1.22 (d, 3H), 0.98 (t, 3H)

Example 254

(R)-2-(3-(4-methylpiperazine-1-carboxamido)phenylamino)-4-(1-phenylethylamino)pyrimidine-5-carboxamide

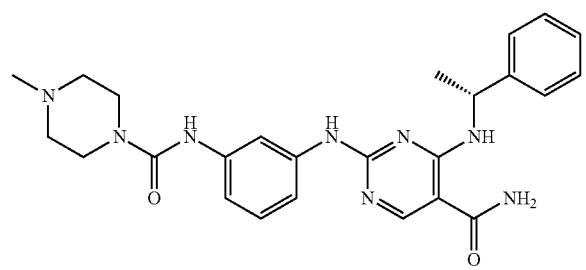 [SMILES: C[C@@H](Nc1nc(Nc2cccc(NC(=O)N3CCN(C)CC3)c2)ncc1C(N)=O)c1ccccc1]

The title compound was synthesized similar to step IV in Scheme 10 for Example 121. MS found for C₂₅H₃₀N₈O₂ as (M+H)⁺ 475.4. UV: λ=249 nm. ¹H NMR: (D-DMSO) δ 8.8 (s, 1H), 8.5 (s, 1H), 7.9 (s, 1H), 7.4 (d, 1H), 7.3 (d, 4H), 7.2 (d, 1H), 7.15 (d, 1H), 7.1 (bs, 1H), 5.4 (t, 1H), 4.2 (d, 2H), 3.2 (t, 4H), 3 (t, 4H0, 2.8 (s, 3H), 1.5 (d, 3H).

Example 255

(R)-N-(3-(5-carbamoyl-4-(1-phenylethylamino)pyrimidin-2-ylamino)phenyl)morpholine-4-carboxamide

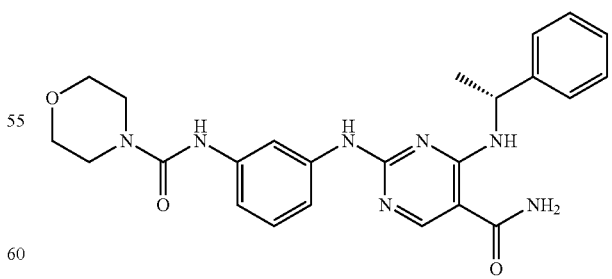

The title compound was synthesized similar to step IV in Scheme 10 for Example 121. MS found for C₂₄H₂₇N₇O₃ as (M+H)⁺ 462.5. UV: λ=207, 249 nm. ¹H NMR: (D-DMSO) δ 8.6 (s, 1H), 8.4 (s, 1H), 7.9 (s, 1H), 7.3 (d, 2H), 7.2 (d, 2H), 7.1 (t, 1H), 7.0 (d, 1H), 6.9 (d, 1H), 5.4 (t, 1H), 3.5 (d, 4H), 3.4 (d, 4H), 1.4 (d, 3H).

Example 256
Preparation of 2-(3-acetamido-4-(2-(pyrrolidin-1-yl)ethoxy)phenylamino)-4-(1-methyl-1H-indazol-4-ylamino)pyrimidine-5-carboxamide
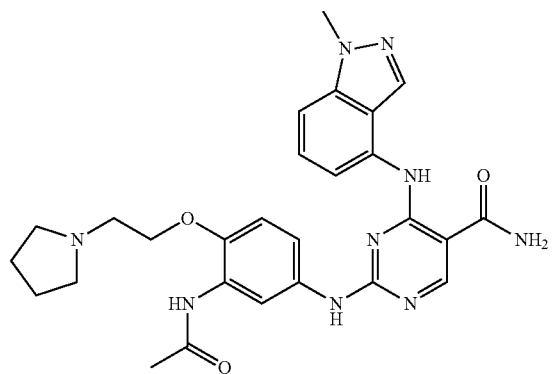 [SMILES: CC(=O)Nc1cc(Nc2ncc(C(N)=O)c(Nc3cccc4c3cnn4C)n2)ccc1OCCN1CCCC1]
The title compound was prepared using the same synthetic scheme demonstrated in Example 223. MS found for $C_{27}H_{31}N_9O_3$ as $(M+H)^+$ 530.5. $\lambda=247.5, 287.8$.
Example 257
2-(3-(2-cyanoacetamido)phenylamino)-4-(3-fluorobenzylamino)-pyrimidine-5-carboxamide
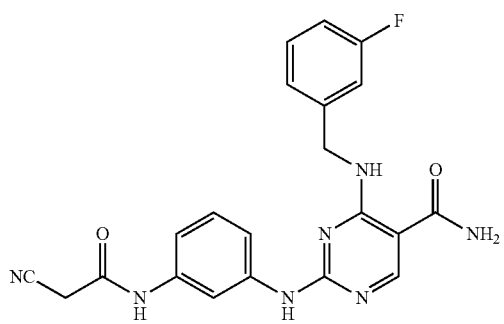 [SMILES: N#CCC(=O)Nc1cccc(Nc2ncc(C(N)=O)c(NCc3cccc(F)c3)n2)c1]
Scheme 16:
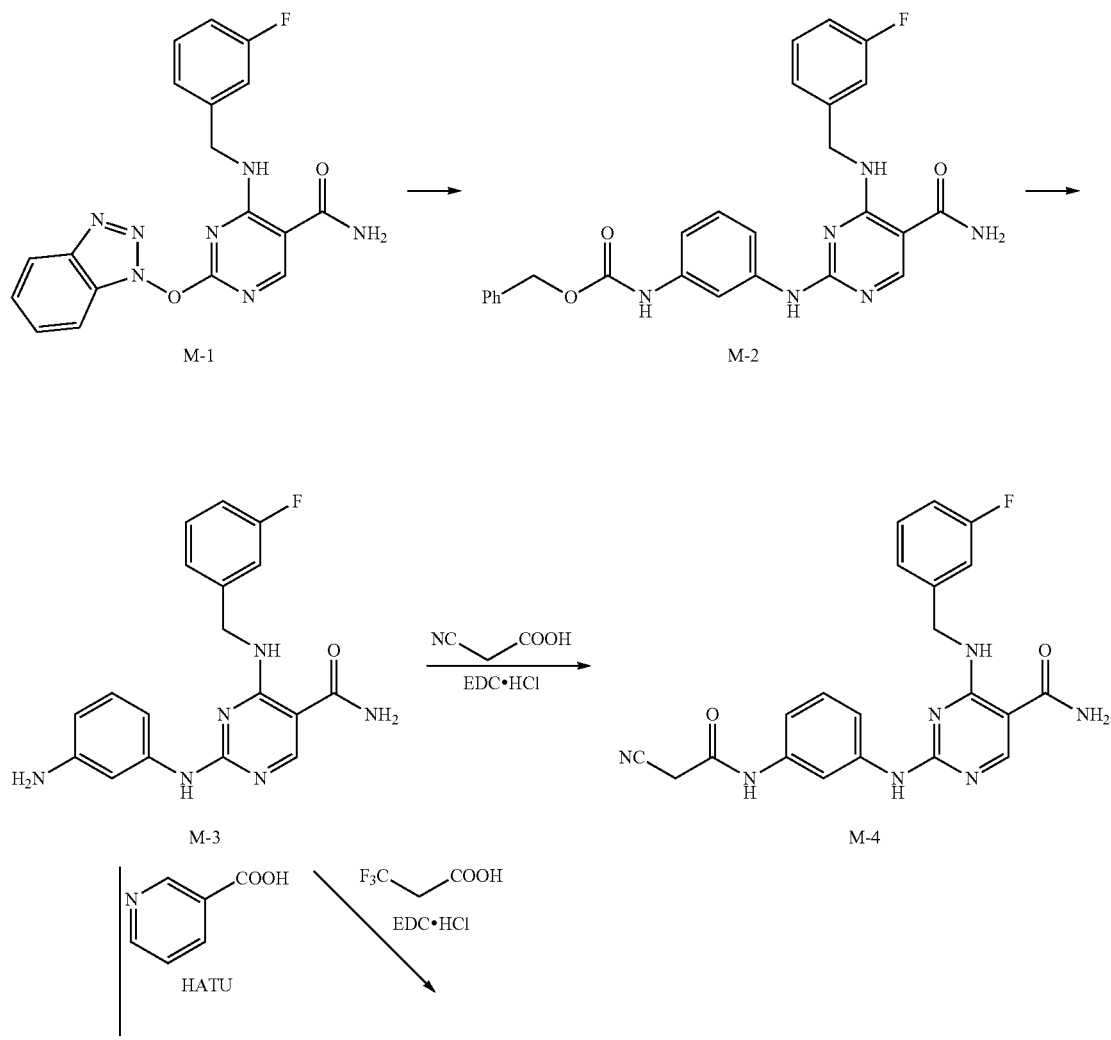

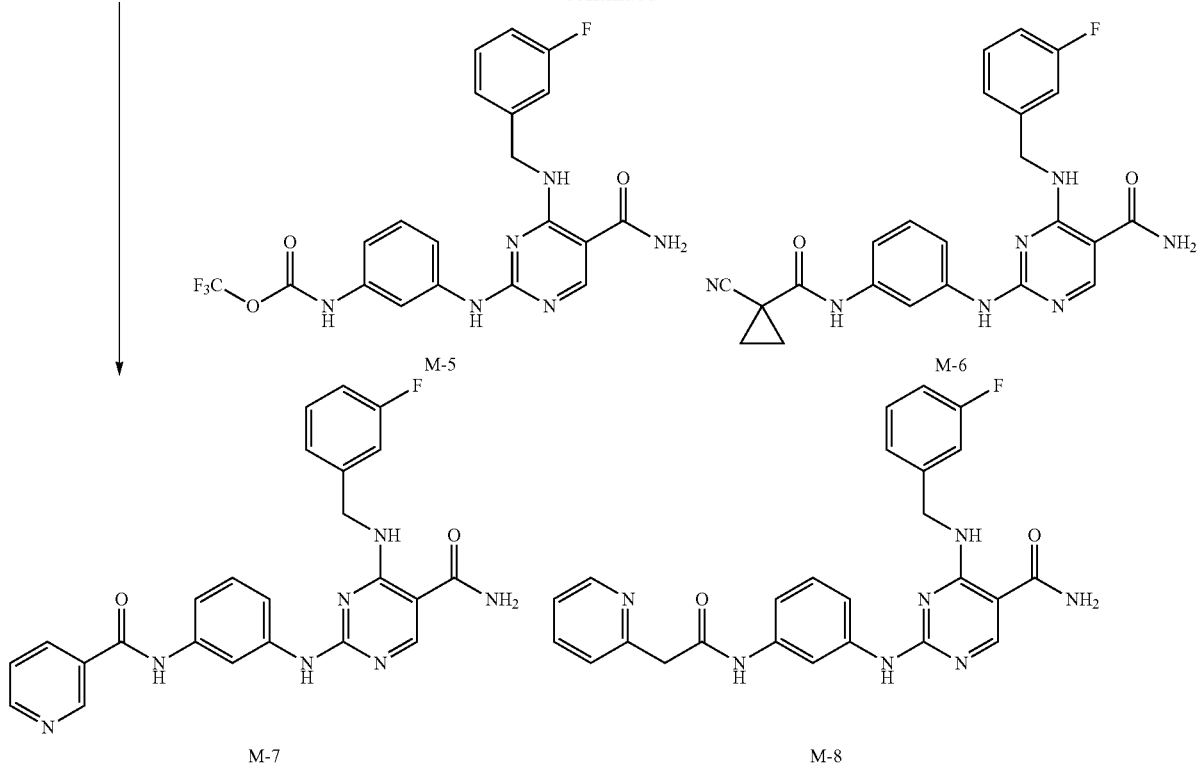

Step 8: The compound, M-2 (Scheme 16) (114 mg), was diluted with EtOAc (50 mL), 10% Pd/C (25 mg) was added, and the mixture was stirred under a hydrogen atmosphere for 18 h. The mixture was filtered through celite and the filtrate was concentrated to yield the free aniline, M-3, as a colorless solid, 78 mg (94%). UV: 253.8 nm. MS: 378.3 (M+H), $C_{19}H_{19}N_7O_2$.

Step 9: The aniline, M-3 (Scheme 16) (48 mg, 0.136 mmol), EDC.HCl (41 mg, 0.213 mmol), and cyanoacetic acid (15 mg, 0.176 mmol), in THF-NMP (2 mL/1 mL)) were stirred at room temperature for 14 h. The reaction mixture was then purified by RP-HPLC to afford the title compound pure, 42 mg (73%). UV: 249.1 nm. MS: 420.5 (M+H), $C_{21}H_{18}FN_7O_2$. $^1$H NMR (400 MHz, DMSO-$d_6$): δ 3.82 (s, 2H), 4.67 (d, 2H, J=5.8 Hz), 6.92-7.18 (m, 6H), 7.20-7.45 (m, 6H), 7.78-8.20 (m, 2H), 8.46 (s, 1H), 9.88 (br s, 1H), 10.06 (br s, 1H), 10.25 (br s, 1H).

Example 258

4-(3-fluorobenzylamino)-2-(3-(4-methylpiperazine-1-carboxamido) phenylamino)pyrimidine-5-carboxamide

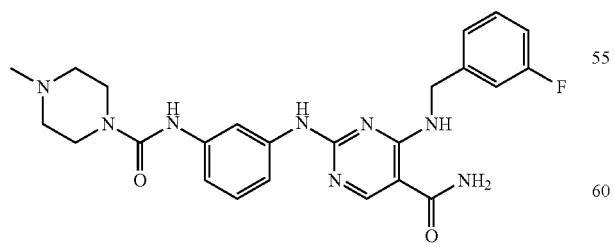

The title compound was synthesized similar to step IV in Scheme 10 for Example 121. MS found for $C_{24}H_{27}FN_8O_2$ as (M+H)$^+$ 479.5. UV: λ=207, 249 nm. $^1$H NMR: (D-DMSO) δ 8.6 (s, 1H), 8.4 (s, 1H), 7.8 (s, 1H), 7.3 (m, 1H), 7.0 (m, 6H), 4.7 (d, 2H), 4.1 (d, 2H), 3.4 (d, 2H), 3.0 (m, 4H), 2.6 (s, 3H).

Example 259

N-(3-(5-carbamoyl-4-(3-fluorobenzylamino)pyrimidin-2-ylamino)phenyl)morpholine-4-carboxamide

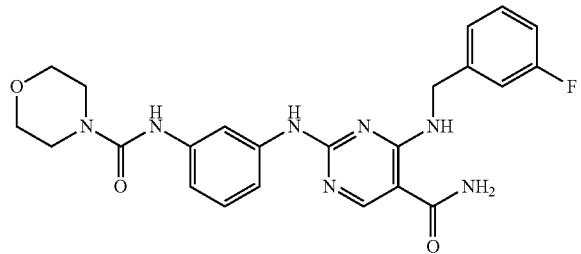 [SMILES: NC(=O)c1cnc(Nc2cccc(NC(=O)N3CCOCC3)c2)nc1NCc1cccc(F)c1]

The title compound was synthesized similar to step IV in Scheme 10 for Example 121. MS found for $C_{23}H_{24}FN_7O_3$ as (M+H)$^+$ 466.5. UV: λ=249 nm. $^1$H NMR: (D-DMSO) δ 8.5 (d, 2H), 7.9 (s, 1H). 7.3 (t, 2H), 6.9-7.1 (m, 3H), 4.7 (d, 2H), 3.4 (d, 8H), Example 260

2-(3-acetamido-5-chlorophenylamino)-4-(benzylamino)pyrimidine-5-carboxamide

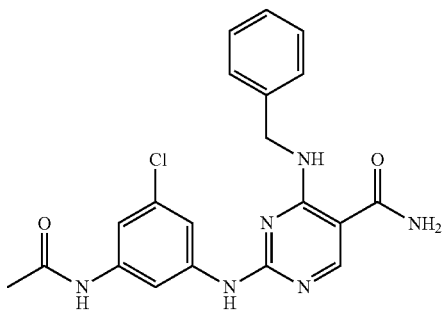 [SMILES: CC(=O)Nc1cc(Cl)cc(Nc2ncc(C(N)=O)c(NCc3ccccc3)n2)c1]

The title compound was synthesized similar to Example 121. MS found for $C_{20}H_{19}ClN_6O_2$ as (M+H)+ 411.6, 413.5. UV: λ=211, 251 nm. $^1$H NMR: (CD$_3$OD) δ 8.49 (s, 1H), 0.94 (s, 1H), 7.38 (m, 6H), 4.83 (s, 2H), 2.13 (s, 3H).

Example 261

2-(3-acetamido-5-chlorophenylamino)-4-(3-fluorobenzylamino)pyrimidine-5-carboxamide

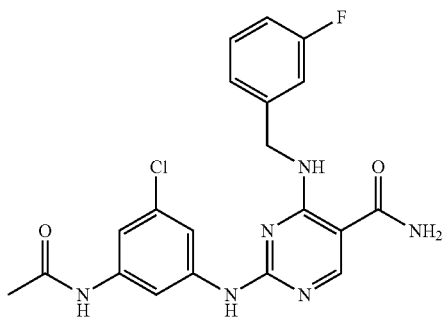 [SMILES: CC(=O)Nc1cc(Cl)cc(Nc2ncc(C(N)=O)c(NCc3cccc(F)c3)n2)c1]

The title compound was synthesized similar to Example 121. MS found for $C_{20}H_{18}ClFN_6O_2$ as (M+H)+ 429.3, 431.3. UV: λ=210, 251 nm. $^1$H NMR: (CD$_3$OD) δ 8.49 (s, 1H), 7.93 (s, 1H), 7.50 (s, 1H), 7.38 (t, 1H), 7.30 (s, 1H), 7.18 (d, 1H), 7.10 (d, 1H), 7.02 (dt, 1H), 4.84 (s, 2H), 2.13 (s, 3H).

Example 262

2-(3-acetamidophenylamino)-4-(cyclobutylmethylamino)pyrimidine-5-carboxamide

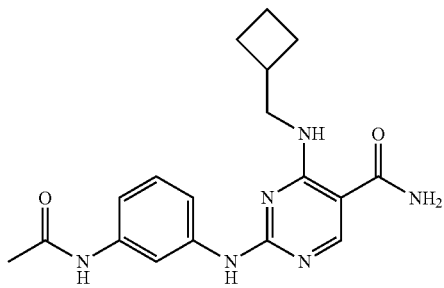 [SMILES: CC(=O)Nc1cccc(Nc2ncc(C(N)=O)c(NCC3CCC3)n2)c1]

The title compound was synthesized similar to Example 121. MS found for $C_{18}H_{22}N_6O_2$ as (M+H)+ 355.4. UV: λ=204, 249 nm. $^1$H NMR: (CD$_3$OD) δ 8.38 (s, 1H), 8.19 (s, 1H), 3.64 (d, 2H), 2.64 (m, 1H), 2.17 (s, 3H), 2.10 (m, 2H), 1.93 (m, 2H), 1.80 (m, 2H).

Example 263

2-(4-chloro-3-(pyrrolidine-1-carboxamido)phenylamino)-4-(cyclobutylmethylamino)pyrimidine-5-carboxamide

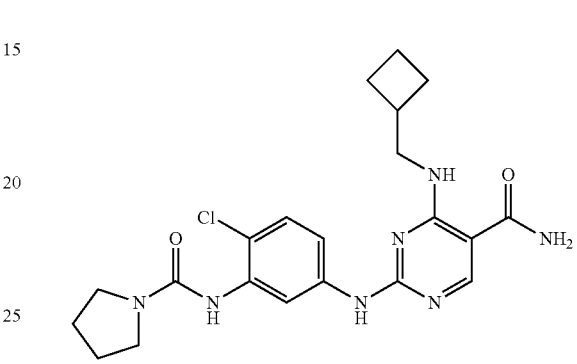

The title compound was synthesized similar to Example 121. MS found for $C_{21}H_{26}ClN_7O_2$ as (M+H+ 444.4, 446.5. UV: λ=256, 276 nm. $^1$H NMR: (CD$_3$OD) δ 8.58 (s, 1H), 8.49 (s, 1H), 8.02 (s, 1H), 7.51 (d, 1H), 7.34 (d, 1H), 3.60 (d, 2H), 3.52 (m, 4H), 2.63 (m, 1H), 1.82-2.19 (m, 8H), 2.83 (m, 2H).

Example 264

2-(3-acetamidophenylamino)-4-(4-aminophenylamino)pyrimidine-5-carboxamide

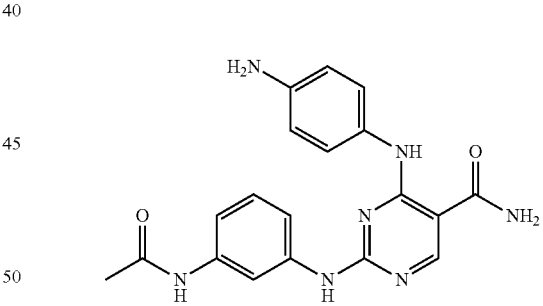

Scheme 17:

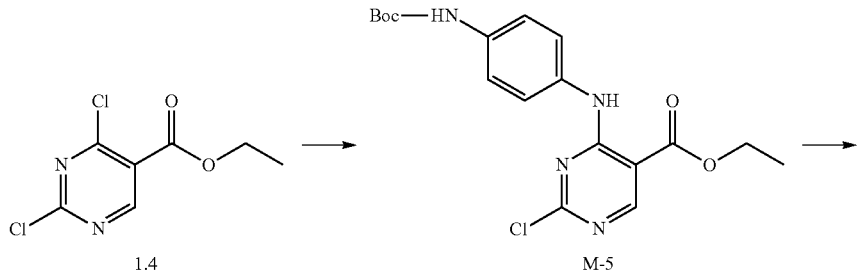

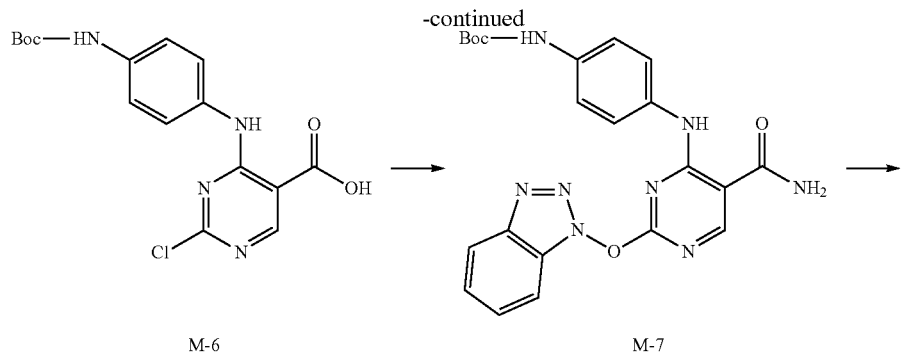
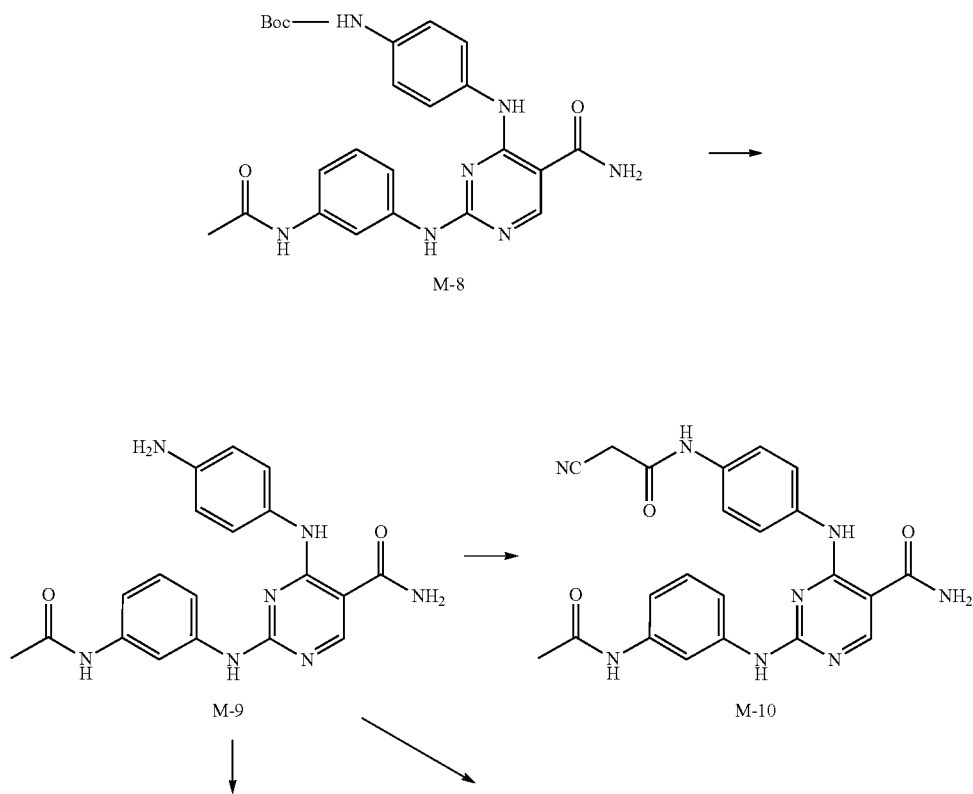
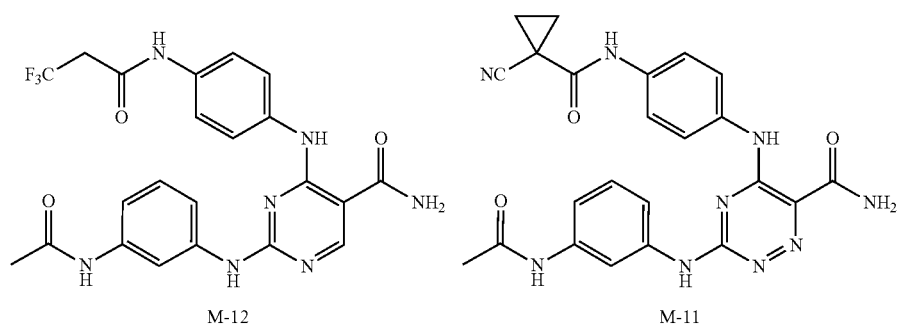

This compound was synthesized using the reactions described in Scheme 17 and following the procedures described for such compounds in scheme 1. UV: 253.8, 201.0 nm. MS: 378.3 (M+H), $C_{19}H_{19}N_7O_2$. $^1$H NMR (400 MHz, DMSO-$d_6$): δ 2.041 (s, 3H), 7.10-7.60 (m, 8H), 7.75 (m, 2H), 8.12 (br s, 1H), 8.68 (s, 1H), 9.85 (br s, 1H), 9.94 (s, 1H), 11.72 (s, 1H).

Example 265

Preparation of 4-(benzylamino)-2-(3-(2-(dimethylamino)acetamido)phenylamino)pyrimidine-5-carboxamide

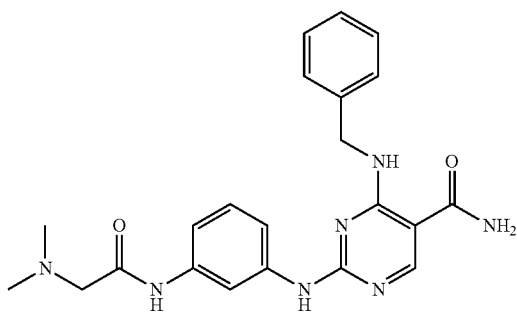 [SMILES: CN(C)CC(=O)Nc1cccc(Nc2ncc(C(N)=O)c(NCc3ccccc3)n2)c1]

The title compound was prepared using the same synthetic scheme demonstrated in Example 184. MS found for $C_{22}H_{25}N_7O_2$ as (M+H)$^+$ 420.4. λ=249.9.

Example 266

Preparation of 2-(3-(2-(dimethylamino)acetamido)phenylamino)-4-(1-methyl-1H-indazol-4-ylamino)pyrimidine-5-carboxamide

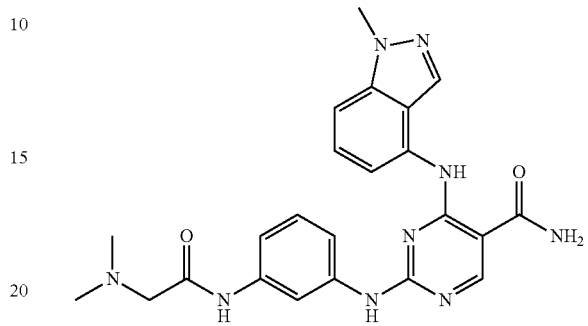

The title compound was prepared using the same synthetic scheme demonstrated in Example 184. MS found for $C_{23}H_{25}N_9O_2$ as (M+H)$^+$ 460.4. λ=250.1.

Examples 145, 153 and 197-199.

The below compounds were prepared using a procedure similar to that described in the above Schemes.

| EXAMPLE NO. | STRUCTURE | MS | MOL. FORMULA |
|---|---|---|---|
| 145 | 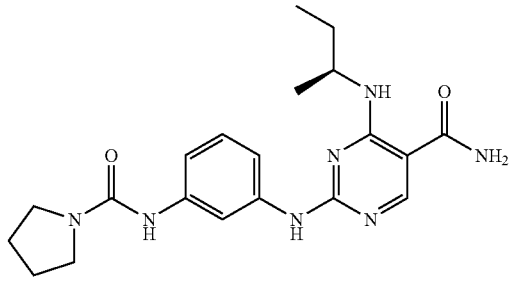 [SMILES: CC[C@H](C)Nc1nc(Nc2cccc(NC(=O)N3CCCC3)c2)ncc1C(N)=O] | 398.4 | C20H27N7O2 |
| 153 | 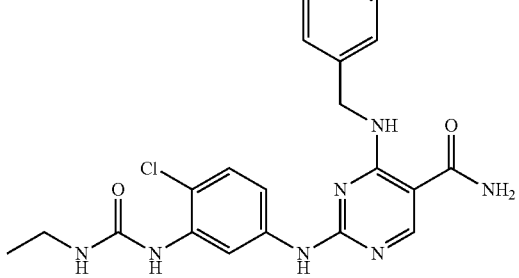 | 440.3, 442.4 | C21H22ClN7O2 |

-continued
| EXAMPLE NO. | STRUCTURE | MS | MOL. FORMULA |
|---|---|---|---|
| 197 | 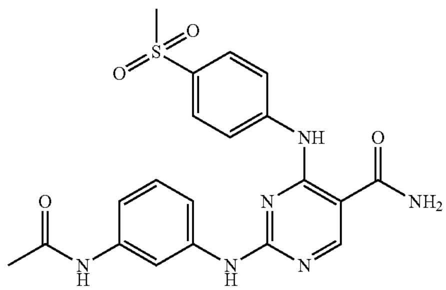 [SMILES: CC(=O)Nc1cccc(Nc2ncc(C(N)=O)c(Nc3ccc(S(C)(=O)=O)cc3)n2)c1] | 441.2 | C20H20N6O4S |
| 198 | 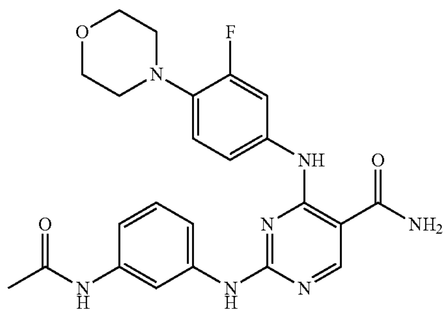 [SMILES: CC(=O)Nc1cccc(Nc2ncc(C(N)=O)c(Nc3ccc(N4CCOCC4)c(F)c3)n2)c1] | 466.2 | C23H24FN7O3 |
| 199 | 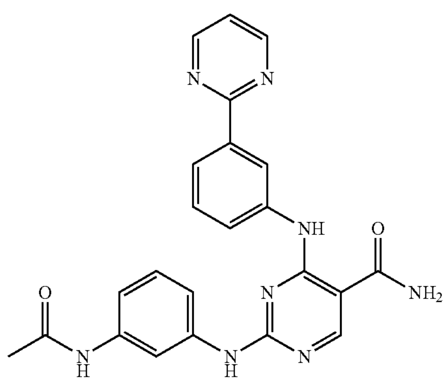 [SMILES: CC(=O)Nc1cccc(Nc2ncc(C(N)=O)c(Nc3cccc(-c4ncccn4)c3)n2)c1] | 441.3 | C23H20N8O2 |
Example 268
Preparation of 2-(3-acetamidophenylamino)-4-(1-phenylcyclopropylamino)pyrimidine-5-carboxamide
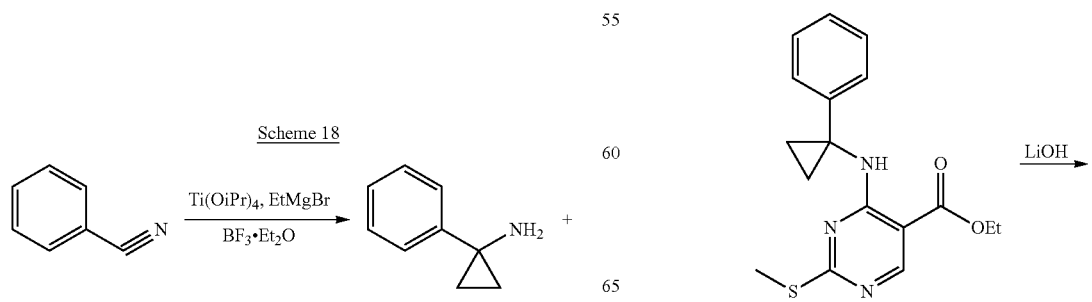
Scheme 18
-continued
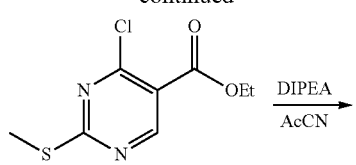

-continued

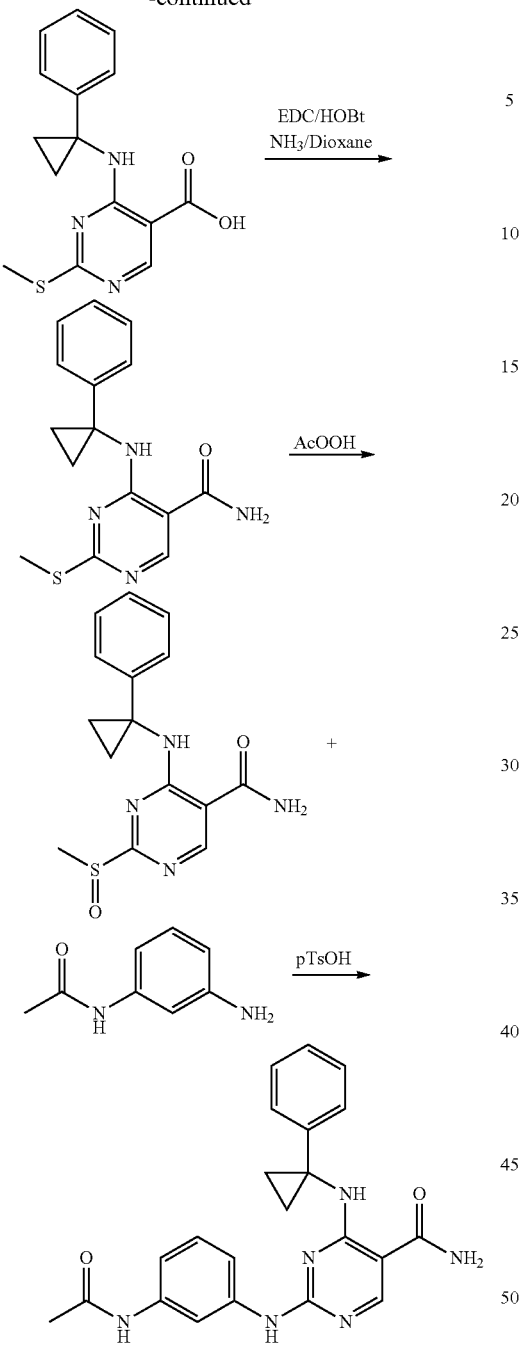

Step 1: To benzonitrile (1.03 g, 10 mmol) in ether (50 ml) at −70° C. was added Ti(OiPr)₄ (3.22 ml, 11 mmol) and EtMgBr (3M in ether, 7.34 mL, 22 mmol) dropwise, the resulting yellow suspension was warmed up to room temperature over 1 h. After stirring for additional 30 min, the dark brown solution was added BF₃.Et₂O (2.47 mL, 20 mL) at room temperature. The mixture was further stirred for 1 h, and was quenched by 1N HCl (30 mL) and 5N NaOH (30 mL), the suspension was extracted with ether, ether layer was combined, concentrated to give crude residue, which was purified by column (Hexanes/EtOAc, 2:1 to 1:9) to give 1-phenylcyclopropanamine (420 mg).

Step 2: To a solution of ethyl 4-chloro-2-(methylthio)pyrimidine-5-carboxylate (550 mg, 2.36 mmol) and 1-phenylcyclopropanamine (420 mg, 3.16 mmol) in CH₃CN (6 mL) at room temperature was added DIEA (0.5 mL, 2.60 mmol). The mixture was stirred at room temperature for 3 h and 50° C. for 3 h. The mixture was diluted with EtOAc, washed with 1N HCl, Sat. NaHCO₃, brine, dried and concentrated to give ethyl 2-(methylthio)-4-(1-phenylcyclopropylamino)pyrimidine-5-carboxylate (810 mg).

Step 3: To a solution of ethyl 2-(methylthio)-4-(1-phenylcyclopropylamino)pyrimidine-5-carboxylate (crude from step 2) in THF (4 mL) was added LiOH.H₂O (150 mg, 3.57 mmol) in H₂O (2 mL). The mixture was stirred at room temperature overnight. THF was removed under vacuum and the residue was acidified with 1N HCl, white solids precipitated out, which were collected by filtration, dried on vacuum to give 2-(methylthio)-4-(1-phenylcyclopropylamino) pyrimidine-5-carboxylic acid (646 mg). MS 302.3 (M+H).

Step 4: To a solution of 2-(methylthio)-4-(1-phenylcyclopropylamino)pyrimidine-5-carboxylic acid (646 mg, 2.15 mmol) and HOBt.H₂O (395 mg, 2.58 mmol) in DMF (3.5 mL), EDC (515 mg, 2.69 mmol) was added. The mixture was stirred at room temperature for 20 min. Ammonium hydroxide (244 mg, 4.30 mmol) was added. It was stirred at room temperature for 1 h. Water was added to induce precipitation, the solids were collected by filtration to give 2-(methylthio)-4-(1-phenylcyclopropylamino) pyrimidine-5-carboxamide (636 mg). MS 301.2 (M+H).

Step 5: To a suspension of 2-(methylthio)-4-(1-phenylcyclopropylamino)pyrimidine-5-carboxamide (636 mg) in AcCN (3 mL) was added AcOOH (39% in AcOH, 0.7 mL). The mixture was stirred at room temperature for 20 h, and the solids were collected by filtration and dried in vacuo to give 2-(methylsulfinyl)-4-(1-phenylcyclopropylamino) pyrimidine-5-carboxamide (530 mg). MS 317.2 (M+H).

Step 6: To a solution of 2-(methylsulfinyl)-4-(1-phenylcyclopropylamino) pyrimidine-5-carboxamide (50 mg, 0.16 mmol) in NMP (1 mL) was added 3-acetamidoaniline (27 mg, 0.18 mmol) and pTsO.RH₂O (30 mg, 0.16 mmol). The mixture was heated at 100° C. for 2 h, cooled to room temperature, and purified by preparative HPLC to give 2-(3-acetamidophenylamino)-4-(1-phenylcyclopropylamino)pyrimidine-5-carboxamide (38 mg). MS found for C₂₂H₂₂N₆O₂ as (M+H)⁺ 403.5. λ=251.1.

Example 269

Preparation of 2-(3-(2-(dimethylamino)acetamido) phenylamino)-4-(1-phenylcyclopropylamino)pyrimidine-5-carboxamide

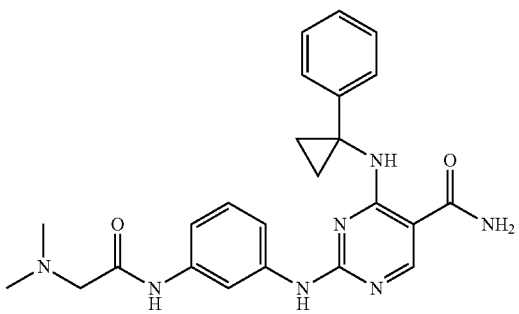 [SMILES: CN(C)CC(=O)Nc1cccc(Nc2ncc(C(N)=O)c(NC3(c4ccccc4)CC3)n2)c1]

The title compound was prepared using the same synthetic scheme demonstrated in Example 268. MS found for C₂₄H₂₇N₇O₂ as (M+H)⁺ 446.6. λ=251.1.

Example 270

Preparation of 2-(3-acetamido-4-methylphenylamino)-4-(1-phenylcyclopropylamino)pyrimidine-5-carboxamide

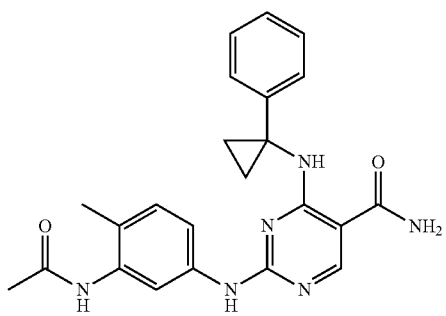 [SMILES: CC(=O)Nc1cc(Nc2ncc(C(N)=O)c(NC3(c4ccccc4)CC3)n2)ccc1C]

The title compound was prepared using the same synthetic scheme demonstrated in Example 268. MS found for C₂₃H₂₄N₆O₂ as (M+H)⁺ 417.5. λ=251.1.

Example 273

Preparation of 4-(benylamino)-2-(3-isobutyraminophenylamino)pyrimidine-5-carboxamide

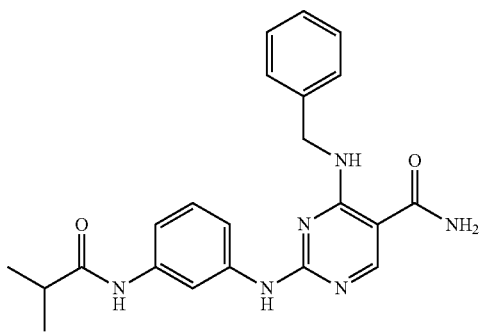 [SMILES: CC(C)C(=O)Nc1cccc(Nc2ncc(C(N)=O)c(NCc3ccccc3)n2)c1]

The title compound was prepared using the same synthetic scheme demonstrated in Example 184. MS found for C₂₂H₂₄N₆O₂ as (M+H)⁺ 405.5. λ=248.7.

Example 274

Preparation of 4-(benylamino)-2-(3-pivalaminophenylamino)pyrimidine-5-carboxamide

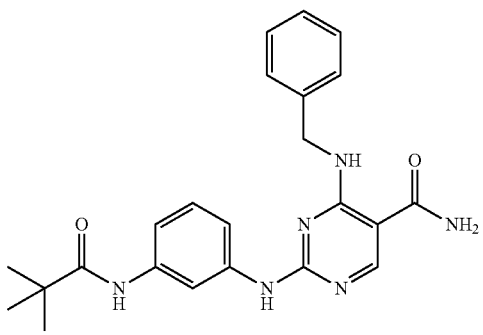 [SMILES: CC(C)(C)C(=O)Nc1cccc(Nc2ncc(C(N)=O)c(NCc3ccccc3)n2)c1]

The title compound was prepared using the same synthetic scheme demonstrated in Example 184. MS found for C₂₃H₂₆N₆O₂ as (M+H)⁺ 419.6. λ=247.5.

Example 275

Preparation of (S)-4-(benylamino)-2-(3-(1-methylpyrrolidine-2-carboxamido)phenylamino)pyrimidine-5-carboxamide

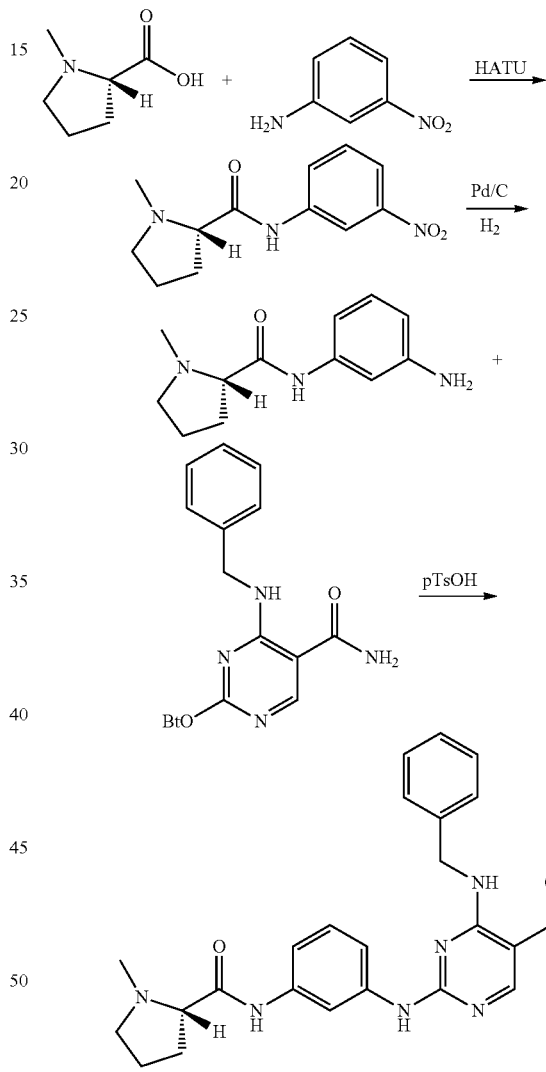

Step 1: To a solution of (S)-1-methylpyrrolidine-2-carboxylic acid (258 mg, 2 mmol) in DMF (4 mL) was added 3-nitroaniline (276 mg, 2 mmol) and HATU (760 mg). After stirring for 20 h, it was added with EtOAc, washed with Sat. NaHCO₃, brine, dried and concentrated to give (S)-1-methyl-N-(3-nitrophenyl)pyrrolidine-2-carboxamide.

Step 2: To a solution of (S)-1-methyl-N-(3-nitrophenyl)pyrrolidine-2-carboxamide (crude from step 1) in MeOH (5 ml) was added Pd/C (50 mg), charged with H₂ (1 atm), after stirring for 3 h, Pd/C was filtered off and the filtrate was concentrated to give (S)-N-(3-aminophenyl)-1-methylpyrrolidine-2-carboxamide (350 mg).

Step 3: To a solution of 2-(1H-benzo[d][1,2,3]triazol-1-yloxy)-4-(benzylamino)pyrimidine-5-carboxamide (50 mg, 0.14 mmol) in NMP (1 mL) was added (S)-N-(3-aminophenyl)-1-methylpyrrolidine-2-carboxamide (33 mg, 0.152 mmol) and pTsO.RH$_2$O (60 mg, 0.28 mmol). The mixture was heated at 100° C. for 2 h, cooled to room temperature, and purified by preparative HPLC to give of (S)-4-(benylamino)-2-(3-(1-methylpyrrolidine-2-carboxamido)phenylamino)pyrimidine-5-carboxamide (48 mg). MS found for C$_{24}$H$_{27}$N$_7$O$_2$ as (M+H)$^+$ 446.5. λ=247.5.

Example 276

Preparation of 2-(3-acetamidophenylamino)-4-((1-methyl-1H-pyrazol-4-yl)methylamino)pyrimidine-5-carboxamide

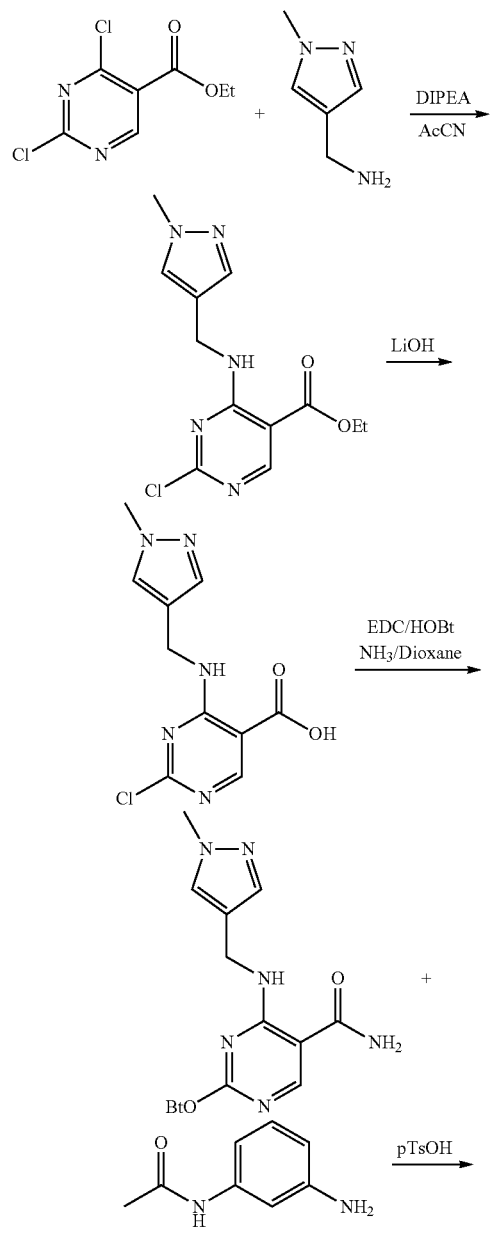

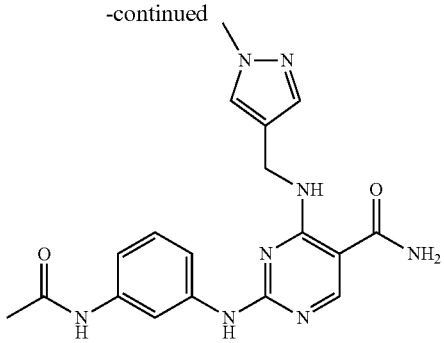

Step 1: To a solution of ethyl 2,4-dichloropyrimidine-5-carboxylate (896 mg, 4 mmol) and (1-methyl-1H-pyrazol-4-yl)methanamine (445 mg, 4 mmol) in CH$_3$CN (6 mL) at room temperature, DIEA (0.783 mL, 4.4 mmol) was added. The mixture was stirred at room temperature for 24 h, and was concentrated to give ethyl 2-chloro-4-((1-methyl-1H-pyrazol-4-yl)methylamino)pyrimidine-5-carboxylate as crude oil.

Step 2: To a solution of give ethyl 2-chloro-4-((1-methyl-1H-pyrazol-4-yl)methylamino)pyrimidine-5-carboxylate (crude from step 1) in THF (9 mL), aq. 1N LiOH (6.6 mL, 6.6 mmol) was added. The mixture was stirred at room temperature overnight. THF was removed under vacuum, and the residue was acidified of with 1N HCl, the precipitated white solids were collected, and dried on vacuum to give 2-chloro-4-((1-methyl-1H-pyrazol-4-yl)methylamino)pyrimidine-5-carboxylic acid (1 g). MS 268.2, 270.2 (M+H, Cl pattern).

Step 3: To a solution of 2-chloro-4-((1-methyl-1H-pyrazol-4-yl)methylamino)pyrimidine-5-carboxylic acid (1 g, 3.74 mmol) and HOBtH$_2$O (858 mg, 5.61 mmol) in DMF (10 mL), EDC (1.08 g, 5.61 mmol) was added. The mixture was stirred at room temperature for 30 min. Ammonia (0.5 M in dioxane, 15 mL, and 7.5 mmol) was added. It was stirred at room temperature overnight. Dioxane was removed under vacuum, the residue was added water to induce precipitation and the resulting solids were isolated by filtration to give 2-(1H-benzo[d][1,2,3]triazol-1-yloxy)-4-((1-methyl-1H-pyrazol-4-yl)methylamino)pyrimidine-5-carboxamide (1.04 g). MS 366.4 (M+H).

Step 4: To a solution of 2-(1H-benzo[d][1,2,3]triazol-1-yloxy)-4-((1-methyl-1H-pyrazol-4-yl)methylamino)pyrimidine-5-carboxamide (51 mg, 0.14 mmol) in NMP (0.8 mL) was added 3-acetamidoaniline (24 mg, 0.16 mmol) and pTsOH.H$_2$O (27 mg, 0.14 mmol). The mixture was heated at 100° C. for 2 h, cooled to room temperature, purified by preparative HPLC to give 2-(3-acetamidophenylamino)-4-((1-methyl-1H-pyrazol-4-yl)methylamino)pyrimidine-5-carboxamide (40 mg). MS found for C$_{18}$H$_{20}$N$_8$O$_2$ as (M+H)$^|$ 381.5. λ=242.8.

Example 280

2-(3-acetamidophenylamino)-4-(cyclopentylmethylamino)pyrimidine-5-carboxamide

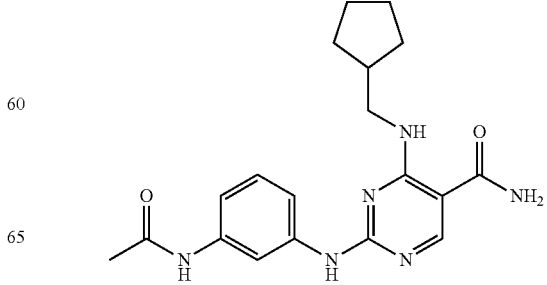

The title compound was synthesized similar to step IV in Scheme 10 for Example 121. MS found for C$_{19}$H$_{24}$N$_6$O$_2$ as (M+H)$^+$ 369.3. UV: λ=202, 249 nm. $^1$H NMR: (CD$_3$OD) δ 8.38 (s, 1H), 8.17 (s, 1H), 7.33 (m, 2H), 7.17 (m, 1H), 3.54 (d, 2H), 2.61 (m, 1), 2.15 (s, 3H), 1.80 (m, 2H), 1.50-1.67 (m, 4H), 1.31 (m, 2H).

Example 281

(4-(cyclopentylmethylamino)-2-(3-(pyrrolidine-1-carboxamido)phenylamino)pyrimidine-5-carboxamide

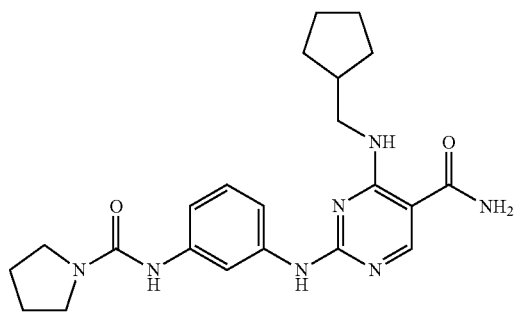 [SMILES: NC(=O)c1cnc(Nc2cccc(NC(=O)N3CCCC3)c2)nc1NCC1CCCC1]

The title compound was synthesized similar to Example 121. MS found for C$_{22}$H$_{29}$N$_7$O$_2$ as (M+H)+ 424.3. UV: λ=207, 246 nm. $^1$H NMR: (CD$_3$OD) δ 8.42 (s, 1H), 8.00 (s, 1H), 7.33 (d, 1H), 7.23 (t, 1H), 7.09 (m, 1H), 3.46 (m, 4H), 2.22 (m, 1H), 1.96 (m, 5), 1.78 (m, 1H), 1.63 (m, 2H), 1.57 (m, 2H), 1.29 (m, 2H).

Example 282

(R)-4-(benzylamino)-2-(3-(3-hydroxypyrrolidine-1-carboxamido)phenylamino)pyrimidine-5-carboxamide

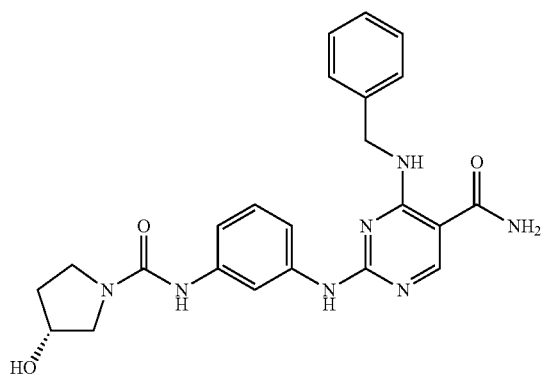 [SMILES: NC(=O)c1cnc(Nc2cccc(NC(=O)N3CC[C@@H](O)C3)c2)nc1NCc1ccccc1]

The title compound was synthesized similar to Example 121. MS found for C$_{23}$H$_{25}$N$_7$O$_3$ as (M+H)$^+$ 448.1. UV: λ=207, 247 nm.

Example 283

(R)-4-(benzylamino)-2-(3-(3-fluoropyrrolidine-1-carboxamido)phenylamino)pyrimidine-5-carboxamide

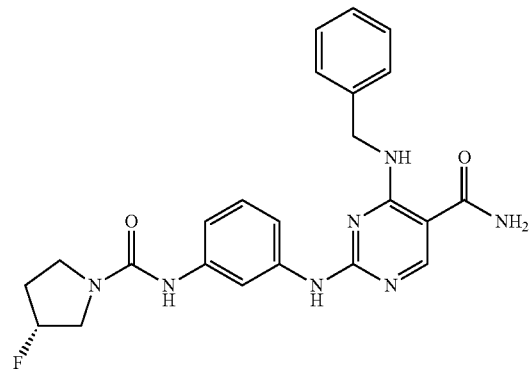 [SMILES: NC(=O)c1cnc(Nc2cccc(NC(=O)N3CC[C@@H](F)C3)c2)nc1NCc1ccccc1]

The title compound was synthesized similar to Example 121. MS found for C$_{23}$H$_{24}$FN$_7$O$_2$ as (M+H)$^+$ 450.2. UV: λ=204, 248 nm. $^1$H NMR: (CD$_3$OD) δ 8.18 (s, 1H), 7.83 (s, 1H), 7.20-7.38 (m, 6H), 7.13 (d, 2H), 5.29 (d, 1H), 4.78 (s, 2H), 3.42-3.78 (m, 4H), 2.01-2.38 (m, 2H).

Example 284

(S)-4-(benzylamino)-2-(3-(3-fluoropyrrolidine-1-carboxamido)phenylamino)pyrimidine-5-carboxamide

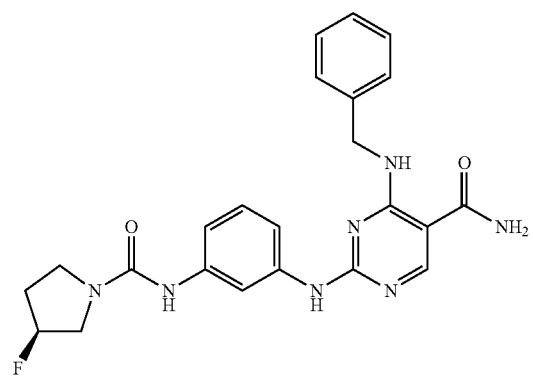 [SMILES: NC(=O)c1cnc(Nc2cccc(NC(=O)N3CC[C@H](F)C3)c2)nc1NCc1ccccc1]

The title compound was synthesized similar to Example 121. MS found for C$_{23}$H$_{24}$FN$_7$O$_2$ as (M+H)$^+$ 450.2. UV: λ=204, 249 nm. $^1$H NMR: (CD$_3$OD) δ 8.18 (s, 1H), 7.83 (s, 1H), 7.20-7.37 (m, 6H), 7.13 (d, 1H), 7.08 (d, 1H), 5.29 (d, 1H), 4.77 (s, 2H), 3.42-3.80 (m, 4H), 2.01-2.38 (m, 2H).

Example 285

2-(3-acetamidophenylamino)-4-(3-cyanobenzylamino)pyrimidine-5-carboxamide

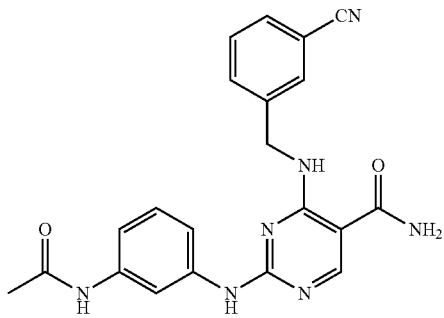 [SMILES: CC(=O)Nc1cccc(Nc2ncc(C(N)=O)c(NCc3cccc(C#N)c3)n2)c1]

The title compound was synthesized similar to step IV in Scheme 10 for Example 121. MS found for $C_{21}H_{19}N_7O_2$ as $(M+H)^+$ 402.2. UV: $\lambda$=202, 249 nm. $^1$H NMR: $(CD_3OD)$ $\delta$ 8.49 (s, 1H), 8.13 (s, 1H), 7.70 (s, 1H), 7.65 (d, 2H), 7.52 (t, 1H), 7.29 (t, 1H), 7.19 (m, 2H), 4.87 (s, 2H), 2.15 (s, 3H).

Example 286

4-(3-cyanobenzylamino)-2-(4-fluoro-3-(pyrrolidine-1-carboxamido)phenylamino)pyrimidine-5-carboxamide

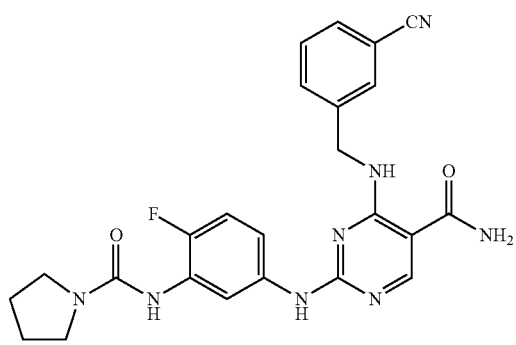 [SMILES: N#Cc1cccc(CNc2nc(Nc3ccc(F)c(NC(=O)N4CCCC4)c3)ncc2C(N)=O)c1]

The title compound was synthesized similar to Example 121. MS found for $C_{24}H_{23}FN_8O_2$ as $(M+H)^+$ 475.3. UV: $\lambda$=210, 244 nm. $^1$H NMR: $(CD_3OD)$ $\delta$ 8.45 (s, 1H), 8.03 (s, 1H), 7.64 (m, 3H), 7.52 (t, 1H), 7.17 (m, 2H), 4.85 (s, 2H), 3.48 (m, 4H), 2.00 (m, 4H).

Example 287

4-(benzylamino)-2-(3-(3,3-difluoropyrrolidine-1-carboxamido)phenylamino)pyrimidine-5-carboxamide

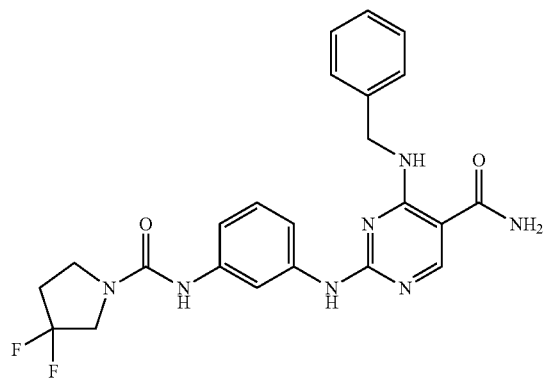 [SMILES: NC(=O)c1cnc(Nc2cccc(NC(=O)N3CCC(F)(F)C3)c2)nc1NCc1ccccc1]

The title compound was synthesized similar to Example 121. MS found for $C_{23}H_{23}F_2N_7O_2$ as $(M+H)^+$ 468.1. UV: $\lambda$=214, 246 nm. $^1$H NMR: $(CD_3OD)$ $\delta$ 8.42 (s, 1H), 8.01 (s, 1H), 7.09-7.37 (m, 8H), 4.69 (s, 2H), 3.61-3.83 (m, 4H), 2.43 (m, 2H).

Example 288

2-(4-fluoro-3-(pyrrolidine-1-carboxamido)phenylamino)-4-(2-fluorobenzylamino)pyrimidine-5-carboxamide

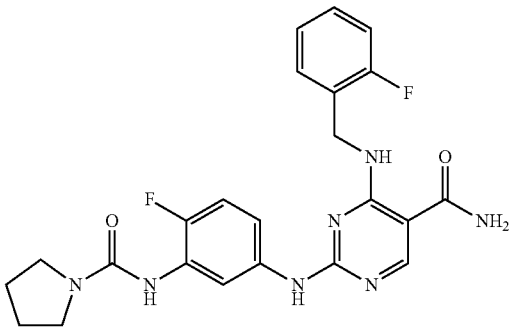 [SMILES: NC(=O)c1cnc(Nc2ccc(F)c(NC(=O)N3CCCC3)c2)nc1NCc1ccccc1F]

The title compound was synthesized similar to Example 121. MS found for $C_{23}H_{23}F_2N_7O_2$ as $(M+H)^+$ 468.3. UV: $\lambda$=207, 246 nm. $^1$H NMR: $(CD_3OD)$ $\delta$ 8.38 (s, 1H), 7.91 (s, 1H), 7.31 (m, 2H), 7.11 (m, 4H), 4.82 (s, 2H), 3.47 (m, 4H), 1.96 (m, 4).

Example 289

(R)-4-(2-fluorobenzylamino)-2-(3-(3-fluoropyrrolidine-1-carboxamido)phenylamino)pyrimidine-5-carboxamide

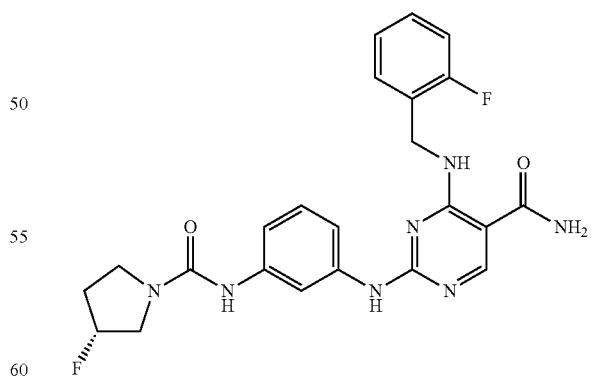

The title compound was synthesized similar to Example 121. MS found for $C_{23}H_{23}F_2N_7O_2$ as $(M+H)^+$ 468.3. UV: $\lambda$=202, 246 nm. $^1$H NMR: $(CD_3OD)$ $\delta$ 8.38 (s, 1H), 7.81 (s, 1H), 7.29 (m, 3H), 7.18 (d, 1H), 7.10 (m, 3H), 5.28 (d, 1H), 4.81 (s, 2H), 3.68 (m, 2H), 3.51 (m, 2H), 2.23 (m, 2H).

Example 290

2-(3-(azetidine-1-carboxamido)-4-fluorophenyl-amino)-4-(2-fluorobenzylamino)pyrimidine-5-carboxamide

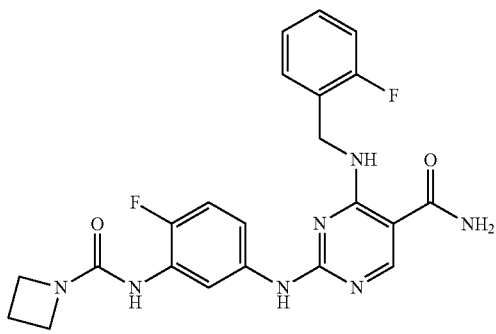 [SMILES: NC(=O)c1cnc(Nc2ccc(F)c(NC(=O)N3CCC3)c2)nc1NCc1ccccc1F]

The title compound was synthesized similar to Example 121. MS found for $C_{22}H_{21}F_2N_7O_2$ as (M+H)$^1$ 454.3. UV: λ=204, 246 nm. $^1$H NMR: (CD$_3$OD) δ 8.34 (m, 2H), 7.24 (m, 2H), 7.13 (m, 3H), 7.03 (m, 1H), 3.58 (m, 2H), 1.95 (m, 2H).

Example 291

4-(3-fluorobenzylamino)-2-(3-(3,3,3-trifluoropropanamido)phenylamino)-pyrimidine-5-carboxamide

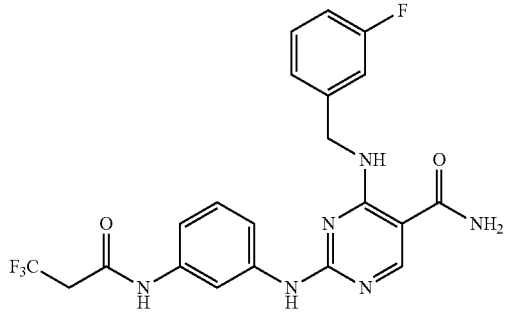 [SMILES: NC(=O)c1cnc(Nc2cccc(NC(=O)CC(F)(F)F)c2)nc1NCc1cccc(F)c1]

The aniline, M-3 (70 mg, 0.198 mmol), 3,3,3-trifluoropropionic acid (45 mg, 0.35 mmol), and EDC.HCl (200 mg, 1.043 mmol), in NMP (2 ml) were stirred for 16 h. Then the reaction mixture was purified by RP-HPLC to afford the title compound as colorless puffs, 67 mg (73%). UV: 249.1, 206.7 nm. MS: 463.2 (M+H), $C_{21}H_{18}F_4N_6O_2$. $^1$H NMR (400 MHz, DMSO-d$_6$): δ 3.43 (q, J=11.4 Hz), 4.68 (d, J=6 Hz), 6.88-7.45 (m, 8H), 7.80-8.00 (m, 2H), 8.46 (s, 1H), 9.78 (br s, 1H), 9.90 (br s, 1H), 10.22 (br s, 1H).

Example 292

Benzyl 3-(5-carbamoyl-4-(3-fluorobenzylamino)pyrimidin-2-ylamino)phenylcarbamate

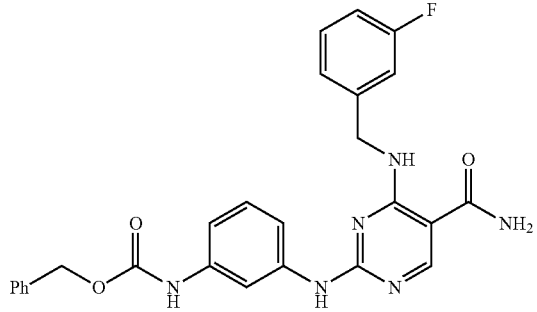 [SMILES: NC(=O)c1cnc(Nc2cccc(NC(=O)OCc3ccccc3)c2)nc1NCc1cccc(F)c1]

The above compound was prepared according to reactions described in Scheme 16. The compound M-1 was prepared using the procedures described in scheme 1 and substituting 3-fluorobenzylamine in the place of cyclobutyl amine.

Step 7: The —OBt derivative (M-1) (100 mg, 0.263 mmol), 3-cbz-aniline (120 mg, 0.495 mmol) and PTSA.H$_2$O (50 mg, 0.262 mmol), dissolved in NMP (1.0 mL) were heated to 50° C. in a sealed tube for 24 h. Then the reaction mixture was cooled to room temperature, and diluted with water to precipitate the compound, 114 mg (89%). UV: 244.4, 206.7 nm. MS: 487.2 (M+H), $C_{26}H_{23}FN_6O_3$. $^1$H NMR (400 MHz, DMSO-d$_6$): δ 4.73 (d, 2H, J=5.8 Hz), 5.10 (s, 2H), 6.98-7.16 (m, 6H), 7.28-7.40 (m, 6H), 8.50 (s, 1H), 9.76 (br s, 1H), 9.84-10.05 (m, 2H).

Example 293

2-(3-(1-cyanocyclopropanecarboxamido)phenylamino)-4-(3-fluorobenzylamino)pyrimidine-5-carboxamide

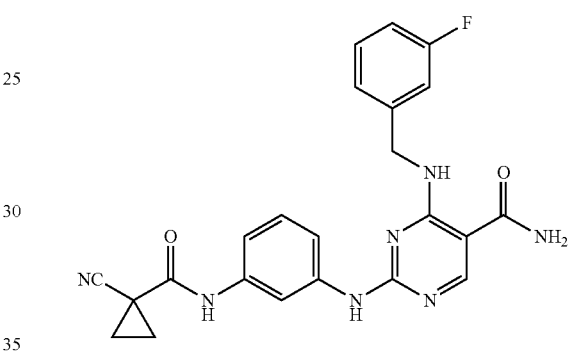

The aniline, M-3, (Scheme 16) (100 mg, 0.283 mmol), 1-cyano-cyclopropanecarboxylic acid (50 mg, 0.450 mmol), and EDC.HCl (257 mg, 1.340 mmol), in NMP (1 mL) were stirred at room temperature for 17 h. Then the reaction mixture was purified by RP-HPLC to afford the title compound, as colorless puffs, 91 mg (72%). UV: 249.1 nm. MS: 446.1 (M+H), $C_{23}H_{20}FN_7O_2$. $^1$H NMR (400 MHz, DMSO-d$_6$): δ 1.50-1.60 (m, 4H), 4.68 (d, 2H, J=6 Hz), 6.92-7.50 (m, 8H), 7.82-8.30 (m, 2H), 8.46 (s, 1H), 9.85 (br s, 1H), 10.02 (br s, 1H).

Example 294

4-(2-fluorobenzylamino)-2-(3-(isonicotinamido)-phenylamino)pyrimidine-5-carboxamide

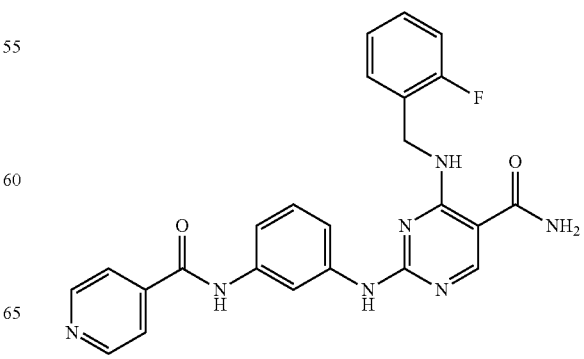

This compound, was synthesized using the procedure described in example 296, using iso-nicotinic acid. UV: 258.6 nm. MS: 458.3 (M+H), $C_{24}H_{20}FN_7O_2$. $^1H$ NMR (400 MHz, DMSO-$d_6$): δ 4.85 (d, 2H, J=5.80 Hz), 7.02-7.20 (m, 4H), 7.28-7.45 (m, 5H), 7.60 (m, 1H), 7.95 (m, 2H), 8.24 (m, 1H), 8.32 (s, 1H), 8.60 (s, 1H), 8.88 (br s, 2H), 10.10 (br s, 1H), 10.36 (br s, 1H), 10.62 (br s, 1H).

Example 295

4-(2-fluorobenzylamino)-2-(3-(picolinamido)-phenylamino)pyrimidine-5-carboxamide

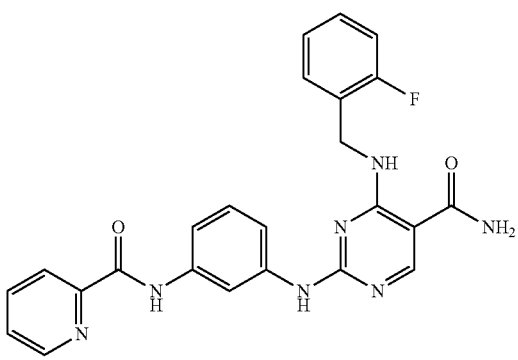 [SMILES: NC(=O)c1cnc(Nc2cccc(NC(=O)c3ccccn3)c2)nc1NCc1ccccc1F]

This compound, was synthesized using the procedure described in example 296, using picolinic acid. UV: 272.8 nm. MS: 458.3 (M+H), $C_{24}H_{20}FN_7O_2$. $^1H$ NMR (400 MHz, DMSO-$d_6$): δ 4.78 (d, 2H, J=6 Hz), 6.95-7.45 (m, 8H), 7.68 (m, 1H), 7.95-8.25 (m, 3H), 8.35 (m, 1H), 8.52 (s, 1H), 8.70 (m, 1H), 9.88 (br s, 1H), 10.02 (br s, 1H), 10.52 (br s, 1H).

Example 296

4-(2-fluorobenzylamino)-2-(3-(nicotinamido)-phenylamino)pyrimidine-5-carboxamide

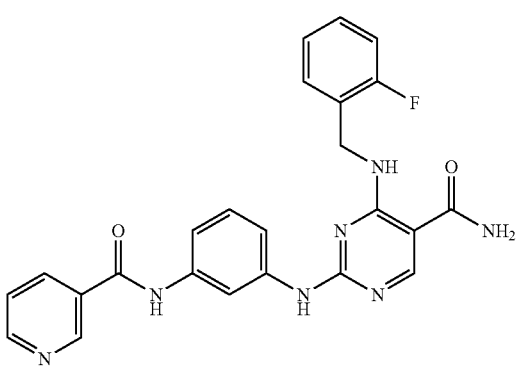 [SMILES: NC(=O)c1cnc(Nc2cccc(NC(=O)c3cccnc3)c2)nc1NCc1ccccc1F]

The aniline.TFA (2-(3-aminophenylamino)-4-(2-fluorobenzylamino)pyrimidine-5-carboxamide) (80 mg, 0.171 mmol), nicotinic acid (32 mg, 0.260 mmol), HATU (104 mg, 0.273 mmol), and DIEA (45 mg, 0.348 mmol), in NMP (2 mL) were stirred at room temperature for 19 h. Then the title compound was obtained by purification through RP-HPLC, 82 mg (84%). UV: 258.6 nm. MS: 458.3 (M+H), $C_{24}H_{20}FN_7O_2$. $^1H$ NMR (400 MHz, DMSO-$d_6$): δ 4.80 (d, 2H), J=5.8 Hz), 6.90-7.12 (m, 4H), 7.22-7.35 (m, 4H), 7.48-7.62 (m, 3H), 8.24 (s, 1H), 8.28 (m, 1H), 8.53 (s, 1H), 8.77 (m, 1H), 9.06 (s, 1H), 10.08 (br s, 1H), 10.32 (br s, 1H), 10.48 (br s, 1H).

Example 297

4-(2-fluorobenzylamino)-2-(3-(2-(pyridin-3-yl)acetamido)-phenylamino)pyrimidine-5-carboxamide

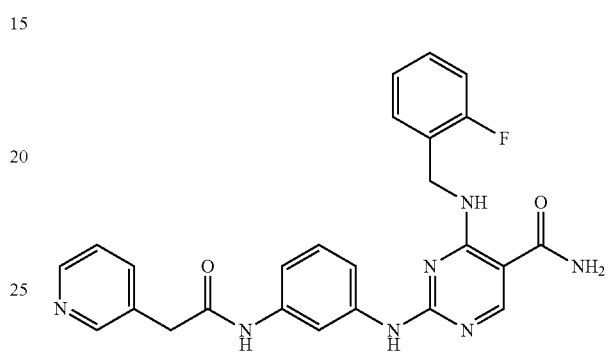

This compound was synthesized using the procedure described in example 296, and using 3-pyridine acetic acid as the acid component. UV: 253.8 nm. MS: 472.3 (M+H), $C_{25}H_{22}FN_7O_2$. $^1H$ NMR (400 MHz, DMSO-$d_6$): δ 3.88 (s, 2H), 4.70 (d, 2H, J=5.80 Hz), 6.98-7.55 (m, 10H), 7.72 (m, 1H), 7.92-8.20 (m, 3H), 8.52 (s, 1H), 8.65-8.75 (m, 2H), 9.92 (br s, 1H), 10.16 (br s, 1H), 10.32 (br s, 1H).

Example 298

4-(2-fluorobenzylamino)-2-(3-(6-hydroxypicolinamido)-phenylamino)pyrimidine-5-carboxamide

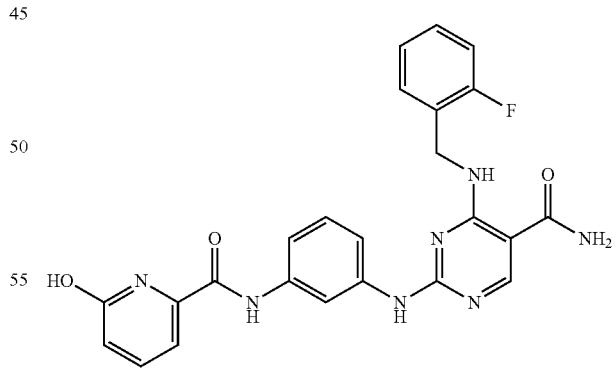

This compound, was synthesized using the procedure described in example 296, using 6-hydroxy-2-pyridine carboxylic acid. UV: 249.1 nm. MS: 474.3 (M+H), $C_{24}H_{20}FN_7O_3$. $^1H$ NMR (400 MHz, DMSO-$d_6$): δ 4.70 (d, 2H, J=6 Hz), 6.75 (m, 1H), 6.90-7.50 (m, 8H), 7.70 (m, 1H), 7.95 (m, 1H), 8.30 (s, 1H), 8.48 (s, 1H), 9.88 (br s, 1H), 10.10 (br s, 2H).

Example 299

4-(2-fluorobenzylamino)-2-(3-(2-(pyridin-4-yl)aceta-mido)-phenylamino)pyrimidine-5-carboxamide

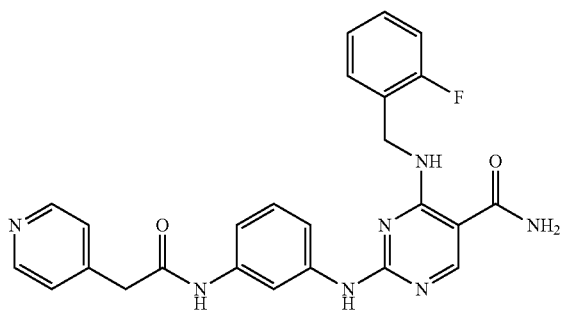 [SMILES: NC(=O)c1cnc(Nc2cccc(NC(=O)Cc3ccncc3)c2)nc1NCc1ccccc1F]

This compound was synthesized using the procedure described in example 296, and using 4-pyridine acetic acid as the acid component. UV: 249.1 nm. MS: 472.4 (M+H), $C_{25}H_{22}FN_7O_2$. $^1$H NMR (400 MHz, DMSO-$d_6$): δ 3.98 (s, 2H), 4.70 (d, 2H, J=6 Hz), 6.98-7.50 (m, 10H), 7.80 (d, 1H, J=7 Hz), 7.90-8.10 (m, 2H), 8.48 (s, 1H), 8.70 (1H, d, J=7 Hz), 9.90 (br s, 1H), 10.15 (br s, 1H), 10.38 (br s, 1H).

Example 300

4-(2-fluorobenzylamino)-2-(3-(2-(pyridin-2-yl)aceta-mido)-phenylamino)pyrimidine-5-carboxamide

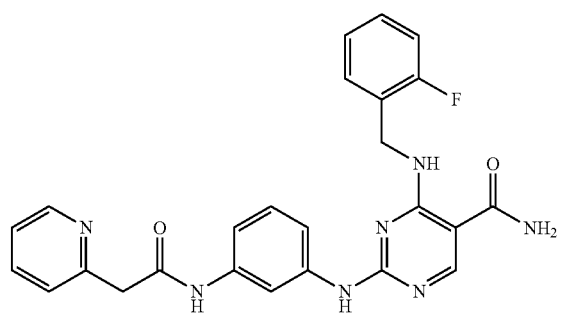 [SMILES: NC(=O)c1cnc(Nc2cccc(NC(=O)Cc3ccccn3)c2)nc1NCc1ccccc1F]

This compound was synthesized using the procedure described in example 296, and using 2-pyridine acetic acid as the acid component. UV: 258.6 nm. MS: 472.2 (M+H), $C_{25}H_{22}FN_7O_2$. $^1$H NMR (400 MHz, DMSO-$d_6$): δ 4.0 (s, 2H), 4.64 (d, 2H, J=6 Hz), 6.90-7.30 (m, 6H), 7.40-7.64 (m, 4H), 7.90-8.16 (m, 3H), 8.44 (s, 1H), 8.60 (m, 1H), (m, 1H), 9.92 (br s, 1H), 10.20 (br s, 1H), 10. 40 (br s, 1H).

Example 301

2-(3-acetamidophenylamino)-4-(4-(2-cyanoaceta-mido)-phenylamino)pyrimidine-5-carboxamide

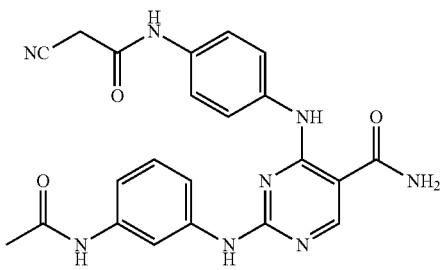 [SMILES: CC(=O)Nc1cccc(Nc2ncc(C(N)=O)c(Nc3ccc(NC(=O)CC#N)cc3)n2)c1]

The reaction mixture, comprising of the aniline.HCl, M-9, (114 mg, 0.231 mmol), cyanoacetic acid (30 mg, 0.352 mmol), EDC.HCl (133 mg, 0.693 mmol), and DIEA (51 mg, 0.394 mmol), in NMP (1.5 mL), was stirred at room temperature for 18 h. Then the title compound was isolated by prep HPLC, 92 mg (71%). UV: 249.1 nm. MS: 445.2 (M+H), $C_{22}H_{20}N_8O_3$.

Example 302

2-(3-acetamidophenylamino)-4-(4-(1-cyanocyclopro-pane-carboxamido)phenylamino)pyrimidine-5-car-boxamide

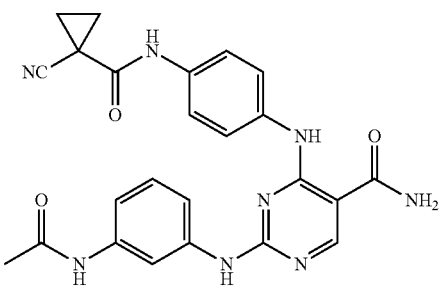 [SMILES: CC(=O)Nc1cccc(Nc2ncc(C(N)=O)c(Nc3ccc(NC(=O)C4(C#N)CC4)cc3)n2)c1]

A mixture of the aniline.HCl, M-9, (117 mg, 0.282 mmol), 1-cyano-cyclopropane carboxylic acid (50 mg, 0.450 mmol), EDC.HCl (257 mg, 1.340 mmol), and DIEA (75 mg, 0.580 mmol) in NMP (1.5 mL) was stirred at room temperature for 19 h. Then the title compound was obtained by purification using RP-HPLC, 125 mg (76%). UV: 249.1 nm. MS: 471.1 (M+H), $C_{24}H_{22}N_8O_3$. $^1$H NMR (400 MHz, DMSO-$d_6$): δ 1.661 (s, 4H), 2.02 (s, 3H), 7.10-7.70 (m, 9H), 7.80 (br s, 1H), 8.12 (br s, 1H), 8.64 (s, 1H), 9.90 (m, 2H), 9.88 (s, 1H), 11.68 (s, 1H).

Example 303

2-(3-acetamidophenylamino)-4-(4-(3,3,3-trifluoro-propanamido) phenylamino)pyrimidine-5-carboxam-ide

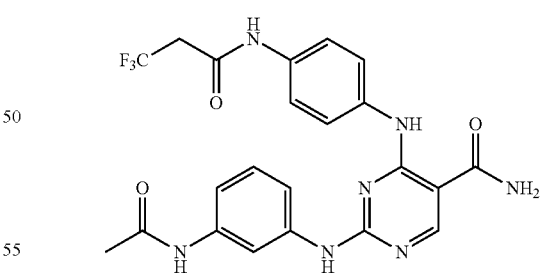

The reaction mixture, consisting of the aniline. HCl, M-9, (95 mg, 0.229 mmol), 3,3,3-trifluoropropionic acid (45 mg, 0.351 mmol), EDC.HCl (133 mg, 0.693 mmol), and DIEA (88 mg, 0.680 mmol), in NMP (1.5 mL) was stirred at room temperature for 18 h. Then the title compound was isolated by purification on RP-HPLC, 109 mg (79%). UV: 249.1 nm. MS: 488.1 (M+H), $C_{22}H_{20}F_3N_7O_3$. $^1$H NMR (400 MHz, DMSO-$d_6$): δ 1.98 (s, 3H), 3.43 (q, 2H, J=11 Hz), 7.05-7.65 (m, 8H), 7.75 (s, 1H), 8.06 (s, 1H), 8.58 (s, 1H), 9.84 (br s, 2H), 10.22 (s, 1H), 11.62 (s, 1H).

Example 304

6-(4-fluoro-3-(pyrrolidine-1-carboxamido)phenylamino)-4-(pyridin-3-ylmethylamino)nicotinamide

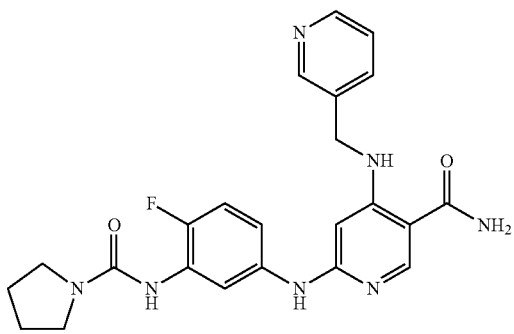 [SMILES: NC(=O)c1cnc(Nc2ccc(F)c(NC(=O)N3CCCC3)c2)cc1NCc1cccnc1]

The title compound was synthesized as scheme 1 described in following procedures.

Step I, 4,6-Dichloronicotinamide (1)

A suspension of 4,6-dihydroxynicotinic acid (3.10 g, 20 mmoles) in phosphoryl trichloride (50 mL) was stirred at 100° C. for 4 hrs. After cooled to room temperature, the reaction solution was poured into a cold ammonium hydroxide solution (27-30%) in several portions and kept the mixture basic. The first portion of desired product as precipitate was collected by filtration. The second portion of desired product was obtained by extraction of mother aqueous liquid with DCM. The total amount of 4,6-Dichloronicotinamide (1) was 2.78 g. MS+: 191.0, UV: λ=201.0; 269.2 nm, $^1$H NMR: (CDCl$_3$) δ8.77 (s, 1H), δ7.45 (s, 1H), δ6.34 (b, 1H), δ6.21 (b, 1H).

Step II, 6-chloro-4-(pyridin-3-ylmethylamino)nicotinamide (2)

A mixture of 4,6-Dichloronicotinamide (1, 950 mg, 5 mmoles), 3-picolylamine (756 mg, 7 mmoles) and DIEA (12 mmoles) in NMP (5 mL) was stirred at 60° C. for 20 hrs. The reaction mixture was concentrated under an oil pump. The residue was washed with water and dried under an oil pump. The desired 6-chloro-4-(pyridin-3-ylmethylamino)nicotinamide (2, 1.085 g) was obtained. MS+: 263.1, UV: λ=220.9; 260.9 nm. $^1$H NMR: (CDCl$_3$) δ8.96 (s, 1H), δ8.60 (s, 1H), δ8.57 (d, J=3.2 Hz, 1H), δ8.30 (s, 1H), δ7.64 (d, J=7.6Hz, 1H), δ7.31 (dd, J1=7.6Hz, J2=3.2Hz, 1H), δ6.51 (s, 1H), δ5.80 (b, 2H), δ4.47 (s, 1H), δ4.45 (s, 1H).

Step III, N-(5-amino-2-fluorophenyl)pyrrolidine-1-carboxamide (3)

A mixture of 1-fluoro-2-isocyanato-4-nitrobenzene (1.125 g, 6.18 mmoles) and pyrrolidine (485 mg, 6.8 mmoles) in DCM (20 mL) was stirred at r.t. for 14 hrs. After concentrated, the mixture was extracted with ethyl acetate. The organic layer was washed with aqueous citric acid solution and dried over MgSO$_4$, followed by hydrogenation with Pd/C (wet, 10%, 0.15 g) under a hydrogen balloon overnight. After filtration and concentration, the reasonable pure N-(5-amino-2-fluorophenyl)pyrrolidine-1-carboxamide (3, 1.44 g) was used for the next reactions. MS+: 224.2, UV: λ=271.6 nm. $^1$H NMR: (DMSO) δ7.44 (s, 1H), δ6.78 (m, 1H), δ6.20 (m, 1H), δ3.32 (m, 4H), 1.83 (m, 4H).

Step IV, 6-(4-fluoro-3-(pyrrolidine-1-carboxamido)phenylamino)-4-(pyridin-3-ylmethylamino) nicotinamide (4)

A mixture of 6-chloro-4-(pyridin-3-ylmethylamino)nicotinamide (2, 27 mg, 0.1 mmoles), N-(5-amino-2-fluorophenyl)pyrrolidine-1-carboxamide (3, 34 mg, 0.15 mmoles), Pd(OAc)$_2$ (2 mg). BINAP (15 mg), Cs$_2$CO$_3$ (100 mg) in dioxane (1 mL) was heated at 120° C. under microwave for 60 min. Purification with reversed phase HPLC, 6-(4-fluoro-3-(pyrrolidine-1-carboxamido)phenylamino)-4-(pyridin-3-ylmethylamino)nicotinamide (4, 10 mg) was obtained. MS found for C$_{23}$H$_{24}$FN$_7$O$_2$ as (M+H)$^+$ 450.5, UV: λ=249.1 nm. $^1$H NMR: (CD$_3$OD) δ8.50 (s, 1H), δ8.42 (d, 1H), δ8.26 (d, 1H), δ7.80 (dd, 1H), δ7.60 (dd, 1H), δ7.40 (dd, 1H), δ7.00 (dd, 1H), δ6.91 (m, 1H), δ5.88 (d, 1H), δ4.49 (s, 2H), δ3.48 (m, 4H), δ1.99 (b, 2H).

Example 305

6-(3-(azetidine-1-carboxamido)-4-fluorophenylamino)-4-(3-fluorobenzylamino)nicotinamide

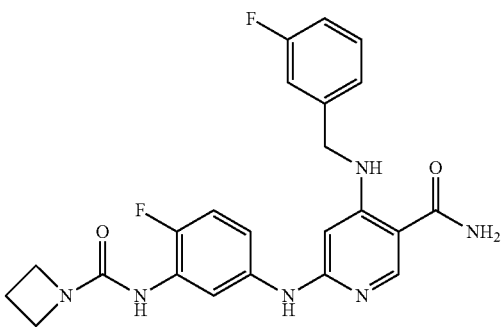 [SMILES: NC(=O)c1cnc(Nc2ccc(F)c(NC(=O)N3CCC3)c2)cc1NCc1cccc(F)c1]

The title compound was synthesized similar to step I-IV in the Scheme for Example 304. MS found for C$_{23}$H$_{22}$F$_2$N$_6$O$_2$ as (M+H)$^+$ 453.3. UV: λ=245.6 nm. $^1$H NMR: (CD$_3$OD) δ8.13 (s, 1H), δ7.64 (dd, 1H), δ7.35 (m, 1H), δ7.17 (dd, 1H), δ7.10 (d, 1H), δ7.02 (m, 2H), δ6.84 (m, 1H), δ5.90 (s, 1H), δ4.53 (s, 2H), δ4.12 (dd, 4H), δ2.34 (m, 2H).

Example 306

(R)-6-(3-(3-(dimethylamino)pyrrolidine-1-carboxamido)phenylamino)-4-(3-fluorobenzylamino)nicotinamide

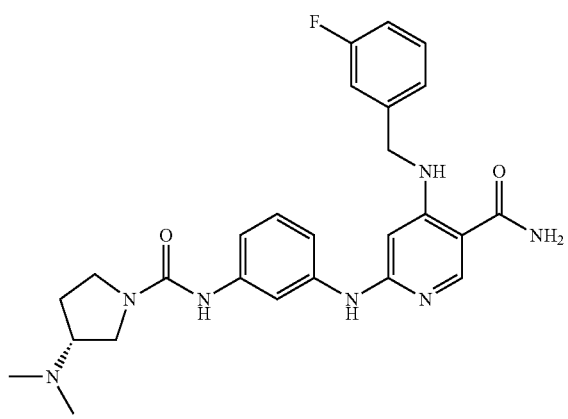 [SMILES: CN(C)[C@@H]1CCN(C(=O)Nc2cccc(Nc3cc(NCc4cccc(F)c4)c(C(N)=O)cn3)c2)C1]

The title compound was synthesized similar to step I-IV in the Scheme for Example 304. MS found for $C_{26}H_{30}FN_7O_2$ as (M+H)$^+$ 492.6. UV: λ=251.5 nm. $^1$H NMR: (CD$_3$OD) δ8.15 (s, 1H), δ7.53 (s, 1H), δ7.33 (m, 2H), δ7.23 (d, 1H), δ7.10 (d, 1H), δ7.02 (m, 2H), δ6.79 (d, 1H), δ6.00 (s, 1H), δ4.53 (s, 2H), δ3.99 (m, 2H), δ3.79 (m, 1H), δ3.60 (m, 2H), δ2.97 (s, 6H), δ2.54 (m, 1H), δ2.25 (m, 1H).

Example 307

(6-(4-fluoro-3-(pyrrolidine-1-carboxamido)phenylamino)-4-(3-fluorobenzylamino)nicotinamide

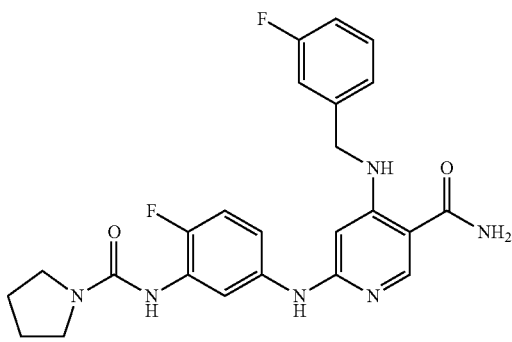 [SMILES: NC(=O)c1cnc(Nc2ccc(F)c(NC(=O)N3CCCC3)c2)cc1NCc1cccc(F)c1]

The title compound was synthesized similar to step I-IV in the Scheme for Example 304. MS found for $C_{24}H_{24}F_2N_6O_2$ as (M+H)$^+$ 467.6. UV: λ=201.0; 250.3 nm.

Example 308

N-(3-(5-carbamoyl-4-(3-fluorobenzylamino)pyridin-2-ylamino)phenyl)morpholine-4-carboxamide

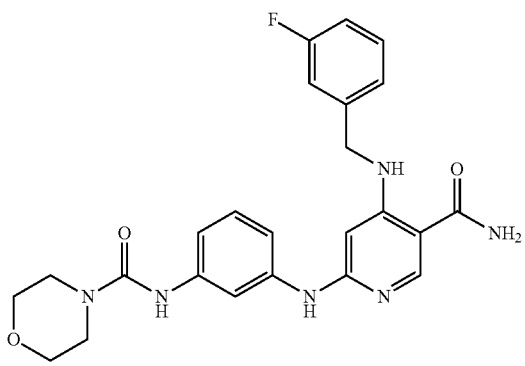 [SMILES: NC(=O)c1cnc(Nc2cccc(NC(=O)N3CCOCC3)c2)cc1NCc1cccc(F)c1]

The title compound was synthesized similar to step I-IV in the Scheme for Example 304. MS found for $C_{24}H_{25}FN_6O_3$ as (M+H)$^+$ 465.3. UV: λ=253.8 nm. $^1$H NMR: (CD$_3$OD) δ8.15 (s, 1H), δ7.46 (s, 1H), δ7.34 (m, 1H), δ7.29 (d, 1H), δ7.13 (m, 2H), δ7.04 (m, 2H), δ6.79 (d, 1H), δ5.98 (s, 1H), δ4.53 (s, 2H), δ3.71 (m, 4H), δ3.52 (m, 4H).

Example 309

4-(3-fluorobenzylamino)-6-(3-(pyrrolidine-1-carboxamido)phenylamino)nicotinamide

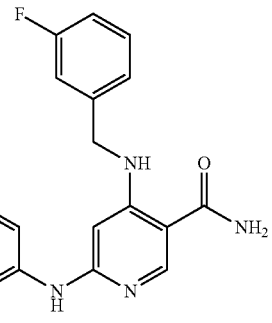

The title compound was synthesized similar to step I-IV in the Scheme for Example 304. MS found for $C_{24}H_{25}FN_6O_2$ as (M+H)$^+$ 449.5. UV: λ=253.8 nm. $^1$H NMR: (CD$_3$OD) δ8.13 (s, 1H), δ7.52 (s, 1H), δ7.32 (m, 2H), δ7.21 (d, 1H), δ7.11 (d, 1H), δ7.04 (m, 2H), δ6.77 (d, 1H), δ5.97 (s, 1H), δ4.53 (s, 2H), δ3.46 (b, 4H), δ1.99 (b, 4H).

Example 310

6-(3-acetamidophenylamino)-4-(3-fluorobenzylamino)nicotinamide

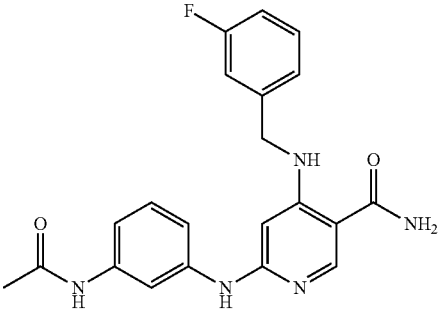 [SMILES: CC(=O)Nc1cccc(Nc2cc(NCc3cccc(F)c3)c(C(N)=O)cn2)c1]

The title compound was synthesized similar to step IV in the Scheme for Example 304. MS found for $C_{21}H_{20}FN_5O_2$ as (M+H)$^+$ 394.5. UV: λ=253.8 nm. $^1$H NMR: (CD$_3$OD) δ8.14 (s, 1H), δ7.74 (t, 1H), δ7.33 (t, 2H), δ7.22 (d, 1H), δ7.08 (d, 1H), δ7.01 (m, 2), δ6.81 (d, 1H), δ5.95 (s, 1H), δ4.51 (s, 2H), δ2.15 (s, 3H).

Example 311

(S)-6-(3-(azetidine-1-carboxamido)-4-fluorophenylamino)-4-(2-hydroxy-1-phenylethylamino)nicotinamide

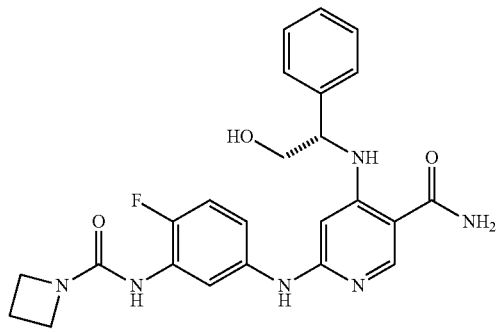 [SMILES: NC(=O)c1cnc(Nc2ccc(F)c(NC(=O)N3CCC3)c2)cc1N[C@H](CO)c1ccccc1]

The title compound was synthesized similar to step I-IV in the Scheme for Example 304. MS found for $C_{24}H_{25}FN_6O_3$ as $(M+H)^+$ 465.5. UV: $\lambda=251.5$ nm. $^1$H NMR: $(CD_3OD)$ δ8.23 (s, 1H), δ7.49 (m, 1H), δ7.30 (m, 5H), δ6.90 (t, 1H), δ6.67 (m, 1H), δ5.75 (s, 1H), δ4.48 (m, 1H), δ4.10 (m, 4H), δ3.89 (m, 1H), δ3.70 (m, 1H), δ2.33 (m, 2H).

Example 312

6-(3-((R)-3-(dimethylamino)pyrrolidine-1-carboxamido)phenylamino)-4-((S)-2-hydroxy-1-phenylethylamino)nicotinamide

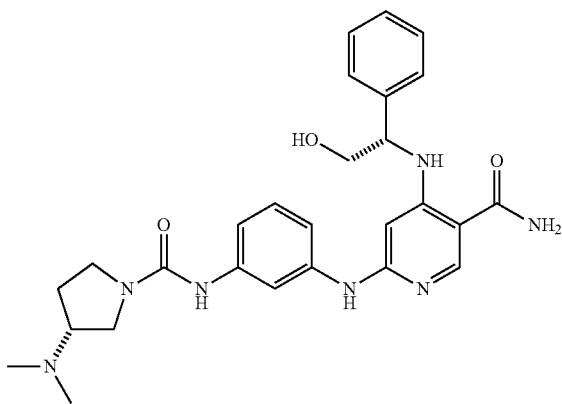 [SMILES: CN(C)[C@@H]1CCN(C(=O)Nc2cccc(Nc3cc(N[C@H](CO)c4ccccc4)c(C(N)=O)cn3)c2)C1]

The title compound was synthesized similar to step I-IV in the Scheme for Example 304. MS found for $C_{27}H_{33}N_7O_3$ as $(M+H)^+$ 504.3. UV: $\lambda=249.1$ nm.

Example 313

(S)-6-(4-fluoro-3-(pyrrolidine-1-carboxamido)phenylamino)-4-(2-hydroxy-1-phenylethylamino)nicotinamide

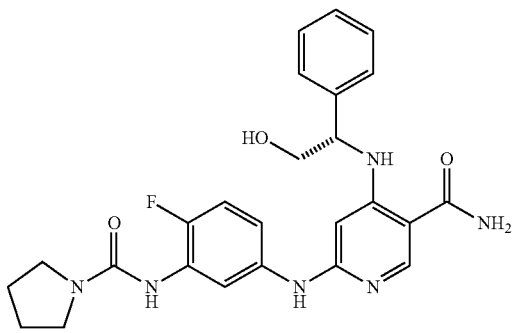 [SMILES: NC(=O)c1cnc(Nc2ccc(F)c(NC(=O)N3CCCC3)c2)cc1N[C@H](CO)c1ccccc1]

The title compound was synthesized similar to step I-IV in the Scheme for Example 304. MS found for $C_{25}H_{27}FN_6O_3$ as $(M+H)^+$ 479.3. UV: $\lambda=251.1$ nm. $^1$H NMR: $(CD_3OD)$ δ8.23 (s, 1H), δ7.46 (m, 1H), δ7.31 (m, 5H), δ6.93 (t, 1H), δ6.68 (m, 1H), δ5.76 (s, 1H), δ4.49 (m, 1), δ3.82 (m, 1H), δ3.71 (m, 1H), δ3.48 (b, 4H), δ1.99 (b, 4H).

Example 314

(S)-N-(3-(5-carbamoyl-4-(2-hydroxy-1-phenylethylamino)pyridin-2-ylamino)phenyl)morpholine-4-carboxamide

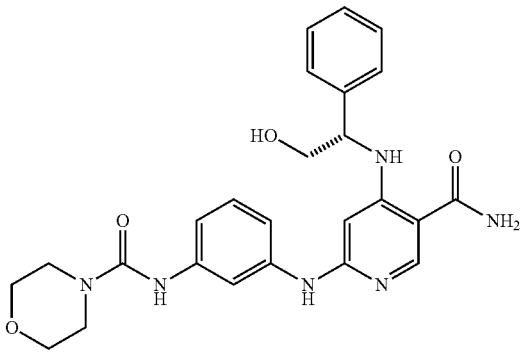 [SMILES: NC(=O)c1cnc(Nc2cccc(NC(=O)N3CCOCC3)c2)cc1N[C@H](CO)c1ccccc1]

The title compound was synthesized similar to step I-IV in the Scheme for Example 304. MS found for $C_{25}H_{28}N_6O_4$ as $(M+H)^+$ 477.5. UV: $\lambda=252.7$ nm.

Example 315

(S)-4-(2-hydroxy-1-phenylethylamino)-6-(3-(pyrrolidine-1-carboxamido)phenylamino)nicotinamide

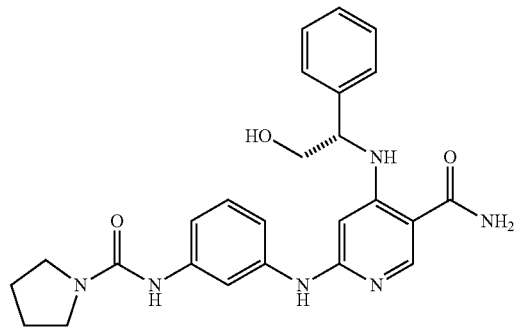 [SMILES: NC(=O)c1cnc(Nc2cccc(NC(=O)N3CCCC3)c2)cc1N[C@H](CO)c1ccccc1]

The title compound was synthesized similar to step I-IV in the Scheme for Example 304. MS found for $C_{25}H_{28}N_6O_3$ as $(M+H)^|$ 461.5. UV: $\lambda=251.5$ nm.

Example 316

(S)-6-(3-acetamidophenylamino)-4-(2-hydroxy-1-phenylethylamino)nicotinamide

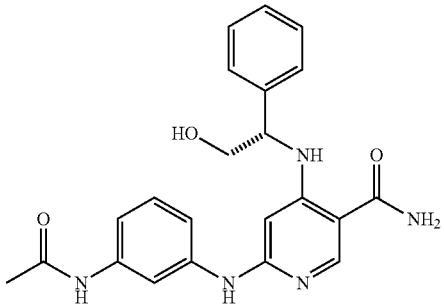 [SMILES: CC(=O)Nc1cccc(Nc2cc(N[C@H](CO)c3ccccc3)c(C(N)=O)cn2)c1]

The title compound was synthesized similar to step IV in the Scheme for Example 304. MS found for $C_{22}H_{23}N_5O_3$ as $(M+H)^+$ 406.5. UV: $\lambda=253.8$ nm. $^1$H NMR: $(CD_3OD)$ δ8.13 (s, 1H), δ7.41 (s, 1H), δ7.18 (m, 5H), δ6.97 (m, 2H), δ6.56 (m, 1H), δ5.70 (s, 1H), δ4.52 (s, 1H), δ4.37 (m, 1H), δ3.71 (m, 1H), δ3.58 (m, 1H), δ2.02 (b, 3H).

Example 317

6-(3-(azetidine-1-carboxamido)-4-fluorophenylamino)-4-(pyridin-3-ylmethylamino)nicotinamide

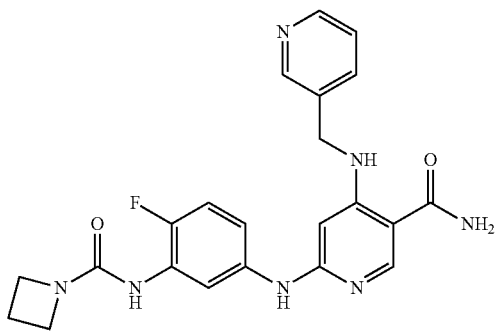 [SMILES: NC(=O)c1cnc(Nc2ccc(F)c(NC(=O)N3CCC3)c2)cc1NCc1cccnc1]

The title compound was synthesized similar to step I-IV in the Scheme for Example 304. MS found for $C_{22}H_{22}FN_7O_2$ as $(M+H)^+$ 436.3. UV: $\lambda=250.3$ nm. $^1$H NMR: $(CD_3CN)$ δ8.49 (s, 1H), δ8.43 (m, 1H), δ8.26 (s, 1H), δ7.80 (d, 1H), δ7.63 (m, 1H), δ7.40 (m, 1), δ6.99 (t, 1H), δ6.89 (m, 1H), δ5.87 (s, 1H), δ4.49 (s, 2H), δ4.10 (t, 4H), δ2.33 (m, 2H).

Example 318

(R)-6-(3-(3-(dimethylamino)pyrrolidine-1-carboxamido)phenylamino)-4-(pyridin-3-ylmethylamino)nicotinamide

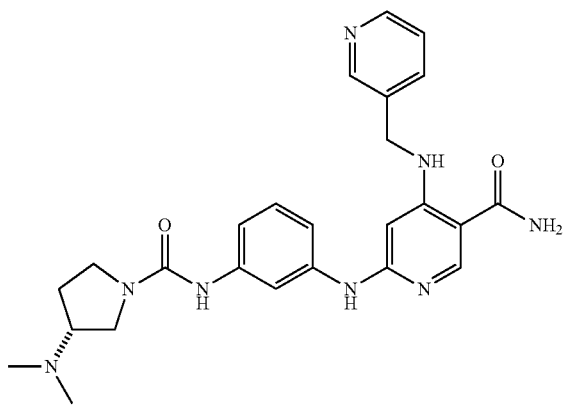 [SMILES: CN(C)[C@@H]1CCN(C(=O)Nc2cccc(Nc3cc(NCc4cccnc4)c(C(N)=O)cn3)c2)C1]

The title compound was synthesized similar to step I-IV in the Scheme for Example 304. MS found for $C_{25}H_{30}N_8O_2$ as $(M+H)^+$ 475.6. UV: $\lambda=252.7$ nm. $^1$H NMR: $(CD_3OD)$ δ8.50 (s, 1H), δ8.43 (m, 1H), δ8.26 (s, 1H), δ7.80 (d, 1H), δ7.50 (m, 1H), δ7.40 (m, 1H), δ7.14 (t, 1H), δ7.02 (m, 1H), δ6.82 (m, 1H), δ5.97 (s, 1H),δ4.50 (s, 2H), δ3.82 (m, 1H), δ3.70 (m, 1H), δ3.48 (m, 1H), δ3.10 (m, 1H), δ2.48 (s, 6H), δ2.31 (m, 1H), δ1.94 (m, 1H).

Example 319

N-(3-(5-carbamoyl-4-(pyridin-3-ylmethylamino)pyridin-2-ylamino)phenyl)morpholine-4-carboxamide

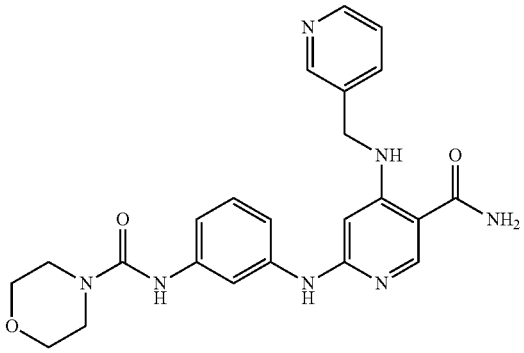 [SMILES: NC(=O)c1cnc(Nc2cccc(NC(=O)N3CCOCC3)c2)cc1NCc1cccnc1]

The title compound was synthesized similar to step I-IV in the Scheme for Example 304. MS found for $C_{23}H_{25}N_7O_3$ as $(M+H)^+$ 448.2. UV: $\lambda=251.5$ nm.

Example 320

4-(pyridin-3-ylmethylamino)-6-(3-(pyrrolidine-1-carboxamido)phenylamino)nicotinamide

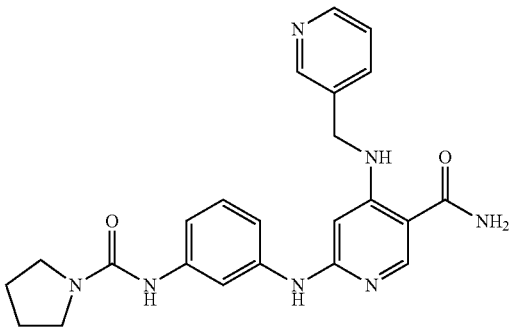 [SMILES: NC(=O)c1cnc(Nc2cccc(NC(=O)N3CCCC3)c2)cc1NCc1cccnc1]

The title compound was synthesized similar to step I-IV in the Scheme for Example 304. MS found for $C_{23}H_{25}N_7O_2$ as $(M+H)^+$ 432.5. UV: $\lambda=250.3$ nm.

Example 321

6-(3-acetamidophenylamino)-4-(pyridin-3-ylmethylamino)nicotinamide

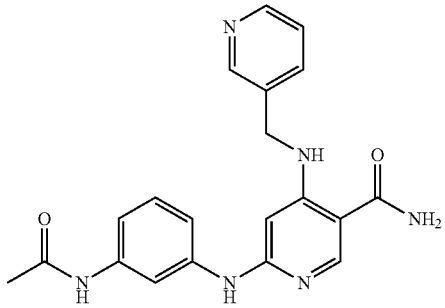 [SMILES: CC(=O)Nc1cccc(Nc2cc(NCc3cccnc3)c(C(N)=O)cn2)c1]

The title compound was synthesized similar to step IV in the Scheme for Example 304. MS found for $C_{20}H_{20}N_6O_2$ as $(M+H)^+$ 477.6. UV: $\lambda=252.7$ nm.

Example 322

(R)-6-(3-acetamidophenylamino)-4-(1-phenylethylamino)nicotinamide

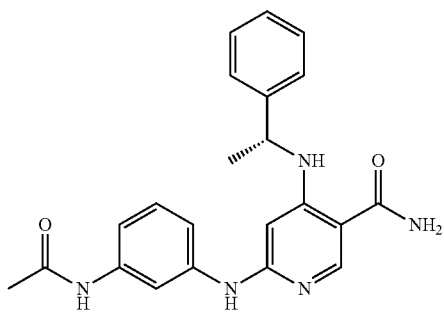 [SMILES: CC(=O)Nc1cccc(Nc2cc(N[C@H](C)c3ccccc3)c(C(N)=O)cn2)c1]

The title compound was synthesized similar to step IV in the Scheme for Example 304. MS found for $C_{22}H_{23}N_5O_2$ as (M+H)⁺ 390.2. UV: λ=205, 256 nm.

Example 323

6-(3-acetamidophenylamino)-4-(isobutylamino)nicotinamide

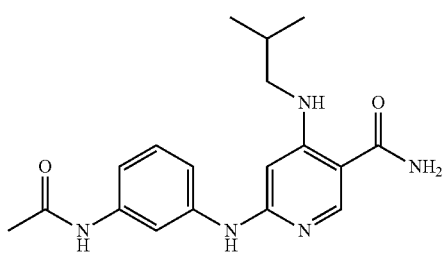 [SMILES: CC(=O)Nc1cccc(Nc2cc(NCC(C)C)c(C(N)=O)cn2)c1]

The title compound was synthesized similar to step IV in the Scheme for Example 304. MS found for $C_{18}H_{23}N_5O_2$ as (M+H)⁺ 342.2. UV: λ=205, 256 nm. ¹H NMR: (CD₃OD) δ 8.15 (s, 1H), 7.88 (s, 1H), 7.41 (m, 1H), 7.23 (d, 1H), 7.01 (d, 1H), 6.08 (s, 1H), 3.08 (d, 2H), 2.13 (s, 3H), 1.98 (m, 1H), 1.03 (d, 6H).

Example 324

4-(isobutylamino)-6-(3-(pyrrolidine-1-carboxamido)phenylamino)nicotinamide

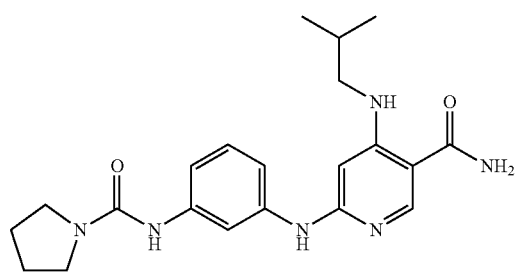 [SMILES: CC(C)CNc1cc(Nc2cccc(NC(=O)N3CCCC3)c2)ncc1C(N)=O]

The title compound was synthesized similar to step IV in the Scheme for Example 304. MS found for $C_{21}H_{28}N_6O_2$ as (M+H)⁺ 397.3. UV: λ=207, 254 nm.

Example 325

(R)-4-(1-phenylethylamino)-6-(3-(pyrrolidine-1-carboxamido)phenylamino)nicotinamide

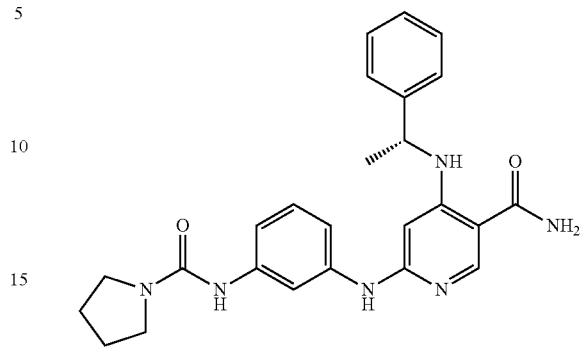

The title compound was synthesized similar to step IV in the Scheme for Example 304. MS found for $C_{25}H_{28}N_6O_2$ as (M+H)⁺ 445.3. UV: λ=207, 254 nm. ¹H NMR: (CD₃OD) δ 8.23 (s, 1H), 7.55 (s, 1H), 7.39 (t, 2H), 7.28 (m, 5H), 6.65 (m, 1H), 5.92 (s, 1H), 4.73 (m, 1H), 3.52 (m, 4H), 2.01 (m, 4H), 1.60 (d, 3H).

Example 326

4-(benzylamino)-6-(3-(pyrrolidine-1-carboxamido)phenylamino)nicotinamide

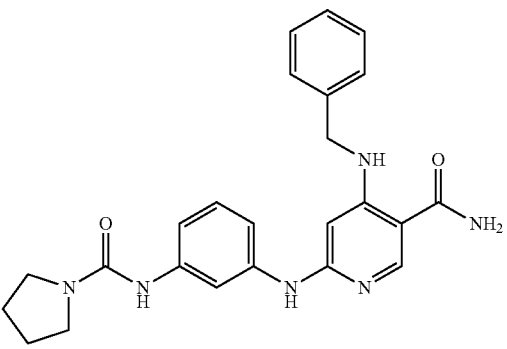 [SMILES: NC(=O)c1cnc(Nc2cccc(NC(=O)N3CCCC3)c2)cc1NCc1ccccc1]

The title compound was synthesized similar to step IV in the Scheme for Example 304. MS found for $C_{24}H_{26}N_6O_2$ as (M+H)⁺ 431.2. UV: λ=204, 254 nm.

Example 327

6-(3-acetamidophenylamino)-4-(isopentylamino)nicotinamide

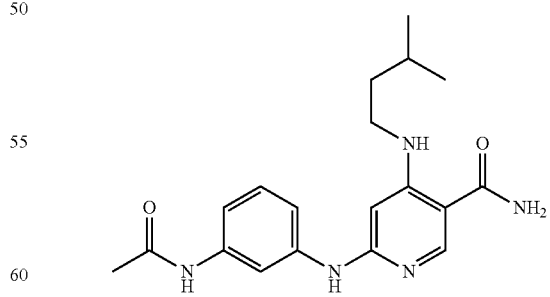

The title compound was synthesized similar to step IV in the Scheme for Example 304. MS found for $C_{19}H_{25}N_5O_2$ as (M+H)⁺ 356.3. UV: λ=205, 254 nm. ¹H NMR: (CD₃OD) δ 8.20 (s, 1H), 7.91 (s, 1H), 7.39 (t, 1H), 7.23 (d, 1H), 7.07 (d, 1H), 6.09 (s, 1H), 3.24 (m, 2H), 2.15 (s, 3H), 1.72 (m, 1H), 1.56 (m, 2H), 0.97 (d, 6H).

Example 328

4-(isopentylamino)-6-(3-(pyrrolidine-1-carboxamido)phenylamino)nicotinamide

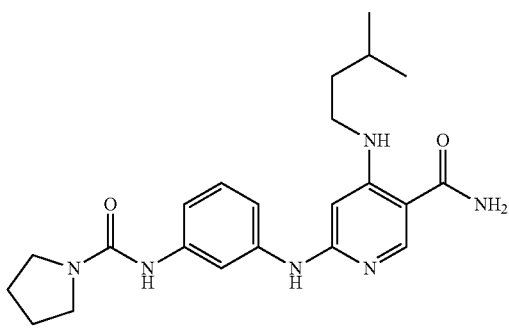 [SMILES: CC(C)CCNc1cc(Nc2cccc(NC(=O)N3CCCC3)c2)ncc1C(N)=O]

The title compound was synthesized similar to step IV in the Scheme for Example 304. MS found for $C_{22}H_{30}N_6O_2$ as (M+H)$^+$ 411.3. UV: λ=207, 254 nm. $^1$H NMR: (CD$_3$OD) δ8.12 (s, 1H), 7.61 (s, 1H), 7.30 (t, 1H), 7.16 (d, 1H), 6.93 (d, 1H), 6.05 (s, 1H), 3.47 (m, 4H), 3.23 (m, 2H), 1.98 (m, 4H), 1.70 (m, 1H), 1.56 (m, 2H), 0.96 (d, 6H).

Example 329

6-(3-acetamidophenylamino)-4-(cyclopropylmethylamino)nicotinamide

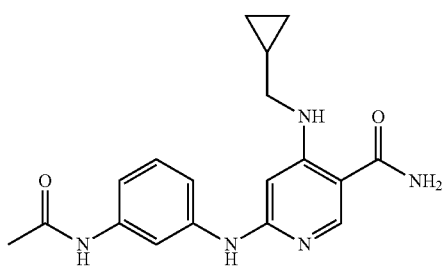 [SMILES: CC(=O)Nc1cccc(Nc2cc(NCC3CC3)c(C(N)=O)cn2)c1]

The title compound was synthesized similar to step IV in the Scheme for Example 304. MS found for $C_{18}H_{21}N_5O_2$ as (M+H)$^+$ 340.2. UV: λ=204, 254 nm. $^1$H NMR: (CD$_3$OD)) δ8.11 (s, 1H), 7.85 (s, 1H), 7.39 (t, 1H), 7.21 (d, 1H), 7.00 (d, 1H), 6.07 (s, 1), 3.12 (d, 2H), 2.15 (s, 3H), 1.27 (m, 1H), 0.62 (m, 2H), 0.31 (m, 2H).

Example 330

6-(3-acetamidophenylamino)-4-(cyclopentylamino)nicotinamide

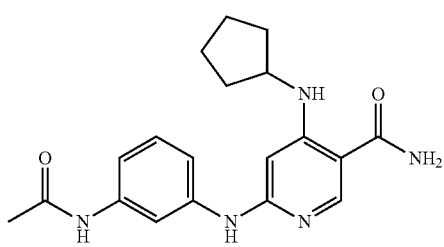 [SMILES: CC(=O)Nc1cccc(Nc2cc(NC3CCCC3)c(C(N)=O)cn2)c1]

The title compound was synthesized similar to step IV in the Scheme for Example 304. MS found for $C_{19}H_{23}N_5O_2$ as (M+H)$^+$ 354.3. UV: λ=354.3 nm. $^1$H NMR: (CD$_3$OD) δ8.11 (s, 1H), 7.86 (s, 1H), 7.39 (m, 1H), 7.22 (m, 1H), 7.01 (m, 1H), 3.88 (m, 1H), 2.15 (s, 3H), 2.03 (m, 4H), 1.69 (m, 4H).

Example 331

6-(3-acetamidophenylamino)-4-(cyclobutylmethylamino)nicotinamide

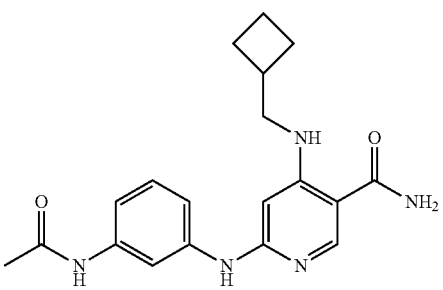 [SMILES: CC(=O)Nc1cccc(Nc2cc(NCC3CCC3)c(C(N)=O)cn2)c1]

The title compound was synthesized similar to step IV in the Scheme for Example 304. MS found for $C_{19}H_{23}N_5O_2$ as (M+H)$^|$ 354.3. UV: λ=205, 256 nm. $^1$H NMR: (CD$_3$OD) δ 8.14 (s, 1H), 7.88 (s, 1H), 7.43 (t, 1H), 7.24 (d, 1H), 7.01 (d, 1H), 6.09 (s, 1H), 2.18 (m, 5H), 1.98 (m, 2H), 1.80 (m, 2H).

Example 332

6-(3-acetamidophenylamino)-4-(4-fluorobenzylamino)nicotinamide

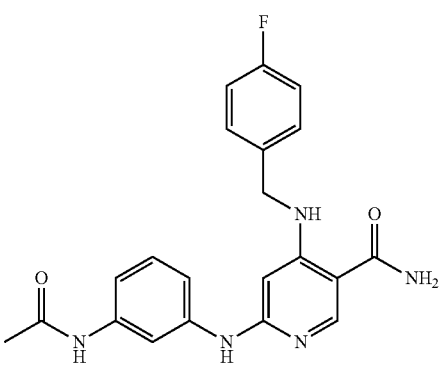 [SMILES: CC(=O)Nc1cccc(Nc2cc(NCc3ccc(F)cc3)c(C(N)=O)cn2)c1]

The title compound was synthesized similar to step IV in the Scheme for Example 304. MS found for $C_{21}H_{20}FN5O_2$ as (M+H)$^+$ 394.1. UV: λ=205, 254 nm. $^1$H NMR: (CD$_3$OD) δ8.13 (s, 1H), 7.74 (t, 1H), 7.35 (t, 1H), 7.23 (m, 3H), 7.05 (t, 2H), 6.86 (dd, 2H), 5.95 (s, 1H), 4.47 (s, 2H), 2.15 (s, 3H).

Example 333

6-(3-acetamidophenylamino)-4-(2,3-dihydro-1H-inden-2-ylamino)nicotinamide

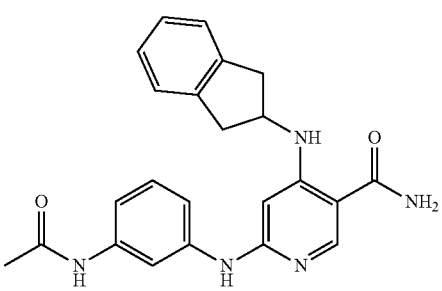 [SMILES: CC(=O)Nc1cccc(Nc2cc(NC3Cc4ccccc4C3)c(C(N)=O)cn2)c1]

The title compound was synthesized similar to step IV in the Scheme for Example 304. MS found for $C_{23}H_{23}N_5O_2$ as (M+H)$^+$ 402.2. UV: λ=209, 251 nm. $^1$H NMR: (CD$_3$OD) δ8.14 (s, 1H), 7.91 (s, 1H), 7.41 (t, 1H), 7.21 (m, 4H), 7.05 (d, 1H), 6.20 (s, 1H), 4.38 (m, 1H), 3.40 (dd, 2H), 2.96 (dd, 2H), 2.15 (s, 3H).

Example 334

6-(3-acetamidophenylamino)-4-(benzo[d][1,3]di-oxol-5-ylmethylamino)nicotinamide

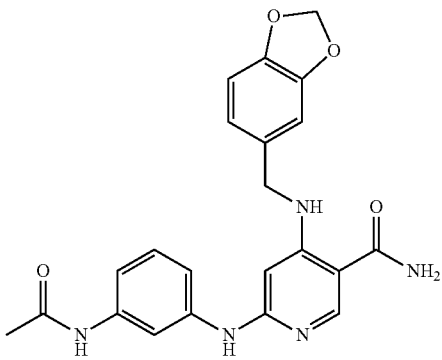 [SMILES: CC(=O)Nc1cccc(Nc2cc(NCc3ccc4c(c3)OCO4)c(C(N)=O)cn2)c1]

The title compound was synthesized similar to step IV in the Scheme for Example 304. MS found for $C_{22}H_{21}N_5O_4$ as $(M+H)^+$ 420.1. UV: $\lambda$=202, 254 nm.

Example 335

(S)-6-(3-acetamidophenylamino)-4-(2,3-dihydro-1H-inden-1-ylamino)nicotinamide

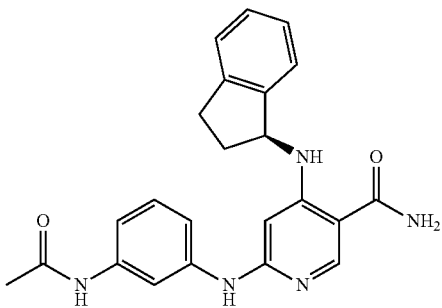 [SMILES: CC(=O)Nc1cccc(Nc2cc(N[C@H]3CCc4ccccc43)c(C(N)=O)cn2)c1]

The title compound was synthesized similar to step IV in the Scheme for Example 304. MS found for $C_{23}H_{23}N_5O_2$ as $(M+H)^+$ 402.2. UV: $\lambda$=209, 258 nm. $^1$H NMR: (CD$_3$OD) $\delta$8.16 (s, 1H), 8.60 (t, 1H), 7.41 (t, 1H), 7.22 (m, 5H), 7.02 (dd, 1H), 6.25 (s, 1H), 5.12 (t, 1H), 3.04 (m, 1H), 2.97 (m, 1H), 2.62 (m, 1H), 1.98 (m, 1H).

Example 336

6-(3-acetamidophenylamino)-4-(2,3-difluorobenzy-lamino)nicotinamide

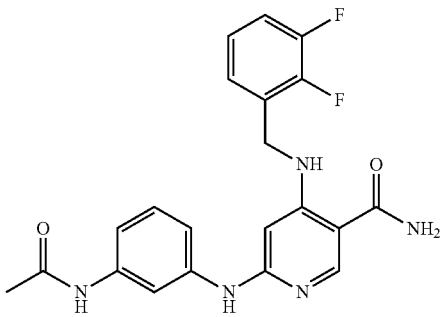

The title compound was synthesized similar to step IV in the Scheme for Example 304. MS found for $C_{21}H_{19}F_2N_5O_2$ as $(M+H)^+$412.2. UV: $\lambda$=205, 254 nm. $^1$H NMR: (CD$_3$OD) $\delta$8.14 (s, 1H), 7.78 (s, 1H), 7.36 (t, 1H), 7.22 (m, 2H), 7.12 (m, 2H), 6.88 (d, 1H), 5.98 (s, 1H), 4.59 (s, 2H), 2.15 (s, 3H).

Example 337

6-(3-acetamidophenylamino)-4-(3-chlorobenzy-lamino)nicotinamide

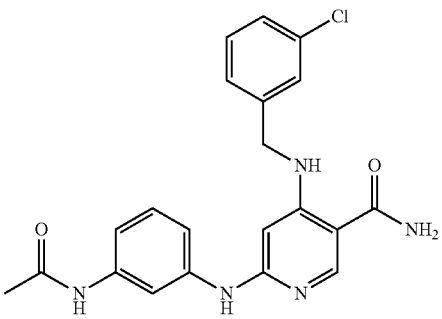 [SMILES: CC(=O)Nc1cccc(Nc2cc(NCc3cccc(Cl)c3)c(C(N)=O)cn2)c1]

The title compound was synthesized similar to step IV in the Scheme for Example 304. MS found for $C_{21}H_{20}ClN_5O_2$ as $(M+H)^+$ 410.1. UV: $\lambda$=202, 254 nm. $^1$H NMR: (CD$_3$OD) $\delta$8.16 (s, 1H), 7.77 (t, 1H), 7.31 (m, 4H), 7.19 (m, 2H), 6.83 (d, 1H), 5.93 (s, 1H), 4.52 (s, 2H), 2.17 (s, 3H).

Example 338

6-(3-acetamidophenylamino)-4-(phenethylamino)nicotinamide

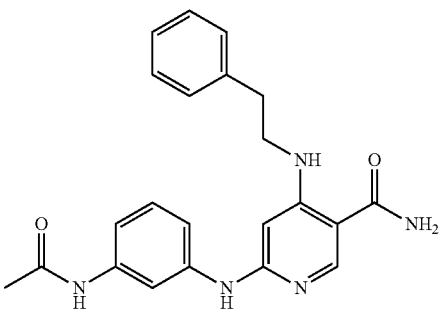 [SMILES: CC(=O)Nc1cccc(Nc2cc(NCCc3ccccc3)c(C(N)=O)cn2)c1]

The title compound was synthesized similar to step IV in the Scheme for Example 304. MS found for $C_{22}H_{23}N_5O_2$ as $(M+H)^+$ 390.1. UV: $\lambda$=205, 256 nm. $^1$H NMR: (CD$_3$OD) $\delta$8.09 (s, 1H), 7.90 (s, 1H), 7.41 (t, 1H), 7.12-7.27 (m, 6H), 6.97 (d, 1H), 6.04 (s, 1H), 3.49 (t, 2H), 2.92 (t, 2H), 2.11 (s, 3H).

Example 339

6-(3-acetamidophenylamino)-4-(benzylamino)-N-methylnicotinamide

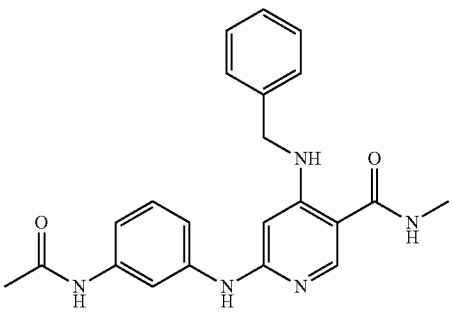 [SMILES: CNC(=O)c1cnc(Nc2cccc(NC(C)=O)c2)cc1NCc1ccccc1]

The title compound was synthesized similar to step IV in the Scheme for Example 304. MS found for $C_{22}H_{23}N_5O_2$ as $(M+H)^+$ 390.4. UV: $\lambda$=207, 254 nm. $^1$H NMR: (CD$_3$OD) $\delta$8.03 (s, 1H), 7.78 (t, 1H), 7.21-7.48 (m, 7H), 6.83 (d, 1H), 6.03 (s, 1H), 4.52 (s, 2H), 2.89 (s, 3H), 2.17 (s, 3H).

Example 340

6-(3-acetamidophenylamino)-4-(2-fluorobenzy-lamino)nicotinamide

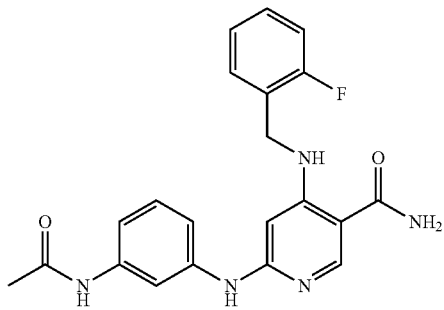 [SMILES: CC(=O)Nc1cccc(Nc2cc(NCc3ccccc3F)c(C(N)=O)cn2)c1]

The title compound was synthesized similar to step IV in the Scheme for Example 304. MS found for $C_{21}H_{20}FN_5O_2$ as $(M+H)^+$ 394.4. UV: $\lambda$=205, 254 nm. $^1$H NMR: $(CD_3OD)$ $\delta$8.22 (s, 1H), 7.83 (s, 1H), 7.18-7.48 (m, 6H), 6.95 (d, 1H), 6.07 (s, 1H), 4.57 (s, 2H), 2.15 (s, 3H).

Example 341

4-(3,5-difluorobenzylamino)-6-(3-(pyrrolidine-1-carboxamido)phenylamino)nicotinamide

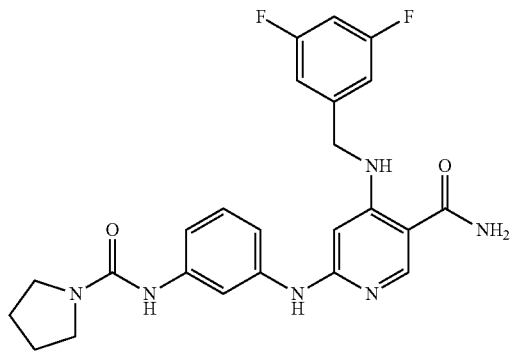 [SMILES: NC(=O)c1cnc(Nc2cccc(NC(=O)N3CCCC3)c2)cc1NCc1cc(F)cc(F)c1]

The title compound was synthesized similar to step IV in the Scheme for Example 304. MS found for $C_{24}H_{24}F_2N_6O_2$ as $(M+H)^+$ 467.3. UV: $\lambda$=219, 261 nm. $^1$H NMR: $(CD_3OD)$ $\delta$8.23 (s, 1H), 7.48 (t, 1H), 7.12 (t, 1H), 7.03 (m, 1H), 6.91 (m, 2H), 6.80 (m, 2H), 5.88 (s, 1H), 4.45 (s, 2H), 3.43 (m, 4H), 1.98 (m, 4H).

Example 342

Kinase Assay Protocols

JAK and TYK2 tyrosine phosphorylation activity is measured using the Z'-LYTE™ Technology developed by Invitrogen Corporation (Carlsbad, Calif.). For JAK1, JAK2 and JAK3 the Z'-LYTE™ Kinase Assay Kit-Tyr6 Peptide (part number PV4122) was used. For TYK2 the Z'-LYTE™ Kinase Assay Kit-Tyr6 Peptide (part number PV3192) was used. The Z'-LYTE™ biochemical assay employs a fluorescence resonance energy transfer (FRET) coupled-enzyme format and is based on the differential sensitivity of phosphorylated and non-phosphorylated peptides to proteolitic cleavage. The assay uses a synthetic peptide substrate that is labelled with a donor fluorophore (coumarin) and an acceptor fluorophore (fluorescein) that make up a FRET pair. In the primary reaction (the Kinase Reaction), the kinase transfers the γ-phosphate of ATP to a single tyrosine residue on the substrate, while the presence of a kinase inhibitor in the primary reaction suppresses phosphorylation. In the secondary reaction (the Development Reaction), a site-specific protease (the Development Reagent) is added. The development buffer quenches the Kinase Reaction, while the protease recognizes and cleaves non-phosphorylated Z'-LYTE™ peptide substrate. Cleavage disrupts FRET between the donor and acceptor fluorophores on the non-phosphoryleted substrate, while uncleaved, phosphorylated substrate maintains FRET.

To test the ability of candidate molecules to inhibit JAK tyrosine phosphorylation activity, molecules are reconstituted in 100% DMSO and serially diluted 1:10 in polypropylene v-bottom microtiter plates. The candidate molecules are then diluted 1:25 into kinase buffer and 2.5 μl transferred into duplicate wells of a 384 well low volume black microtiter assay plate (Corning, USA). The final DMSO concentration in the assay is 1%. The kinase reaction contains 2.5 μl of a candidate molecule, 5 μl of catalytic domain recombinant Kinase enzyme+Tyr peptide substrate (Invitrogen, CA) and 2.5 μl ATP (Invitrogen, CA). The kinase reaction is allowed to procede for 1 hour at room temperature. The protease reaction is initiated by the addition of 5 μl Development Reagent (Invitrogen, CA). After 1 hour incubation at room temperature the fluorescence is measured using a FlexStation plate reader (Molecular Devices, Sunnyvale, Calif.). The reader settings used are as follows: Fluorescence mode, endpoint, top read, excitation 400 nm, emission 445 nm and 520 nm, Auto Cutoff 435 nm and 515 nm, PMT sensitivity high, 6 reads per well Inhibition of JAK activity is calculated as the percent phosphorylation of substrate in the presence of inhibitor compared to the percent phosphorylation of substrate in the absence of inhibitor. IC50's were derived using Xlfit 4.3 (IDBS, UK), 4 parameter logistic model 205: $Y=(A+4B-A)/(1+((C/x)^D))$).

Inhibition of IL4-induced phospho STAT6 formation was measured by pre-incubating 0.5 million Ramos B lymphocytes (ATCC) with 5 μl compound or DMSO vehicle for 1 hour at 37° C./5% $CO_2$. Cells were activated by addition of 1 ng/ml [f] IL4 (R & D Research Systems) for 10 min at 37° C./5% $CO_2$ and then fixed by addition of 1.6% [f] PFA (Electron Microscopy Services). Following a PBS wash step and permaeabilization with 100% methanol, cells were incubated with ALEXA-conjugated anti-phosphoSTAT6 (Y641) antibody (BD 612600). The extent of cell associated-fluorescence was determined by flow cytomentry and data expressed as mean fluorescent intensity. The extent of inhibition of the IL4-induced signal was then calculated.

In the table below, activity in the Jak assays is provided as follows: +++++=$IC_{50}$<0.0010 μM; ++++=0.0010 μM<$IC_{50}$<0.010 μM, +++=0.010 μM<$IC_{50}$<0.10 μM, ++=0.10 μM<$IC_{50}$<1 μM, +=$IC_{50}$>1 μM.

TABLE 1

Select data for Examples.

| Example No. | Syk IC50 | JAK1 IC50 | JAK2 IC50 | JAK3 IC50 | Tyk2 IC50 | % Inhibition of IL-4 Induced STAT6 Phosphorylation 200 nM | 1 μM |
|---|---|---|---|---|---|---|---|
| 1 | ++ | +++ | +++ | ++++ | NT | | |
| 2 | NT | +++ | +++ | ++++ | +++ | | |
| 3 | + | +++ | ++++ | ++++ | NT | | |
| 4 | ++ | +++ | +++ | +++ | +++ | | |
| 5 | ++ | ++ | ++ | +++ | +++ | | |
| 6 | ++ | +++ | +++ | +++ | +++ | | |
| 7 | ++ | +++ | +++ | ++++ | ++++ | | |
| 8 | ++ | NT | NT | NT | NT | | |
| 9 | ++ | NT | NT | NT | NT | | |
| 10 | ++ | NT | NT | NT | NT | | |
| 11 | ++ | NT | NT | NT | NT | | |
| 12 | ++ | NT | NT | NT | NT | | |

TABLE 1-continued

Select data for Examples.

| Example No. | Syk IC50 | JAK1 IC50 | JAK2 IC50 | JAK3 IC50 | Tyk2 IC50 | % Inhibition of IL-4 Induced STAT6 Phosphorylation 200 nM | % Inhibition of IL-4 Induced STAT6 Phosphorylation 1 μM |
|---|---|---|---|---|---|---|---|
| 13 | ++ | NT | NT | NT | NT | | |
| 14 | ++ | NT | NT | NT | NT | | |
| 15 | ++ | +++ | +++ | ++++ | NT | | |
| 16 | ++ | NT | NT | NT | NT | | |
| 17 | ++ | +++ | ++++ | +++++ | ++++ | 34.0 | 73.7 |
| 18 | + | + | ++ | +++ | NT | | |
| 19 | ++ | +++ | +++ | ++++ | NT | | |
| 20 | ++ | +++ | +++ | ++++ | ++++ | 41.3 | 89.6 |
| 21 | ++ | +++ | +++ | ++++ | NT | | |
| 22 | ++ | +++ | +++ | ++++ | NT | | |
| 23 | ++ | +++ | +++ | ++++ | NT | | |
| 24 | ++ | ++ | ++ | +++ | +++ | 24.7 | 71.3 |
| 25 | ++ | +++ | +++ | ++++ | NT | | |
| 26 | + | ++ | +++ | ++++ | ++++ | 7.3 | 45.7 |
| 27 | + | ++ | +++ | ++++ | +++ | 7.0 | 54.3 |
| 28 | + | +++ | +++ | ++++ | ++++ | 32.0 | 77.7 |
| 29 | + | +++ | +++ | ++++ | ++++ | 37.5 | 80.0 |
| 30 | ++ | ++ | +++ | ++++ | ++++ | 8.3 | 63.0 |
| 31 | + | ++ | ++ | ++++ | +++ | 13.7 | 37.0 |
| 32 | + | ++ | ++ | +++ | +++ | 27.0 | 65.0 |
| 33 | ++ | +++ | +++ | ++++ | NT | | |
| 34 | ++ | +++ | +++ | ++++ | NT | | |
| 35 | ++ | +++ | +++ | ++++ | NT | | |
| 36 | ++ | +++ | +++ | ++++ | NT | | |
| 37 | + | +++ | +++ | ++++ | ++++ | | |
| 38 | ++ | +++ | +++ | ++++ | ++++ | 41.3 | 82.7 |
| 39 | + | +++ | +++ | ++++ | ++++ | 15.0 | 60.0 |
| 40 | + | +++ | +++ | +++++ | ++++ | 47.2 | 78.8 |
| 41 | + | + | ++ | +++ | +++ | 50.7 | 95.3 |
| 42 | + | ++ | ++ | ++ | NT | | |
| 43 | + | ++ | ++ | +++ | NT | | |
| 44 | + | ++ | ++ | +++ | NT | | |
| 45 | + | + | ++ | ++ | NT | | |
| 46 | + | + | + | ++ | NT | | |
| 47 | + | ++ | +++ | ++++ | +++ | 25.3 | 77.7 |
| 48 | + | ++ | +++ | ++++ | NT | | |
| 49 | ++ | ++ | +++ | ++++ | NT | | |
| 50 | + | ++ | ++ | ++ | NT | | |
| 51 | ++ | ++ | +++ | +++ | NT | | |
| 52 | ++ | +++ | +++ | ++++ | ++++ | 63.0 | 94.0 |
| 53 | ++ | +++ | +++ | ++++ | NT | | |
| 54 | + | ++ | ++ | ++ | NT | | |
| 55 | ++ | +++ | +++ | ++++ | NT | | |
| 56 | ++ | ++ | +++ | +++ | NT | | |
| 57 | ++ | +++ | +++ | ++++ | +++ | 55.0 | 76.5 |
| 58 | ++ | +++ | ++++ | ++++ | NT | | |
| 59 | ++ | +++ | +++ | ++++ | NT | | |
| 60 | + | ++ | ++ | +++ | ++ | 12.5 | 23.0 |
| 61 | + | +++ | ++ | +++ | NT | | |
| 62 | + | +++ | ++ | +++ | NT | | |
| 63 | + | + | + | ++ | NT | | |
| 64 | + | ++ | ++ | +++ | NT | | |
| 65 | + | + | ++ | +++ | +++ | | |
| 66 | + | ++ | ++ | ++ | ++ | | |
| 67 | + | ++ | ++ | +++ | NT | | |
| 68 | + | ++ | ++ | +++ | NT | | |
| 69 | + | ++ | ++ | +++ | NT | | |
| 70 | + | + | ++ | ++ | NT | | |
| 71 | + | ++ | +++ | ++++ | NT | | |
| 72 | + | ++ | ++ | +++ | NT | | |
| 73 | + | +++ | +++ | ++++ | ++++ | 17.1 | 55.6 |
| 74 | ++ | +++ | +++ | +++ | NT | | |
| 75 | + | +++ | +++ | ++++ | ++++ | 53.3 | 90.3 |
| 76 | + | ++ | +++ | +++ | +++ | | |
| 77 | + | ++ | +++ | ++++ | +++ | | |
| 78 | + | +++ | ++++ | ++++ | +++ | | |
| 79 | + | +++ | +++ | ++++ | +++ | | |
| 80 | + | ++ | ++ | +++ | +++ | | |
| 81 | + | ++ | +++ | +++ | +++ | | |
| 82 | ++ | ++ | +++ | +++ | +++ | | |
| 83 | + | ++ | ++ | +++ | +++ | | |
| 84 | ++ | +++ | +++ | ++++ | +++ | | |
| 85 | + | ++ | ++ | +++ | +++ | | |
| 86 | + | ++ | ++++ | ++++ | +++ | | |
| 87 | + | ++ | ++++ | ++++ | +++ | | |
| 88 | + | +++ | +++ | +++ | +++ | | |
| 89 | + | +++ | ++++ | ++++ | +++ | | |
| 90 | + | +++ | +++ | ++++ | +++ | | |
| 91 | NT | +++ | +++ | +++ | +++ | | |
| 92 | NT | +++ | +++ | +++ | +++ | | |
| 93 | + | ++ | +++ | ++++ | +++ | 20.0 | 53.0 |
| 94 | NT | +++ | +++ | ++++ | +++ | | |
| 95 | NT | +++ | +++ | ++++ | +++ | | |
| 96 | NT | +++ | +++ | +++ | +++ | | |
| 97 | NT | +++ | +++ | ++++ | ++++ | | |
| 98 | NT | ++ | ++ | +++ | ++ | | |
| 99 | NT | ++ | +++ | +++ | +++ | | |
| 100 | NT | +++ | +++ | ++++ | ++++ | 43.5 | 95.3 |
| 101 | NT | +++ | ++++ | ++++ | +++ | | |
| 102 | NT | ++ | +++ | ++++ | +++ | | |
| 103 | NT | ++ | +++ | +++ | +++ | | |
| 104 | NT | ++ | +++ | +++ | +++ | | |
| 105 | NT | ++ | +++ | ++++ | +++ | | |
| 106 | NT | ++ | ++ | +++ | +++ | 16.8 | 27.8 |
| 107 | NT | + | + | ++ | ++ | | |
| 108 | NT | ++ | +++ | ++++ | +++ | 21.3 | 70.0 |
| 109 | NT | ++ | ++ | +++ | ++ | | |
| 110 | NT | ++ | ++ | +++ | ++ | 48.3 | 97.7 |
| 111 | NT | + | + | ++ | ++ | | |
| 112 | NT | + | + | + | + | | |
| 113 | NT | + | + | ++ | ++ | | |
| 114 | NT | +++ | +++ | +++ | +++ | | |
| 115 | + | ++ | ++ | +++ | ++ | 12.3 | 53.7 |
| 116 | NT | +++ | +++ | +++ | +++ | | |
| 117 | ++ | +++ | ++++ | +++++ | ++++ | 4.5 | 29.5 |
| 118 | NT | +++ | ++++ | ++++ | +++ | | |
| 119 | ++ | +++ | +++ | ++++ | +++ | 9.0 | 63.0 |
| 120 | NT | +++ | +++ | ++++ | +++ | | |
| 121 | + | ++ | +++ | ++++ | +++ | 18.3 | 61.7 |
| 122 | NT | ++ | +++ | ++++ | ++ | | |
| 123 | NT | +++ | +++ | ++++ | ++++ | | |
| 124 | NT | +++ | +++ | ++++ | ++++ | | |
| 125 | NT | +++ | +++ | +++ | +++ | | |
| 126 | NT | +++ | +++ | +++ | +++ | | |
| 127 | NT | ++ | +++ | +++ | ++ | | |
| 128 | + | +++ | +++ | +++++ | +++ | 31.7 | 82.7 |
| 129 | + | + | ++ | +++ | ++ | 4.0 | 16.7 |
| 130 | + | ++ | +++ | ++++ | +++ | 0.7 | 19.0 |
| 131 | + | + | ++ | ++++ | +++ | 0.3 | 4.3 |
| 132 | NT | ++ | ++ | +++ | ++ | 7.5 | 53.7 |
| 133 | NT | ++ | ++ | +++ | +++ | | |
| 134 | NT | +++ | +++ | +++ | +++ | | |
| 135 | NT | +++ | +++ | ++++ | ++++ | 42.3 | 89.7 |
| 136 | NT | +++ | +++ | +++ | +++ | | |
| 137 | NT | ++ | +++ | ++++ | +++ | 14.7 | 57.3 |
| 138 | NT | ++ | +++ | ++++ | +++ | | |
| 139 | NT | +++ | +++ | ++++ | +++ | 25.3 | 74.3 |
| 140 | NT | +++ | +++ | ++++ | ++++ | 21.7 | 69.0 |
| 141 | NT | ++ | +++ | ++++ | ++ | | |
| 142 | NT | +++ | +++ | ++++ | ++++ | 41.3 | 79.3 |
| 143 | NT | +++ | +++ | ++++ | ++++ | 44.7 | 85.7 |
| 144 | NT | ++ | ++ | +++ | +++ | | |
| 145 | NT | +++ | +++ | ++++ | +++ | | |
| 146 | NT | +++ | +++ | ++++ | ++++ | 40.7 | 82.0 |
| 147 | NT | +++ | +++ | ++++ | ++++ | 28.7 | 82.0 |
| 148 | NT | ++ | +++ | ++++ | +++ | | |
| 149 | NT | ++ | +++ | ++++ | +++ | 6.7 | 44.0 |
| 150 | NT | + | + | ++ | ++ | | |
| 151 | NT | + | + | + | + | | |
| 152 | NT | ++ | ++ | +++ | ++ | | |
| 153 | NT | ++ | ++ | +++ | +++ | 22.3 | 51.7 |
| 154 | NT | + | + | +++ | ++ | 11.7 | 33.7 |
| 155 | NT | +++ | +++ | ++++ | ++++ | 71.7 | 88.0 |
| 156 | NT | +++ | +++ | ++++ | ++++ | 28.0 | 71.3 |

TABLE 1-continued

Select data for Examples.

| Example No. | Syk IC50 | JAK1 IC50 | JAK2 IC50 | JAK3 IC50 | Tyk2 IC50 | % Inhibition of IL-4 Induced STAT6 Phosphorylation | |
|---|---|---|---|---|---|---|---|
| | | | | | | 200 nM | 1 µM |
| 157 | NT | +++ | +++ | ++++ | ++++ | 23.0 | 31.7 |
| 158 | NT | + | +++ | ++++ | +++ | | |
| 159 | NT | ++ | +++ | ++++ | +++ | | |
| 160 | NT | +++ | +++ | ++++ | +++ | 12.3 | 50.3 |
| 161 | NT | ++ | +++ | ++++ | ++ | | |
| 162 | NT | +++ | +++ | ++++ | +++ | | |
| 163 | NT | +++ | +++ | ++++ | ++++ | 20.7 | 61.0 |
| 164 | NT | +++ | +++ | ++++ | ++++ | 34.7 | 68.7 |
| 165 | NT | + | ++ | +++ | + | 57.3 | 89.7 |
| 166 | NT | +++ | +++ | +++ | +++ | | |
| 167 | NT | +++ | ++ | +++ | +++ | | |
| 168 | NT | +++ | +++ | ++++ | ++++ | 54.0 | 92.0 |
| 169 | NT | ++ | ++ | ++++ | +++ | 3.3 | 16.7 |
| 170 | NT | + | + | ++++ | +++ | 5.7 | 53.7 |
| 171 | NT | ++ | ++ | +++ | ++ | 7.3 | 15.3 |
| 172 | NT | ++ | ++ | +++ | ++ | 11.3 | 33.0 |
| 173 | NT | + | ++ | +++ | ++ | | |
| 174 | NT | +++ | ++ | +++ | +++ | | |
| 175 | NT | ++ | ++ | +++ | +++ | | |
| 176 | NT | +++ | ++ | +++ | +++ | | |
| 177 | NT | + | ++ | ++++ | ++ | 2.3 | 7.3 |
| 178 | NT | ++ | +++ | +++ | +++ | | |
| 179 | NT | +++ | +++ | ++++ | +++ | 11.3 | 10.7 |
| 180 | NT | +++ | +++ | ++++ | +++ | | |
| 181 | NT | +++ | +++ | ++++ | ++++ | 23.7 | 38.7 |
| 182 | NT | +++ | +++ | ++++ | ++++ | 42.3 | 89.0 |
| 183 | NT | ++ | +++ | ++++ | +++ | | |
| 184 | NT | ++++ | ++++ | ++++ | ++++ | | |
| 185 | NT | +++ | +++ | ++++ | ++++ | | |
| 186 | NT | + | +++ | +++ | + | | |
| 187 | NT | ++ | +++ | +++ | +++ | | |
| 188 | NT | ++ | +++ | +++ | +++ | | |
| 189 | NT | ++ | ++ | +++ | +++ | | |
| 190 | NT | +++ | +++ | ++++ | +++ | 17.0 | 39.3 |
| 191 | NT | +++ | +++ | ++++ | +++ | | |
| 192 | NT | + | +++ | ++++ | +++ | | |
| 193 | NT | ++ | ++ | ++++ | ++ | 13.7 | 51.3 |
| 194 | NT | ++ | ++ | ++++ | +++ | 10.0 | 22.7 |
| 195 | NT | ++ | +++ | ++++ | +++ | 3.3 | 27.3 |
| 196 | NT | ++ | ++ | ++++ | +++ | 8.3 | 65.0 |
| 197 | NT | + | +++ | +++ | +++ | | |
| 198 | NT | + | +++ | +++ | +++ | | |
| 199 | NT | +++ | +++ | +++ | +++ | | |
| 200 | NT | + | + | +++ | ++ | | |
| 201 | NT | + | + | +++ | ++ | | |
| 202 | NT | +++ | +++ | ++++ | ++++ | 23.5 | 48.5 |
| 203 | NT | +++ | +++ | ++++ | ++++ | 80.0 | 106.3 |
| 204 | NT | ++ | ++ | ++ | ++ | | |
| 205 | NT | + | ++ | +++ | ++ | | |
| 206 | NT | +++ | +++ | +++ | ++++ | | |
| 207 | NT | ++ | +++ | +++ | +++ | | |
| 208 | NT | +++ | +++ | ++++ | +++ | 22.7 | 67.7 |
| 209 | NT | + | + | ++++ | ++ | 0.3 | 1.0 |
| 210 | NT | +++ | +++ | ++++ | ++++ | 48.0 | 81.7 |
| 211 | NT | + | + | + | + | | |
| 212 | NT | NT | ++ | ++ | ++ | | |
| 213 | NT | ++ | ++ | +++ | ++ | 11.3 | 35.3 |
| 214 | NT | NT | NT | NT | NT | | |
| 215 | NT | +++ | +++ | ++++ | +++ | | |
| 216 | NT | +++ | +++ | +++++ | ++++ | 57.3 | 91.0 |
| 217 | NT | +++ | +++ | ++++ | ++++ | 61.3 | 92.0 |
| 218 | NT | +++ | +++ | ++++ | ++++ | 28.7 | 76.0 |
| 219 | NT | +++ | +++ | ++++ | ++++ | 19.0 | 65.3 |
| 220 | NT | ++ | +++ | ++++ | +++ | | |
| 221 | NT | + | ++ | +++ | ++ | 2.3 | 6.3 |
| 222 | NT | +++ | +++ | ++++ | ++++ | 47.7 | 86.7 |
| 223 | NT | +++ | ++++ | ++++ | +++ | | |
| 224 | NT | ++ | +++ | +++ | ++ | | |
| 225 | NT | ++ | ++ | +++ | ++ | | |
| 226 | NT | +++ | ++ | +++ | ++ | | |
| 227 | NT | +++ | ++++ | ++++ | +++ | | |
| 228 | NT | ++ | +++ | ++++ | +++ | | |
| 229 | NT | + | +++ | +++ | ++ | | |
| 230 | NT | +++ | ++++ | ++++ | +++ | | |
| 231 | NT | +++ | ++++ | +++++ | +++ | | |
| 232 | NT | ++ | +++ | +++ | ++ | | |
| 233 | NT | ++ | ++ | ++++ | +++ | 7.0 | 37.7 |
| 234 | NT | +++ | +++ | ++++ | +++ | 34.3 | 77.0 |
| 235 | NT | +++ | +++ | ++++ | ++++ | | |
| 236 | NT | +++ | +++ | +++ | +++ | | |
| 237 | NT | +++ | +++ | ++++ | +++ | | |
| 238 | NT | ++++ | ++++ | +++++ | ++++ | | |
| 239 | NT | ++ | +++ | +++ | +++ | | |
| 240 | NT | + | + | ++ | + | | |
| 241 | NT | ++ | ++ | +++ | ++ | | |
| 242 | NT | + | + | ++ | + | | |
| 243 | NT | +++ | ++++ | ++++ | ++++ | | |
| 244 | NT | +++ | +++ | +++++ | ++++ | 51.3 | 94.7 |
| 245 | NT | +++ | +++ | +++++ | ++++ | 51.3 | 87.0 |
| 246 | NT | +++ | +++ | ++++ | +++ | 23.7 | 37.7 |
| 247 | NT | +++ | +++ | +++ | +++ | | |
| 248 | NT | +++ | + | +++ | +++ | 61.3 | 94.7 |
| 249 | NT | +++ | ++++ | +++++ | ++++ | | |
| 250 | NT | +++ | ++ | ++++ | +++ | | |
| 251 | NT | +++ | +++ | ++++ | ++++ | | |
| 252 | NT | ++++ | ++++ | +++++ | +++++ | | |
| 253 | NT | +++ | +++ | ++++ | ++++ | | |
| 254 | NT | +++ | ++++ | ++++ | +++ | | |
| 255 | NT | +++ | ++++ | +++++ | +++ | | |
| 256 | NT | +++ | ++++ | ++++ | +++ | | |
| 257 | NT | +++ | ++++ | +++++ | ++++ | | |
| 258 | NT | +++ | ++++ | +++++ | ++++ | | |
| 259 | NT | +++ | ++++ | ++++ | ++++ | | |
| 260 | NT | + | ++ | +++ | +++ | | |
| 261 | NT | + | +++ | +++ | +++ | | |
| 262 | NT | +++ | +++ | ++++ | ++++ | | |
| 263 | NT | + | + | + | + | | |
| 264 | NT | NT | NT | NT | NT | | |
| 265 | NT | NT | NT | NT | NT | | |
| 266 | NT | NT | NT | NT | NT | | |
| 267 | | | | | ++++ | | |
| 280 | | | | | +++++ | | |
| 281 | | | | | ++ | | |
| 282 | | | | | +++++ | | |
| 283 | | | | | +++++ | | |
| 284 | | | | | +++++ | | |
| 288 | | | | | ++++ | | |
| 289 | | | | | +++ | | |
| 290 | | | | | ++++ | | |
| 295 | | | | | +++ | | |
| 296 | | | | | +++++ | | |
| 297 | | | | | ++++ | | |
| 298 | | | | | ++++ | | |
| 299 | | | | | +++++ | | |
| 300 | | | | | +++++ | | |
| 301 | | | | | ++++ | | |
| 302 | | | | | +++ | | |
| 303 | | | | | +++ | | |
| 304 | | + | + | +++ | | | |
| 305 | + | ++ | ++ | ++++ | | | |
| 306 | + | ++ | +++ | +++++ | | | |
| 307 | ++ | ++ | ++ | +++ | | | |
| 308 | | ++ | +++ | ++++ | | | |
| 309 | | ++ | +++ | ++++ | | | |
| 310 | | ++ | ++ | ++++ | | | |
| 311 | | + | ++ | ++++ | | | |
| 312 | + | + | ++ | ++++ | | | |
| 313 | | + | + | +++ | | | |
| 314 | | ++ | ++ | ++++ | | | |
| 315 | | + | ++ | ++++ | | | |
| 316 | | ++ | ++ | +++ | | | |
| 317 | | + | + | +++ | | | |
| 318 | | + | ++ | +++ | | | |
| 319 | | + | ++ | +++ | | | |

TABLE 1-continued

Select data for Examples.

| Example No. | Syk IC50 | JAK1 IC50 | JAK2 IC50 | JAK3 IC50 | Tyk2 IC50 | % Inhibition of IL-4 Induced STAT6 Phosphorylation | |
|---|---|---|---|---|---|---|---|
| | | | | | | 200 nM | 1 μM |
| 320 | | + | ++ | +++ | | | |
| 321 | | ++ | ++ | +++ | | | |
| 322 | | ++ | ++ | +++ | ++ | | |
| 323 | | ++ | ++ | +++ | +++ | | |
| 324 | | ++ | ++ | +++ | ++ | | |
| 325 | | ++ | ++ | ++++ | ++ | | |
| 326 | | ++ | ++ | ++++ | +++ | | |
| 327 | | ++ | ++ | +++ | +++ | | |
| 328 | | ++ | ++ | +++ | +++ | | |
| 329 | | + | ++ | ++ | ++ | | |
| 330 | | ++ | ++ | ++ | +++ | | |
| 331 | | ++ | ++ | +++ | +++ | | |
| 332 | | + | ++ | ++ | + | | |
| 333 | | + | + | ++ | ++ | | |
| 334 | | + | + | ++ | + | | |
| 335 | | ++ | + | +++ | +++ | | |
| 336 | | ++ | ++ | ++++ | ++ | | |
| 337 | | ++ | ++ | +++ | ++ | | |
| 338 | | + | + | ++ | ++ | | |
| 339 | | + | + | + | | | |
| 340 | + | ++ | ++ | +++ | | | |
| 341 | | + | ++ | ++++ | | | |

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the formula I:

(I)

[Structure]

or a tautomer or pharmaceutically acceptable salt thereof, wherein:
  $Y^1$ is N or $CR^{1c}$;
  $R^{1a}$ is benzyl, optionally substituted with from 1 to 3 substituents selected from the group consisting of $C_{2-8}$alkenyl, $C_{2-8}$alkynyl, amino, hydroxy, halogen, $C_{1-8}$heteroalkyl, cyano, $C_{3-8}$cycloalkyl, aryl, haloaryl, $C_{1-8}$alkylaryl, and $C_{1-8}$alkoxyaryl, heteroaryl, $C_{3-8}$heterocyclyl and $C_{3-8}$heterocyclylcarbonyl;
  $R^{1b}$ is H or $C_{1-8}$alkyl;
  $R^{1c}$ is H, $C_{1-8}$alkyl or halogen;
  $R^2$ is H, $C_{1-8}$alkyl, $C_{1-8}$heteroalkyl, heterocyclyl $C_{1-8}$alkoxy, halogen or heterocyclyl;
  $R^3$ is H or $C_{1-8}$alkyl or $C_{3-8}$cycloalkyl;
  $R^4$ is selected from the group consisting amino, $C_{1-8}$alkyl, amino$C_{1-8}$alkyl, $C_{2-8}$alkenyl, $C_{2-8}$alkynyl, $C_{1-8}$heteroalkyl, $C_{3-8}$cycloalkyl, aryl, heteroaryl and $C_{3-8}$heterocyclyl; and
  m is 0, 1, 2 or 3.

2. A compound having the formula I:

(I)

[Structure]

or a tautomer or pharmaceutically acceptable salt thereof, wherein:
  $Y^1$ is N or $CR^{1c}$;
  $R^{1a}$ is benzyl, optionally substituted with from 1 to 3 substituents selected from the group consisting of $C_{2-8}$alkenyl, $C_{2-8}$alkynyl, amino, hydroxy, halogen, $C_{1-8}$heteroalkyl, cyano, $C_{3-8}$cycloalkyl, aryl, haloaryl, $C_{1-8}$alkylaryl, $C_{1-8}$alkoxyaryl, heteroaryl, $C_{3-8}$heterocyclyl and $C_{3-8}$heterocyclylcarbonyl;
  $R^{1b}$ is H or $C_{1-8}$alkyl;
  $R^{1c}$ is H, $C_{1-8}$alkyl or halogen;
  $R^2$ is H, $C_{1-8}$alkyl, $C_{1-8}$alkoxy or halogen;
  $R^3$ is H or $C_{1-8}$alkyl;
  $R^4$ is selected from the group consisting amino, $C_{1-8}$alkyl, $C_{2-8}$alkenyl, $C_{2-8}$alkynyl, $C_{1-8}$heteroalkyl, $C_{3-8}$cycloalkyl, aryl, heteroaryl and $C_{3-8}$heterocyclyl; and
  m is 0, 1, 2 or 3.

3. The compound of claim 1 wherein $Y^1$ is N.
4. The compound of claim 1 wherein $Y^1$ is CH.
5. The compound of claim 1 having the formula Ia:

(Ia)

[Structure]

or a tautomer or pharmaceutically acceptable salt thereof, wherein:
  $R^{1a}$ is benzyl, optionally substituted with from 1 to 3 substituents selected from the group consisting of $C_{2-8}$alkenyl, $C_{2-8}$alkynyl, amino, hydroxy, halogen, $C_{1-8}$heteroalkyl, cyano, $C_{3-8}$cycloalkyl, aryl, haloaryl, $C_{1-8}$alkylaryl, $C_{1-8}$alkoxyaryl, heteroaryl, $C_{3-8}$heterocyclyl and $C_{3-8}$heterocyclylcarbonyl;
  $R^{1b}$ is H or $C_{1-8}$alkyl;
  $R^2$ is H, $C_{1-8}$alkyl, $C_{1-8}$alkoxy or halogen;
  $R^3$ is H or $C_{1-8}$alkyl;

$R^4$ is selected from the group consisting $C_{1-8}$alkyl, $C_{1-8}$heteroalkyl, $C_{3-8}$cycloalkyl, and amino; and
m is 0, 1, 2 or 3.

6. The compound of claim 1 wherein $R^3$ is H.

7. The compound of claim 1 having the formula (Ib):

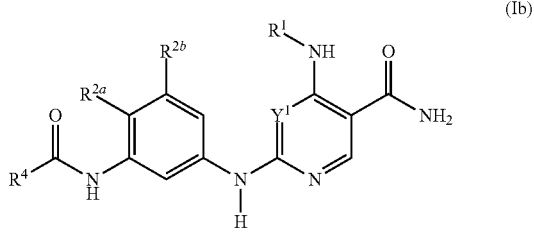

(Ib)

or a tautomer or pharmaceutically acceptable salt thereof, wherein:
$R^1$ is benzyl, optionally substituted with from 1 to 3 substituents selected from the group consisting of $C_{2-8}$alkynyl, hydroxy, halogen, $C_{1-8}$alkoxy, cyano, aminocarbonyl, $C_{3-8}$cycloalkyl, aryl, haloaryl, $C_{1-8}$alkylaryl, $C_{1-8}$alkoxyaryl, heteroaryl, and heterocyclyl, heterocyclylcarbonyl;
$R^{2a}$ is H, $C_{1-8}$alkyl, $C_{1-8}$alkoxy or halogen;
$R^{2b}$ is H, $C_{1-8}$alkyl, $C_{1-8}$alkoxy or halogen; and
$R^4$ is selected from the group consisting $C_{1-8}$alkyl, $C_{1-8}$alkoxy$C_{1-8}$alkylene, $C_{3-8}$ cycloalkyl, $C_{1-8}$alkoxy, and amino.

8. The compound of claim 7 wherein $R^1$ is benzyl, optionally substituted with from 1 to 3 substituents selected from the group consisting of $C_{2-8}$alkynyl, hydroxy, halogen, $C_{1-8}$alkoxy, cyano, aminocarbonyl, $C_{3-8}$cycloalkyl, aryl, haloaryl, heteroaryl, heterocyclyl, and heterocyclylcarbonyl.

9. The compound of claim 7 wherein $R^1$ is benzyl, substituted with from 1 to 3 substituents selected from the group consisting of $C_{2-8}$alkynyl, hydroxy, halogen, $C_{1-8}$alkoxy, cyano, aminocarbonyl and $C_{3-8}$cycloalkyl.

10. The compound of claim 7 wherein $R^1$ is benzyl, substituted with from 1 to 3 substituents selected from the group consisting of aryl, haloaryl, $C_{1-8}$alkylaryl, $C_{1-8}$alkoxyaryl, heteroaryl, heterocyclyl and heterocyclylcarbonyl.

11. The compound of claim 1 wherein $R^{2a}$ is H, methyl, methoxy, fluoro or chloro and $R^{2b}$ is H, methyl, methoxy, fluoro or chloro.

12. A compound having the formula (Ic):

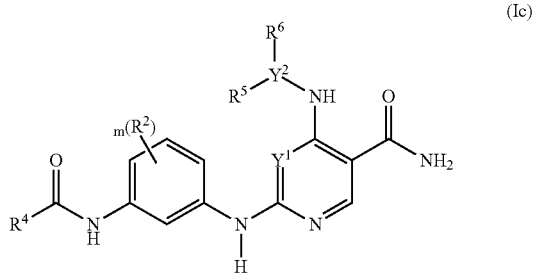

(Ic)

or a tautomer or pharmaceutically acceptable salt thereof, wherein:
$Y^2$ is —CH or —CH—CH—;
$R^5$ is H, $C_{1-8}$alkyl or hydroxy$C_{1-8}$alkylene; and
$R^6$ is benzyl, optionally substituted with from 1 to 3 substituents selected from the group consisting of $C_{2-8}$alkynyl, hydroxy, halogen, $C_{1-8}$alkoxy, cyano, aminocarbonyl, $C_{3-8}$cyclopropyl, aryl, haloaryl, $C_{1-8}$alkylaryl, $C_{1-8}$alkoxyaryl, heteroaryl, heterocyclyl and heterocyclylcarbonyl.

13. The compound of claim 12 wherein $R^5$ is selected from the group consisting of $CH_3$; and
$R^6$ is Ph or

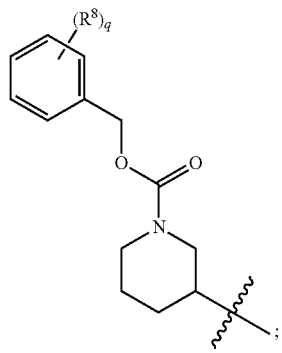

$R^8$ is selected from the group consisting of $C_{1-8}$alkyl, halogen, $C_{1-8}$alkoxy, or may be taken together to form a heterocyclic ring; and
q is 0, 1, 2 or 3; the wavy line indicates the point of attachment to the rest of the molecule.

14. The compound of claim 1 having the formula (Id):

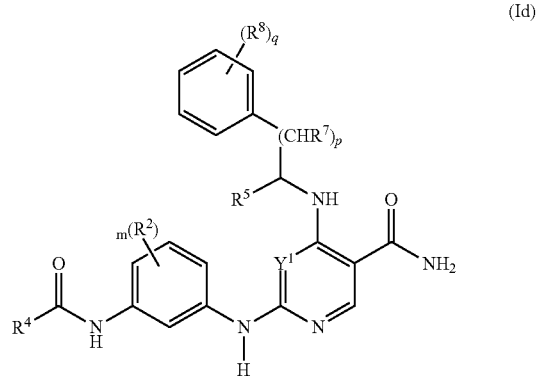

(Id)

or a tautomer or pharmaceutically acceptable salt thereof, wherein:
$R^5$ is $C_{1-8}$alkyl or hydroxy$C_{1-8}$alkylene; or may be taken together with $R^8$ to form a cyclic ring;
$R^7$ is $C_{1-8}$alkyl, hydroxy or $C_{1-8}$alkoxy;
$R^8$ is selected from the group consisting of $C_{1-8}$alkyl, halogen and $C_{1-8}$alkoxy, or may be taken together to form a heterocyclic ring; and
p is 0,1,2, or 3; and q is 0,1, 2 or 3.

15. The compound of claim 1 having the formula (Ie):

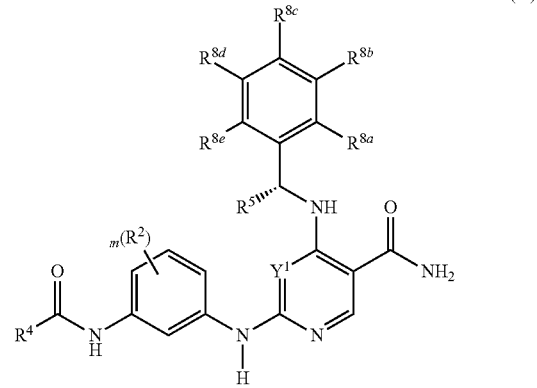

(Ie)

or a tautomer or pharmaceutically acceptable salt thereof, wherein:
R$^5$ is C$_{1-8}$alkyl or hydroxyC$_{1-8}$alkylene; or may be taken together with R$^{8a}$ or R$^{8b}$ to form a cyclic ring;
R$^{8a}$ is H, halogen, or may be taken together with R$^5$ to form 5-6 membered carbocyclic ring;
R$^{8b}$ is H, halogen or, or may be taken together with R$^{8a}$ to form a heterocyclic ring;
R$^{8c}$ is H, C$_{1-8}$alkyl, halogen or C$_{1-8}$alkoxy, or may be taken together with R$^{8b}$ to form a heterocyclic ring;
R$^{8d}$ is H; and
R$^{8e}$ is H, halogen or may be taken together with R$^5$ to form 5-6 membered carbocyclic ring.

16. The compound of claim 1 wherein R$^2$ is selected from the group consisting of: H and C$_{1-8}$alkyl.

17. The compound of claim 1 wherein R$^4$ is selected from the group consisting of: C$_{1-8}$alkyl and C$_{3-8}$cycloalkyl.

18. The compound of claim 1 wherein R$^5$ is selected from the group consisting of: H and C$_{1-8}$alkyl.

19. The compound of claim 1 wherein having formula (Ii):

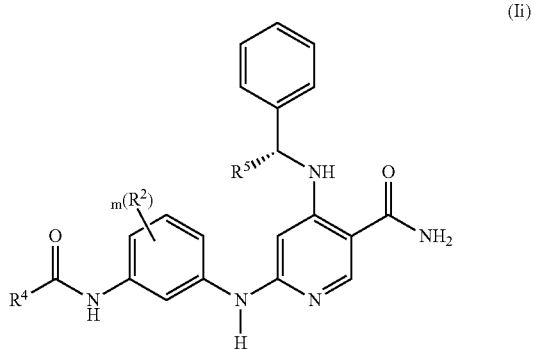

(Ii)

or a tautomer or pharmaceutically acceptable salt thereof, wherein:
R$^5$ is H or C$_{1-8}$alkyl;
R$^4$ is C$_{1-8}$alkyl or heterocyclyl.

20. The compound of claim 1 wherein R$^4$ is selected from the group consisting of —CH$_3$, —CH$_2$CH$_3$, —NH$_2$, —NHCH$_3$, —NCH$_2$CH$_3$, —N(CH$_3$)$_2$, —OCH$_3$, —OCH$_2$CH$_3$, —OCH(CH$_3$)$_2$, —CH$_2$OCH$_3$, —CH$_2$CONH$_2$, cPr, and cBu.

21. The compound of claim 1 wherein:
R$^4$ has the formula:

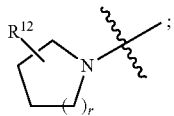

wherein R$^{12}$ is selected from the group consisting of H and OH,
r is 0 or 1; and
the wavy line indicates the point of attachment to the rest of the molecule.

22. The compound of claim 1 wherein:
R$^4$ has the formula:

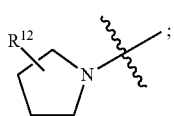

wherein R$^{12}$ is selected from the group consisting of H and OH; and
the wavy line indicates the point of attachment to the rest of the molecule.

23. The compound of claim 1 selected from the group consisting of: methyl 3-(5-carbamoyl-4-(2,2,2-trifluoroethylamino)pyrimidin-2-ylamino)phenylcarbamate; 2-(3-(cyclopropanecarboxamido)phenylamino)-4-(2,2,2-trifluoroethylamino)pyrimidine-5-carboxamide; 2-(3-(2-methoxyacetamido)phenylamino)-4-(2,2,2-trifluoroethylamino)pyrimidine-5-carboxamide; 2-(3-acetamidophenylamino)-4-(2,2,2-trifluoroethylamino)pyrimidine-5-carboxamide; 2-(3-acetamidophenylamino)-4-(methylamino)pyrimidine-5-carboxamide; 2-(3-acetamidophenylamino)-4-(ethylamino)pyrimidine-5-carboxamide; 2-(3-acetamidophenylamino)-4-(prop-2-ynylamino)pyrimidine-5-carboxamide; 2-(3-acetamidophenylamino)-4-(isopropylamino)pyrimidine-5-carboxamide; 2-(3-acetamidophenylamino)-4-(cyclopropylmethylamino)pyrimidine-5-carboxamide; 2-(3-acetamidophenylamino)-4-(tert-butylamino)pyrimidine-5-carboxamide; 2-(3-acetamidophenylamino)-4-(2-methoxyethylamino)pyrimidine-5-carboxamide; 2-(3-acetamidophenylamino)-4-(cyclopentylamino)pyrimidine-5-carboxamide; 2-(3-acetamidophenylamino)-4-(3-methoxypropylamino)pyrimidine-5-carboxamide; 2-(3-acetamidophenylamino)-4-(benzylamino)pyrimidine-5-carboxamide; methyl 5-(5-carbamoyl-4-(2,2,2-trifluoroethylamino)pyrimidin-2-ylamino)-2-chlorophenylcarbamate; 4-(cyclopentylamino)-2-(3-(cyclopropanecarboxamido)phenylamino)pyrimidine-5-carboxamide; 2-(3-(cyclobutanecarboxamido)phenylamino)-4-(cyclopentylamino)pyrimidine-5-carboxamide; 4-(cyclopentylamino)-2-(3-propionamidophenylamino)pyrimidine-5-carboxamide; 4-(cyclopentylamino)-2-(3-(2-methoxyacetamido)phenylamino)pyrimidine-5-carboxamide; methyl 3-(5-carbamoyl-4-(cyclopentylamino)pyrimidin-2-ylamino)phenylcarbamate; ethyl 3-(5-carbamoyl-4-(cyclopentylamino)pyrimidin-2-ylamino)phenylcarbamate; methyl 5-(5-carbamoyl-4-(cyclopentylamino)pyrimidin-2-ylamino)-2-chlorophenylcarbamate; 4-(benzylamino)-2-(3-(cyclopropanecarboxamido)phenylamino)pyrimidine-5-carboxamide; 4-(benzylamino)-2-(3-(cyclobutanecarboxamido)phenylamino)pyrimidine-5-carboxamide; 4-(benzylamino)-2-(3-propionamidophenylamino)pyrimidine-5-carboxamide; 4-(benzylamino)-2-(3-(2-methoxyacetamido)phenylamino)pyrimidine-5-carboxamide; methyl 3-(4-(benzylamino)-5-carbamoylpyrimidin-2-ylamino)phenylcarbamate; ethyl 3-(4-(benzylamino)-5-carbamoylpyrimidin-2-ylamino)phenylcarbamate; methyl 5-(4-(benzylamino)-5-carbamoylpyrimidin-2-ylamino)-2-chlorophenylcarbamate; 4-(cyclopentylamino)-2-(3-ureidophenylamino)pyrimidine-5-carboxamide; 4-(cyclopentylamino)-2-(3-(3-methylureido)phenylamino)pyrimidine-5-carboxamide; 4-(cyclopentylamino)-2-(3-(3,3-dimethylureido)phenylamino)pyrimidine-5-carboxamide; 4-(cyclopentylamino)-2-(3-(3-ethylureido)phenylamino)pyrimidine-5-carboxamide; 4-(cyclopentylamino)-2-(3-(pyrrolidine-1-carboxamido)phenylamino)pyrimidine-5-carboxamide; 4-(benzylamino)-2-(3-ureidophenylamino)pyrimidine-5-carboxamide; 4-(benzylamino)-2-(3-(3-methylureido)phenylamino)pyrimidine-5-carboxamide; 4-(benzylamino)-2-(3-(pyrrolidine-1-carboxamido)phenylamino)pyrimidine-5-carboxamide; isopropyl 3-(4-(benzylamino)-5-carbamoylpyrimidin-2-ylamino)phenylcarbamate; (S)-2-(3-(2-methoxyacetamido)phenylamino)-4-(1-phenylethylamino)pyrimidine-5-carboxamide; 2-(3-(2-methoxyacetamido)phenylamino)-4-(4-methylbenzylamino)pyrimidine-5-carboxamide; 2-(3-(2- methoxyacetamido)phenylamino)-4-(4-methoxybenzylamino)pyrimidine-5-carboxamide; 4-(4-chlorobenzylamino)-2-(3-(2-methoxyacetamido)phenylamino)pyrimidine-5-carboxamide; 4-(3,4-dichlorobenzylamino)-2-(3-(2-methoxyacetamido)phenylamino)pyrimidine-5-carboxamide; (R)-2-(3-(2-methoxyacetamido)phenylamino)-4-(1-phenylethylamino)pyrimidine-5-carboxamide; (S)-2-(3-acetamidophenylamino)-4-(2-hydroxy-2-phenylethylamino)pyrimidine-5-carboxamide; (R)-2-(3-acetamidophenylamino)-4-(2-hydroxy-2-phenylethylamino)pyrimidine-5-carboxamide; 2-(3-acetamidophenylamino)-4-(2-amino-2-oxoethylamino)pyrimidine-5-carboxamide; 2-(3-acetamidophenylamino)-4-(2-phenylcyclopropylamino)pyrimidine-5-carboxamide; 2-(3-acetamidophenylamino)-4-(cyclohexylamino)pyrimidine-5-carboxamide; 2-(3-acetamidophenylamino)-4-((trans)-2-hydroxycyclopentylamino)pyrimidine-5-carboxamide; 2-(3-acetamidophenylamino)-4-(benzyl(methyl)amino)pyrimidine-5-carboxamide; 4-(cyclobutylamino)-2-(3-(2-methoxyacetamido)phenylamino)pyrimidine-5-carboxamide; 2-(3-acetamidophenylamino)-4-(cyclobutylamino)pyrimidine-5-carboxamide; 2-(3-acetamidophenylamino)-4-(phenethylamino)pyrimidine-5-carboxamide; 4-(isopropylamino)-2-(3-(2-methoxyacetamido)phenylamino)pyrimidine-5-carboxamide; 2-(3-(2-methoxyacetamido)phenylamino)-4-(2,3,6-trifluorobenzylamino)pyrimidine-5-carboxamide; 2-(3-acetamidophenylamino)-4-(2,3,6-trifluorobenzylamino)pyrimidine-5-carboxamide; (S)-2-(3-acetamidophenylamino)-4-(2-phenylpropylamino)pyrimidine-5-carboxamide; (S)-2-(3-acetamidophenylamino)-4-(1-hydroxy-3-(1H-imidazol-5-yl)propan-2-ylamino)pyrimidine-5-carboxamide; 2-(3-acetamidophenylamino)-4-(3-amino-3-oxopropylamino)pyrimidine-5-carboxamide; (R)-2-(3-acetamidophenylamino)-4-(1-hydroxy-4-methylpentan-2-ylamino)pyrimidine-5-carboxamide; 2-(3-acetamidophenylamino)-4-(2-(pyrrolidin-1-yl)ethylamino)pyrimidine-5-carboxamide; (S)-2-(3-acetamidophenylamino)-4-(1-phenylethylamino)pyrimidine-5-carboxamide; 2-(3-acetamidophenylamino)-4-(2-oxo-2-(pyrrolidin-1-yl)ethylamino)pyrimidine-5-carboxamide; (R)-2-(3-acetamidophenylamino)-4-(piperidin-3-ylamino)pyrimidine-5-carboxamide; 2-(3-acetamidophenylamino)-4-(4-methylbenzylamino)pyrimidine-5-carboxamide; 2-(3-acetamidophenylamino)-4-(4-methoxybenzylamino)pyrimidine-5-carboxamide; 2-(3-acetamidophenylamino)-4-(4-chlorobenzylamino)pyrimidine-5-carboxamide; 2-(3-acetamidophenylamino)-4-(3,4-dichlorobenzylamino)pyrimidine-5-carboxamide; (R)-2-(3-acetamidophenylamino)-4-(1-phenylethylamino)pyrimidine-5-carboxamide; 2-(3-acetamidophenylamino)-4-(2-(methylamino)-2-oxoethylamino)pyrimidine-5-carboxamide; 2-(3-acetamidophenylamino)-4-((2S,3S)-1-hydroxy-3-methylpentan-2-ylamino)pyrimidine-5-carboxamide; 2-(3-acetamidophenylamino)-4-(cyanomethylamino)pyrimidine-5-carboxamide; 2-(3-acetamidophenylamino)-4-(tetrahydro-2H-pyran-4-ylamino)pyrimidine-5-carboxamide; (S)-2-(3-acetamidophenylamino)-4-(1-hydroxy-3-phenylpropan-2-ylamino)pyrimidine-5-carboxamide; 4-(isopropylamino)-2-(3-(N-methylacetamido)phenylamino)pyrimidine-5-carboxamide; 4-(cyclopentylamino)-2-(3-(N-methylacetamido)phenylamino)pyrimidine-5-carboxamide; 4-(benzylamino)-2-(3-(N-methylacetamido)phenylamino)pyrimidine-5-carboxamide; 2-(3-acetamidophenylamino)-4-(2-morpholinoethylamino)pyrimidine-5-carboxamide; (R)-2-(3-acetamidophenylamino)-4-(2-phenylpropylamino)pyrimidine-5-carboxamide; (S)-2-(3-acetamidophenylamino)-4-(2-hydroxypropylamino)pyrimidine-5-carboxamide; (R)-2-(3-acetamidophenylamino)-4-(2,3-dihydroxypropylamino)pyrimidine-5-carboxamide; 2-(3-acetamidophenylamino)-4-(2-methoxy-2-phenylethylamino)pyrimidine-5-carboxamide; (S)-2-(3-acetamidophenylamino)-4-(1-amino-1-oxopropan-2-ylamino)pyrimidine-5-carboxamide; (R)-2-(3-(2-methoxy-N-methylacetamido)phenylamino)-4-(1-phenylethylamino)pyrimidine-5-carboxamide; (R)-2-(3-(N-methylacetamido)phenylamino)-4-(1-phenylethylamino)pyrimidine-5-carboxamide; 4-(isopropylamino)-2-(3-(2-methoxy-N-methylacetamido)phenylamino)pyrimidine-5-carboxamide; 4-(cyclopentylamino)-2-(3-(2-methoxy-N-methylacetamido)phenylamino)pyrimidine-5-carboxamide; 4-(benzylamino)-2-(3-(2-methoxy-N-methylacetamido)phenylamino)pyrimidine-5-carboxamide; (R)-2-(3-acetamidophenylamino)-4-(1-amino-1-oxopropan-2-ylamino)pyrimidine-5-carboxamide; 2-(3-acetamidophenylamino)-4-(2,3-dihydro-1H-inden-2-ylamino)pyrimidine-5-carboxamide; (S)-2-(3-acetamidophenylamino)-4-(2-hydroxy-1-phenylethylamino)pyrimidine-5-carboxamide; 2-(3-acetamidophenylamino)-4-(3-fluorobenzylamino)pyrimidine-5-carboxamide; 2-(3-acetamidophenylamino)-4-(2,3-difluorobenzylamino)pyrimidine-5-carboxamide; (S)-2-(3-acetamidophenylamino)-4-(2,3-dihydro-1H-inden-1-ylamino)pyrimidine-5-carboxamide; (R)-2-(3-acetamidophenylamino)-4-(2,3-dihydro-1H-inden-1-ylamino)pyrimidine-5-carboxamide; (R)-2-(3-acetamidophenylamino)-4-(2-hydroxy-1-phenylethylamino)pyrimidine-5-carboxamide; 2-(3-acetamidophenylamino)-4-(benzo[d][1,3]dioxol-5-ylmethylamino)pyrimidine-5-carboxamide; 2-(3-acetamidophenylamino)-4-(2-fluorobenzylamino)pyrimidine-5-carboxamide; 2-(3-acetamidophenylamino)-4-(3-chlorobenzylamino)pyrimidine-5-carboxamide; 2-(3-acetamidophenylamino)-4-(2,5-difluorobenzylamino)pyrimidine-5-carboxamide; 2-(3-acetamidophenylamino)-4-(4-fluorobenzylamino)pyrimidine-5-carboxamide; 4-(4-fluorobenzylamino)-2-(3-(2-methoxyacetamido)phenylamino)pyrimidine-5-carboxamide; and (R)-4-(1-phenylethylamino)-2-(3-(pyrrolidine-1-carboxamido)phenylamino)pyrimidine-5-carboxamide; 2-(3-acetamido-4-chlorophenylamino)-4-(benzylamino)pyrimidine-5-carboxamide; 4-(benzylamino)-2-(4-chloro-3-(2-methoxyacetamido)phenylamino)pyrimidine-5-carboxamide; 4-(benzylamino)-2-(4-chloro-3-(3-cyclobutylureido)phenylamino)pyrimidine-5-carboxamide; (R)-2-(3-acetamido-4-chlorophenylamino)-4-(1-phenylethylamino)pyrimidine-5-carboxamide; (R)-2-(4-chloro-3-(2-methoxyacetamido)phenylamino)-4-(1-phenylethylamino)pyrimidine-5-carboxamide; (R)-2-(4-chloro-3-(cyclopropanecarboxamido)phenylamino)-4-(1-phenylethylamino)pyrimidine-5-carboxamide; (R)-2-(4-chloro-3-(3-cyclobutylureido)phenylamino)-4-(1-phenylethylamino)pyrimidine-5-carboxamide; 2-(3-acetamidophenylamino)-4-(benzylamino)-N-methylpyrimidine-5-carboxamide; 4-(benzylamino)-2-(3-(2-methoxyacetamido)phenylamino)-N-methylpyrimidine-5-carboxamide; methoxyacetamido)phenylamino)-N-methylpyrimidine-5-carboxamide; benzyl 3-((2-(3-acetamidophenylamino)-5-carbamoylpyrimidin-4-ylamino)methyl)piperidine-1-carboxylate; and 6-(3-acetamidophenylamino)-4-(benzylamino)nicotinamide.

24. A composition comprising a compound of claim 1 in combination with a pharmaceutically acceptable carrier or diluent.

25. A kit comprising a composition of claim 24, packaging and instructions for use.

26. A compound of claim 1 that is 2-(4-chloro-3-(pyrrolidine-1-carboxamido)phenylamino)-4-(2-fluorobenzylamino)pyrimidine-5-carboxamide or a pharmaceutically acceptable salt thereof.

27. A composition comprising a compound of claim 26 in combination with a pharmaceutically acceptable carrier or diluent.

* * * * *

UNITED STATES PATENT AND TRADEMARK OFFICE
CERTIFICATE OF CORRECTION

PATENT NO. : 8,367,689 B2  
APPLICATION NO. : 12/775358  
DATED : February 5, 2013  
INVENTOR(S) : Bauer et al.

Page 1 of 1

It is certified that error appears in the above-identified patent and that said Letters Patent is hereby corrected as shown below:

On the Title Page:

References Cited, item (56), in the OTHER PUBLICATIONS subsection, page 1, second col., line 26: delete "Singnaling" and insert --Signaling--.

References Cited, item (56), in the OTHER PUBLICATIONS subsection, page 1, second col., line 31: delete "Hematpoietic" and insert --Hematopoietic--.

In the Claims:

In column 208, line 48, delete "3;andqis-0,1," and insert --3; and q is -0, 1,--.

Signed and Sealed this  
Seventeenth Day of September, 2013

Teresa Stanek Rea  
*Deputy Director of the United States Patent and Trademark Office*